US012065428B2

(12) United States Patent
Bardiot et al.

(10) Patent No.: US 12,065,428 B2
(45) Date of Patent: Aug. 20, 2024

(54) ANTI-VIRAL COMPOUNDS

(71) Applicants: Aligos Therapeutics, Inc., South San Francisco, CA (US); Katholieke Universiteit Leuven, Leuven (BE)

(72) Inventors: Dorothée Alice Marie-Eve Bardiot, Leuven (BE); Koen Vandyck, Paal (BE); Sandro Boland, Leuven (BE); Antitsa Dimitrova Stoycheva, Half Moon Bay, CA (US); Arnaud Didier Marie Marchand, Leuven (BE); Pierre Jean-Marie Bernard Raboisson, Wavre (BE); Leonid Beigelman, San Mateo, CA (US)

(73) Assignees: Aligos Therapeutics, Inc., South San Francisco, CA (US); Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 17/932,218

(22) Filed: Sep. 14, 2022

(65) Prior Publication Data
US 2023/0140238 A1    May 4, 2023

Related U.S. Application Data

(60) Provisional application No. 63/367,791, filed on Jul. 6, 2022, provisional application No. 63/265,481, filed on Dec. 15, 2021, provisional application No. 63/261,339, filed on Sep. 17, 2021.

(51) Int. Cl.
| | | |
|---|---|---|
| *C07D 401/14* | (2006.01) | |
| *C07D 401/12* | (2006.01) | |
| *C07D 405/14* | (2006.01) | |
| *C07D 409/14* | (2006.01) | |
| *C07D 417/14* | (2006.01) | |
| *C07D 487/04* | (2006.01) | |

(52) U.S. Cl.
CPC ......... *C07D 401/14* (2013.01); *C07D 401/12* (2013.01); *C07D 405/14* (2013.01); *C07D 409/14* (2013.01); *C07D 417/14* (2013.01); *C07D 487/04* (2013.01)

(58) Field of Classification Search
CPC .. C07D 401/14; C07D 401/12; C07D 405/14; C07D 409/14; C07D 417/14; C07D 487/04; A61P 31/16; A61P 31/14
See application file for complete search history.

(56) References Cited

U.S. PATENT DOCUMENTS

| | | | |
|---|---|---|---|
| 4,388,305 A | 6/1983 | Trouet et al. | |
| 4,639,456 A | 1/1987 | Trouet et al. | |
| 4,970,297 A | 1/1990 | Castelhano et al. | |
| 5,147,865 A | 9/1992 | Habich et al. | |
| 5,364,931 A | 11/1994 | Haebich et al. | |
| 5,510,333 A | 4/1996 | Angelastro et al. | |
| 5,514,694 A | 5/1996 | Powers et al. | |
| 5,741,812 A | 4/1998 | Burk et al. | |
| 5,756,528 A | 5/1998 | Anthony et al. | |
| 5,847,135 A | 12/1998 | Bemis et al. | |
| 5,856,309 A | 1/1999 | Konetschny-Rapp et al. | |
| 5,874,424 A | 2/1999 | Batchelor et al. | |
| 5,955,616 A | 9/1999 | Ohtani et al. | |
| 6,159,984 A | 12/2000 | Guzi et al. | |
| 6,162,791 A | 12/2000 | Karimian et al. | |
| 6,174,887 B1 | 1/2001 | Haruta et al. | |
| 9,603,864 B2 | 3/2017 | Blatt et al. | |
| 11,124,497 B1 * | 9/2021 | Arnold | C07D 207/26 |
| 11,174,231 B1 | 11/2021 | Arnold et al. | |
| 2003/0153788 A1 | 8/2003 | Kobayashi et al. | |
| 2003/0216325 A1 | 11/2003 | Saksena et al. | |
| 2004/0110945 A1 | 6/2004 | Nakayama et al. | |
| 2004/0171489 A1 | 9/2004 | Hacker et al. | |
| 2006/0111303 A1 | 5/2006 | Hatayama et al. | |
| 2007/0032433 A1 | 2/2007 | Saksena et al. | |
| 2007/0208001 A1 | 9/2007 | Zhou et al. | |
| 2007/0238769 A1 | 10/2007 | Ochi et al. | |
| 2013/0109661 A1 | 5/2013 | Hermann et al. | |
| 2013/0164694 A1 | 6/2013 | Wang et al. | |

(Continued)

FOREIGN PATENT DOCUMENTS

| | | |
|---|---|---|
| AU | 2002318741 | 3/2003 |
| CA | 2851462 | 7/2004 |

(Continued)

OTHER PUBLICATIONS

Good et al., "AT-527 a Double Prodrug of a Guanosine Nucleotide Analog, Is a Potent Inhibitor of SARA-CoV-2 In Vitro and a Promising Oral Antiviral for Treatment of COVID-19" Antimicrobial Agents and Chemotherapy (2021) 65(4):e02479-20.
Hoffmann et al., "SARA-COV-2 Cell Entry Depends on ACE2 and TMPRSS2 and Is Blocked by a Clinically Proven Protease Inhibitor" Cell (2020) 181:271-280.
"IUPAC-IUB Commission on Biochemical Nomenclature Abbreviated Nomenclature of Synthetic Polypeptides (Polymerized Amino Acids)* Revised Recommendations (1971)" *Biochemistry.* (1972) 11(5) :942-944.
Kim et al., "Broad-Spectrum Antivirals against 3C or 3C-Like Proteases of Picornaviruses, Noroviruses, and Coronaviruses" Journal of Virology (2012) 86(21):11754-11762.

(Continued)

*Primary Examiner* — Matthew P Coughlin
*Assistant Examiner* — Ashli Ariana Chicks
(74) *Attorney, Agent, or Firm* — Knobbe, Martens, Olson & Bear, LLP

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

23 Claims, No Drawings

(56) References Cited

U.S. PATENT DOCUMENTS

| | | |
|---|---|---|
| 2013/0178478 A1 | 7/2013 | Hermann et al. |
| 2014/0194386 A1 | 7/2014 | Burns et al. |
| 2014/0374657 A1 | 12/2014 | Matsuyama et al. |
| 2017/0324007 A1 | 11/2017 | Pentlehmer |
| 2021/0355111 A1 | 11/2021 | Arnold et al. |
| 2022/0009903 A1 * | 1/2022 | Vandyck ............ C07D 405/14 |
| 2022/0033383 A1 † | 2/2022 | Panarese |
| 2022/0259145 A1 | 8/2022 | Liu et al. |
| 2022/0396550 A1 | 12/2022 | Ghosh et al. |
| 2022/0402905 A1 | 12/2022 | Soliman et al. |
| 2022/0411401 A1 | 12/2022 | Ghosh et al. |
| 2023/0002413 A1 | 1/2023 | Wu et al. |
| 2023/0024012 A1 † | 1/2023 | Chattrejee |
| 2023/0031213 A1 | 2/2023 | Wu et al. |
| 2023/0065527 A1 | 3/2023 | Wu et al. |
| 2023/0093249 A1 | 3/2023 | Vandyck et al. |
| 2023/0140238 A1 | 5/2023 | Bardiot et al. |
| 2023/0192713 A1 | 6/2023 | Wu et al. |
| 2024/0018126 A1 | 1/2024 | Vandyck et al. |

FOREIGN PATENT DOCUMENTS

| | | |
|---|---|---|
| CA | 3201360 | 6/2023 |
| CN | 103254129 | 8/2013 |
| CN | 103288832 | 9/2013 |
| CN | 107540726 | 1/2018 |
| CN | 113444144 | 9/2021 |
| CN | 114149415 | 3/2022 |
| CN | 114426568 | 5/2022 |
| DE | 4016994 | 11/1991 |
| EP | 0393445 | 10/1990 |
| EP | 0402646 | 12/1990 |
| EP | 472077 | 2/1992 |
| EP | 472078 | 2/1992 |
| EP | 520336 | 12/1992 |
| EP | 525420 | 2/1993 |
| EP | 0530537 | 3/1993 |
| EP | 0641800 | 3/1995 |
| EP | 0644198 | 3/1995 |
| EP | 1881001 | 3/1995 |
| EP | 0805147 | 11/1997 |
| EP | 1217000 | 6/2002 |
| EP | 1760076 | 3/2007 |
| EP | 1881002 | 1/2008 |
| EP | 2270025 | 1/2011 |
| EP | 3835296 A1 | 6/2021 |
| IN | 2006DEL01558 | 1/2008 |
| JP | 63144084 | 6/1988 |
| JP | 06192199 | 7/1994 |
| JP | 04334357 | 11/1995 |
| JP | 07309866 A | 11/1995 |
| JP | 09124571 | 5/1997 |
| JP | 2002145848 | 5/2002 |
| JP | 2005336172 | 12/2005 |
| JP | 2006232707 | 9/2006 |
| JP | 2013032343 | 2/2013 |
| JP | 2015174929 | 10/2015 |
| JP | 7055528 B1 | 4/2022 |
| WO | WO 89/04833 | 6/1989 |
| WO | WO 92/00954 | 1/1992 |
| WO | WO 92/07869 | 5/1992 |
| WO | WO 92/20357 | 11/1992 |
| WO | WO 93/02057 | 2/1993 |
| WO | WO 93/12796 | 7/1993 |
| WO | WO 93/17003 | 9/1993 |
| WO | WO 94/00421 | 1/1994 |
| WO | WO 94/11339 | 5/1994 |
| WO | WO 95/07294 | 3/1995 |
| WO | WO 95/09858 | 4/1995 |
| WO | WO 95/12611 | 5/1995 |
| WO | WO 95/35308 | 12/1995 |
| WO | WO 96/16981 | 6/1996 |
| WO | WO 96/20725 | 7/1996 |
| WO | WO 96/20949 | 7/1996 |
| WO | WO 96/39137 | 12/1996 |
| WO | WO 96/40732 | 12/1996 |
| WO | WO 97/05135 | 2/1997 |
| WO | WO 97/08133 | 3/1997 |
| WO | WO 97/22619 | 6/1997 |
| WO | WO 97/31939 | 9/1997 |
| WO | WO 98/01133 | 1/1998 |
| WO | WO 98/53814 | 12/1998 |
| WO | WO 98/53817 | 12/1998 |
| WO | WO 98/57945 | 12/1998 |
| WO | WO 99/67230 | 12/1999 |
| WO | WO 2000/016627 | 3/2000 |
| WO | WO 2000/051974 | 9/2000 |
| WO | WO 2000/055125 | 9/2000 |
| WO | WO 2000/071572 | 11/2000 |
| WO | WO 2001/012186 | 2/2001 |
| WO | WO 01/79167 | 10/2001 |
| WO | WO 2002/008244 | 1/2002 |
| WO | WO 2002/053534 | 7/2002 |
| WO | WO 2002/085899 | 10/2002 |
| WO | WO 2003/004468 | 1/2003 |
| WO | WO 2003/008380 | 1/2003 |
| WO | WO 2003/029284 | 4/2003 |
| WO | WO 2003/035060 | 5/2003 |
| WO | WO 2003/039529 | 5/2003 |
| WO | WO 2003/062265 | 7/2003 |
| WO | WO 2003/091202 | 11/2003 |
| WO | WO 2004/032846 | 4/2004 |
| WO | WO 2004/046107 | 6/2004 |
| WO | WO 2004/062601 | 7/2004 |
| WO | WO 2005/014532 | 2/2005 |
| WO | WO 2005/061475 | 7/2005 |
| WO | WO 2005/102381 | 11/2005 |
| WO | WO 2006/061714 | 6/2006 |
| WO | WO 2007/022459 | 2/2007 |
| WO | WO 2007/067836 | 6/2007 |
| WO | WO 2007/085895 | 8/2007 |
| WO | WO 2007109080 | 9/2007 |
| WO | WO 2008/074035 | 6/2008 |
| WO | WO 2008/110008 | 9/2008 |
| WO | WO 2008/121065 | 10/2008 |
| WO | WO 2008/141227 | 11/2008 |
| WO | WO 2008/154642 | 12/2008 |
| WO | WO 2009/043889 | 4/2009 |
| WO | WO 2009/103160 | 8/2009 |
| WO | WO 2009/105782 | 8/2009 |
| WO | WO 2010/077836 | 7/2010 |
| WO | WO 2010/126881 | 11/2010 |
| WO | WO 2010/132601 | 11/2010 |
| WO | WO 2011/043994 | 4/2011 |
| WO | WO 2011/047287 | 4/2011 |
| WO | WO 2011/048390 | 4/2011 |
| WO | WO 2011/050160 | 4/2011 |
| WO | WO 2011/082337 | 7/2011 |
| WO | WO 2011/094426 | 8/2011 |
| WO | WO 2011/103932 | 9/2011 |
| WO | WO 2011/103933 | 9/2011 |
| WO | WO 2011/129457 | 10/2011 |
| WO | WO 2012/020747 | 2/2012 |
| WO | WO 2012/058645 | 5/2012 |
| WO | WO 2012/065963 | 5/2012 |
| WO | WO 2012/083048 | 6/2012 |
| WO | WO 2012/122420 | 9/2012 |
| WO | WO 2012/122422 | 9/2012 |
| WO | WO 2012/123938 | 9/2012 |
| WO | WO 2012/140500 | 10/2012 |
| WO | WO 2012/163724 | 12/2012 |
| WO | WO 2013/003720 | 1/2013 |
| WO | WO 2013/133178 | 9/2013 |
| WO | WO 2013/178816 | 12/2013 |
| WO | WO 2013/188344 | 12/2013 |
| WO | WO 2014/151958 | 9/2014 |
| WO | WO 2014/154682 | 10/2014 |
| WO | WO 2014/188178 | 11/2014 |
| WO | WO 2016/075150 | 5/2016 |
| WO | WO 2016/187712 | 12/2016 |
| WO | WO 2017/091616 | 6/2017 |
| WO | WO 2017/160269 | 9/2017 |
| WO | WO 2017/197377 | 11/2017 |
| WO | WO 2018/020357 | 2/2018 |

(56) References Cited

FOREIGN PATENT DOCUMENTS

| | | |
|---|---|---|
| WO | WO 2018/042343 | 3/2018 |
| WO | WO 2018/045084 | 3/2018 |
| WO | WO 2018/064119 | 4/2018 |
| WO | WO 2018/112626 | 6/2018 |
| WO | WO 2018/152633 | 8/2018 |
| WO | WO 2018/167269 | 9/2018 |
| WO | WO 2019/190885 | 10/2019 |
| WO | WO 2019/190999 | 10/2019 |
| WO | WO 2020/006294 | 1/2020 |
| WO | WO 2020/030143 | 2/2020 |
| WO | WO 2020/123675 | 6/2020 |
| WO | WO 2020/136298 | 6/2020 |
| WO | WO 2020/160707 | 8/2020 |
| WO | WO 2020/185830 | 9/2020 |
| WO | WO 2021/146211 | 7/2021 |
| WO | WO 2021/151265 | 8/2021 |
| WO | WO 2021/151387 | 8/2021 |
| WO | WO 2021/207632 | 10/2021 |
| WO | WO 2021/221043 | 11/2021 |
| WO | WO 2021/226546 | 11/2021 |
| WO | WO 2021/231872 | 11/2021 |
| WO | WO 2021/234668 | 11/2021 |
| WO | WO 2021/236771 | 11/2021 |
| WO | 2021252644 A1 † | 12/2021 |
| WO | WO 2021/250648 | 12/2021 |
| WO | WO 2021/252491 | 12/2021 |
| WO | WO 2021/252644 | 12/2021 |
| WO | WO-2021252491 A1 * | 12/2021 ........... A61K 31/404 |
| WO | WO 2022/020242 | 1/2022 |
| WO | WO 2022/020711 | 1/2022 |
| WO | WO 2022/040002 | 2/2022 |
| WO | WO 2022/119858 | 6/2022 |
| WO | WO 2022/133069 | 6/2022 |
| WO | WO 2022/187491 | 9/2022 |
| WO | 2022208262 A1 † | 10/2022 |
| WO | WO 2022/208113 | 10/2022 |
| WO | WO 2022/218442 | 10/2022 |
| WO | WO-2022208262 A1 * | 10/2022 |
| WO | WO-2022218442 A1 * | 10/2022 .............. A61P 31/14 |
| WO | WO 2022/266236 | 12/2022 |
| WO | WO 2022/266363 | 12/2022 |
| WO | WO 2022/266368 | 12/2022 |
| WO | WO 2023/030459 | 3/2023 |
| WO | WO 2023/036093 | 3/2023 |
| WO | WO 2023/036140 | 3/2023 |
| WO | WO 2023/043816 | 3/2023 |
| WO | WO 2023/044171 | 3/2023 |
| WO | WO 2023/052638 | 4/2023 |
| WO | WO 2023/088418 | 5/2023 |
| WO | WO 2023/122260 | 6/2023 |
| WO | WO 2023/283256 | 6/2023 |
| WO | WO 2023/125846 | 7/2023 |
| WO | WO 2023/133174 | 7/2023 |
| WO | WO 2023/149982 | 8/2023 |
| WO | WO 2023/180189 | 9/2023 |
| WO | WO 2023/194840 | 10/2023 |
| WO | WO 2023/196307 | 10/2023 |
| WO | WO 2024/008196 | 1/2024 |
| WO | WO 2024/010585 | 1/2024 |
| WO | WO 2024/010794 | 1/2024 |

OTHER PUBLICATIONS

Mellott et al., "A cysteine protein inhibitor blocks SARS-COV-2 infection of human and monkey cells" bioRxiv (2020) 2020.2010.2023.347534.

Shang et al., "Cell entry mechanisms of SARS-COV-2" PNAS (2020) 117(21):11727.

Steuten et al., "Challenges for targeting SARS-COV-2 proteases as a therapeutics strategy for COVID-19" bioRxiv (2020) 2020.2011.2021.392753.

Zhang et al, "a-Ketoamides as Broad-Spectrum Inhibitors of Coronavirus and Enterovirus Replication: Structure-Based Design, Synthesis, and Activity Assessment" JACS (2020) 63:4562-4578 (https://dx.doi.org/10.1021/acs.jmedchem.9b01828).

International Search Report and Written Opinion mailed Nov. 17, 2022 for PCT Application No. PCT/US2022/043496, filed Sep. 14, 2022.

Abdelnabi et al., "Comparing infectivity and virulence of emerging SARS-COV-2 variants in Syrian hamsters" EBioMedicine Jun. 202168:103403. doi: 10.1016/j.ebiom.2021.103403.

Ahmad et al., "Exploring the Binding Mechanism of PF-07321332 SARS-COV-2 Protease Inhibitor through Molecular Dynamics and Binding Free Energy Simulations" Int. J. Mol. Sci. (2021) 22(17):91242.

Alugubelli et al., "A systemic exploration of beceprevir-based main protease inhibitos as SARS-CoV-2 antivirals" European J. of Med. Chem. (2022) 240:114596.

Arakawa et al., "Synthetic Study of Optically Active 3-Azabicyclo[3.3.0]octane-2,6,8-tricarboxylic Acid" Chemical & Pharmaceutical Bulletin (2003) 51(8), 1015-1020.

Breuning et al., "Enantioselective synthesis of tricyclic amino acid derivatives based on a rigid 45-azatricyclo[5.2.1.02,6]decane skeleton" Beilstein Journal of Organic Chemistry (2009) 5(81):1-5.

CAS Reg. No. 1040187-41-4, Entry Date Aug. 11, 2008.

CAS Reg. No. 1212645-49-2, Entry Date Mar. 21, 2010.

CAS Reg. No. 1240410-37-0, Entry Date Sep. 9, 2010.

Calaza et al., "Synthesis of [c]-Fused Bicyclic Proline Analogues" Eur. J. Org. Chem. (2015), 2015(8):1633-1658.

Chia et al., "Novel Coronavirus Main Protease Di- and Tripeptide Inhibitors for Treating COVID-19" ACS Med. Chem. Lett. (2002) 13:1388-1389.

Cox et al., "Escaping form Flatland: Substituted Bridged Pyrrolidine Fragments with Inherent Three-Dimensional Character" ACS Med. Chem. Lett. (2020) 11(6):1185-1190.

De Graaff et al., "IBX-mediated oxidation of unactivated cyclic amines: application in highly diastereoselective oxidative Ugi-type and aza-Friedel-Crafts reactions" Org. Biomol. Chem. (2015) 13:10108-10112.

Eiden et al., "Synthesis of a 3-Amino-2,3-dihdropyrid-4-one and Related Heterocyclic Anaalogues as Mechanism-Based Inhibitors of BioA, a Pyridoxal Phosphate-Dependent Enzyme" J. Org. Chem. (2017) 82(15):7806-7819.

Farmer et al., "Inhibitors of hepatitis C virus NS3•4A protease: P2 proline variants." Letters in Drug Design & Discovery (2005) 2(7):497-502.

Gansauer et al., "R-exo Cyclizations by Template Catalysis" Ang. Chem. Int. Ed. (2009) 48(47), 8882-8885, S8882/1-S8882/32.

Gupton et al., "Application of 2-Substituted Vinamidinium Salts to the Synthesis of 2,4-Disubstituted Pyrroles" J. Org. Chem. (1990) 55(15):4735-4740.

Hartford, B., "To conquer COVID-19, create the perfect pill" Chemical & Engineering News (2021) 99(19):28-31.

Hartford, B., "Pfizer unveils its oral SARS-COV-2 inhibitor" Chemical & Engineering News (2021), 99(13):7.

Johnson et al., "Synthesis and Characterization of Novel Bi- And Tricyclic α-Amino Acids" Synthetic Communications (2011) 41(18):2769-2793.

Liu et al., "Modular and Stereoselective Synthesis of Tetrasubstituted Helical Alkenes via a Palladium-Catalyzed Domino Reaction" Org. Lett. (2012) 14(14):3648-3651.

Liu et al., "An Improved and Enantioselective Preparation of the Telaprevir Bicyclic [3.3.0] Proline Intermediate and Reuse of Unwanted Enantiomer" Org. Process Res. Dev. (2016) 20(2):320-324.

Macchiagodena et al., "Virtual Double-System Single-Box for Absolute Dissociation Free Energy Calculations in GROMACS" J. Chem. Inf. Model (2021) 61:5320-5326.

Macchiagodena et al., "Characterization of the non-covalent interaction between the PF-07321332 inhibitor and the SARS-CoV-2 main protease" J. Mol. Graphics & Modelling (2022) 110:108042.

Moody et al., "Stereospecific synthesis of naturally-occurring 4-alkylideneglutamic acids, 4-alkylglutates and 4-alkylprolines" J. Chem. Soc., Perkin Trans. 1 (1997) 23:3519-3530.

Mulamreddy et al., "4-Vinylproline" J. Org. Chem. (2018) 83(21):13580-13586.

(56) References Cited

OTHER PUBLICATIONS

Ngo et al., "Insights into the Binding and Covalent Inhibition Mechanism of PF-07321332 to SARS-CoV-2 Mpro" ChemRxiv (2021) 1-10.
Owen et al., "An oral SARS-COV Mpro inhibitor clinical candidate for the treatment of COVID-19" Science (2021) 374(6575):1586-1593.
Pavan et al., "Supervised Molecular Dynamics (SuMD) Insights into the mechanism of action of SARS-Co-V-2 main protease inhibitor PF-07321332" Journal of Enzyme Inhibition and Medicinal Chemistry (2021) 36(1):1646-1650.
Ramos-Guzman et al., "Computational simulations on the binding and reactivity of a nitrile inhibitor of the SARS-COV-2 main protease" Chem. Commun. (2021) 57(72):9096-9099 & Supporting Information.
Roy et al., "The Hemetsberger-Knittel Synthesis of Substituted 5-,6-, and 7-Azaindoles" Synthesis (2005) 16:2751-2757.
Rulíšek et al., "An Experimental and Theoretical Study of Stereoselectivity of Furan-Maleic Anhydride and Furan-Maleimide Diels-Alder Reactions" J. Org. Chem. (2005) 70(16):6295-6302.
Zhao et al., "Crystal Structure of SARS-COV-2 main protease in complex with protease inhibitor PF-07321332" Protein & Cell (2021) https://doi.org/10.1007/s13238-021-00883-2.
Znabet et al., "Asymmetric synthesis of synthetic alkaloids by a tandem biocatalysis/Ugi/Pictet-Spengler-type cyclization sequence" Chem. Commun. (2010) 46(41):7706-7708 & Supplemental Information.
Znabet et al., "Highly stereoselective synthesis of substituted prolyl peptides using a combination of biocatalytic desymmetrization and multicomponent reactions." Angewandte Chemie International Edition (2010) 49(31):5298-5292.
https://www.cdc.gov/coronavirus/2019-ncov/need-extra-precautions/groups-at-higher-risk.html.
Balasubramaniam et al., "The Growing Synthetic Utility of the Weinreb Amide" Synthesis (2008) 23:3707-3738.
CAS Reg. No. 2321331-16-0, Entered May 30, 2019.
CAS Reg. No. 2582799-51-5, Entered Feb. 4, 2021.
CAS Reg. No. 2582799-50-4, Entered Feb. 4, 2021.
Concellon et al., "Enantiopure Preparation of the Two Enantiomers of the Pseudo-$C_2$-Symmetric N,N-Dibenzyl-1,2:4,5-diepoxypentan-3-amine" J. Org. Chem. (2001) 66(25):8661-8665.
Corey et al., "Enantioselective Synthesis of α-Amino Nitriles from N-Benzhydryl Imines and HCN with a Chiral Bicyclic Guanidine as Catalyst" Org. Lett. (1999) 1(1):157-160.
Cowley et al., "Spirocyclic systems derived from pyroglutamic acid" Org. Biomol. Chem. (2011) 9:7042-7056.
Evans et al., "Directed Reduction of β-Hydroxy Ketones Employing Tetramethylammonium Triacetoxyborohydride" J. Am. Chem. Soc. (1988) 110(11):3560-3578.
Fukuda et al. "Construction of Tetrasubstituted Carbon by an Organocatalyst: Cyanation Reaction of Ketones and Ketimines Catalyzed by a Nucleophilic-N-Heterocyclic Carbene" Synthesis, (2006) 16:2649-2652.
Kim et al., "Direct C(sp3)-H Cyanation Enabled by a Highly Active Decatungstate Photocatalyst" Org. Lett. (2021) 23(14): 5501-5505.
Mendonca et al., "Novel route to the synthesis of peptides containing 2-amino-1'-hydroxymethyl ketones and their application as cathepsin K inhibitors" Bioorganic & Medicinal Chemistry Letters (2002) 12(20): 2887-2891.
Nahm et al., "N-Methoxy-N-Methylamides as Effective Acylating Agents" Tetrahedron Lett. (1981) 22(39), 3815-3818.
Nicolaou et al., "New Synthetic Technologies for the Construction of Heterocycles and Tryptamines" J. Am. Chem. Soc. (2009) 131(10):3690-3699.
Pace et al., "Chemoselective Synthesis of N-Substituted α-Amino-α'-chloro Ketones via Chloromethylation of Glycine-Derived Weinreb Amides" Advanced Synthesis & Catalysis (2013) 355(5):919-926.
Pedregal et al., "Highly chemoselective reduction of N-Boc protected lactams" Tetrahedron Lett. (1994) 35(13):2053-2056.
Rasnick, D., "Synthesis of peptide fluoromethyl ketones and the inhibition of human cathepsin B" Anal. Biochem. (1985) 149(2):461-465.
Sakaine et al., "Modified Julia-Kocienski Reagents for a Stereoselective Introduction of Trisubstituted Double Bonds: A Formal Total Synthesis of Limazepine E and Barmumycin" J. Org. Chem. (2018) 83(9):5323-5330.
Shi et al., "Direct Synthesis of α-Amino Nitriles from Sulfonamides via Base-Mediated C—H Cyanation" Org. Lett. (2021) 23(10):4018-4022.
Sun et al., "Synthesis of EF24-Tripeptide Chloromethyl Ketone: A Novel Curcumin-Related Anticancer Drug Delivery System" J. Med. Chem. (2006) 49(11):3153-3158.

\* cited by examiner
† cited by third party

1

ANTI-VIRAL COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application Nos. 63/261,339, filed Sep. 17, 2021, 63/265,481, filed Dec. 15, 2021 and 63/367,791, filed Jul. 6, 2022, each of which is incorporated by reference in there entireties.

BACKGROUND

Field

The present application relates to the fields of chemistry, biochemistry and medicine. Disclosed herein are compounds of Formula (I), or pharmaceutically acceptable salt thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

A positive-sense single-stranded RNA virus ((+)ssRNA virus) is a virus that uses positive sense, single stranded, RNA as its genetic material. Positive-sense single-stranded RNA viruses can be enveloped or non-enveloped. Coronaviridae, Picornaviridae and Noroviruses are each a (+)ssRNA virus. Each of the aforementioned viruses are known to infect mammals, including humans.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a coronavirus infection that can include administering to a subject identified as suffering from the coronavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a coronavirus infection.

Some embodiments disclosed herein relate to a method of inhibiting replication of a coronavirus that can include contacting a cell infected with the coronavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication a coronavirus.

Some embodiments described herein relate to a method of treating a picornavirus infection that can include administering to a subject identified as suffering from the picornavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a picornavirus infection.

Some embodiments disclosed herein relate to a method of inhibiting replication of a picornavirus that can include contacting a cell infected with the picornavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication a picornavirus.

Some embodiments described herein relate to a method of treating a norovirus infection that can include administering to a subject identified as suffering from the norovirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a norovirus infection.

Some embodiments disclosed herein relate to a method of inhibiting replication of a norovirus that can include contacting a cell infected with the norovirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication a norovirus.

These are other embodiments are described in greater detail below.

DETAILED DESCRIPTION

Coronaviridae viruses are a family of enveloped, positive-stranded, single-stranded, spherical RNA viruses. Coronaviruses are named for the crown-like spikes on their surface.

The Coronaviridae family includes two sub-families, Coronavirus and Torovirus. The Coronavirus genus has a helical nucleocapsid, and Torovirus genus has a tubular nucleocapsid. The Coronaviridae family of viruses includes Middle East respiratory syndrome coronavirus (MERS-CoV), SARS and SARS-CoV-2.

Coronavirus disease 2019 (COVID-19) (also referred to as novel coronavirus pneumonia or 2019-nCoV acute respiratory disease) is an infectious disease caused by the virus severe respiratory syndrome coronavirus 2 (SARS-CoV-2) (also referred to as novel coronavirus 2019, or 2019-nCoV). The disease was first identified in December 2019 and spread globally, causing a pandemic. Symptoms of COVID-19 include fever, cough, shortness of breath, fatigue, headache, loss of smell, nasal congestion, sore throat, coughing up sputum, pain in muscles or joints, chills, nausea, vomiting, and diarrhea. In severe cases, symptoms can include difficulty waking, confusion, blueish face or lips, coughing up blood, decreased white blood cell count, and kidney failure. Complications can include pneumonia, viral sepsis, acute respiratory distress syndrome, and kidney failure.

COVID-19 is especially threatening to public health. The virus is highly contagious, and studies currently indicate that it can be spread by asymptomatic carriers or by those who are pre-symptomatic. Likewise, the early stage of the disease is slow-progressing enough that carriers do not often realize they are infected, leading them to expose numerous others to the virus. The combination of COVID-19's ease of transmission, its high rate of hospitalization of victims, and its death rate make the virus a substantial public health risk, especially for countries without a healthcare system equipped to provide supportive care to pandemic-level numbers of patients. There is not yet a vaccine or specific antiviral treatment for COVID-19 and accordingly, there is a pressing need for treatments or cures.

SARS-CoV-2 is not the only coronavirus that causes disease. It is a β-coronavirus, a genus of coronaviruses that includes other human pathogens, including SARS-CoV (the causative agent of SARS), MERS-CoV (the causative agent of MERS), and HCoV-OC43 (a causative agent of the common cold). The infectivity of these viruses, and the severity of the diseases they cause, varies widely. β-coronavirus can also manifest as zoonotic infections, spread to and from humans and animals. Additionally, non-human species such as camels, bats, tigers, non-human primates, and rabbits can be susceptible to β-coronavirus. Accordingly, there is a pressing need for treatments or cures to multiple coronaviruses.

The present disclosure provides molecules useful against coronaviruses, and especially SARS-CoV-2, the causative agent of COVID-19 in humans. Accordingly, the present disclosure fulfills the need in the art for compounds that can be safely and effectively treat or prevent coronavirus infections in humans.

Picornaviruses are a family of positive strand RNA, nonenveloped viruses. A picornavirus has 60 identical subunits (vertices) which contain five protomers. Each protomer is made up of one copy of four proteins, named VP1, VP2, VP3 and VP4. There are several genera of picornaviruses, including, Enterovirus, Aphthovirus, Cardiovirus and Hepatovirus. Enteroviruses known to infect human include, but are not limited to, Rhinovirus A, Rhinovirus B, Rhinovirus C, Coxsackievirus A, Coxsackievirus B and Poliovirus. There is no specific treatment for a picornavirus infection.

Noroviruses are single-stranded positive-sense RNA, non-enveloped viruses belonging to the Caliciviridae family. Noroviruses are often spread by the fecal-oral route, and are a common cause of gastroenteritis. Infected subjects can experience nausea, non-bloody diarrhea, vomiting and/or abdominal pain. Those suffering from a norovirus infection can become severely dehydrated and require medical attention. As with a picornavirus infection, there is no specific treatment for a norovirus infection. Accordingly, there is a need for compounds that effectively treat or prevent a picornavirus and/or a norovirus infection.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) (such as 1, 2 or 3) individually and independently selected from deuterium, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, C-amido(alkyl), isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amine and a di-substituted amine.

As used herein, "$C_a$ to $C_b$" or "$C_{a-b}$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused- or spiro-fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused- or spiro-fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "cycloalkyl(alkyl)" refers to a cycloalkyl group connected, as a substituent, via a lower alkylene group. The lower alkylene and cycloalkyl group of a cycloalkyl(alkyl) may be substituted or unsubstituted. A cycloalkyl(alkyl) group may be unsubstituted or substituted.

As used herein, "aryl(alkyl)" refers to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "heterocyclyl(alkyl)" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group with a substituent(s) listed under the definition of "substituted." Further, when a lower alkylene group is substituted, the lower alkylene can be substituted by replacing both hydrogens on the same carbon with a cycloalkyl group

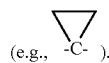

(e.g., -C- ).

As used herein, "alkoxy" refers to the formula —OR wherein R is an alkyl, an alkenyl, an alkynyl, a cycloalkyl, a cycloalkenyl, an aryl, a heteroaryl, a heterocyclyl, a cycloalkyl(alkyl), an aryl(alkyl), a heteroaryl(alkyl) or a heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzyloxy. In some instances, an alkoxy can be —OR, wherein R is an unsubstituted C$_{1-4}$ alkyl. An alkoxy may be substituted or unsubstituted.

As used herein, "acyl" refers to a hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl) connected, as substituents, via a carbonyl group. Examples include formyl, acetyl, propanoyl, benzoyl and acryl. An acyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group and O-monocyclic cycloalkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy, 2-fluoroisobutoxy, chloro-substituted cyclopropyl, fluoro-substituted cyclopropyl, chloro-substituted cyclobutyl and fluoro-substituted cyclobutyl. In some instances, a haloalkoxy can be —OR, wherein R is a C$_{1-4}$ alkyl substituted by 1, 2 or 3 halogens. A haloalkoxy may be substituted or unsubstituted.

A "sulfenyl" group refers to an "—SR" group in which R can be hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl (alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ is hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—SCN" group.

An "isothiocyanato" group refers to an "—NCS" group.

A "mercapto" group refers to an "—SH" group.

A "carbonyl" group refers to a —C(=O)— group.

An "S-sulfonamido" group refers to a "—SO$_2$N(R$_A$R$_B$)" group in which R$_A$ and R$_B$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). An N-sulfonamido may be substituted or unsubstituted.

An "O-carbamyl" group refers to a "—OC(=O)N(R$_A$R$_B$)" group in which R$_A$ and R$_B$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). An O-carbamyl may be substituted or unsubstituted.

An "N-carbamyl" group refers to an "ROC(=O)N(R$_A$)—" group in which R and R$_A$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). An O-thiocarbamyl may be substituted or unsubstituted.

An "N-thiocarbamyl" group refers to an "ROC(=S)N($R_A$)—" group in which R and $R_A$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). An N-thiocarbamyl may be substituted or unsubstituted.

A "C-amido" group refers to a "—C(=O)N($R_AR_B$)" group in which $R_A$ and $R_B$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). A C-amido may be substituted or unsubstituted.

An "N-amido" group refers to a "RC(=O)N($R_A$)—" group in which R and $R_A$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl (alkyl) or a heterocyclyl(alkyl). An N-amido may be substituted or unsubstituted.

A "mono-substituted amine" refers to a "—$NHR_A$" in which $R_A$ can be independently an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). A mono-substituted amine may be substituted or unsubstituted. In some instances, a mono-substituted amine can be —$NHR_A$, wherein $R_A$ can be an unsubstituted $C_{1-6}$ alkyl or an unsubstituted or a substituted benzyl.

A "di-substituted amine" refers to a "—$NR_AR_B$" in which $R_A$ and $R_B$ can be independently can be independently an alkyl, an alkenyl, an alkynyl, a cycloalkyl, a cycloalkenyl, an aryl, a heteroaryl, a heterocyclyl, an aryl(alkyl), a heteroaryl (alkyl) or a heterocyclyl(alkyl). A mono-substituted amine may be substituted or unsubstituted. In some instances, a mono-substituted amine can be —$NR_AR_B$, wherein $R_A$ and $R_B$ can be independently an unsubstituted $C_{1-6}$ alkyl or an unsubstituted or a substituted benzyl.

A "ketoamide" group refers to a —C(=O)—C(=O)N ($R_AR_B$) group in which $R_A$ and $R_B$ can be independently hydrogen, an alkyl, an alkenyl, an alkynyl, a cycloalkyl, a cycloalkenyl, an aryl, a heteroaryl, a heterocyclyl, an aryl (alkyl), a heteroaryl(alkyl) or a heterocyclyl(alkyl). A ketoamide may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the number of substituents is not specified (e.g., haloalkyl), there may be one or more substituents present. For example, "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

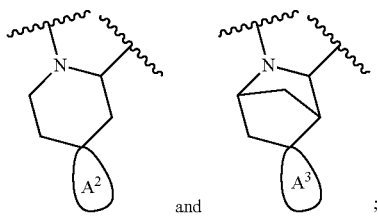
(I)

wherein: Ring $A^1$ can be selected from

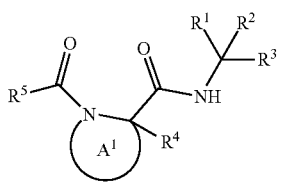
and ;

Ring $A^2$ can be an unsubstituted or a substituted monocyclic $C_{3-6}$ cycloalkyl; Ring $A^3$ can be an unsubstituted or a substituted monocyclic $C_{3-6}$ cycloalkyl; $R^1$ can be selected from cyano, an unsubstituted or a substituted $C_{2-5}$ alkynyl, an unsubstituted or a substituted acyl, an unsubstituted or a substituted ketoamide, —CH(OH)—(S(═O)$_2$—O—), —CH(OH)((P═O)(OR$^6$)$_2$) and —C(═O)CH$_2$—O—((P═O)(OR$^7$)$_2$), $R^2$ can be hydrogen, deuterium or halogen; $R^3$ can be an unsubstituted or a substituted C-amido($C_{1-4}$ alkyl), an unsubstituted or a substituted monocyclic nitrogen-containing heteroaryl($C_{1-4}$ alkyl), an unsubstituted or a substituted monocyclic nitrogen-containing heterocyclyl ($C_{1-4}$ alkyl), an unsubstituted or a substituted bicyclic nitrogen-containing heteroaryl($C_{1-4}$ alkyl) or an unsubstituted or a substituted bicyclic nitrogen-containing heterocyclyl($C_{1-4}$ alkyl); $R^4$ can be hydrogen, deuterium or halogen; $R^5$ can be an unsubstituted or a substituted naphthyl, an unsubstituted or a substituted

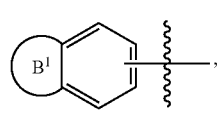, an unsubstituted or a substituted

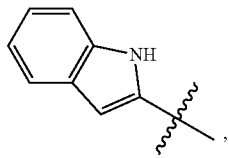 [SMILES: *c1cc2ccccc2[nH]1], an unsubstituted or a substituted

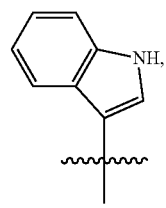 [SMILES: *c1c[nH]c2ccccc12]

an unsubstituted or a substituted

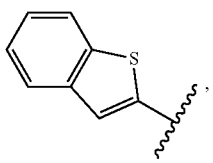 [SMILES: *c1cc2ccccc2s1], an unsubstituted or a substituted

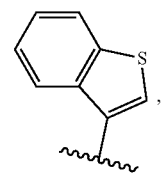 [SMILES: *c1csc2ccccc12], an unsubstituted or a substituted

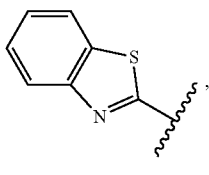 [SMILES: *c1nc2ccccc2s1], an unsubstituted or a substituted

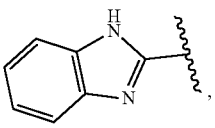 [SMILES: *c1nc2ccccc2[nH]1], an unsubstituted or a substituted

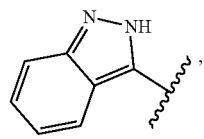 [SMILES: *c1[nH]nc2ccccc12]

an unsubstituted or a substituted

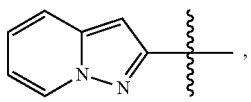 [SMILES: *c1cc2ccccn2n1]

an unsubstituted or a substituted

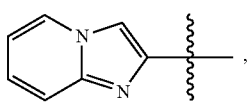

an unsubstituted or a substituted

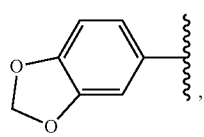 [SMILES: *c1ccc2c(c1)OCO2]

an unsubstituted or a substituted

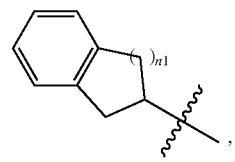

an unsubstituted or a substituted

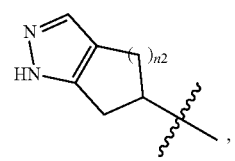

an unsubstituted or a substituted

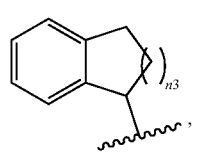

an unsubstituted or a substituted

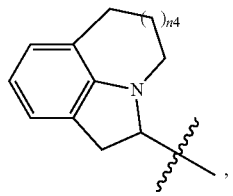

an unsubstituted or a substituted

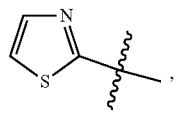 [SMILES: *c1nccs1]

an unsubstituted or a substituted

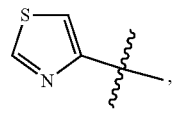

an unsubstituted or a substituted

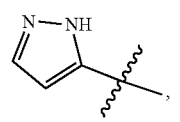 [SMILES: *c1ccn[nH]1]

an unsubstituted or a substituted

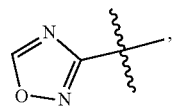

an unsubstituted or a substituted

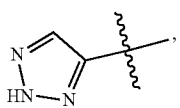 [SMILES: *c1cn[nH]n1]

an unsubstituted or a substituted

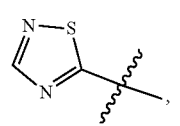 [SMILES: *c1ncns1]

an unsubstituted or a substituted

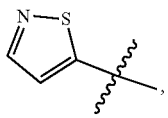 [SMILES: *c1ccns1]

an unsubstituted or a substituted pyridine, an unsubstituted or a substituted phenyl, an unsubstituted or a substituted monocyclic $C_{3-6}$ cycloalkyl and an unsubstituted or a substituted 4- to 6-membered monocyclic heterocyclyl; wherein $B^1$ is an unsubstituted or a substituted monocyclic 5-6-membered heteroaryl; and wherein when $R^5$ is substituted, $R^5$ is substituted with one or more substituents independently selected from deuterium, halogen, an unsubstituted or a substituted $C_{1-6}$ alkyl, an unsubstituted or a substituted monocyclic $C_{3-6}$ cycloalkyl, an unsubstituted $C_{1-6}$ haloalkyl, an unsubstituted $C_{1-6}$ alkoxy, an unsubstituted or a substituted phenyl, an unsubstituted or a substituted 5- to 6-membered monocyclic heteroaryl, an unsubstituted or a substituted 5- to 6-membered monocyclic heterocyclyl, an unsubstituted or a substituted bicyclic cycloalkenyl and an unsubstituted or a substituted bicyclic heterocyclyl; or $R^5$ can be

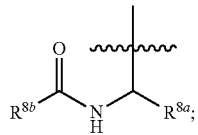

$R^{8a}$ can be selected from an unsubstituted or a substituted $C_{2-6}$ alkyl, an unsubstituted or a substituted $C_{2-6}$ alkenyl, an unsubstituted or a substituted $C_{2-6}$ alkynyl, an unsubstituted or a substituted monocyclic $C_{3-6}$ cycloalkyl, an unsubstituted or a substituted bicyclic $C_{5-8}$ cycloalkyl and an unsubstituted or a substituted monocyclic 4- to 6-membered heterocyclyl, wherein when the $C_{2-6}$ alkyl is substituted, the $C_{2-6}$ can be is substituted 1, 2, 3 or 4 times with a substituent independently selected from halogen, cyano, an unsubstituted or a substituted monocyclic $C_{3-6}$ cycloalkyl, an unsubstituted $C_{1-4}$ alkoxy and an unsubstituted $C_{1-4}$ haloalkoxy, or the $C_{2-6}$ alkyl is substituted 1 to 13 times with deuterium; wherein when the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted, the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl can be substituted 1, 2, 3 or 4 times with a substituent independently selected from the group consisting of halogen, an unsubstituted $C_{1-4}$ alkyl, an unsubstituted $C_{2-4}$ alkenyl, an unsubstituted $C_{2-4}$ alkynyl, an unsubstituted $C_{1-6}$ haloalkyl, an unsubstituted or a substituted monocyclic $C_{3-6}$ cycloalkyl and an unsubstituted $C_{1-4}$ alkoxy; and $R^{8b}$ can be selected from an unsubstituted or a substituted $C_{1-6}$ alkyl, an unsubstituted or a substituted $C_{1-6}$ haloalkyl, an unsubstituted or a substituted monocyclic $C_{3-6}$ cycloalkyl, an unsubstituted or a substituted bicyclic $C_{5-6}$ cycloalkyl, an unsubstituted or a substituted monocyclic heteroaryl and an unsubstituted or a substituted monocyclic heterocyclyl, wherein the substituted $C_{1-6}$ alkyl is substituted 1 or 2 times with an unsubstituted $C_{1-4}$ alkoxy, wherein the substituted monocyclic $C_{3-6}$ cycloalkyl is substituted 1, 2, 3 or 4 times with a substituent independently selected from the group consisting of halogen, an unsubstituted $C_{1-4}$ alkyl, an unsubstituted $C_{2-4}$ alkenyl, an unsubstituted $C_{1-4}$ alkoxy, an unsubstituted $C_{1-4}$ haloalkyl and an unsubstituted monocyclic $C_3$-6 cycloalkyl, and wherein the substituted $C_{1-6}$ haloalkyl is substituted 1 or 2 times with an unsubstituted $C_{1-4}$ alkoxy; each $R^6$ and each $R^7$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl); n1, n2 and n3 can be independently 1 or 2; and n4 can be 0 or 1.

The substituent $R^1$ can be various moieties. In some embodiments, $R^1$ can be an unsubstituted ketoamide. In some embodiments, $R^1$ can be a substituted ketoamide. The ketoamide can have the structure —C(=O)—C(=O)NR$^{y1}$R$^{z1}$. In some embodiments, $R^1$ can be an acyl, for example, $R^1$ can be —C(=O)H, —C(=O)(an unsubstituted $C_{1-4}$ alkyl), —C(=O)(an unsubstituted to a substituted benzyl), —C(=O)(an unsubstituted to a substituted monocyclic heteroaryl) or —C(=O)(an unsubstituted to a substituted bicyclic heteroaryl). In some embodiments, $R^1$ can be a substituted acyl. The acyl for $R^1$ can have the structure —C(=O)R$^{y2}$. When the acyl is substituted, the possible groups that can be present on the acyl include hydroxy, a substituted or an unsubstituted alkoxy (such as —O-(an unsubstituted $C_{1-4}$ alkyl), —O-(an unsubstituted $C_{3-6}$ cycloalkyl), a substituted or an unsubstituted phenoxy or a substituted or an unsubstituted benzyloxy) or —O—(C=O)-(an unsubstituted $C_{1-6}$ alkyl). In some embodiments, $R^1$ can be an unsubstituted can be —C(=O)—N-sulfonamido.

$R^{y1}$, $R^{y2}$ and $R^{z1}$ can be a variety of groups. In some embodiments, $R^{y1}$, $R^{y2}$ and $R^{z1}$ can be independently selected from hydrogen, $C_{1-8}$ alkyl, $C_{2-8}$ alkenyl, $C_{2-8}$ alkynyl, $C_3$-8 cycloalkyl (for example, a monocyclic $C_{3-8}$ cycloalkyl), $C_{3-8}$ cycloalkenyl (such as a monocyclic $C_{3-8}$ cycloalkenyl), aryl (such as phenyl or naphthyl), heteroaryl (including a monocyclic or a bicyclic heteroaryl), heterocyclyl (for example, a monocyclic or a bicyclic heterocyclyl), aryl(alkyl) (such as benzyl), heteroaryl(alkyl) (including a monocyclic heteroaryl(CH$_2$)— and a monocyclic (heteroaryl(CH$_2$CH$_2$)—) or heterocyclyl(alkyl) (such as a monocyclic heterocyclyl(CH$_2$)— and a monocyclic heterocyclyl(CH$_2$CH$_2$)—), wherein each of the aforementioned $R^{y1}$, $R^{y2}$ and $R^{z1}$ groups can be unsubstituted or substituted. In some embodiments, $R^{y1}$, $R^{y2}$ and $R^{z1}$ can be independently selected from H, $C_{1-8}$ alkyl, an unsubstituted $C_{1-4}$ haloalkyl (including —CF$_3$, —CCl$_3$, —CHF$_2$, —C(CH$_3$)F$_2$, —CHCl$_2$, —CH$_2$F, —CH(CH$_3$)F, —CH$_2$CF$_3$, —CH$_2$Cl, —CH$_2$CH$_2$F, —CH$_2$CH$_2$Cl, —CH$_2$CH$_2$CH$_2$F and —CH$_2$CH$_2$CH$_2$Cl), —C$_{1-4}$ alkyl(OH) (including —CH$_2$OH, —CH$_2$CH$_2$OH and —CH(CH$_3$)OH), —C$_{1-4}$ alkyl($C_{1-4}$ alkoxy) (such as —CH$_2$O (an unsubstituted $C_{1-4}$ alkyl) and —CH$_2$CH$_2$O (an unsubstituted $C_{1-4}$ alkyl)), —C$_{1-4}$ alkyl-O-(a monocyclic $C_{3-6}$ cycloalkyl) (such as —CH$_2$O (a monocyclic $C_{3-6}$ cycloalkyl), —CH$_2$CH$_2$O (a monocyclic $C_{3-6}$ cycloalkyl)), —C$_{1-4}$ alkyl-O-(phenyl) (for example, —CH$_2$O(phenyl) and —CH$_2$CH$_2$O(phenyl)), —C$_{1-4}$ alkyl-O-(5- to 6-membered monocyclic heteroaryl) (such as —CH$_2$O (5- to 6-membered monocyclic heteroaryl) and —CH$_2$CH$_2$O (5- to 6-membered monocyclic heteroaryl)), —C$_{1-4}$ alkyl-O-(5- to 6-membered monocyclic heterocyclyl) (for example, —CH$_2$O (5- to 6-membered monocyclic heterocyclyl) and —CH$_2$CH$_2$O (5- to 6-membered monocyclic heterocyclyl)), —C$_{1-4}$ alkyl-O-(a monocyclic $C_{3-6}$ cycloalkyl($C_{1-4}$ alkyl) (such as —C$_{1-4}$ alkyl-O—

CH₂-(monocyclic C₃₋₆ cycloalkyl) and —C₁₋₄ alkyl-O—CH₂CH₂-(monocyclic C₃₋₆ cycloalkyl)), —C₁₋₄ alkyl-O-(benzyl) (for example, —CH₂O(benzyl) and —CH₂CH₂O(benzyl)), —C₁₋₄ alkyl-O-(5- to 6-membered monocyclic heteroaryl(C₁₋₄ alkyl), —C₁₋₄ alkyl-O-(5- to 6-membered monocyclic heterocyclyl(C₁₋₄ alkyl), —C₁₋₄ alkyl-O(C=O)(an unsubstituted C₁₋₆ alkyl) (for example, —CH₂O(C=O)(an unsubstituted C₁₋₆ alkyl)), a monocyclic C₃₋₈ cycloalkyl (such as cyclopropyl, cyclobutyl, cyclopentyl, cyclohexyl, cycloheptyl and cyclooctyl), a monocyclic heteroaryl (such as imidazole, 1,3,4-oxadiazole and pyridinyl), a monocyclic heterocyclyl (for example, tetrahydrofuran and tetrahydropyran), a bicyclic heteroaryl (for example, benzothiazole, benzoimidazole and benzooxazole), a bicyclic heterocyclyl, a monocyclic C₃₋₆ cycloalkyl(alkyl), aryl(alkyl) (such as benzyl), heteroaryl(alkyl) (for example, a monocyclic heteroaryl-(CH₂)—, such as pyridinyl-(CH₂)—) and heterocyclyl(alkyl) (for example, a monocyclic heterocyclyl-(CH₂)—), wherein each of the aforementioned $R^{y1}$, $R^{y2}$ and $R^{z1}$ groups can be unsubstituted or substituted.

In some embodiments, $R^1$ can be —C(=O)$R^{y2}$, wherein $R^{y2}$ can be —C₁₋₄ alkyl(OH) (such as —CH₂OH). In some embodiments, $R^1$ can be —C(=O)—C(=O)NR$^{y1}$R$^{z1}$; wherein $R^{y1}$ can be H; and $R^{z1}$ can be any of the moieties listed for $R^{z1}$ in the previous paragraph. In some embodiments, $R^1$ can be —C(=O)—C(=O)NR$^{y1}$R$^{z1}$; wherein $R^{y1}$ can be H; and $R^{z1}$ can be a monocyclic C₃₋₈ cycloalkyl (for example, cyclopropyl, cyclobutyl, cyclopentyl, cyclohexyl, cycloheptyl and cyclooctyl).

Prodrug-type and phosphate-containing moieties can be present at $R^1$. In some embodiments, $R^1$ can be —CH(OH)—(S(=O)₂—O—). In other embodiments, $R^1$ can be —CH(OH)((P=O)(OR⁶)₂), wherein each R⁶ can be independently hydrogen, an unsubstituted C₁₋₆ alkyl, an unsubstituted C₂₋₆ alkenyl, an unsubstituted C₁₋₆ haloalkyl, an unsubstituted or a substituted aryl or an unsubstituted or a substituted aryl(C₁₋₄ alkyl). In still other embodiments, $R^1$ can be —C(=O)CH₂—O—((P=O)(OR⁷)₂), wherein each R⁷ can be independently hydrogen, an unsubstituted C₁₋₆ alkyl, an unsubstituted C₂₋₆ alkenyl, an unsubstituted C₁₋₆ haloalkyl, an unsubstituted or a substituted aryl or an unsubstituted or a substituted aryl(C₁₋₄ alkyl). Other examples of R⁶ and R⁷ groups include methyl, ethyl, n-propyl, iso-propyl, n-butyl, iso-butyl, sec-butyl, tert-butyl, pentyl (straight-chained and branched), hexyl (straight-chained and branched), ethenyl, propenyl, butenyl, pentenyl, hexenyl, chloromethyl, fluoromethyl, difluoromethyl, dichloromethyl, trifluoromethyl, trichloromethyl, an unsubstituted or a substituted phenyl and an unsubstituted or a substituted benzyl.

In some embodiments, $R^1$ can be cyano. In other embodiments, $R^1$ can be an unsubstituted C₂₋₅ alkynyl. In still other embodiments, $R^1$ can be a substituted C₂₋₅ alkynyl. The C₂₋₅ alkynyl can have various structures. For example, the C₂₋₅ alkynyl can have the structure —(CH₂)₁—C₂₋₄ alkynyl or —(CH₂)₂—C₂₋₃ alkynyl.

As described herein, Ring A¹ can be

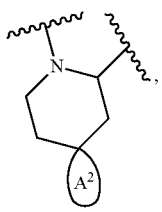

wherein Ring A² can be an unsubstituted or a substituted monocyclic C₃₋₆ cycloalkyl. In some embodiments, Ring A¹ can be

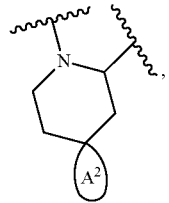

wherein Ring A² can be an unsubstituted monocyclic C₃₋₆ cycloalkyl. In other embodiments, Ring A¹ can be

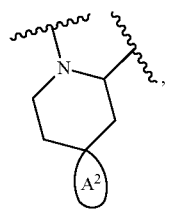

wherein Ring A² can be a substituted monocyclic C₃₋₆ cycloalkyl.

As also described herein, Ring A¹ can be

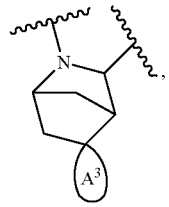

wherein Ring A³ can be an unsubstituted or a substituted monocyclic C₃₋₆ cycloalkyl. In some embodiments, Ring A¹ can be

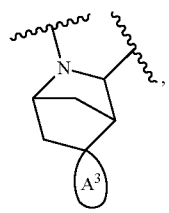

wherein Ring A³ can be an unsubstituted monocyclic C₃₋₆ cycloalkyl. In other embodiments, Ring A¹ can be

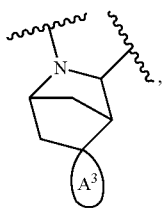

wherein Ring $A^3$ can be a substituted monocyclic $C_{3-6}$ cycloalkyl. Examples of monocyclic $C_{3-6}$ cycloalkyls that can be connected in a spiro-manner to Ring $A^2$ and/or Ring $A^3$ include cyclopropyl, cyclobutyl, cyclopentyl and cyclohexyl, including unsubstituted and substituted versions thereof. Example of suitable substituents that can be present on a monocyclic $C_{3-6}$ cycloalkyl that can be connected in a spiro-manner to Ring $A^2$ and/or Ring $A^3$ include, but are not limited to, =O, deuterium, halogen (such as F or Cl), hydroxy, an unsubstituted $C_{1-4}$ alkyl (for example, methyl, ethyl, n-propyl, iso-propyl, n-butyl, iso-butyl, sec-butyl and tert-butyl), an unsubstituted $C_{1-4}$ haloalkyl (including —CF$_3$, —CCl$_3$, —CHF$_2$, —C(CH$_3$)F$_2$, —CHCl$_2$, —CH$_2$F, —CH(CH$_3$)F, —CH$_2$CF$_3$, —CH$_2$Cl, —CH$_2$CH$_2$F, —CH$_2$CH$_2$Cl, —CH$_2$CH$_2$CH$_2$F and —CH$_2$CH$_2$CH$_2$Cl), an unsubstituted $C_{2-4}$ alkenyl (such as ethenyl, propenyl (branched and straight-chained) and butenyl (branched and straight-chained)) and an unsubstituted $C_{2-4}$ alkynyl (for example, ethynyl, propynyl and butynyl (branched and straight-chained)). Examples of Ring $A^1$ include, but are not limited to, the following

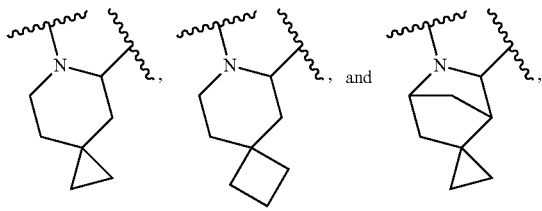 [SMILES: *C1CC2(CCN1*)CC2 ; *C1CC2(CCC2)CCN1* ; *C1C2CC(CC23CC3)N1*]

wherein each of these rings can be unsubstituted or substituted as described herein (including those paragraph).

In some embodiments, $R^4$ can be hydrogen. In other embodiments, $R^4$ can be deuterium. In still other embodiments, $R^4$ can be halogen (such as fluoro or chloro).

As provided herein, $R^3$ can be a non-hydrogen substituent. In some embodiments, $R^3$ can be an unsubstituted C-amido ($C_{1-4}$ alkyl). In other embodiments, $R^3$ can be a substituted C-amido($C_{1-4}$ alkyl). For example, $R^3$ can be an unsubstituted or a substituted C-amido-(CH$_2$)—.

Cyclic groups can also be present at $R^3$, such as, an unsubstituted or a substituted monocyclic nitrogen-containing heteroaryl($C_{1-4}$ alkyl), an unsubstituted or a substituted monocyclic nitrogen-containing heterocyclyl($C_{1-4}$ alkyl), an unsubstituted or a substituted bicyclic nitrogen-containing heteroaryl($C_{1-4}$ alkyl) or an unsubstituted or a substituted bicyclic nitrogen-containing heterocyclyl($C_{1-4}$ alkyl). In some embodiments, $R^3$ can be an unsubstituted monocyclic nitrogen-containing heterocyclyl($C_{1-4}$ alkyl). In other embodiments, $R^3$ can be a substituted monocyclic nitrogen-containing heterocyclyl($C_{1-4}$ alkyl). In still other embodiments, $R^3$ can be an unsubstituted monocyclic nitrogen-containing heteroaryl($C_{1-4}$ alkyl). In yet still other embodiments, $R^3$ can be a substituted monocyclic nitrogen-containing heteroaryl($C_{1-4}$ alkyl). In some embodiments, $R^3$ can be an unsubstituted bicyclic nitrogen-containing heterocyclyl($C_{1-4}$ alkyl). In other embodiments, $R^3$ can be a substituted bicyclic nitrogen-containing heterocyclyl($C_{1-4}$ alkyl). When $R^3$ is a bicyclic nitrogen-containing heterocyclyl($C_{1-4}$ alkyl), the two rings of the bicyclic heterocyclyl can be connected in a fused-fashion (including bridged-fashion) or a spiro-fashion.

Those skilled in the art understand that when two rings are connected in a spiro-fashion, the two rings are connected by a single ring atom. For example, in the structure

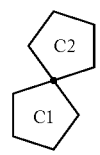

rings C1 and C2 are joined in a spiro-fashion. When two rings described herein are connected in a fused-fashion, the two rings are connected by two or more ring atoms. In some instances, the two rings can be connected by two adjacent ring atoms. As an example, rings D1 and D1 are connected in a fused-fashion by two adjacent ring atoms

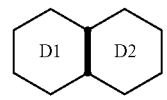

In some instances, two rings described herein can be connected by three or more atoms are shared between the two rings. The following structure:

is an example of two rings being connected by three or more ring atoms. When two rings are connected by three or more ring atoms, the three or more ring atoms connecting the two rings would be referred to by those skilled in the art as "bridging" atoms. Further, those skilled in the art would understand based on the disclosure provided herein that two rings connected in a "bridged" fashion is an example of two rings connected in a fused-fashion.

The number of ring atoms for a monocyclic and a bicyclic nitrogen-containing heterocyclyl($C_{1-4}$ alkyl) can vary. Non-limiting examples include an unsubstituted or a substituted 5-membered monocyclic nitrogen-containing heterocyclyl ($C_{1-4}$ alkyl), 6-membered monocyclic nitrogen-containing heterocyclyl($C_{1-4}$ alkyl), an unsubstituted or a substituted 9-membered bicyclic nitrogen-containing heterocyclyl($C_{1-4}$ alkyl) and 10-membered bicyclic nitrogen-containing heterocyclyl($C_{1-4}$ alkyl). Examples of suitable $R^3$ groups include the following: azepan-2-one($C_{1-4}$ alkyl), imidazolidin-2-one($C_{1-4}$ alkyl), tetrahydropyrimidin-2-one($C_{1-4}$ alkyl), pyrrolidin-2-one($C_{1-4}$ alkyl), piperidin-2-one($C_{1-4}$ alkyl), pyrazolidin-3-one($C_{1-4}$ alkyl), oxazolidin-4-one($C_{1-4}$ alkyl), 1,4-oxazepan-3-one($C_{1-4}$ alkyl), morpholin-3-one ($C_{1-4}$ alkyl),

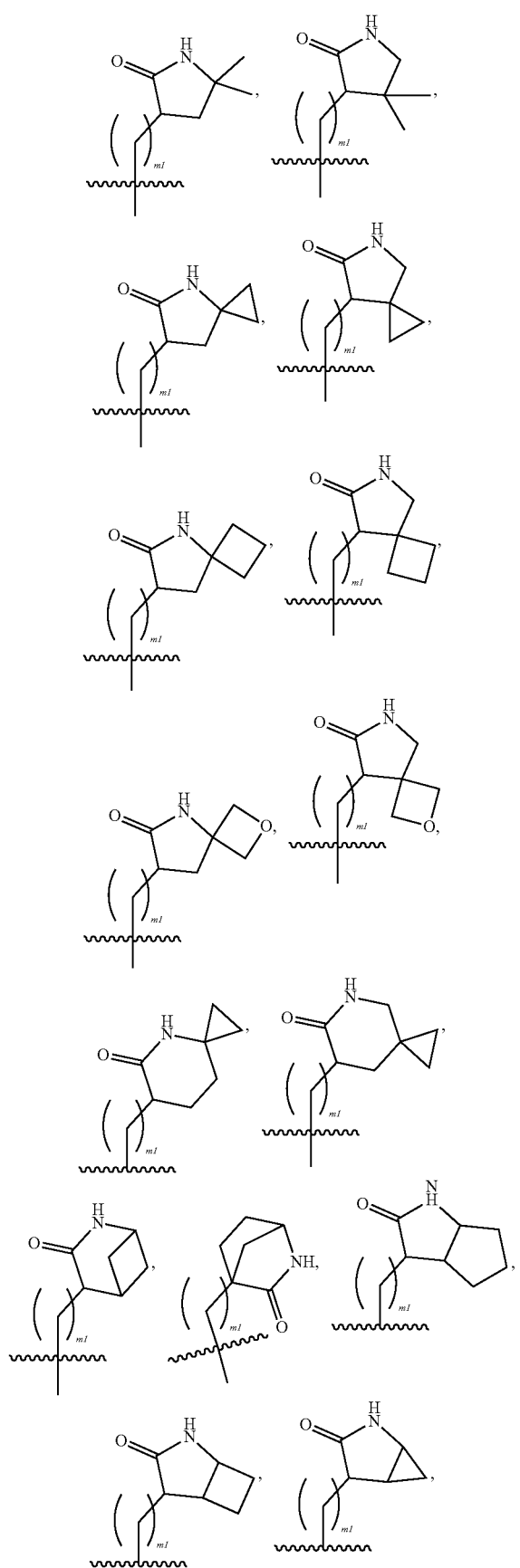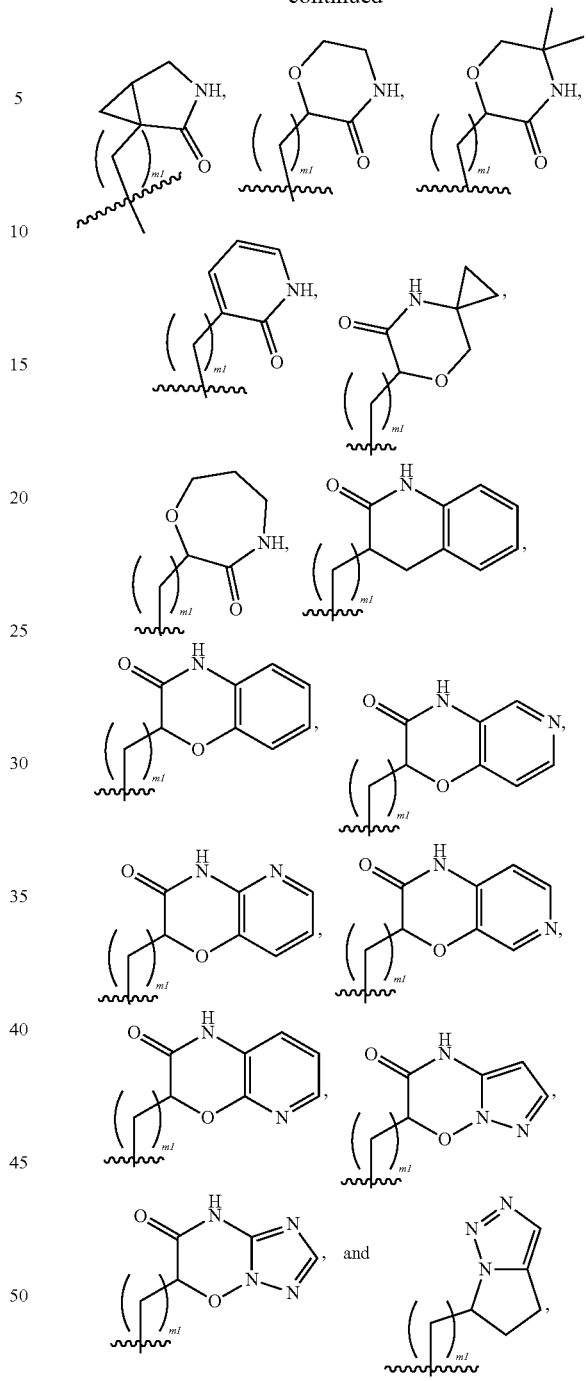

wherein each m1 can be independently 1, 2, 3 or 4, (including substituted or unsubstituted versions of the aforementioned). The R³ groups provided herein can be substituted with one or more moieties independently selected from those listed for "optionally substituted." In some embodiments, a R³ group provided herein can be substituted with one or more moieties selected from deuterium, halogen, hydroxy, an unsubstituted $C_{1-4}$ alkyl, an unsubstituted $C_{2-4}$ alkenyl an unsubstituted $C_{1-4}$ alkoxy, amino, -(an unsubstituted $C_{1-4}$ alkyl)-O—P—$(OH)_2$ (such as —$CH_2$—O—P—$(OH)_2$) and -(an unsubstituted $C_{1-4}$ alkyl)-O—P—(O(an unsubstituted $C_{1-4}$ alkyl))$_2$ (such as —$CH_2$—O—P—$(OCH_3)_2$).

Non-limiting examples of R³ moieties include the following:
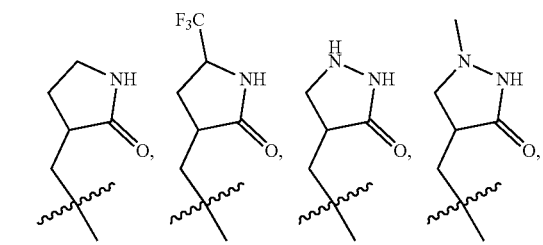
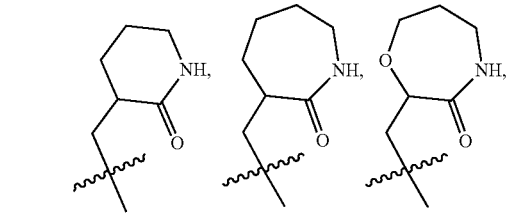
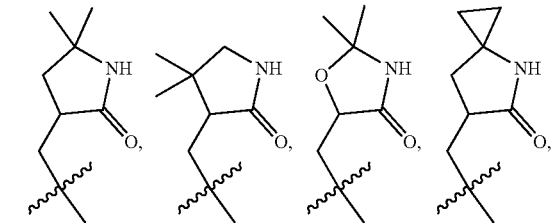
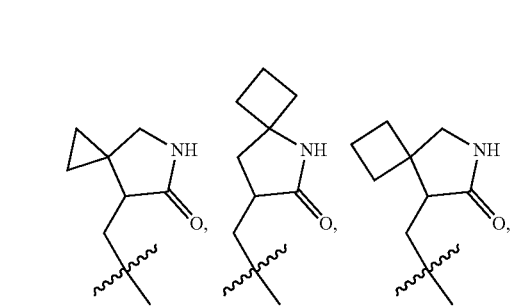
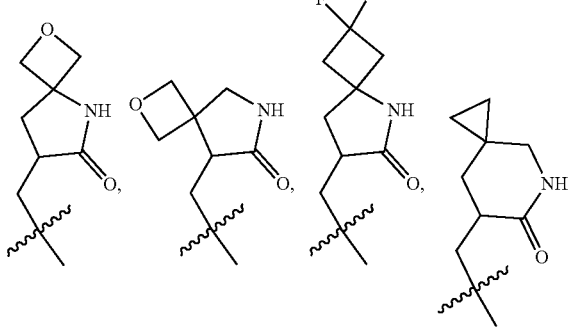
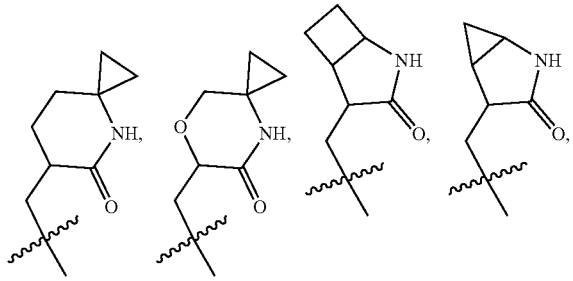
-continued
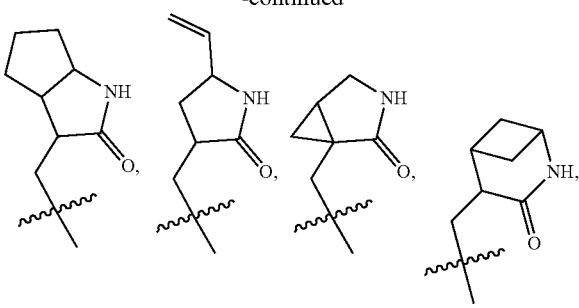
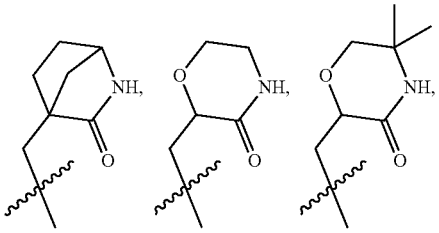
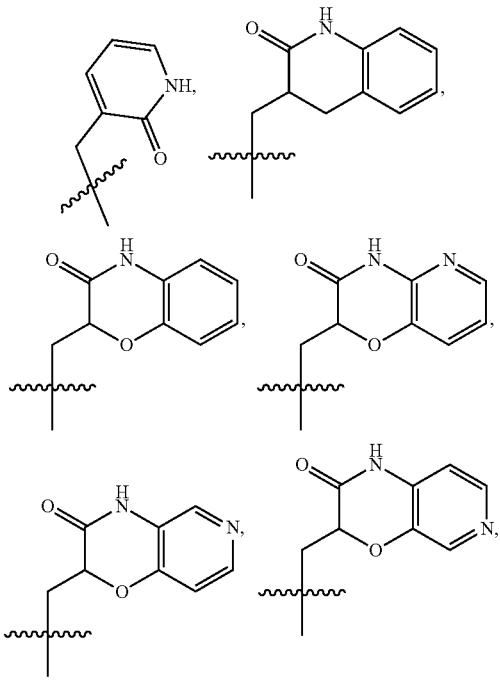
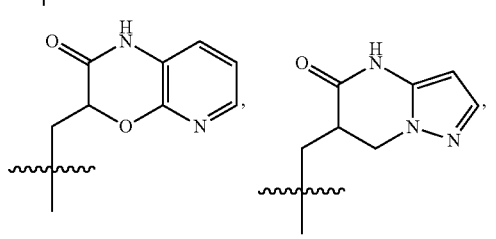
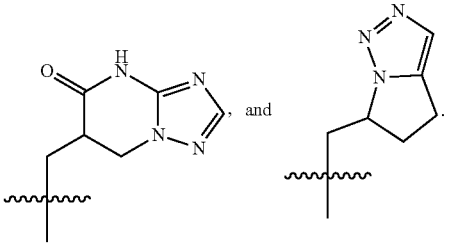

In some embodiments, $R^2$ can be hydrogen. In other embodiments, $R^2$ can be deuterium. In still other embodiments, $R^2$ can be halogen (for example, fluoro or chloro).

As provided herein, $R^5$ can be a variety of monocyclic, bicyclic tricyclic ring structures. For example, $R^5$ can be 5-membered monocyclic structure, 6-membered monocyclic structure, 6,5-bicyclic structure, a 5,6 bicyclic structure or a tricyclic structure, each of which can be unsubstituted or substituted. In some embodiments, $R^5$ can be an aromatic carbocyclyl. For example, $R^5$ can be an unsubstituted or a substituted naphthyl or an unsubstituted or a substituted phenyl. In other embodiments, $R^5$ can be a non-aromatic carbocyclyl. Examples of non-aromatic carbocyclyls include the following: a monocyclic $C_{3-6}$ cycloalkyl (such as cyclopropyl, cyclobutyl, cyclopentyl and cyclohexyl),

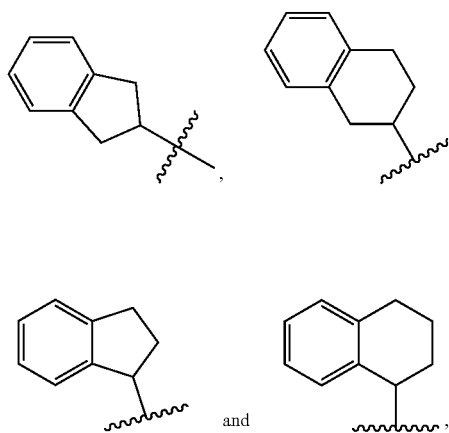

and wherein each can be unsubstituted or a substituted.

A variety of bicyclic and tricyclic ring structures can be present for $R^5$. In some embodiments, $R^5$ can be an unsubstituted or a substituted

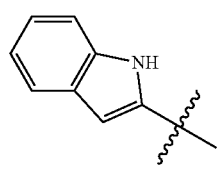

In other embodiments, $R^5$ can be an unsubstituted or a substituted

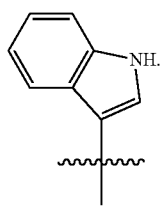 [SMILES: *c1c[nH]c2ccccc12]

In still other embodiments, $R^5$ can be an unsubstituted or a substituted

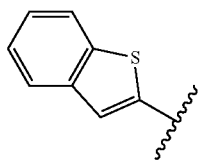

In yet still other embodiments, $R^5$ can be an unsubstituted or a substituted

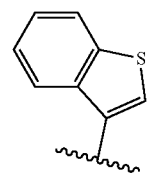

In some embodiments, $R^5$ can be an unsubstituted or a substituted

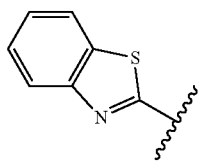

In other embodiments, $R^5$ can be an unsubstituted or a substituted

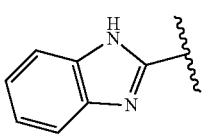

In still other embodiments, $R^5$ can be an unsubstituted or a substituted

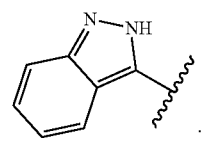 [SMILES: *c1[nH]nc2ccccc12]

In yet still other embodiments, $R^5$ can be an unsubstituted or a substituted

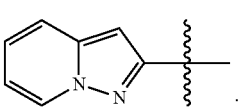 [SMILES: *c1cc2ccccn2n1]

In some embodiments, $R^5$ can be an unsubstituted or a substituted

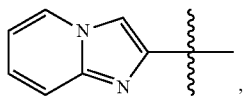 [SMILES: *c1cn2ccccc2n1]

In some embodiments, R⁵ can be an unsubstituted or a substituted

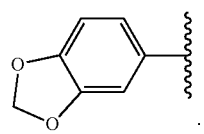 [SMILES: *c1ccc2c(c1)OCO2]

In other embodiments, R⁵ can be an unsubstituted or a substituted

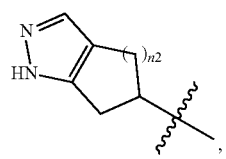

wherein n2 can be 1 or 2. In still other embodiments, R⁵ can be an unsubstituted or a substituted

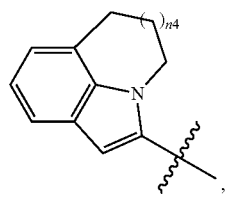

wherein n4 can be 0 or 1. In yet still other embodiments, R⁵ can be

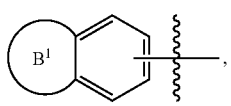

wherein B¹ can be an unsubstituted or a substituted monocyclic 5-6-membered heteroaryl. The heteroatoms that can be present in the ring of an unsubstituted or a substituted monocyclic 5-6-membered heteroaryl of B¹ include, but are not limited to, N (nitrogen), O (oxygen) and S (sulfur).

Various monocyclic rings can be also present for R⁵. In some embodiments, R⁵ can be an unsubstituted or a substituted

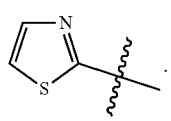

In other embodiments, R⁵ can be an unsubstituted or a substituted

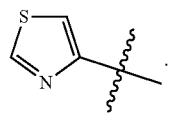

In still other embodiments, R⁵ can be an unsubstituted or a substituted

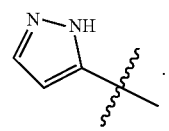 [SMILES: *c1ccn[nH]1]

In yet other embodiments, R⁵ can be an unsubstituted or a substituted

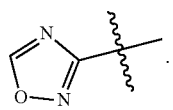

In some embodiments, R⁵ can be an unsubstituted or a substituted

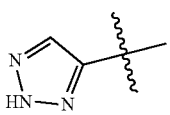

In other embodiments, R can be an unsubstituted or a substituted

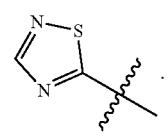 [SMILES: *c1ncns1]

In still other embodiments, R⁵ can be an unsubstituted or a substituted

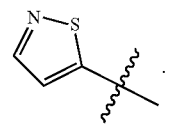 [SMILES: *c1ccns1]

In yet still other embodiments, R⁵ can be an unsubstituted or a substituted pyridine. In some embodiments, R⁵ can be an unsubstituted or a substituted 4- to 6-membered monocyclic heterocyclyl. For example, R⁵ can be an unsubstituted or a substituted 4- to 6-membered monocyclic heterocyclyl that includes 1, 2 or 3 heteroatoms selected from N (nitrogen), O (oxygen) and S (sulfur).

In some embodiments, Ring A¹ can be

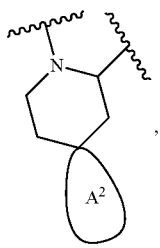

wherein R⁵ can be selected from an unsubstituted or a substituted naphthyl, an unsubstituted or a substituted

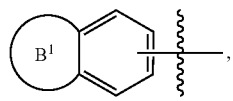

an unsubstituted or a substituted

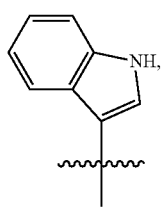 [SMILES: *c1c[nH]c2ccccc12]

an unsubstituted or a substituted

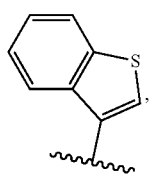

an unsubstituted or a substituted

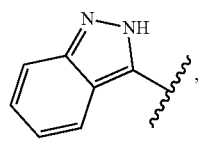 [SMILES: *c1[nH]nc2ccccc12]

an unsubstituted or a substituted

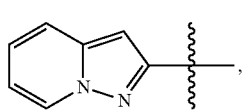 [SMILES: *c1cc2ccccn2n1]

an unsubstituted or a substituted

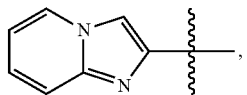 [SMILES: *c1cn2ccccc2n1]

an unsubstituted or a substituted

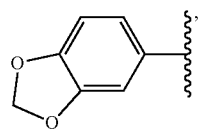

an unsubstituted or a substituted

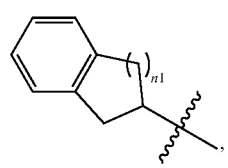

an unsubstituted or a substituted

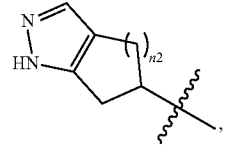

an unsubstituted or a substituted

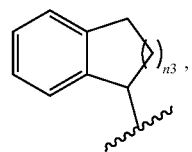

an unsubstituted or a substituted

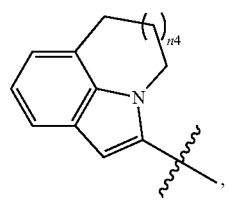

an unsubstituted or a substituted

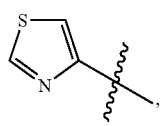

an unsubstituted or a substituted

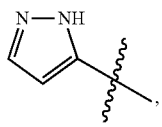

an unsubstituted or a substituted

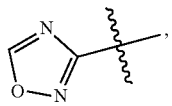 [SMILES: *c1ncon1]

an unsubstituted or a substituted

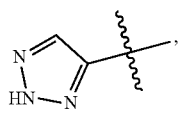

an unsubstituted or a substituted

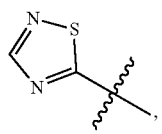

an unsubstituted or a substituted

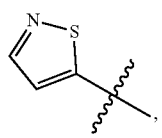 [SMILES: *c1ccns1]

an unsubstituted or a substituted pyridine, an unsubstituted or a substituted phenyl, an unsubstituted or a substituted monocyclic $C_{3-6}$ cycloalkyl and an unsubstituted or a substituted 4- to 6-membered monocyclic heterocyclyl.

In some embodiments, Ring $A^1$ can be

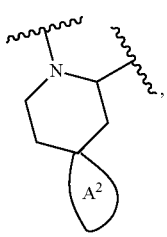

wherein $R^5$ can be an unsubstituted or a substituted

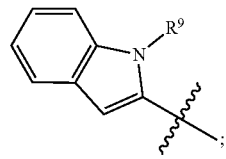

and wherein $R^9$ can be selected from an unsubstituted $C_{4-6}$ alkyl, an unsubstituted or a substituted monocyclic $C_{3-6}$ cycloalkyl, an unsubstituted or a substituted phenyl, an unsubstituted or a substituted 5- to 6-membered monocyclic heteroaryl and an unsubstituted or a substituted 5- to 6-membered monocyclic heterocyclyl.

In some embodiments, Ring $A^1$ can be

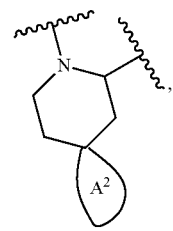

wherein $R^5$ can be selected from an unsubstituted or a substituted

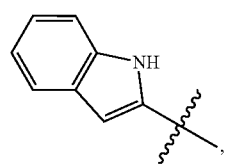 [SMILES: *c1cc2ccccc2[nH]1]

an unsubstituted or a substituted

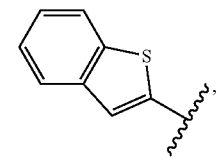 [SMILES: *c1cc2ccccc2s1]

an unsubstituted or a substituted

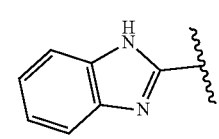 [SMILES: *c1nc2ccccc2[nH]1]

and an unsubstituted or a substituted

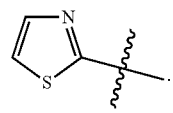

In some embodiments of this paragraph, Ring $A^2$ can be an unsubstituted or a substituted monocyclic $C_{4-6}$ cycloalkyl.

As described herein, $R^5$ can be unsubstituted or substituted with various substituents. Exemplary substituents that can be present on $R^5$ include the following: deuterium, halogen, an unsubstituted or a substituted $C_{1-6}$ alkyl, an unsubstituted or a substituted monocyclic $C_{3-6}$ cycloalkyl, an unsubstituted $C_{1-6}$ haloalkyl, an unsubstituted $C_{1-6}$ alkoxy, an unsubstituted or a substituted phenyl, an unsubstituted or a substituted 5- to 6-membered monocyclic heteroaryl and an unsubstituted or a substituted 5- to 6-membered monocyclic heterocyclyl. For example, a $R^5$ ring structure, such as those described herein, can be substituted with a substituents that includes chloro, fluoro, methyl, ethyl, n-propyl, isopropyl, n-butyl, isobutyl, sec-butyl, tert-butyl, pentyl (straight-chained and/or branched), hexyl (straight-chained and/or branched), cyclopropyl, cyclobutyl, cyclopentyl, cyclohexyl, —CF$_3$, —CCl$_3$, —CHF$_2$, —C(CH$_3$)F$_2$, —CHCl$_2$, —CH$_2$F, —CH(CH$_3$)F, —CH$_2$CF$_3$, —CH$_2$Cl, —CH$_2$CH$_2$F, —CH$_2$CH$_2$Cl, —CH$_2$CH$_2$CH$_2$F, —CH$_2$CH$_2$CH$_2$Cl, methoxy, ethoxy, n-propoxy, isopropoxy, n-butoxy, isobutoxy, sec-butoxy, tert-butoxy, pentoxy (straight-chained and/or branched), hexoxy (straight-chained and/or branched), a 5- to 6-membered monocyclic heteroaryl that includes 1, 2 or 3 heteroatoms selected from N (nitrogen), O (oxygen) and S (sulfur), and a 5- to 6-membered monocyclic heterocyclyl that includes 1, 2 or 3 heteroatoms selected from N (nitrogen), O (oxygen) and S (sulfur).

When $R^5$ is substituted, one or more (such as 1, 2 or 3) substituents can be present. As provided herein a $C_{1-6}$ alkyl, a monocyclic $C_{3-6}$ cycloalkyl, a phenyl, a 5- to 6-membered monocyclic heteroaryl and a 5- to 6-membered monocyclic heterocyclyl that is substituted on $R^5$ can be unsubstituted or further substituted. For example, a monocyclic $C_{3-6}$ cycloalkyl, a phenyl, a 5- to 6-membered monocyclic heteroaryl and a 5- to 6-membered monocyclic heterocyclyl present on a $R^5$ ring structure can substituted one or more times, for example, 1, 2 or 3 times with a moiety selected from deuterium, halogen (such as fluoro and/or chloro), an unsubstituted $C_{1-6}$ alkyl, an unsubstituted $C_{1-6}$ haloalkyl and an unsubstituted $C_{1-6}$ alkoxy.

Further, when $R^5$ is a monocyclic $C_{3-6}$ cycloalkyl or a 4- to 6-membered monocyclic heterocyclyl, the monocyclic $C_{3-6}$ cycloalkyl or the 4- to 6-membered monocyclic heterocyclyl can be substituted in a spiro-fashion by an unsubstituted or a substituted bicyclic cycloalkenyl or an unsubstituted or a substituted bicyclic heterocyclyl. The bicyclic cycloalkenyl can be an unsubstituted or a substituted 8- to 10-membered bicyclic cycloalkenyl. An unsubstituted or a substituted bicyclic heterocyclyl can be an unsubstituted or a substituted 8- to 10-membered bicyclic heterocyclyl, for example, an unsubstituted or a substituted 8- to 10-membered bicyclic heterocyclyl that includes 1, 2 or 3 heteroatoms in the rings selected from N (nitrogen), O (oxygen) and S (sulfur). In some embodiments, the bicyclic cycloalkenyl and/or the bicyclic heterocyclyl can be substituted one or more times (such as 1, 2, 3 or 4 times) with a moiety independently selected from halogen, an unsubstituted $C_{1-4}$ alkyl, an unsubstituted $C_{1-6}$ haloalkyl (such as —CF$_3$, —CCl$_3$, —CHF$_2$, —C(CH$_3$)F$_2$, —CHCl$_2$, —CH$_2$F, —CH(CH$_3$)F, —CH$_2$CF$_3$, —CH$_2$Cl, —CH$_2$CH$_2$F, —CH$_2$CH$_2$Cl, —CH$_2$CH$_2$CH$_2$F, —CH$_2$CH$_2$CH$_2$Cl) and an unsubstituted $C_{1-4}$ alkoxy. Examples of $R^5$ as a monocyclic $C_{3-6}$ cycloalkyl or a 4- to 6-membered monocyclic heterocyclyl substituted in a spiro-fashion by an unsubstituted or a substituted bicyclic cycloalkenyl or an unsubstituted or a substituted bicyclic heterocyclyl include the following:

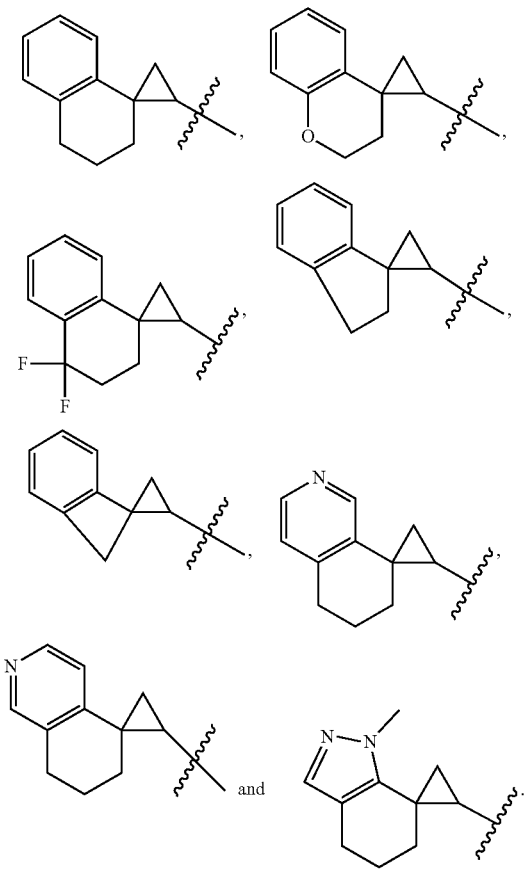

In some embodiments, $R^1$ can be an unsubstituted or a substituted ketoamide (such as those described herein); $R^2$ can be hydrogen; $R^3$ can be an unsubstituted or a substituted monocyclic nitrogen-containing heterocyclyl($C_{1-4}$ alkyl); $R^4$ can be hydrogen; and $R^5$ can be selected from an unsubstituted or a substituted naphthyl, an unsubstituted or a substituted

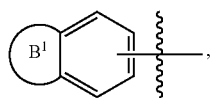

an unsubstituted or a substituted

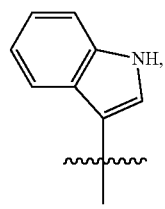 [SMILES: *c1c[nH]c2ccccc12]

an unsubstituted or a substituted

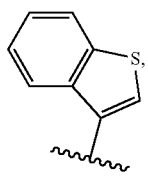 [SMILES: *c1csc2ccccc12]

an unsubstituted or a substituted

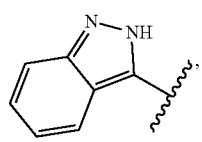

an unsubstituted or a substituted

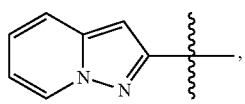 [SMILES: *c1cc2ccccn2n1]

an unsubstituted or a substituted

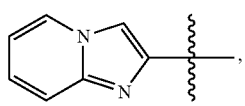 [SMILES: *c1cn2ccccc2n1]

an unsubstituted or a substituted

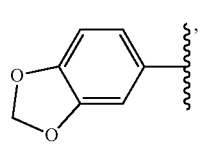

an unsubstituted or a substituted

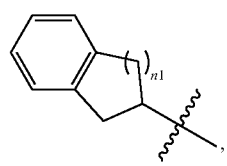

an unsubstituted or a substituted

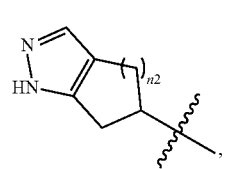

an unsubstituted or a substituted

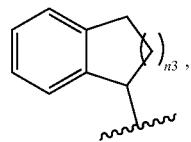

an unsubstituted or a substituted

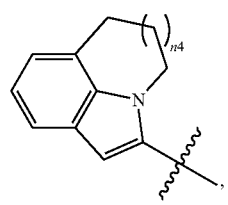

an unsubstituted or a substituted

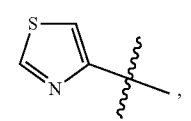 [SMILES: *c1cscn1]

an unsubstituted or a substituted an

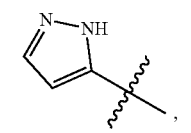 [SMILES: *c1ccn[nH]1]

an unsubstituted or a substituted

an unsubstituted or a substituted

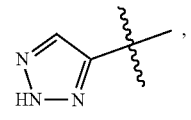

an unsubstituted or a substituted

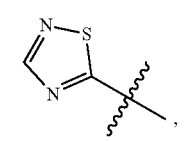 [SMILES: *c1ncns1]

an unsubstituted or a substituted

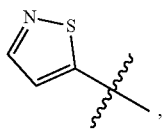 [SMILES: *c1ccns1], an unsubstituted or a substituted pyridine, an unsubstituted or a substituted phenyl and an unsubstituted or a substituted monocyclic $C_{3-6}$ cycloalkyl and an unsubstituted or a substituted 4- to 6-membered monocyclic heterocyclyl. In some embodiments, $R^1$ can be an unsubstituted or a substituted ketoamide (such as those described herein); $R^2$ can be hydrogen; $R^3$ can be an unsubstituted or a substituted monocyclic nitrogen-containing heterocyclyl($C_{1-4}$ alkyl); $R^4$ can be hydrogen; and $R^5$ can be a substituted

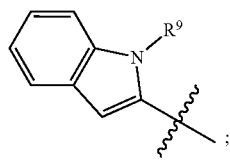;

and wherein $R^9$ can be selected from an unsubstituted $C_{4-6}$ alkyl, an unsubstituted or a substituted monocyclic $C_{3-6}$ cycloalkyl, an unsubstituted or a substituted phenyl, an unsubstituted or a substituted 5- to 6-membered monocyclic heteroaryl and an unsubstituted or a substituted 5- to 6-membered monocyclic heterocyclyl.

As provided herein, $R^5$ can be

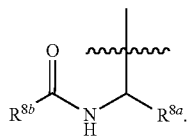

In some embodiments, $R^{8b}$ can be an unsubstituted $C_{1-6}$ haloalkyl. For example, $R^{8b}$ can be —$CF_3$, —$CCl_3$, —$CHF_2$, —$C(CH_3)F_2$, —$CHCl_2$, —$CH_2F$, —$CH(CH_3)F$, —$CH_2CF_3$, —$CH_2Cl$, —$CH_2CH_2F$, —$CH_2CH_2Cl$, —$CH_2CH_2CH_2F$ and —$CH_2CH_2CH_2Cl$. In some embodiments, $R^{8b}$ can be —$CF_3$. In other embodiments, $R^{8b}$ can be a substituted $C_{1-6}$ haloalkyl where the $C_{1-6}$ haloalkyl can be substituted 1 or 2 times with an unsubstituted $C_{1-4}$ alkoxy. When the $C_{1-6}$ haloalkyl is substituted with 1 or 2 unsubstituted $C_{1-4}$ alkoxys, one or more hydrogens of the $C_{1-6}$ haloalkyl can be replaced with an unsubstituted $C_{1-4}$ alkoxy (such as methoxy, ethoxy, n-propoxy, isopropoxy, n-butoxy, isobutoxy, sec-butoxy and tert-butoxy). Exemplary $C_{1-6}$ haloalkyls substituted with an unsubstituted $C_{1-4}$ alkoxy include —$C(OCH_3)F_2$, —$C(OCH_3)Cl_2$, —$CH(OCH_3)F$, —$C(OCH_3)(CH_3)F$, —$CH(OCH_3)CF_3$, —$C(OCH_3)(CH_3)CF_3$, —$CH_2CH(OCH_3)CF_3$, —$CH_2C(OCH_3)(CH_3)CF_3$, —$CH(OCH_3)Cl$, —$CH_2CH(OCH_3)F$, —$CH_2CH(OCH_3)Cl$, —$CH_2CH_2CH(OCH_3)F$ and —$CH_2CH_2CH(OCH_3)Cl$. In still other embodiments, $R^{8b}$ can be an unsubstituted $C_{1-6}$ alkyl, such as methyl, ethyl, n-propyl, iso-propyl, n-butyl, iso-butyl, sec-butyl, tert-butyl, pentyl (straight-chained or branched) and hexyl (straight-chained or branched). In yet still other embodiments, $R^{8b}$ can be a $C_{1-6}$ alkyl substituted 1 or 2 times with an unsubstituted $C_{1-4}$ alkoxy. When the $C_{1-6}$ alkyl is substituted with an unsubstituted $C_{1-4}$ alkoxy, a hydrogen of the $C_{1-6}$ alkyl can be replaced with an unsubstituted $C_{1-4}$ alkoxy such as those described herein. A non-limiting list of $C_{1-6}$ alkyls substituted 1 or 2 times with an unsubstituted $C_{1-4}$ alkoxy include —$CH_2(OCH_3)$, —$CH(OCH_3)_2$, —$CH(CH_3)(OCH_3)$ and —$C(CH_3)_2(OCH_3)$. In some embodiments, $R^{8b}$ can be an unsubstituted or a substituted monocyclic heteroaryl. A variety of an unsubstituted or a substituted monocyclic heteroaryls can be present for $R^{8b}$. For example, the heteroaryl can be a 5- or 6-membered heteroaryl that includes 1, 2 or 3 heteroatoms selected from nitrogen (N), oxygen (O) and sulfur (S). Exemplary heteroaryls for an unsubstituted or a substituted monocyclic heteroaryl include, but are not limited to, furane, isoxazole, isothiazole pyridine, pyridazine, pyrimidine and pyrazine. In yet still other embodiments, $R^{8b}$ can be an unsubstituted or a substituted monocyclic heterocyclyl. A non-limiting list of monocyclic heterocyclyls for $R^{8b}$ include oxetane, tetrahydrofuran, tetrahydrothiophene, pyrrolidine, tetrahydropyran, tetrahydrothiopyran, piperidine and morpholine. Various substituents can be present on a substituted heteroaryl and/or a substituted heterocyclyl of $R^{8b}$. For example, the heteroaryl can be substituted 1, 2 or 3 times with a moiety selected from halogen, an unsubstituted $C_{1-6}$ alkyl, an unsubstituted $C_{1-6}$ haloalkyl and an unsubstituted $C_{1-6}$ alkoxy. Suitable halogens, unsubstituted $C_{1-6}$ alkyls, unsubstituted $C_{1-6}$ haloalkyls and unsubstituted $C_{1-6}$ alkoxys are described herein.

In some embodiments, $R^{8b}$ can be an unsubstituted monocyclic $C_{3-6}$ cycloalkyl, such as cyclopropyl, cyclobutyl, cyclobutyl, cyclopentyl and cyclohexyl. In other embodiments, $R^{8b}$ can be halogen-substituted monocyclic $C_{3-6}$ cycloalkyl. In some embodiments, $R^{8b}$ can be a monocyclic $C_{3-6}$ cycloalkyl substituted with an unsubstituted $C_{1-4}$ alkyl. In yet still other embodiments, $R^{8b}$ can be a monocyclic $C_{3-6}$ cycloalkyl substituted with an unsubstituted $C_{1-4}$ alkoxy. In some embodiments, $R^{8b}$ can be a monocyclic $C_{3-6}$ cycloalkyl substituted with an unsubstituted $C_{2-4}$ alkenyl. In some embodiments, $R^{8b}$ can be a monocyclic $C_{3-6}$ cycloalkyl substituted with an unsubstituted $C_{1-4}$ haloalkyl. In still other embodiments, $R^{8b}$ can be a monocyclic $C_{3-6}$ cycloalkyl substituted with an unsubstituted monocyclic $C_{3-6}$ cycloalkyl, such as cyclopropyl, cyclobutyl, cyclopentyl or cyclohexyl. In some embodiments, $R^{8b}$ can be an unsubstituted bicyclic $C_{5-6}$ cycloalkyl. In other embodiments, $R^{8b}$ can be a substituted bicyclic $C_{5-6}$ cycloalkyl. The two rings of a bicyclic $C_{5-6}$ cycloalkyl can be connected in a spiro-fashion or a fused-fashion. In some embodiments, $R^{8b}$ can be a halogen-substituted bicyclic $C_{5-6}$ cycloalkyl. In still other embodiments, $R^{8b}$ can be a bicyclic $C_{5-6}$ cycloalkyl substituted with an unsubstituted $C_{1-4}$ alkyl. In yet still other embodiments, $R^{8b}$ can be a bicyclic $C_{5-6}$ cycloalkyl substituted with an unsubstituted $C_{1-4}$ alkoxy. In some embodiments, $R^{8b}$ can be a bicyclic $C_{5-6}$ cycloalkyl substituted with an unsubstituted $C_{2-4}$ alkenyl. In other embodiments, $R^{8b}$ can be a bicyclic $C_{5-6}$ cycloalkyl substituted with an unsubstituted $C_{1-4}$ haloalkyl. In still other embodiments, $R^{8b}$ can be a bicyclic $C_{5-6}$ cycloalkyl substituted with an unsubstituted monocyclic $C_{3-6}$ cycloalkyl (including cyclopropyl, cyclobutyl, cyclopentyl and cyclohexyl). A non-liming list of bicyclic $C_{5-6}$ cycloalkyls include spiro[2.2]pentane, spiro [2.3]hexane, bicyclo[1.1.1]pentane and bicyclo[2.1.1] hexane.

Suitable halogen-substituted monocyclic $C_{3-6}$ cycloalkyls include halogen-substituted cyclopropyl, halogen-substituted cyclobutyl, halogen-substituted cyclopentyl and halogen-substituted cyclohexyl. Additional monocyclic $C_{3-6}$ cycloalkyls include cyclopropyl substituted with an unsubstituted $C_{1-4}$ alkyl, an unsubstituted $C_{1-4}$ alkoxy, an unsubstituted $C_{2-4}$ alkenyl, an unsubstituted $C_{1-4}$ haloalkyl, and/or an unsubstituted monocyclic $C_{3-6}$ cycloalkyl, cyclobutyl substituted with an unsubstituted $C_{1-4}$ alkyl, an unsubstituted $C_{1-4}$ alkoxy, an unsubstituted $C_{2-4}$ alkenyl, an unsubstituted $C_{1-4}$ haloalkyl and/or an unsubstituted monocyclic $C_{3-6}$ cycloalkyl, cyclopentyl substituted with an unsubstituted $C_{1-4}$ alkyl, an unsubstituted $C_{1-4}$ alkoxy, an unsubstituted $C_{2-4}$ alkenyl, an unsubstituted $C_{1-4}$ haloalkyl and/or an unsubstituted monocyclic $C_{3-6}$ cycloalkyl, cyclohexyl substituted with an unsubstituted $C_{1-4}$ alkyl, an unsubstituted $C_{1-4}$ alkoxy, an unsubstituted $C_{2-4}$ alkenyl, an unsubstituted $C_{1-4}$ haloalkyl and/or an unsubstituted monocyclic $C_{3-6}$ cycloalkyl. The number halogens on a halogen-substituted monocyclic $C_{3-6}$ cycloalkyl and/or a bicyclic $C_{5-6}$ cycloalkyl, the number of unsubstituted $C_{1-4}$ alkyls on a monocyclic $C_{3-6}$ cycloalkyl and/or a bicyclic $C_{5-6}$ cycloalkyl, the number of unsubstituted $C_{1-4}$ alkoxys on a monocyclic $C_{3-6}$ cycloalkyl and/or a bicyclic $C_{5-6}$ cycloalkyl, the number of unsubstituted $C_{2-4}$ alkenyls on a monocyclic $C_{3-6}$ cycloalkyl and/or a bicyclic $C_{5-6}$ cycloalkyl, the number of unsubstituted $C_{1-4}$ haloalkyls on a monocyclic $C_{3-6}$ cycloalkyl and/or a bicyclic $C_{5-6}$ cycloalkyl, and the number of unsubstituted monocyclic $C_{3-6}$ cycloalkyls on a monocyclic $C_{3-6}$ cycloalkyl and/or a bicyclic $C_{5-6}$ cycloalkyl can vary. For example, 1, 2, 3 or 4 halogens can be present on a halogen-substituted monocyclic $C_{3-6}$ cycloalkyl, 1, 2, 3 or 4 unsubstituted $C_{1-4}$ alkyls can be present on a monocyclic $C_{3-6}$ cycloalkyl substituted with an unsubstituted $C_{1-4}$ alkyl, 1, 2, 3 or 4 unsubstituted $C_{1-4}$ alkoxys can be present on a monocyclic $C_{3-6}$ cycloalkyl substituted with an unsubstituted $C_{1-4}$ alkoxy, 1, 2, 3 or 4 unsubstituted $C_{2-4}$ alkenyls can be present on a monocyclic $C_{3-6}$ cycloalkyl substituted with an unsubstituted $C_{2-4}$ alkenyl, 1, 2, 3 or 4 unsubstituted $C_{1-4}$ haloalkyls can be present on a monocyclic $C_{3-6}$ cycloalkyl substituted with an unsubstituted $C_{1-4}$ haloalkyl, 1 or 2 unsubstituted monocyclic $C_{3-6}$ cycloalkyls can be present on a monocyclic $C_{3-6}$ cycloalkyl substituted with an unsubstituted monocyclic $C_{3-6}$ cycloalkyl, 1, 2, 3 or 4 halogens can be present on a halogen-substituted bicyclic $C_{5-6}$ cycloalkyl, 1, 2, 3 or 4 unsubstituted $C_{1-4}$ alkyls can be present on a bicyclic $C_{5-6}$ cycloalkyl substituted with an unsubstituted $C_{1-4}$ alkyl, 1, 2, 3 or 4 unsubstituted $C_{1-4}$ alkoxys can be present on a bicyclic $C_{5-6}$ cycloalkyl substituted with an unsubstituted $C_2$-4 alkoxy, 1, 2, 3 or 4 unsubstituted $C_{2-4}$ alkenyls can be present on a bicyclic $C_{5-6}$ cycloalkyl substituted with an unsubstituted $C_{2-4}$ alkenyl, 1, 2, 3 or 4 unsubstituted $C_{1-4}$ haloalkyls can be present on a bicyclic $C_{5-6}$ cycloalkyl substituted with an unsubstituted $C_{1-4}$ haloalkyl and 1 or 2 unsubstituted monocyclic $C_{3-6}$ cycloalkyls can be present on a bicyclic $C_{5-6}$ cycloalkyl substituted with an unsubstituted monocyclic $C_{3-6}$ cycloalkyl. In some embodiments, a monocyclic $C_{3-6}$ cycloalkyl can be substituted with 1 or more substituents (such as 1, 2, 3 or 4 substituents) selected from halogen, an unsubstituted $C_{1-4}$ alkyl, an unsubstituted $C_{1-4}$ alkoxy, an unsubstituted $C_{2-4}$ alkenyl and an unsubstituted $C_{1-4}$ haloalkyl. In other embodiments, a bicyclic $C_{5-6}$ cycloalkyl can be substituted with 1 or more substituents (such as 1, 2, 3 or 4 substituents) selected from halogen, an unsubstituted $C_{1-4}$ alkyl, an unsubstituted $C_{1-4}$ alkoxy an unsubstituted $C_{2-4}$ alkenyl, and an unsubstituted $C_{1-4}$ haloalkyl. Suitable halogens that can be present on a substituted monocyclic $C_{3-6}$ cycloalkyl include, but are not limited to, fluoro (F) and chloro (Cl). Examples of unsubstituted $C_{1-4}$ haloalkyls include, but are not limited to, —$CF_3$, —$CCl_3$, —$CHF_2$, —$C(CH_3)F_2$, —$CHCl_2$, —$CH_2F$, —$CH(CH_3)F$, —$CH_2CF_3$, —$CH_2Cl$, —$CH_2CH_2F$, —$CH_2CH_2Cl$, —$CH_2CH_2CH_2F$ and —$CH_2CH_2CH_2Cl$. Exemplary unsubstituted $C_{1-4}$ alkoxys include, but are not limited to methoxy, ethoxy, n-propoxy, iso-propoxy, n-butoxy, iso-butoxy, sec-butoxy and tert-butoxy.

The $R^{8a}$ moiety can be a substituted or an unsubstituted version of a $C_{2-6}$ alkyl, a $C_{2-6}$ alkenyl, a $C_{2-6}$ alkynyl, a monocyclic $C_{3-6}$ cycloalkyl, a bicyclic $C_{5-8}$ cycloalkyl or a monocyclic 4- to 6-membered heterocyclyl. In some embodiments, $R^{8a}$ can be an unsubstituted $C_{2-6}$ alkyl. In other embodiments, $R^{8a}$ can be a substituted $C_{2-6}$ alkyl. Exemplary $C_{2-6}$ alkyls include methyl, ethyl, n-propyl, iso-propyl, n-butyl, isobutyl, sec-butyl, tert-butyl, pentyl (straight-chained and branched) and hexyl (straight-chained and branched). In some embodiments, $R^{8a}$ can be an unsubstituted $C_{2-6}$ alkenyl. In other embodiments, $R^{8a}$ can be a substituted $C_{2-6}$ alkenyl. In still other embodiments, $R^{8a}$ can be an unsubstituted $C_{2-6}$ alkynyl. In yet still other embodiments, $R^{8a}$ can be a substituted $C_{2-6}$ alkynyl.

Cyclic moieties, including monocyclic and bicyclic moieties, can also be present for $R^{8a}$. In some embodiments, $R^{8a}$ can be an unsubstituted monocyclic $C_{3-6}$ cycloalkyl. In some embodiments, $R^{8a}$ can be a substituted monocyclic $C_{3-6}$ cycloalkyl. For example, $R^{8a}$ can be a substituted or an unsubstituted cyclopropyl, a substituted or an unsubstituted cyclobutyl, a substituted or an unsubstituted cyclopentyl or a substituted or an unsubstituted cyclohexyl. In some embodiments, $R^{8a}$ can be an unsubstituted bicyclic $C_{5-8}$ cycloalkyl. In other embodiments, $R^{8a}$ can be an unsubstituted bicyclic $C_{5-8}$ cycloalkyl. The two rings of the bicyclic $C_{5-8}$ cycloalkyl can joined in a fused or a spiro-fashion. Examples of rings connected in a fused and a spiro-fashion are provided herein. In some embodiments, $R^{8a}$ can be an unsubstituted or a substituted bicyclo[1.1.1]pentyl. In still other embodiments, $R^{8a}$ can be an unsubstituted monocyclic 4- to 6-membered heterocyclyl. In yet still other embodiments, $R^{8a}$ can be an unsubstituted monocyclic 4- to 6-membered heterocyclyl. The number of heteroatoms present in a monocyclic 4- to 6-membered heterocyclyl for $R^{8a}$ can vary. Suitable heteroatoms include, but are not limited to, O (oxygen), S (sulfur) and N (nitrogen). Examples of monocyclic 4- to 6-membered heterocyclyls are oxetane, thietane, azetidine, pyrrolidine, tetrahydrofuran, tetrahydrothiophene, tetrahydropyran, tetrahydrothiopyran and piperidine (including unsubstituted or substituted versions of each of the aforementioned). In some embodiments, $R^{8a}$ can be an unsubstituted monocyclic $C_{3-6}$ cycloalkyl($CH_2$)—. Various monocyclic $C_{3-6}$ cycloalkyl are described herein. As examples, $R^{8a}$ can be selected from cyclopropyl($CH_2$)—, cyclobutyl($CH_2$)—, cyclopentyl($CH_2$)— and cyclohexyl ($CH_2$)—.

As described herein, $R^{8a}$ can be substituted. In some embodiments, when $R^{8a}$ is a $C_{2-6}$ alkyl that is substituted, the $C_{2-6}$ alkyl can be substituted 1, 2, 3 or 4 times with a substituent independently selected from halogen, cyano, an unsubstituted or a substituted monocyclic $C_{3-6}$ cycloalkyl, an unsubstituted $C_{1-4}$ alkoxy and an unsubstituted $C_{1-4}$ haloalkoxy. In some embodiments, $R^{8a}$ can be a $C_{2-6}$ alkyl that is substituted 1 to 13 times with deuterium. In some embodiments, $R^{8a}$ can be a $C_{2-6}$ alkyl that is substituted 1 to 9 times with deuterium, 1 to 6 times with deuterium, 1 to 5 times with deuterium or 1 to 3 times with deuterium. Each halogen can be independently F (fluoro) or Cl (chloro). Exemplary unsubstituted and substituted monocyclic $C_{3-6}$ cycloalkyls that can be present on a substituted $C_{2-6}$ alkyl for $R^{8a}$ include cyclopropyl, cyclobutyl, cyclopentyl, cyclohexyl and halogen-substituted monocyclic $C_{3-6}$ cycloalkyls. Suitable unsubstituted $C_{1-4}$ alkoxys that can be substituted on a $C_{2-6}$ alkyl of $R^{8a}$ include methoxy, ethoxy, n-propoxy, isopropoxy, n-butoxy, isobutoxy, sec-butoxy and tert-butoxy. Examples of an unsubstituted $C_{1-4}$ haloalkoxy can be substituted on a $C_{2-6}$ alkyl of $R^{8a}$ include —OCl₃, —OCF₃, —OCH₂Cl, —OCH₂F, —OCHCl₂ and —OCHF₂. In some embodiments, when $R^{8a}$ is a substituted $C_{2-6}$ alkenyl, a substituted $C_{2-6}$ alkynyl, a substituted monocyclic $C_{3-6}$ cycloalkyl, a substituted bicyclic $C_{5-8}$ cycloalkyl or a substituted monocyclic 4- to 6-membered heterocyclyl, each of the aforementioned can be substituted 1, 2, 3 or 4 times with a substituents independently selected from halogen, an unsubstituted $C_{1-4}$ alkyl, an unsubstituted $C_{2-4}$ alkenyl, an unsubstituted $C_{2-4}$ alkynyl, an unsubstituted $C_{1-6}$ haloalkyl, an unsubstituted or a substituted monocyclic $C_{3-6}$ cycloalkyl and an unsubstituted $C_{1-4}$ alkoxy. Examples of unsubstituted $C_{1-4}$ alkyls, unsubstituted $C_{2-4}$ alkenyls and unsubstituted $C_{2-4}$ alkynyls that can be substituted on a substituted $C_{2-6}$ alkenyl, a substituted $C_{2-6}$ alkynyl, a substituted monocyclic $C_{3-6}$ cycloalkyl, a substituted bicyclic $C_{5-8}$ cycloalkyl or a substituted monocyclic 4- to 6-membered heterocyclyl include methyl, ethyl, n-propyl, isopropyl, n-butyl, iso-butyl, sec-butyl, tert-butyl, ethenyl, propenyl, butenyl, ethynyl, propynyl and butynyl. Suitable halogens and unsubstituted $C_{1-4}$ alkoxys that can be present on a substituted $C_{2-6}$ alkenyl, a substituted $C_{2-6}$ alkynyl, a substituted monocyclic $C_{3-6}$ cycloalkyl, a substituted bicyclic $C_{5-8}$ cycloalkyl or a substituted monocyclic 4- to 6-membered heterocyclyl are described herein, such as in this paragraph. Non-limiting list of unsubstituted and substituted monocyclic $C_{3-6}$ cycloalkyls include cyclopropyl, cyclobutyl, cyclopentyl, cyclohexyl and halogen-substituted monocyclic $C_{3-6}$ cycloalkyls. Examples of unsubstituted $C_{1-6}$ haloalkyls that can be present on a substituted $C_{2-6}$ alkenyl, a substituted $C_{2-6}$ alkynyl, a substituted monocyclic $C_{3-6}$ cycloalkyl, a substituted bicyclic $C_{5-8}$ cycloalkyl or a substituted monocyclic 4- to 6-membered heterocyclyl include, but are not limited to, —CF₃, —CCl₃, —CHF₂, —C(CH₃)F₂, —CHCl₂, —CH₂F, —CH(CH₃)F, —CH₂CF₃, —CH₂Cl, —CH₂CH₂F, —CH₂CH₂Cl, —CH₂CH₂CH₂F and —CH₂CH₂CH₂Cl.

Exemplary $R^5$ groups include the following:

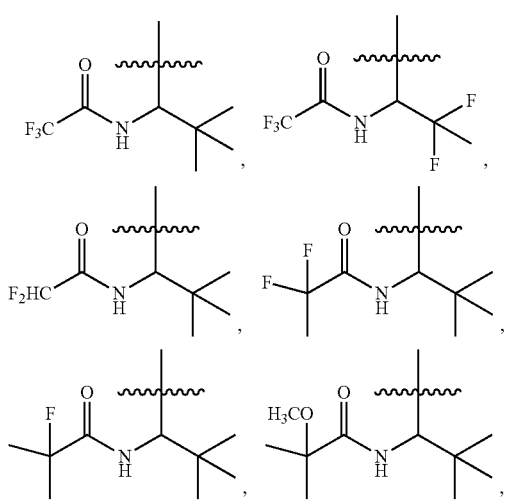

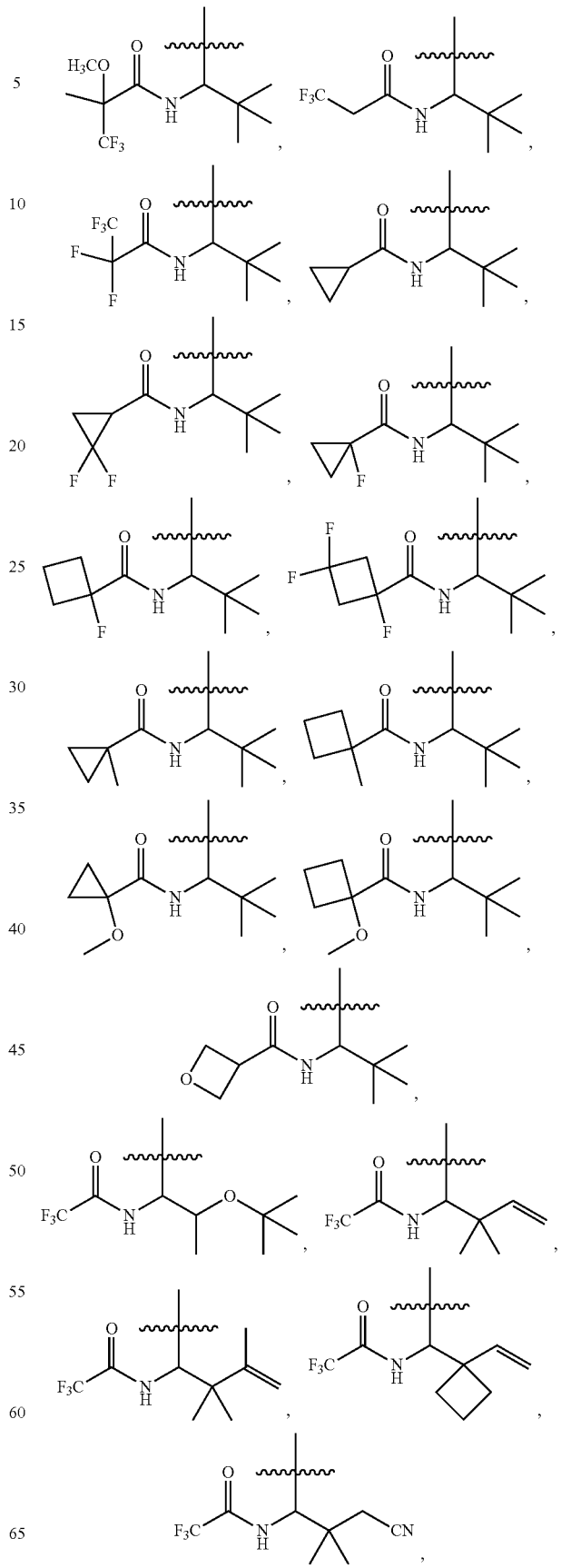

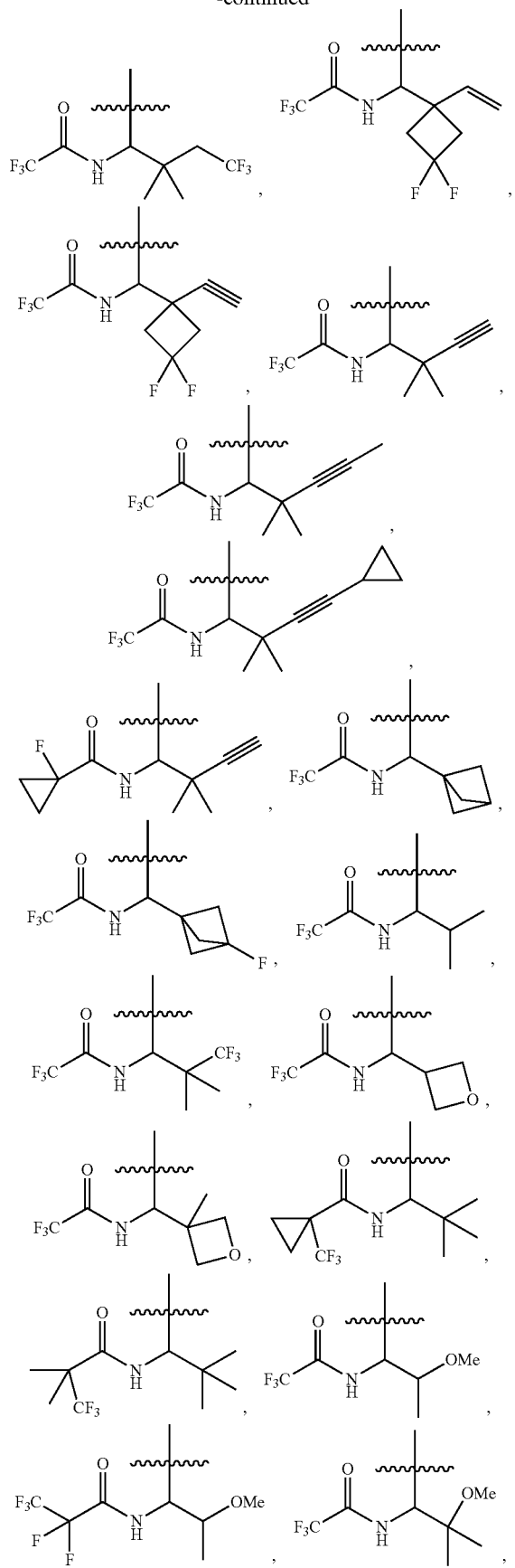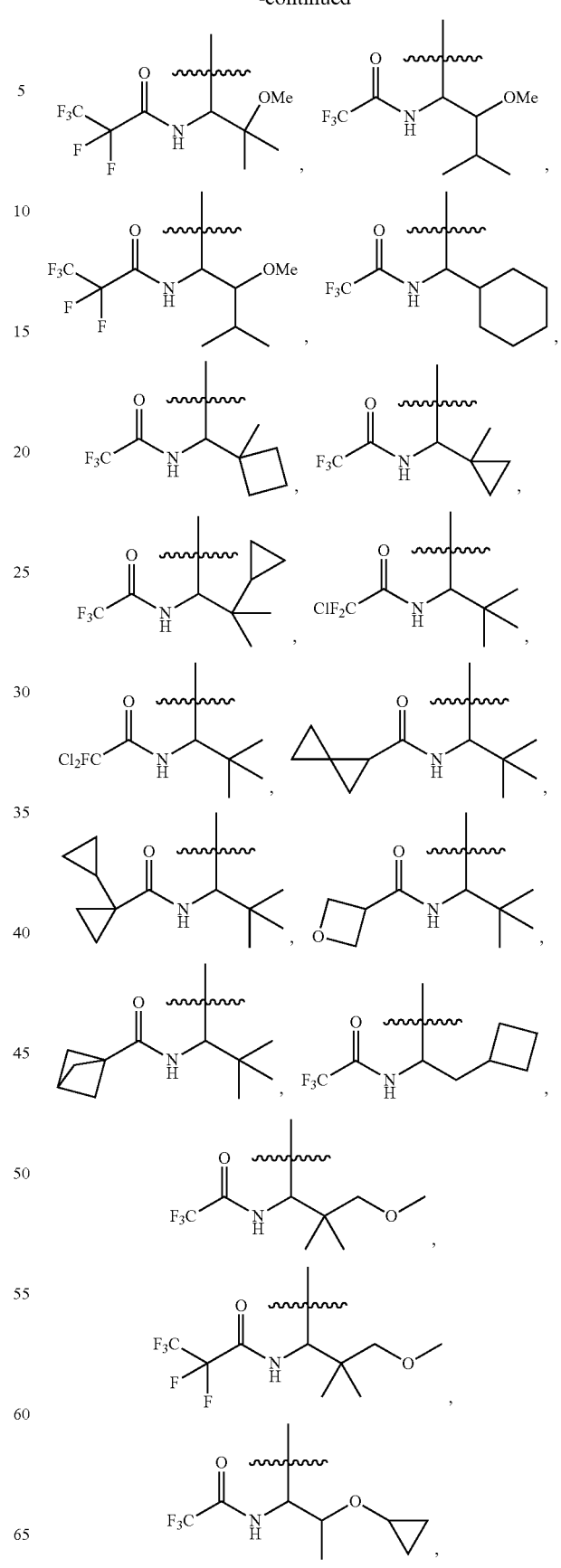

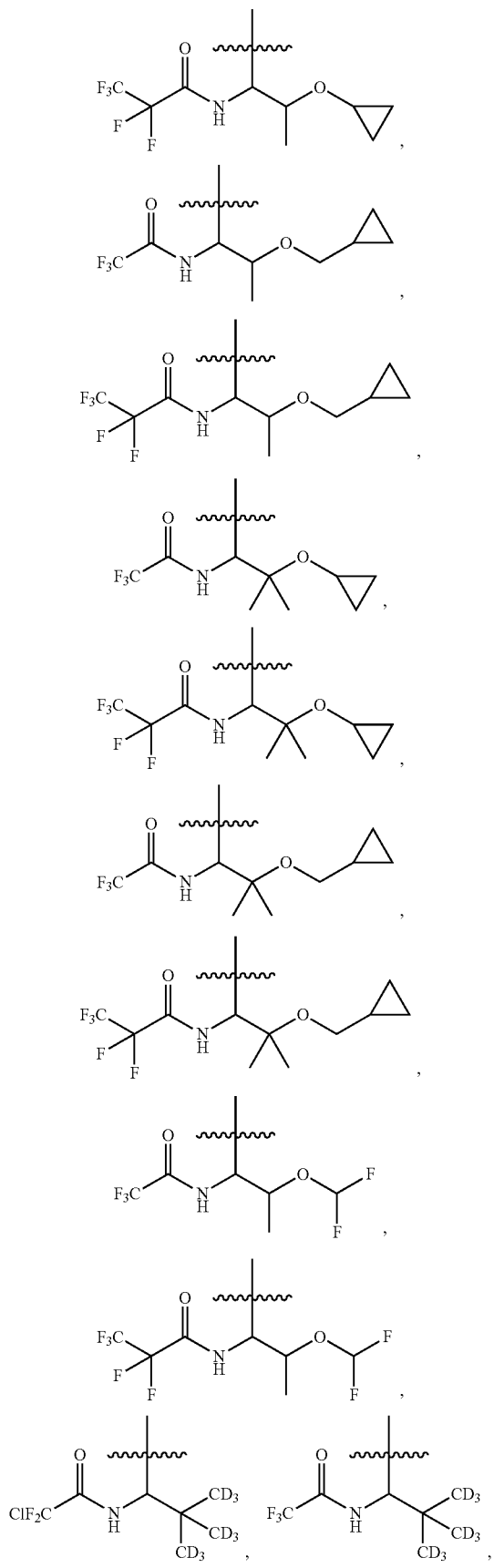

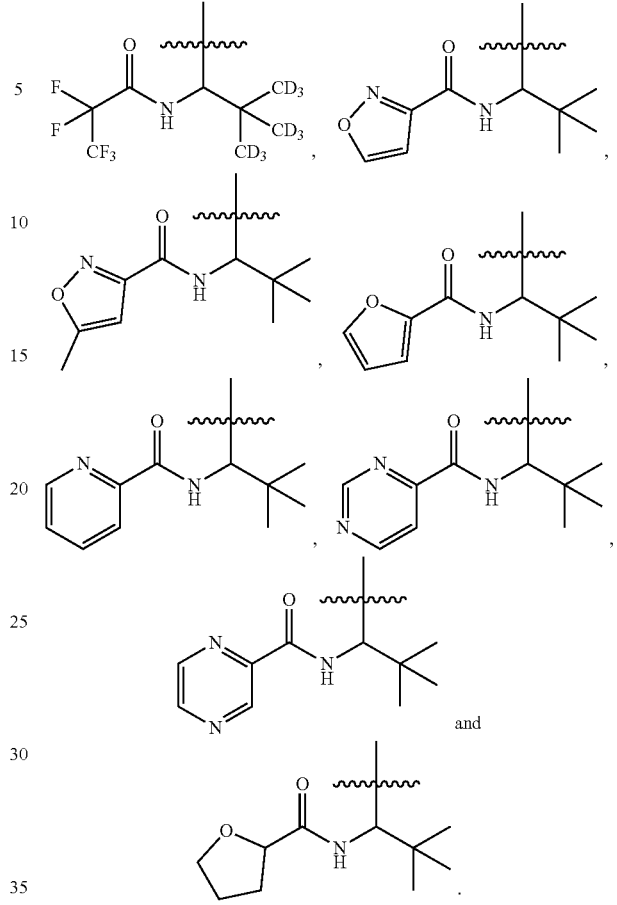

In some embodiments, a compound of Formula (I), or a pharmaceutically acceptable salt thereof, can be where Ring $A^1$ can be selected from

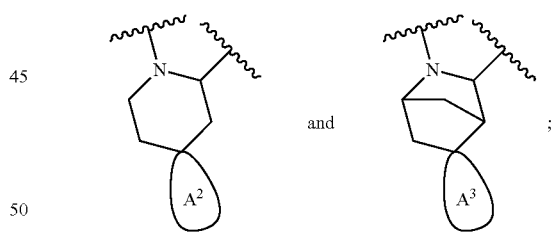

Ring $A^2$ can be an unsubstituted or a substituted monocyclic $C_{3-6}$ cycloalkyl; Ring $A^3$ can be an unsubstituted or a substituted monocyclic $C_{3-6}$ cycloalkyl; $R^1$ can be selected from cyano, an unsubstituted or a substituted $C_{2-5}$ alkynyl, an unsubstituted or a substituted acyl, an unsubstituted or a substituted ketoamide, —CH(OH)—(S(=O)$_2$—O—), —CH(OH)((P=O)(OR$^6$)$_2$) and —C(=O)CH$_2$—O—((P=O)(OR$^7$)$_2$), $R^2$ can be hydrogen, deuterium or halogen; $R^3$ can be an unsubstituted or a substituted C-amido($C_{1-4}$ alkyl), an unsubstituted or a substituted monocyclic nitrogen-containing heteroaryl($C_{1-4}$ alkyl), an unsubstituted or a substituted monocyclic nitrogen-containing heterocyclyl ($C_{1-4}$ alkyl), an unsubstituted or a substituted bicyclic nitrogen-containing heteroaryl($C_{1-4}$ alkyl) or an unsubstituted or a substituted bicyclic nitrogen-containing heterocyclyl($C_{1-4}$ alkyl); $R^4$ can be hydrogen, deuterium or halogen; $R^5$ can be selected from

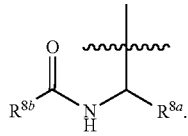

an unsubstituted or a substituted naphthyl, an unsubstituted or a substituted

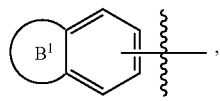

an unsubstituted or a substituted

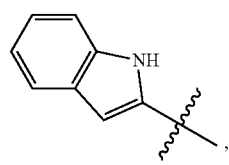 [SMILES: *c1cc2ccccc2[nH]1]

an unsubstituted or a substituted

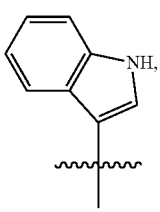

an unsubstituted or a substituted

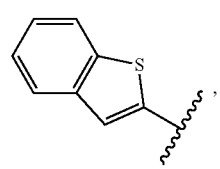 [SMILES: *c1cc2ccccc2s1]

an unsubstituted or a substituted

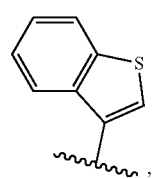 [SMILES: *c1csc2ccccc12]

an unsubstituted or a substituted

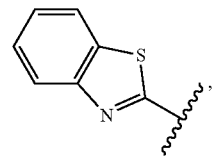 [SMILES: *c1nc2ccccc2s1]

an unsubstituted or a substituted

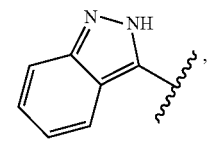 [SMILES: *c1[nH]nc2ccccc12]

an unsubstituted or a substituted

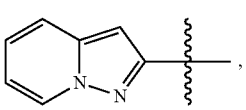

an unsubstituted or a substituted

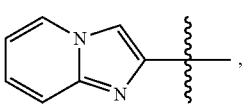 [SMILES: *c1cn2ccccc2n1]

an unsubstituted or a substituted

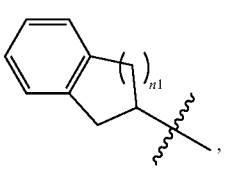

an unsubstituted or a substituted an unsubstituted or a substituted

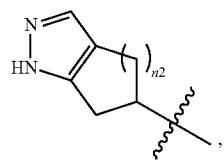

substituted an unsubstituted or a substituted

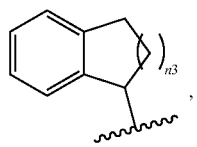

an unsubstituted or a substituted

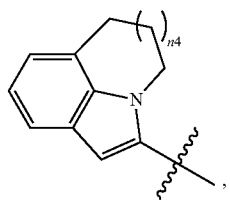

an unsubstituted or a substituted

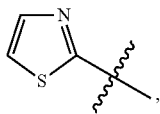 [SMILES: *c1nccs1]

an unsubstituted or a substituted

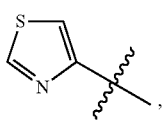 [SMILES: *c1cscn1]

an unsubstituted or a substituted

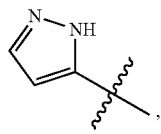

an unsubstituted or a substituted

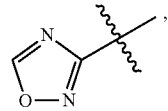

an unsubstituted or a substituted

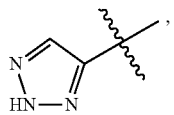

an unsubstituted or a substituted

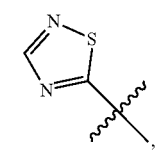

an unsubstituted or a substituted

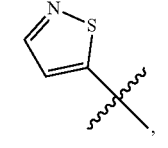 [SMILES: *c1ccns1]

an unsubstituted or a substituted pyridine, an unsubstituted or a substituted phenyl, an unsubstituted or a substituted monocyclic $C_{3-6}$ cycloalkyl and an unsubstituted or a substituted 4- to 6-membered monocyclic heterocyclyl; wherein $B^1$ is an unsubstituted or a substituted monocyclic 5-6-membered heteroaryl; and wherein when $R^5$ is substituted, $R^5$ is substituted with one or more substituents independently selected from the group consisting of deuterium, halogen, an unsubstituted or a substituted $C_{1-6}$ alkyl, an unsubstituted or a substituted monocyclic $C_{3-6}$ cycloalkyl, an unsubstituted $C_{1-6}$ haloalkyl, an unsubstituted $C_{1-6}$ alkoxy, an unsubstituted or a substituted phenyl, an unsubstituted or a substituted 5- to 6-membered monocyclic heteroaryl, an unsubstituted or a substituted 5- to 6-membered monocyclic heterocyclyl, an unsubstituted or a substituted bicyclic cycloalkenyl and an unsubstituted or a substituted bicyclic heterocyclyl; and each $R^6$ and each $R^7$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl); $R^{8a}$ can be selected from an unsubstituted or a substituted $C_{2-6}$ alkyl, an unsubstituted or a substituted $C_{2-6}$ alkenyl, an unsubstituted or a substituted $C_{2-6}$ alkynyl, an unsubstituted or a substituted monocyclic $C_{3-6}$ cycloalkyl, an unsubstituted or a substituted bicyclic $C_{5-8}$ cycloalkyl and an unsubstituted or a substituted monocyclic 4- to 6-membered heterocyclyl, wherein when the $C_{2-6}$ alkyl is substituted, the $C_{2-6}$ can be is substituted 1, 2, 3 or 4 times with a substituent independently selected from the group consisting of halogen and an unsubstituted $C_{1-4}$ alkoxy; wherein when the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted, the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl can be substituted 1, 2, 3 or 4 times with a substituent independently selected from the group consisting of halogen, an unsubstituted $C_{1-4}$ alkyl, an unsubstituted $C_{1-6}$ haloalkyl and an unsubstituted $C_{1-4}$ alkoxy; and $R^{8b}$ can be selected from an unsubstituted $C_{1-6}$ alkyl, an unsubstituted $C_{1-6}$ haloalkyl and an unsubstituted or a substituted monocyclic $C_{3-6}$ cycloalkyl, wherein the substituted monocyclic $C_{3-6}$ cycloalkyl is substituted 1, 2, 3 or 4 times with a substituent independently selected from the group consisting of halogen, an unsubstituted $C_{1-4}$ alkyl and an unsubstituted $C_{1-4}$ haloalkyl; n1, n2 and n3 can be independently 1 or 2; and n4 can be 0 or 1.

In some embodiments, a compound of Formula (I), or a pharmaceutically acceptable salt thereof, can be where Ring $A^1$ can be selected from

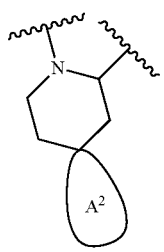 and 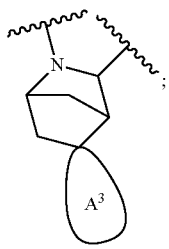;

Ring $A^2$ can be an unsubstituted or a substituted monocyclic $C_{3-6}$ cycloalkyl; Ring $A^3$ can be an unsubstituted or a substituted monocyclic $C_{3-6}$ cycloalkyl; $R^1$ can be selected from cyano, an unsubstituted or a substituted $C_{2-5}$ alkynyl, an unsubstituted or a substituted acyl, an unsubstituted or a substituted ketoamide, $-CH(OH)-(S(=O)_2-O-)$, $-CH(OH)((P=O)(OR^6)_2)$ and $-C(=O)CH_2-O-((P=O)(OR^7)_2)$, $R^2$ can be hydrogen, deuterium or halogen; $R^3$ can be an unsubstituted or a substituted C-amido($C_{1-4}$ alkyl), an unsubstituted or a substituted monocyclic nitrogen-containing heteroaryl($C_{1-4}$ alkyl), an unsubstituted or a substituted monocyclic nitrogen-containing heterocyclyl ($C_{1-4}$ alkyl), an unsubstituted or a substituted bicyclic nitrogen-containing heteroaryl($C_{1-4}$ alkyl) or an unsubstituted or a substituted bicyclic nitrogen-containing heterocyclyl($C_{1-4}$ alkyl); $R^4$ can be hydrogen, deuterium or halogen; $R^5$ can be selected from

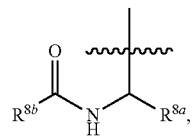

an unsubstituted or a substituted naphthyl, an unsubstituted or a substituted

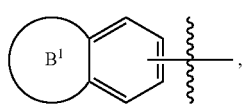

an unsubstituted or a substituted

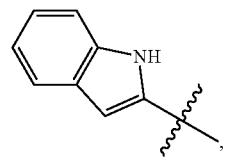 [SMILES: *c1cc2ccccc2[nH]1]

an unsubstituted or a substituted

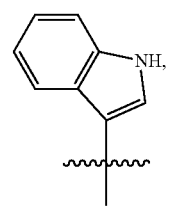 [SMILES: *c1c[nH]c2ccccc12]

an unsubstituted or a substituted

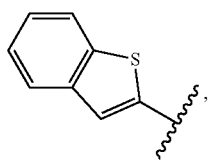 [SMILES: *c1cc2ccccc2s1]

an unsubstituted or a substituted

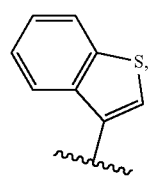

an unsubstituted or a substituted

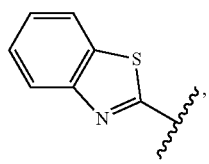 [SMILES: *c1nc2ccccc2s1]

an unsubstituted or a substituted

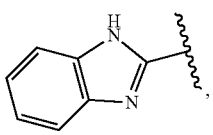 [SMILES: *c1nc2ccccc2[nH]1]

an unsubstituted or a substituted

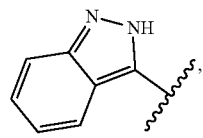 [SMILES: *c1[nH]nc2ccccc12]

an unsubstituted or a substituted

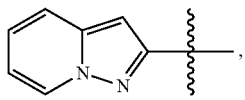

an unsubstituted or a substituted

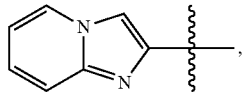

an unsubstituted or a substituted

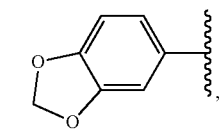

an unsubstituted or a substituted

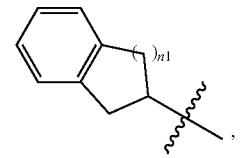

an unsubstituted or a substituted

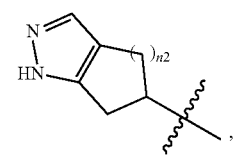

an unsubstituted or a substituted

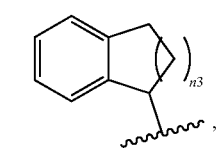

an unsubstituted or a substituted

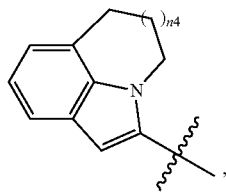

an unsubstituted or a substituted

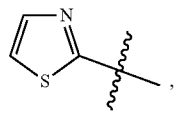

an unsubstituted or a substituted

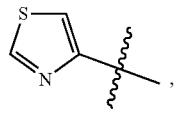 [SMILES: *c1cscn1]

an unsubstituted or a substituted

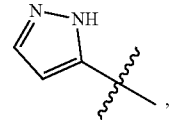 [SMILES: *c1ccn[nH]1]

an unsubstituted or a substituted

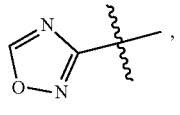

an unsubstituted or a substituted

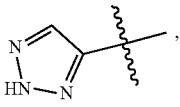 [SMILES: *c1cn[nH]n1]

an unsubstituted or a substituted

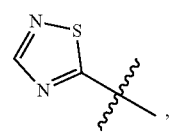 [SMILES: *c1ncns1]

an unsubstituted or a substituted

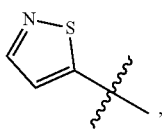 [SMILES: *c1ccns1]

an unsubstituted or a substituted pyridine, an unsubstituted or a substituted phenyl, an unsubstituted or a substituted monocyclic $C_{3-6}$ cycloalkyl and an unsubstituted or a substituted 4- to 6-membered monocyclic heterocyclyl; wherein $B^1$ is an unsubstituted or a substituted monocyclic 5-6-membered heteroaryl; and wherein when $R^5$ is substituted, $R^5$ is substituted with one or more substituents independently selected from the group consisting of deuterium, halogen, an unsubstituted or a substituted $C_{1-6}$ alkyl, an unsubstituted or a substituted monocyclic $C_{3-6}$ cycloalkyl, an unsubstituted $C_{1-6}$ haloalkyl, an unsubstituted $C_{1-6}$ alkoxy, an unsubstituted or a substituted phenyl, an unsubstituted or a substituted 5- to 6-membered monocyclic heteroaryl, an unsubstituted or a substituted 5- to 6-membered monocyclic heterocyclyl, an unsubstituted or a substituted bicyclic cycloalkenyl and an unsubstituted or a substituted bicyclic heterocyclyl; and each $R^6$ and each $R^7$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl); $R^{8a}$ can be selected from an unsubstituted or a substituted $C_{2-6}$ alkyl, an unsubstituted or a substituted $C_{2-6}$ alkenyl, an unsubstituted or a substituted $C_{2-6}$ alkynyl, an unsubstituted or a substituted monocyclic $C_{3-6}$ cycloalkyl, an unsubstituted or a substituted bicyclic $C_{5-8}$ cycloalkyl and an unsubstituted or a substituted monocyclic 4- to 6-membered heterocyclyl, wherein when the $C_{2-6}$ alkyl is substituted, the $C_{2-6}$ can be is substituted 1, 2, 3 or 4 times with a substituent independently selected from the group consisting of halogen, cyano, an unsubstituted or a substituted monocyclic $C_{3-6}$ cycloalkyl and an unsubstituted $C_{1-4}$ alkoxy; wherein when the $C_2$-6 alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted, the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl can be substituted 1, 2, 3 or 4 times with a substituent independently selected from the group consisting of halogen, an unsubstituted $C_{1-4}$ alkyl, an unsubstituted $C_2$-4 alkenyl, an unsubstituted $C_{2-4}$ alkynyl, an unsubstituted $C_{1-6}$ haloalkyl, an unsubstituted or a substituted monocyclic $C_{3-6}$ cycloalkyl and an unsubstituted $C_{1-4}$ alkoxy; and $R^{8b}$ can be selected from an unsubstituted $C_{1-6}$ alkyl, an unsubstituted $C_{1-6}$ haloalkyl, an unsubstituted or a substituted monocyclic $C_{3-6}$ cycloalkyl, an unsubstituted or a substituted bicyclic $C_{5-6}$ cycloalkyl, an unsubstituted or a substituted monocyclic heteroaryl and an unsubstituted or a substituted monocyclic heterocyclyl, wherein the substituted monocyclic $C_{3-6}$ cycloalkyl is substituted 1, 2, 3 or 4 times with a substituent independently selected from the group consisting of halogen, an unsubstituted $C_{1-4}$ alkyl, an unsubstituted $C_{1-4}$ haloalkyl and an unsubstituted monocyclic $C_{3-6}$ cycloalkyl; n1, n2 and n3 can be independently 1 or 2; and n4 can be 0 or 1.

In some embodiments, a compound of Formula (I), or a pharmaceutically acceptable salt thereof, can be where Ring $A^1$ can be selected from

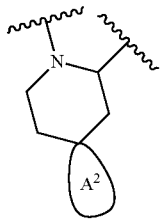 and 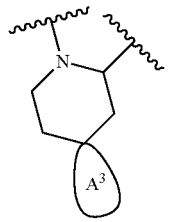 ;

Ring $A^2$ can be an unsubstituted or a substituted monocyclic $C_{3-6}$ cycloalkyl; Ring $A^3$ can be an unsubstituted or a substituted monocyclic $C_{3-6}$ cycloalkyl; $R^1$ can be selected from cyano, an unsubstituted or a substituted $C_{2-5}$ alkynyl, an unsubstituted or a substituted acyl, an unsubstituted or a substituted ketoamide, —CH(OH)—(S(=O)$_2$—O—), —CH(OH)((P=O)(OR$^6$)$_2$) and —C(=O)CH$_2$—O—((P=O)(OR$^7$)$_2$), $R^2$ can be hydrogen, deuterium or halogen; $R^3$ can be an unsubstituted or a substituted C-amido($C_{1-4}$ alkyl), an unsubstituted or a substituted monocyclic nitrogen-containing heteroaryl($C_{1-4}$ alkyl), an unsubstituted or a substituted monocyclic nitrogen-containing heterocyclyl ($C_{1-4}$ alkyl), an unsubstituted or a substituted bicyclic nitrogen-containing heteroaryl($C_{1-4}$ alkyl) or an unsubstituted or a substituted bicyclic nitrogen-containing heterocyclyl($C_{1-4}$ alkyl); $R^4$ can be hydrogen, deuterium or halogen; $R^5$ can be an unsubstituted or a substituted naphthyl, an unsubstituted or a substituted

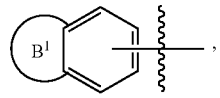

an unsubstituted or a substituted

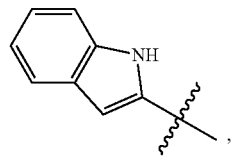 [SMILES: *c1cc2ccccc2[nH]1]

an unsubstituted or a substituted

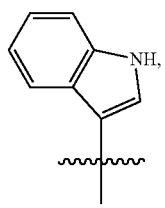 [SMILES: *c1c[nH]c2ccccc12]

an unsubstituted or a substituted

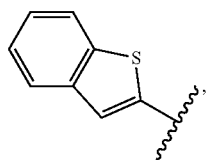 [SMILES: *c1cc2ccccc2s1]

an unsubstituted or a substituted

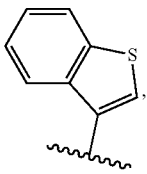 [SMILES: *c1csc2ccccc12]

an unsubstituted or a substituted

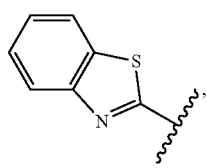 [SMILES: *c1nc2ccccc2s1]

an unsubstituted or a substituted

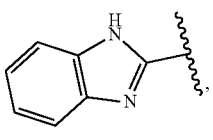 [SMILES: *c1nc2ccccc2[nH]1]

an unsubstituted or a substituted

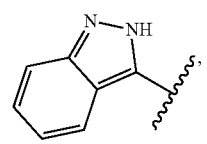 [SMILES: *c1[nH]nc2ccccc12]

an unsubstituted or a substituted

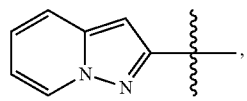 [SMILES: *c1cc2ccccn2n1]

an unsubstituted or a substituted

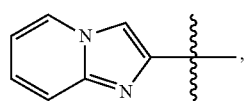 [SMILES: *c1cn2ccccc2n1]

an unsubstituted or a substituted

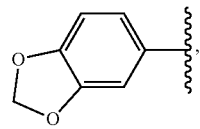 [SMILES: *c1ccc2c(c1)OCO2]

an unsubstituted or a substituted

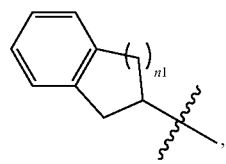

an unsubstituted or a substituted

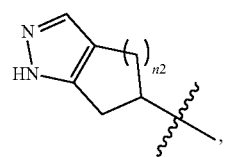

an unsubstituted or a substituted

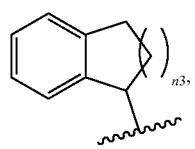

an unsubstituted or a substituted

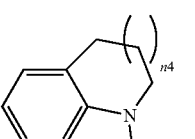

an unsubstituted or a substituted

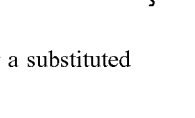

an unsubstituted or a substituted

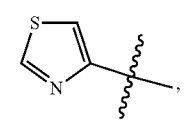 [SMILES: *c1cscn1]

an unsubstituted or a substituted

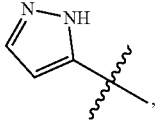 [SMILES: *c1ccn[nH]1], an unsubstituted or a substituted

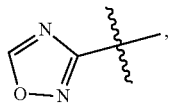 [SMILES: *c1ncon1], an unsubstituted or a substituted

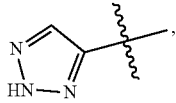, an unsubstituted or a substituted

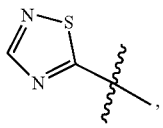 [SMILES: *c1ncns1], an unsubstituted or a substituted

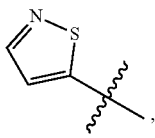 [SMILES: *c1ccns1], an unsubstituted or a substituted pyridine, an unsubstituted or a substituted phenyl, an unsubstituted or a substituted monocyclic $C_{3-6}$ cycloalkyl and an unsubstituted or a substituted 4- to 6-membered monocyclic heterocyclyl; wherein $B^1$ is an unsubstituted or a substituted monocyclic 5-6-membered heteroaryl; and wherein when $R^5$ is substituted, $R^5$ is substituted with one or more substituents independently selected from the group consisting of deuterium, halogen, an unsubstituted or a substituted $C_{1-6}$ alkyl, an unsubstituted or a substituted monocyclic $C_{3-6}$ cycloalkyl, an unsubstituted $C_{1-6}$ haloalkyl, an unsubstituted $C_{1-6}$ alkoxy, an unsubstituted or a substituted phenyl, an unsubstituted or a substituted 5- to 6-membered monocyclic heteroaryl, an unsubstituted or a substituted 5- to 6-membered monocyclic heterocyclyl, an unsubstituted or a substituted bicyclic cycloalkenyl and an unsubstituted or a substituted bicyclic heterocyclyl; or $R^5$ can be

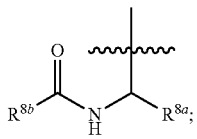

each $R^6$ and each $R^7$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl); $R^{8a}$ can be selected from an unsubstituted or a substituted $C_{2-6}$ alkyl, an unsubstituted or a substituted $C_{2-6}$ alkenyl, an unsubstituted or a substituted $C_{2-6}$ alkynyl, an unsubstituted or a substituted monocyclic $C_{3-6}$ cycloalkyl, an unsubstituted or a substituted bicyclic $C_{5-8}$ cycloalkyl and an unsubstituted or a substituted monocyclic 4- to 6-membered heterocyclyl, wherein when the $C_{2-6}$ alkyl is substituted, the $C_{2-6}$ can be is substituted 1, 2, 3 or 4 times with a substituent independently selected from the group consisting of halogen, cyano, an unsubstituted or a substituted monocyclic $C_{3-6}$ cycloalkyl, an unsubstituted $C_{1-4}$ alkoxy and an unsubstituted $C_{1-4}$ haloalkoxy, or the $C_{2-6}$ alkyl is substituted 1 to 13 times with deuterium; wherein when the $C_2$-6 alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted, the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl can be substituted 1, 2, 3 or 4 times with a substituent independently selected from the group consisting of halogen, an unsubstituted $C_{1-4}$ alkyl, an unsubstituted $C_2$-4 alkenyl, an unsubstituted $C_{2-4}$ alkynyl, an unsubstituted $C_{1-6}$ haloalkyl, an unsubstituted or a substituted monocyclic $C_{3-6}$ cycloalkyl and an unsubstituted $C_{1-4}$ alkoxy; and $R^{8b}$ can be selected from an unsubstituted $C_{1-6}$ alkyl, an unsubstituted $C_{1-6}$ haloalkyl, an unsubstituted or a substituted monocyclic $C_{3-6}$ cycloalkyl, an unsubstituted or a substituted bicyclic $C_{5-6}$ cycloalkyl, an unsubstituted or a substituted monocyclic heteroaryl and an unsubstituted or a substituted monocyclic heterocyclyl, wherein the substituted monocyclic $C_{3-6}$ cycloalkyl is substituted 1, 2, 3 or 4 times with a substituent independently selected from the group consisting of halogen, an unsubstituted $C_{1-4}$ alkyl, an unsubstituted $C_{1-4}$ alkoxy, an unsubstituted $C_{1-4}$ haloalkyl and an unsubstituted monocyclic $C_{3-6}$ cycloalkyl; n1, n2 and n3 can be independently 1 or 2; and n4 can be 0 or 1.

Examples of compounds of Formula (I), include the following:

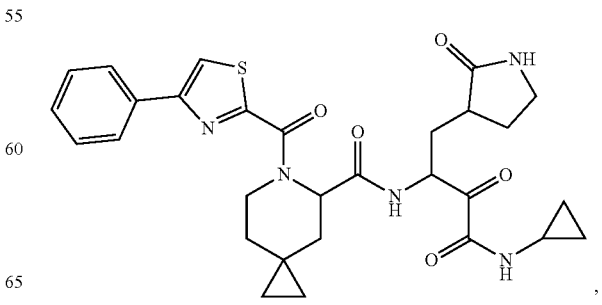

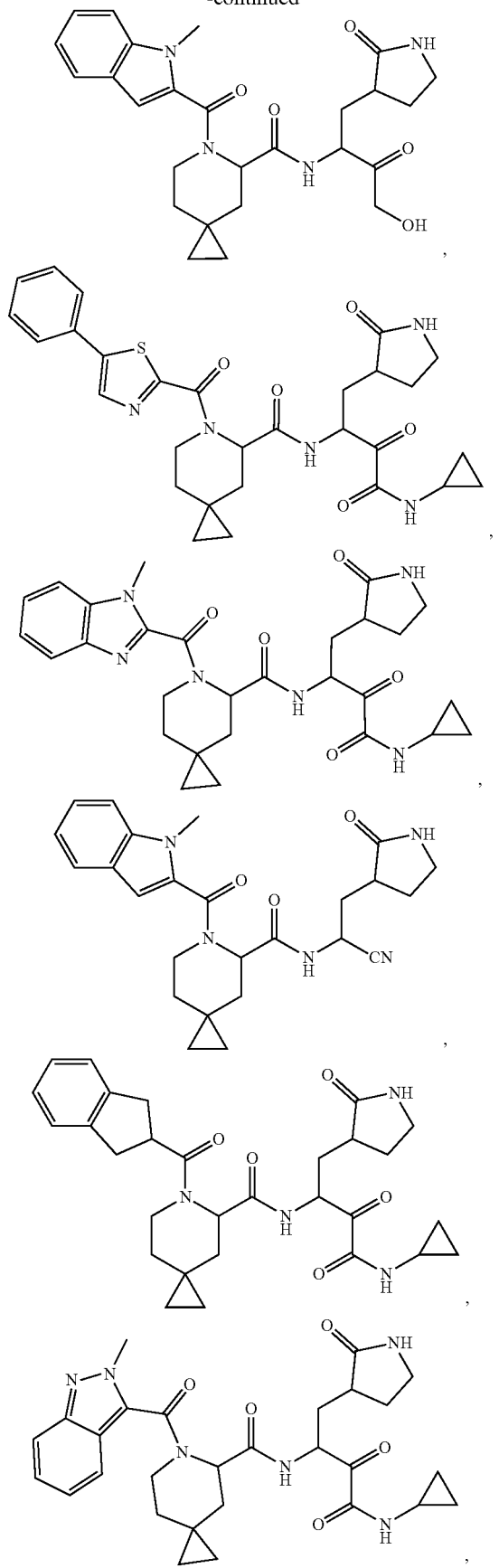
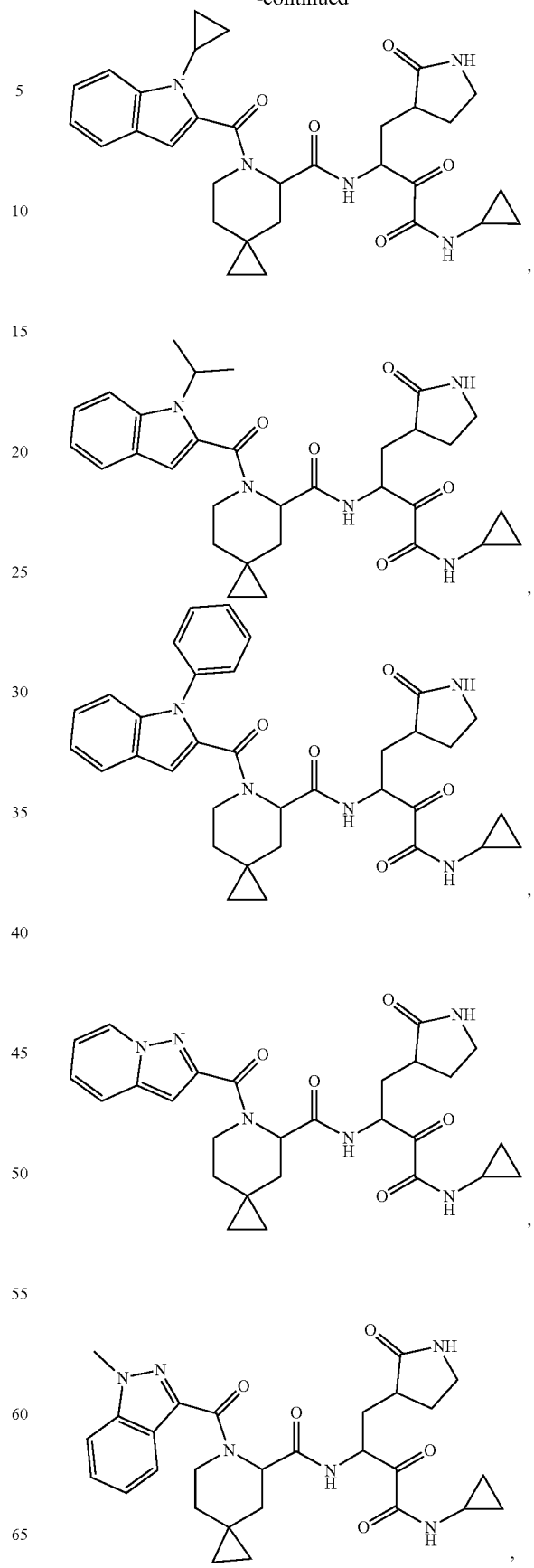

63
-continued
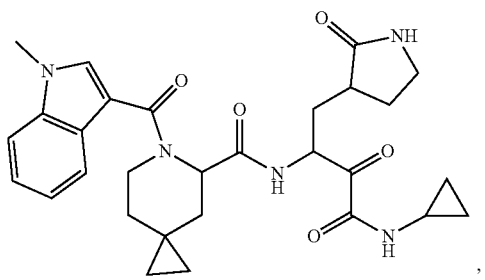
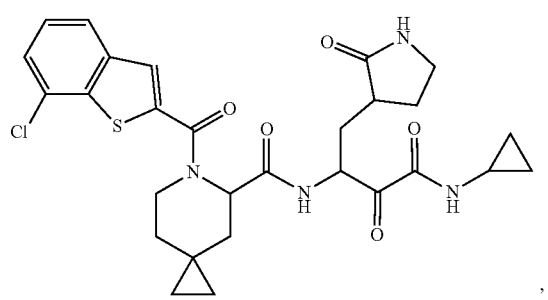
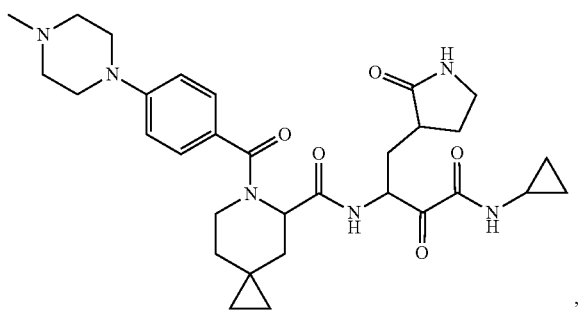
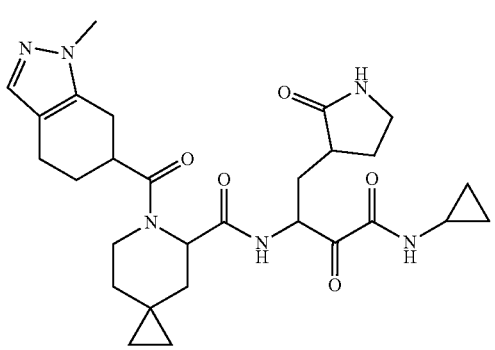
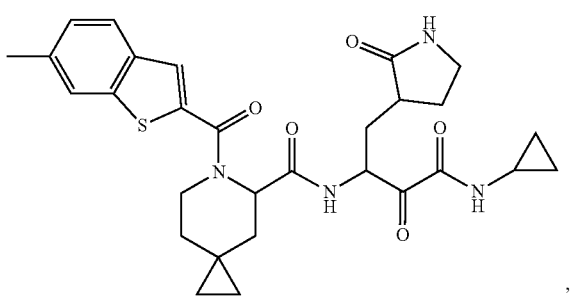
64
-continued
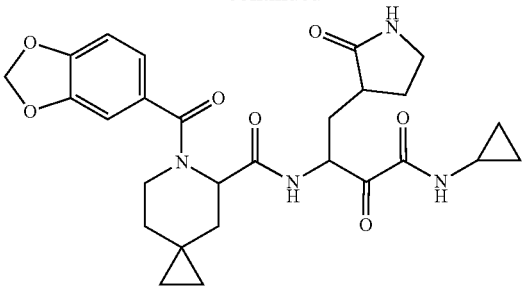
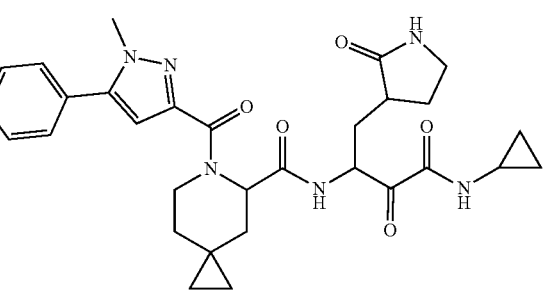
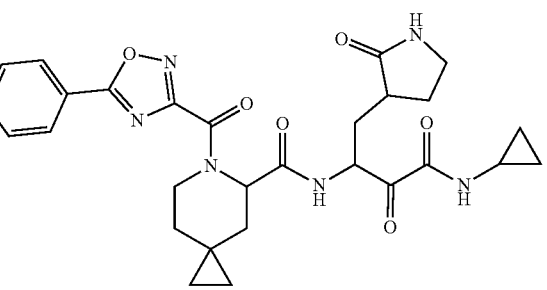
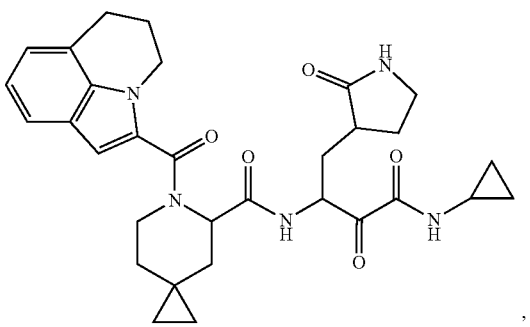
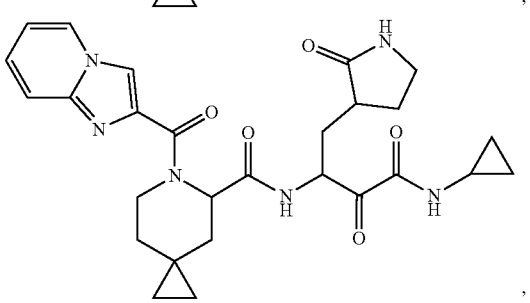

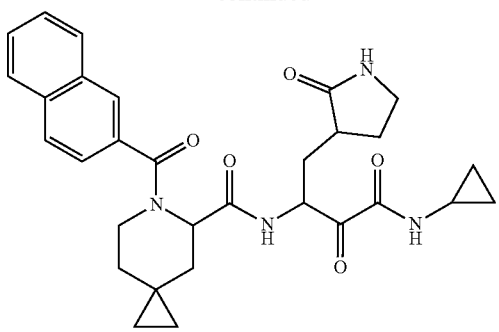
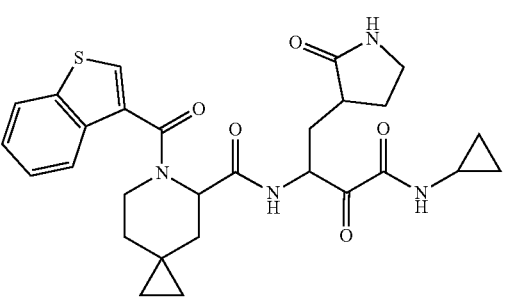
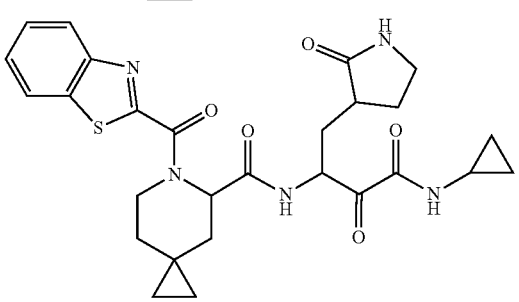
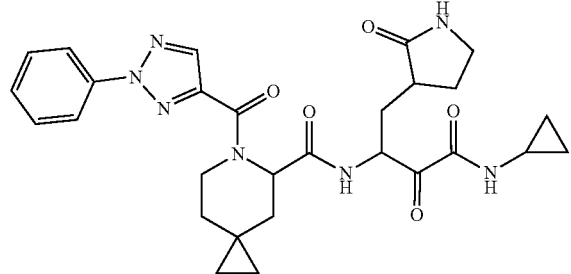
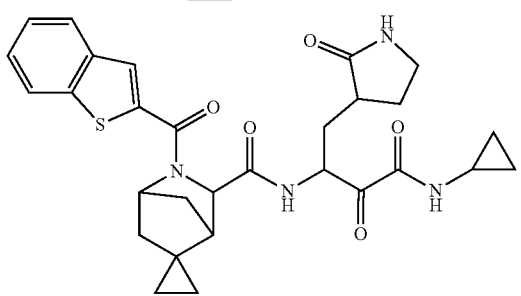
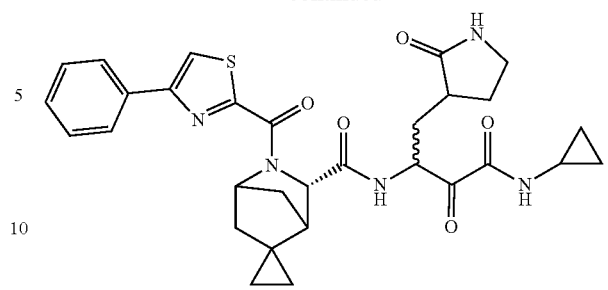
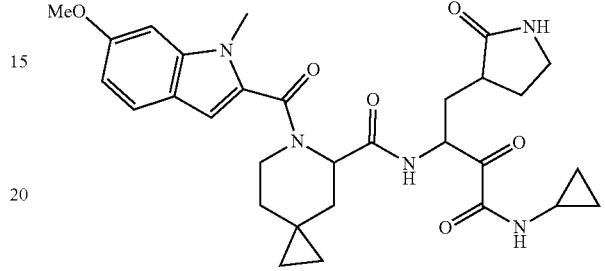
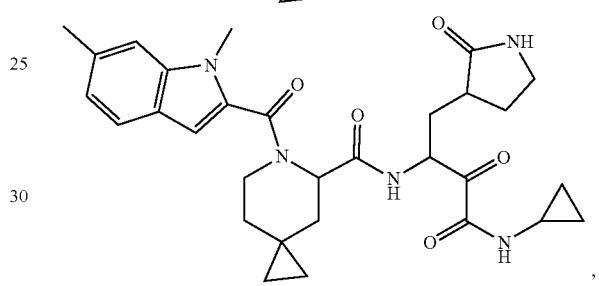
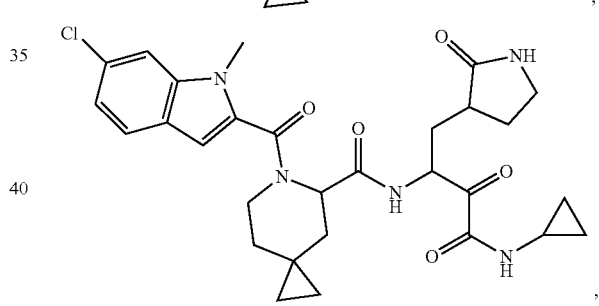
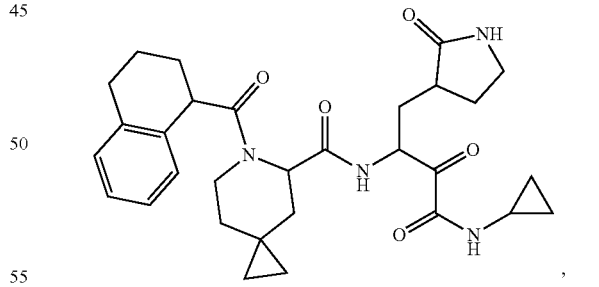
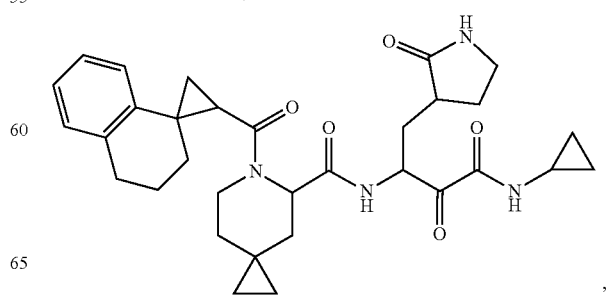

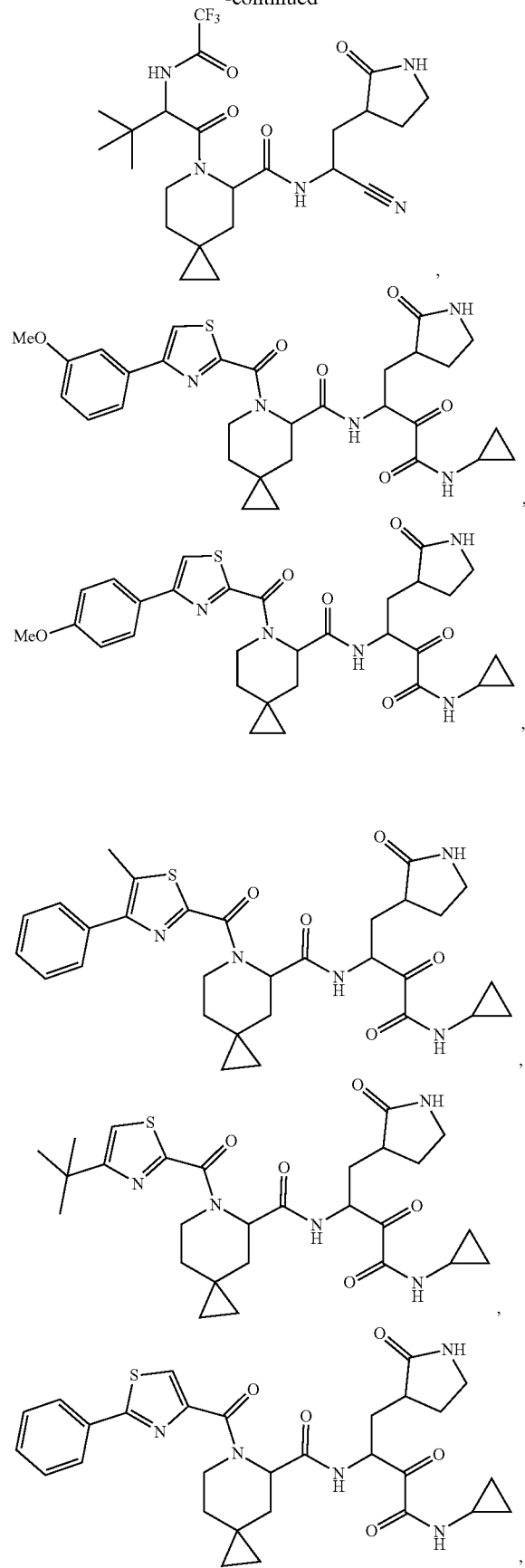
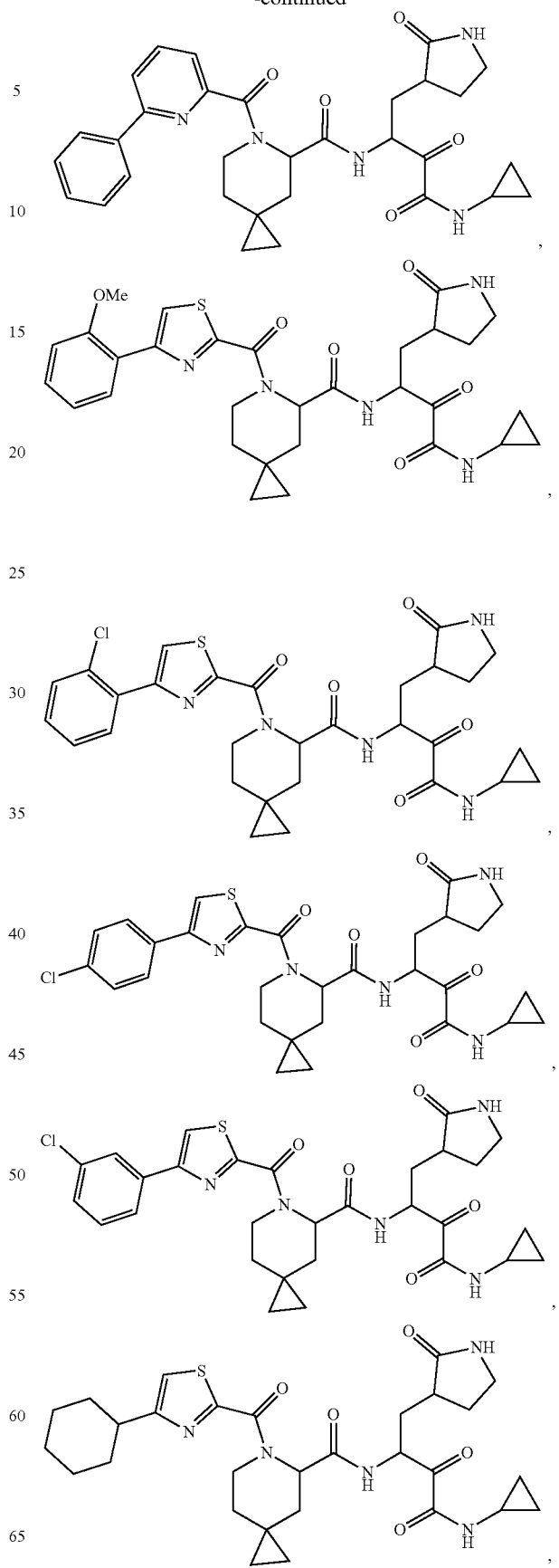

-continued
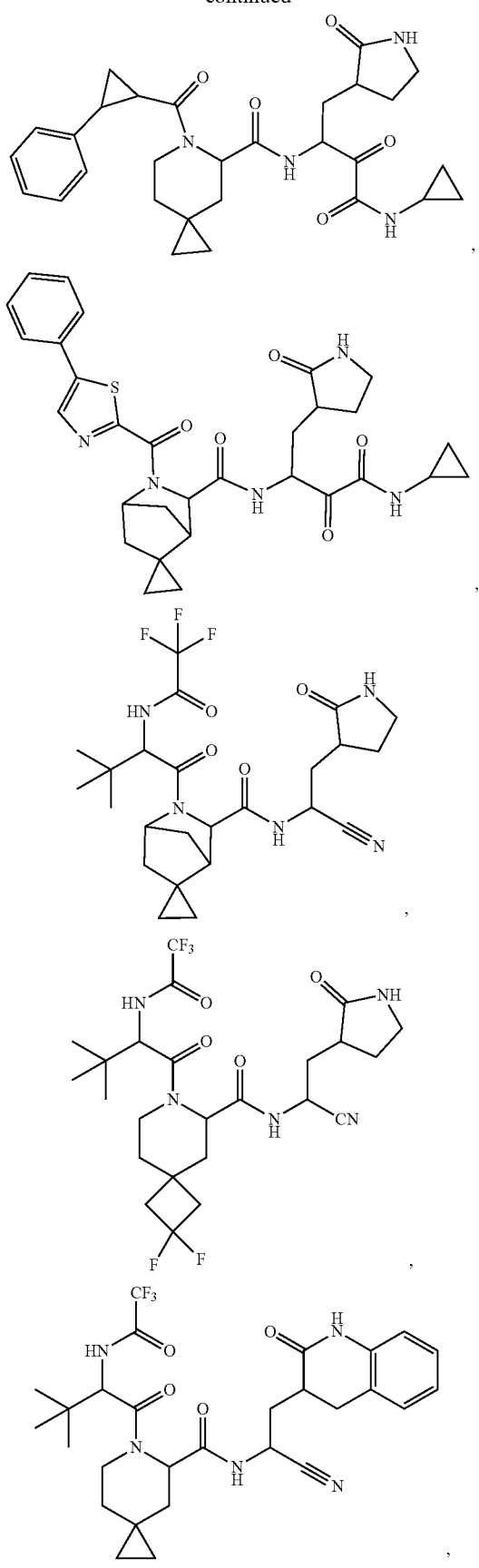
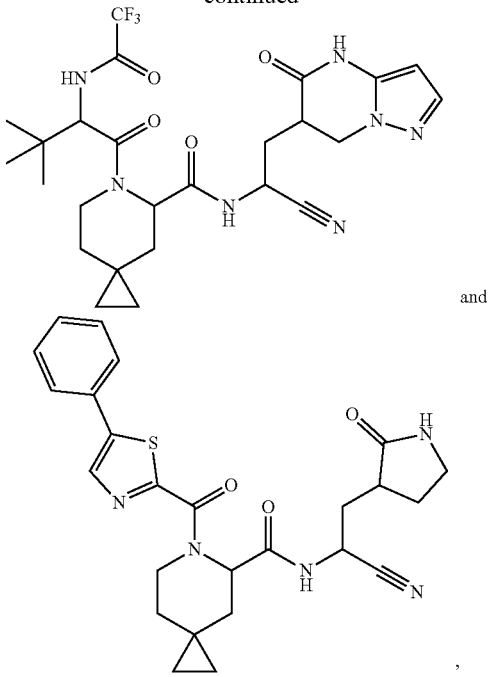
or pharmaceutically acceptable salt of any of the foregoing.
Additional examples of compounds of Formula (I), include the following:
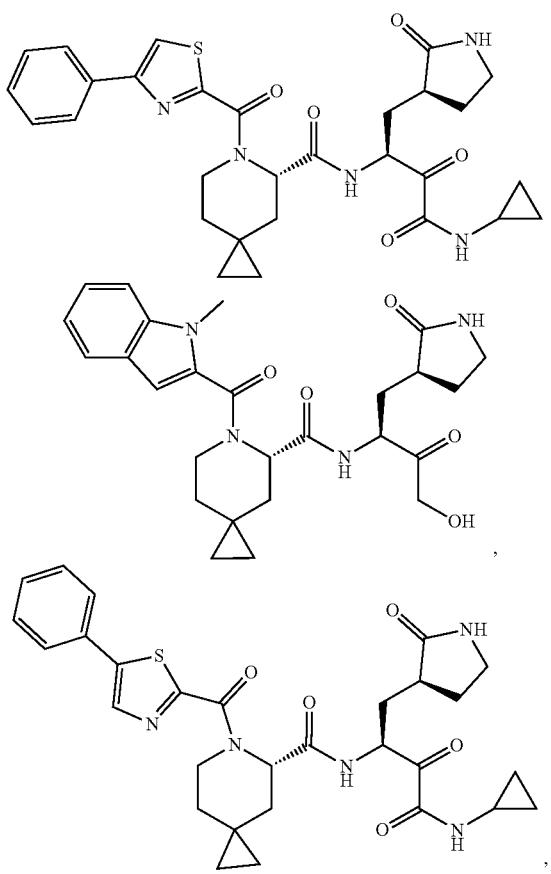

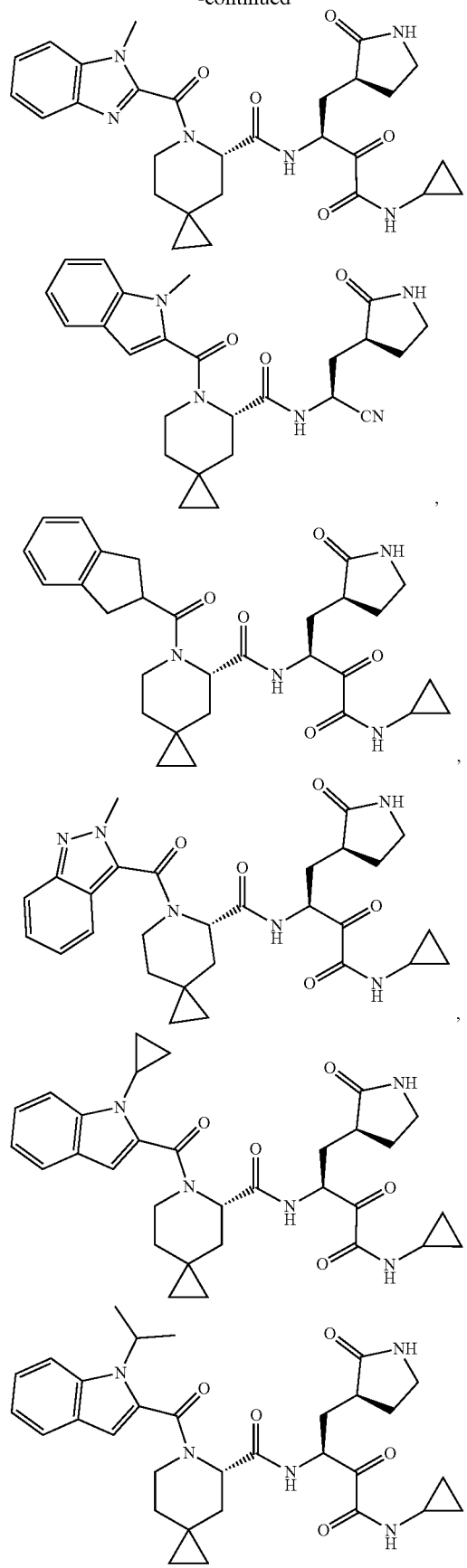
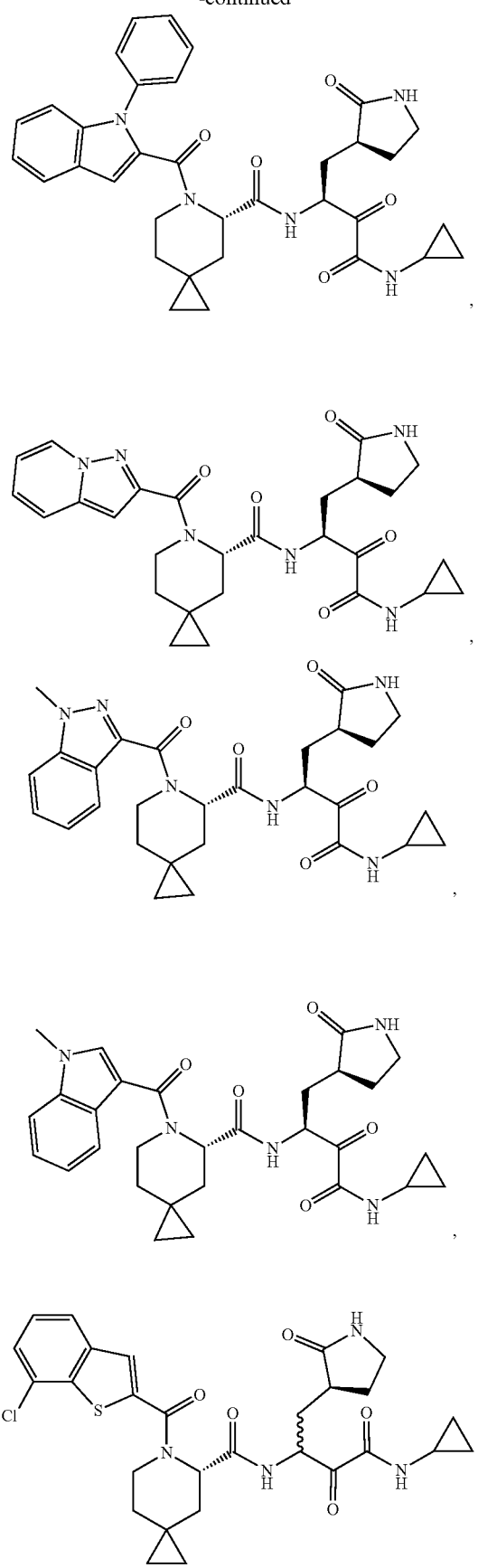

73
-continued
74
-continued
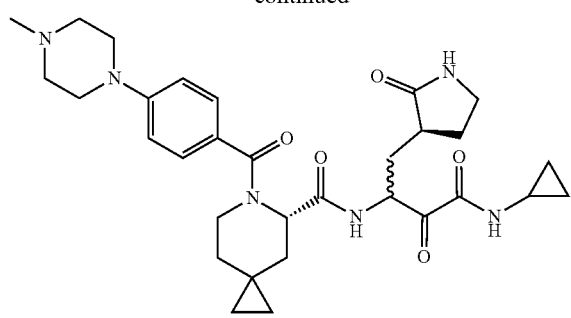
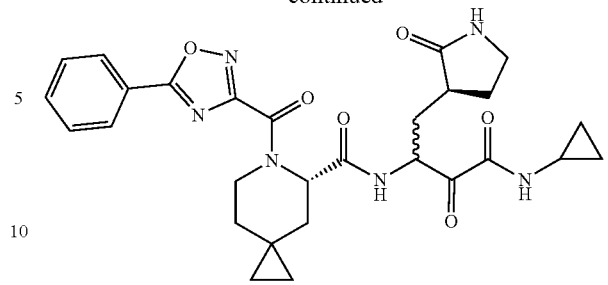
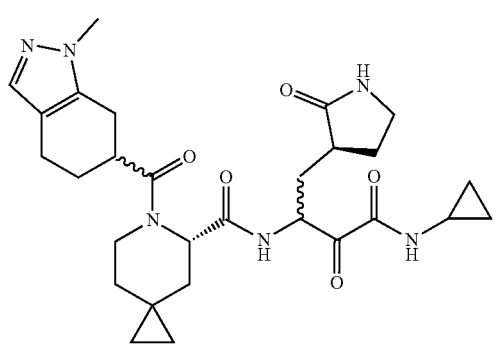
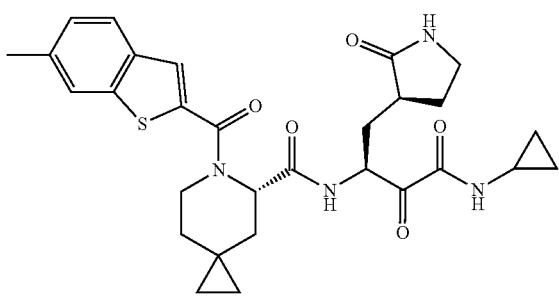
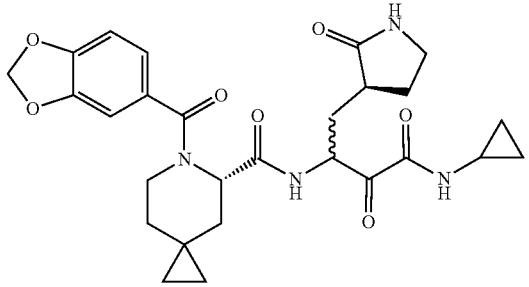
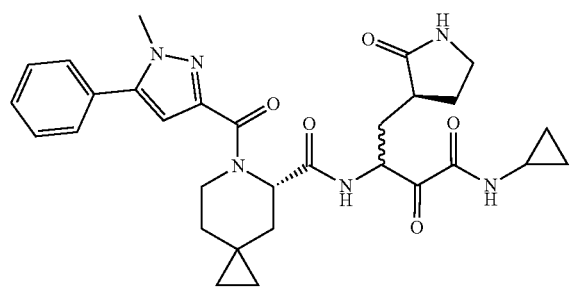

75
-continued
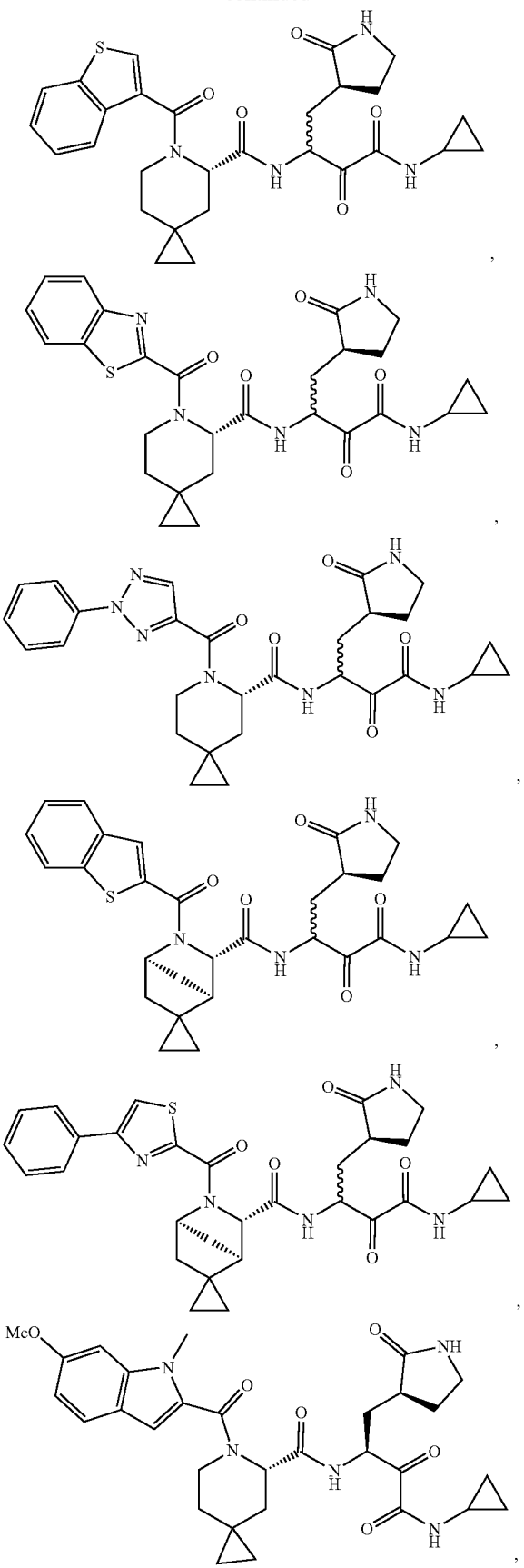
76
-continued
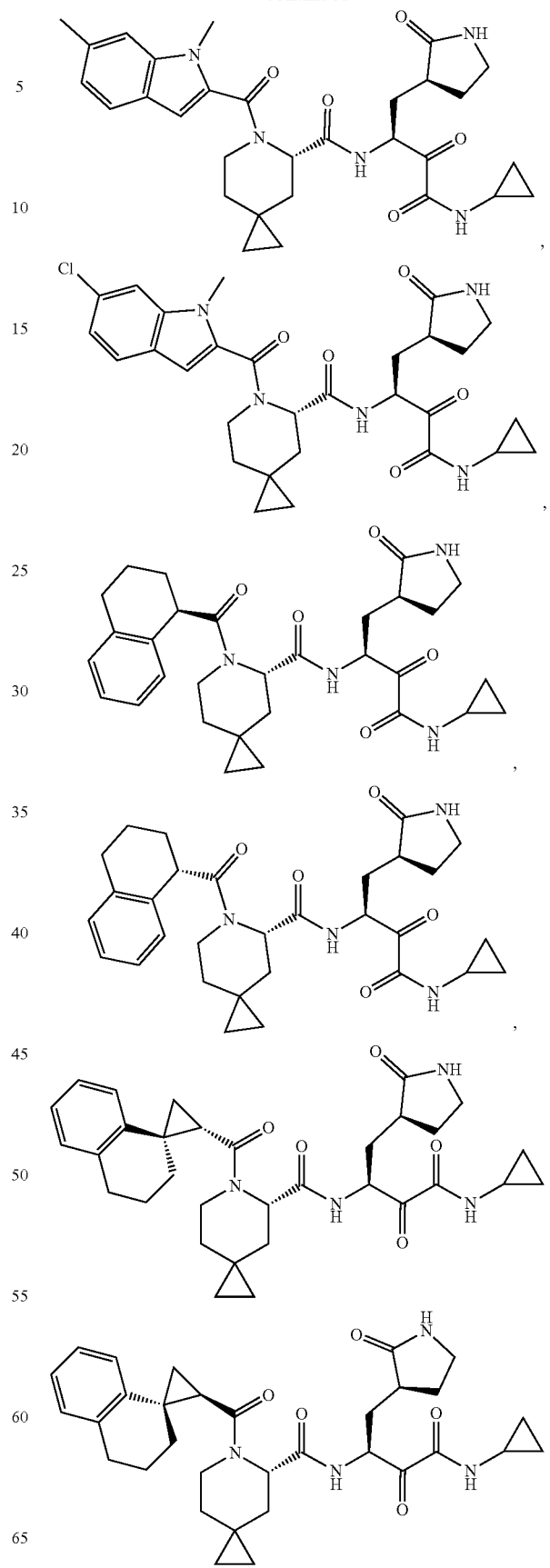

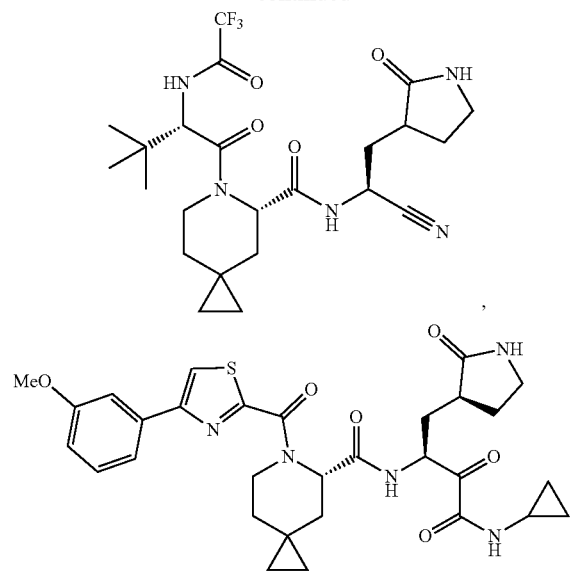
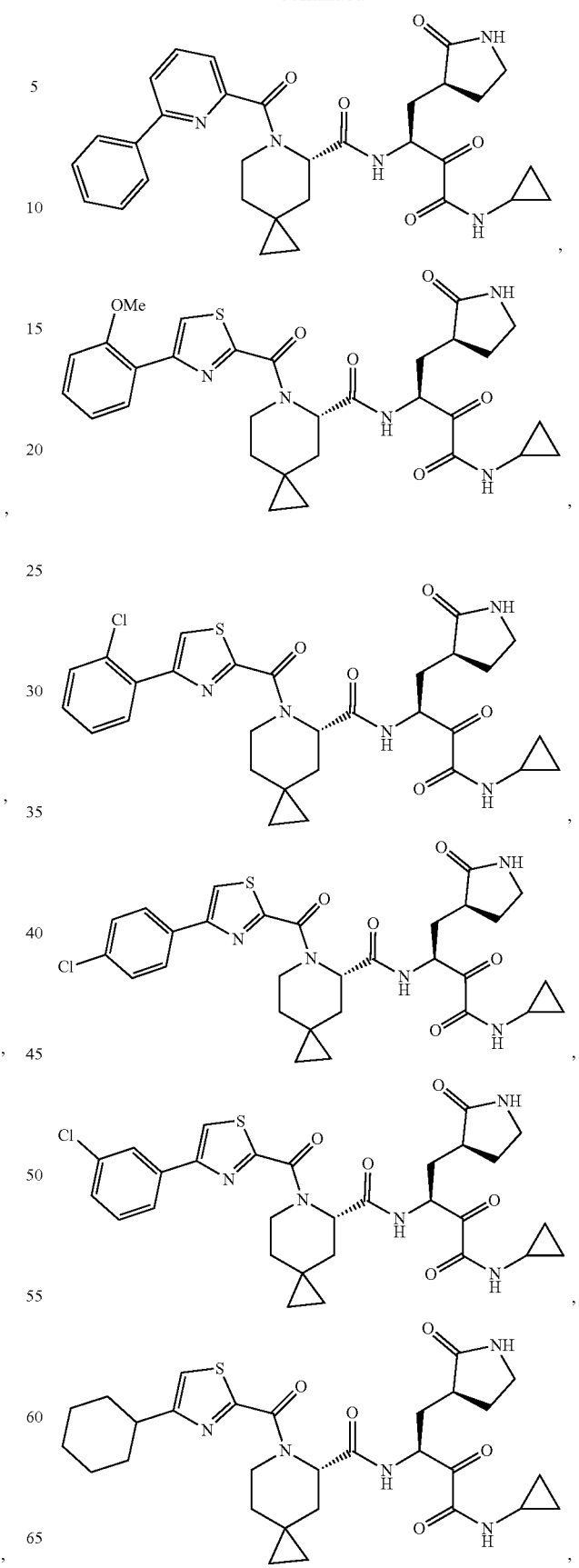

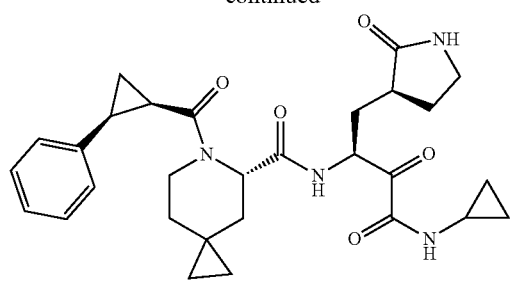
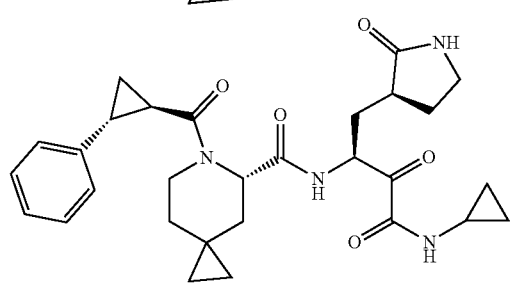
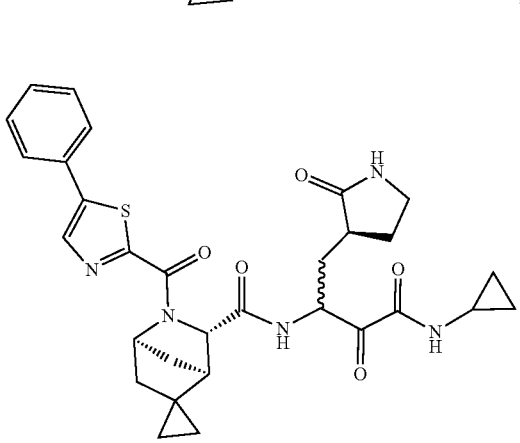
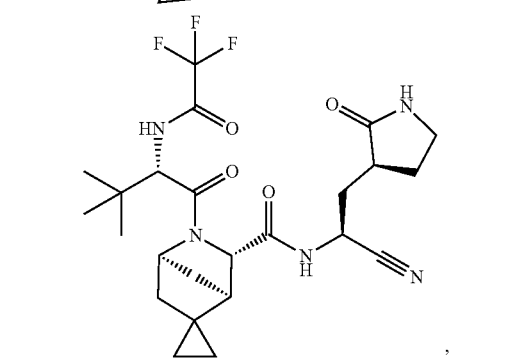
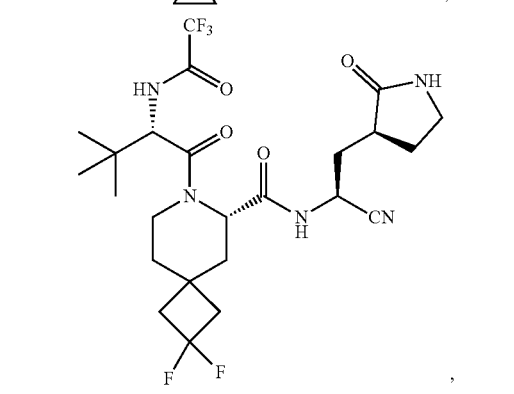
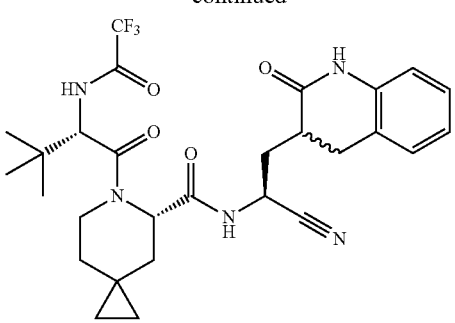
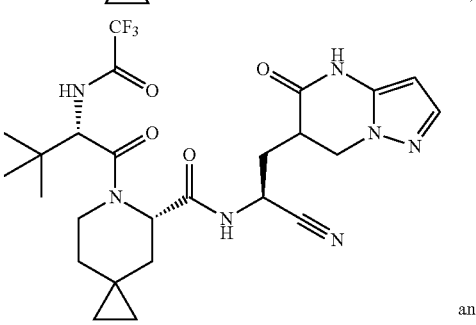
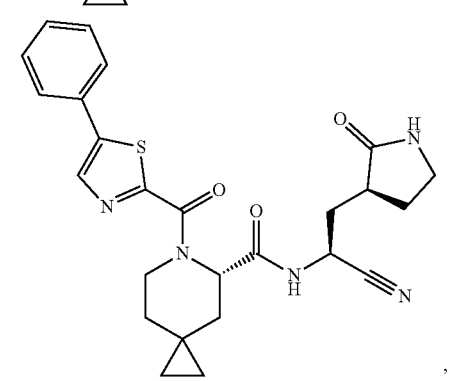
and
or pharmaceutically acceptable salt of any of the foregoing.
In some embodiments, $R^5$ cannot be one or more of the $R^5$ cyclic structure provided herein. For example, $R^5$ cannot be an unsubstituted or a substituted
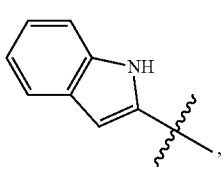 [SMILES: *c1cc2ccccc2[nH]1]
an unsubstituted or a substituted
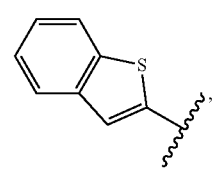 [SMILES: *c1cc2ccccc2s1]

an unsubstituted or a substituted

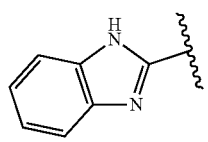 [SMILES: *c1nc2ccccc2[nH]1]

and/or an unsubstituted or a substituted

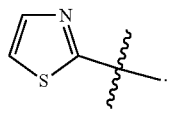 [SMILES: *c1nccs1]

In some embodiments, when $R^5$ is

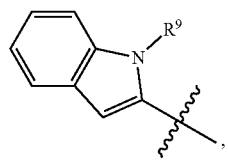

$R^9$ cannot be an unsubstituted $C_{1-4}$ alkyl, such as methyl. In some embodiments, including those of this paragraph, Ring $A^2$ cannot be an unsubstituted or a substituted cyclopropyl. In some embodiments, including those of this paragraph, Ring $A^2$ cannot be an unsubstituted cyclopropyl. In some embodiments, a compound of Formula (I), or a pharmaceutically acceptable salt thereof, cannot be a compound or salt provided in WO 2021/252491. In some embodiments, a compound of Formula (I), or a pharmaceutically acceptable salt thereof, cannot be selected from

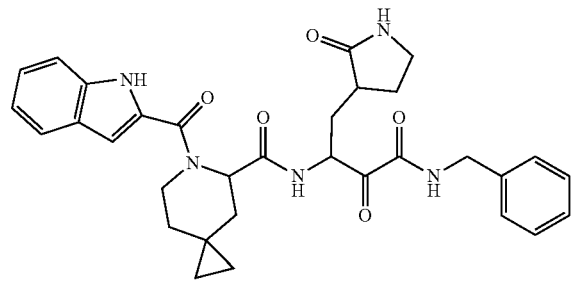

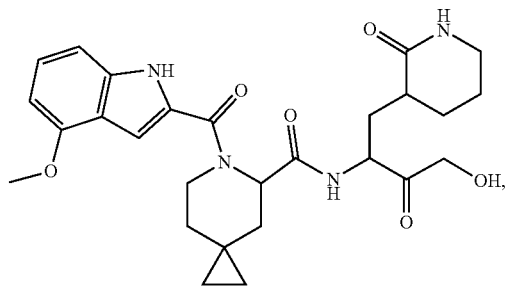

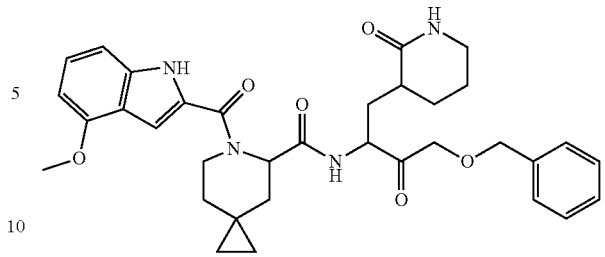

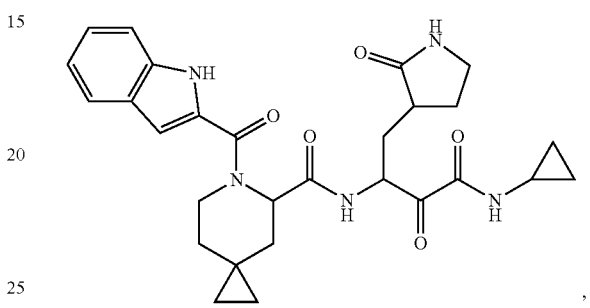

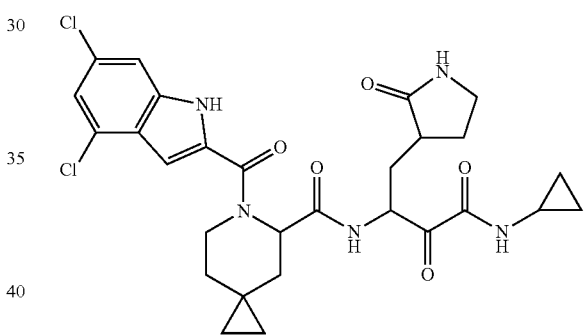

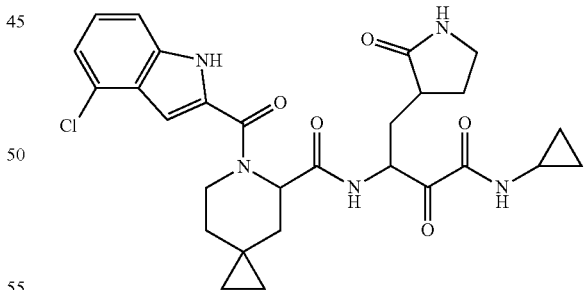

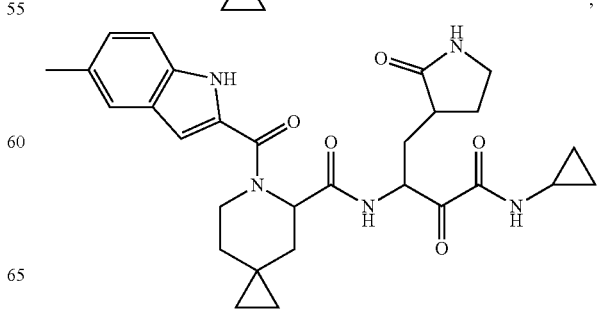

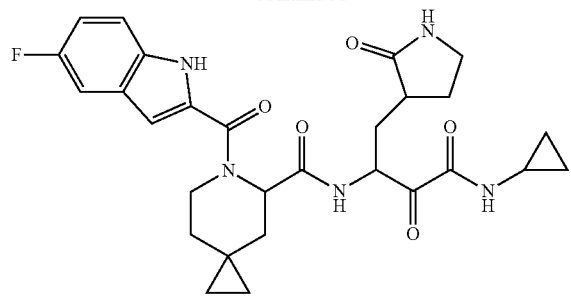
,
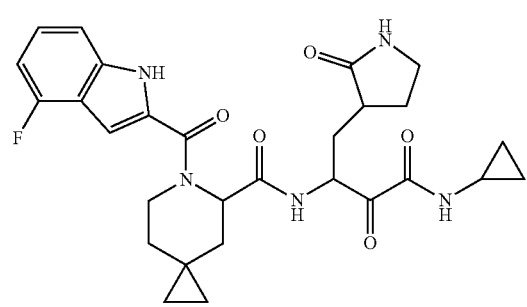
,
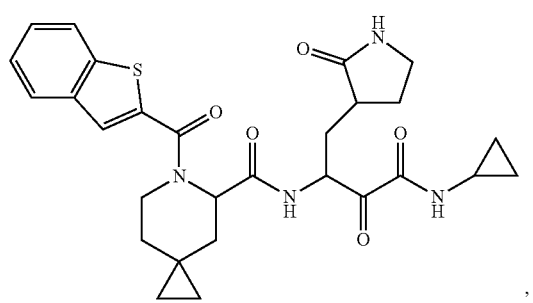
,
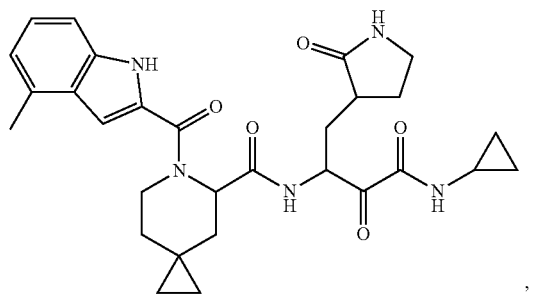
,
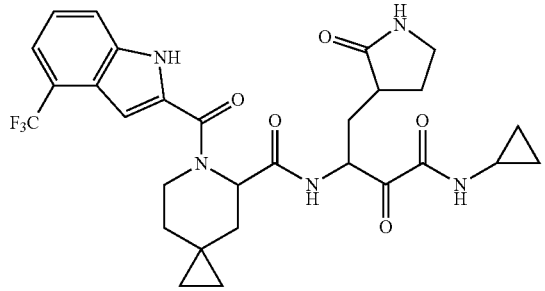
,
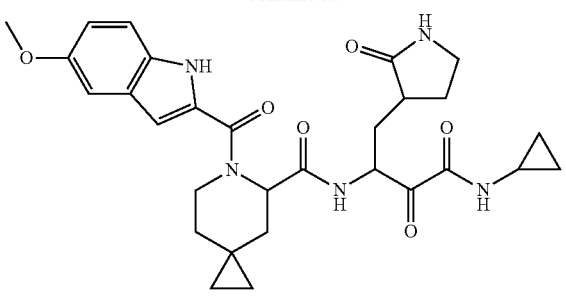
,
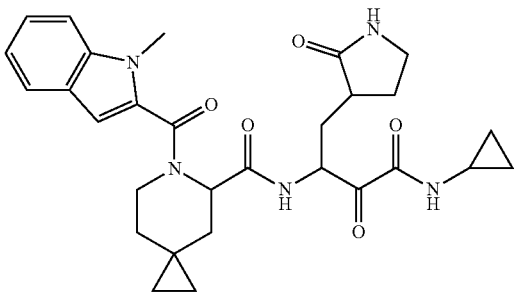
,
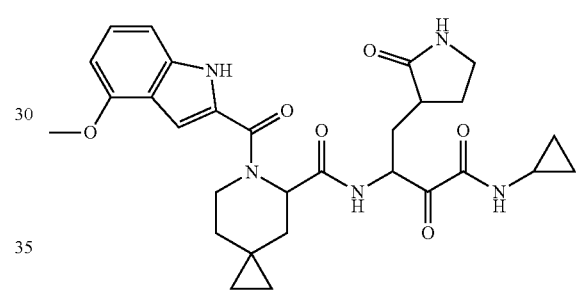
and
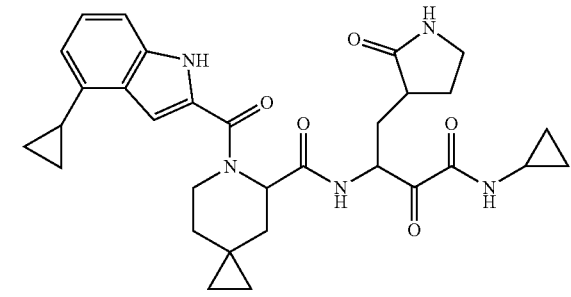
,
or a pharmaceutically acceptable salt of any of the foregoing. In some embodiments, a compound of Formula (I), or a pharmaceutically acceptable salt thereof, cannot be selected from
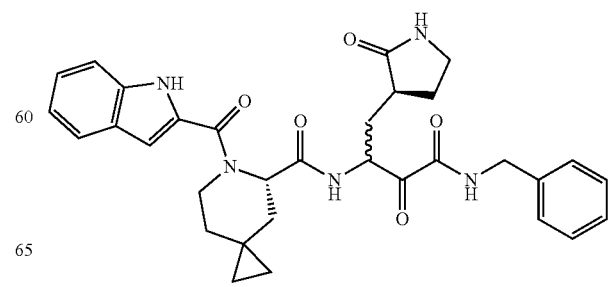
, 85
-continued
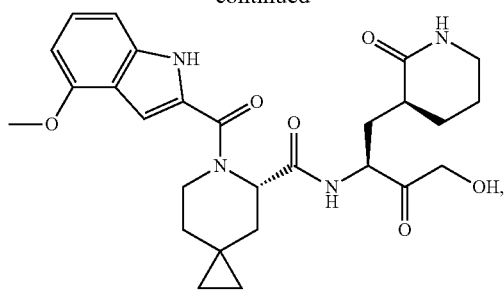
,
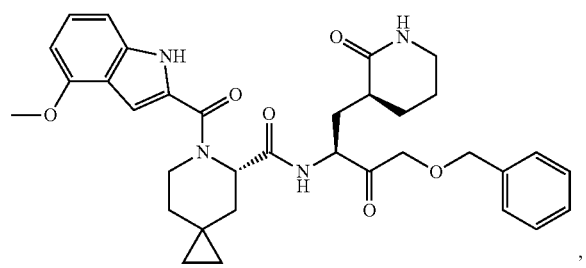
,
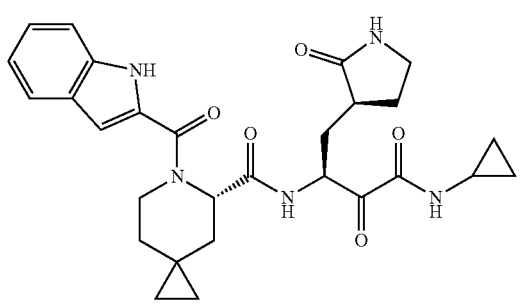
,
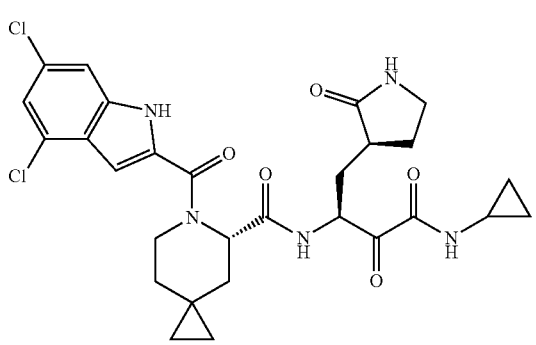
,
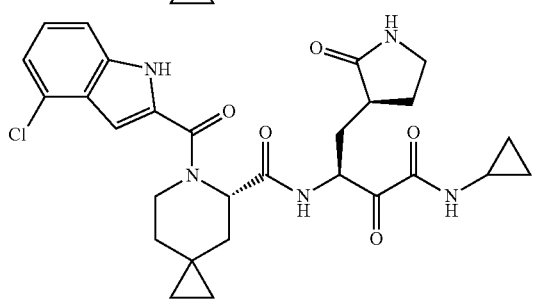
,
86
-continued
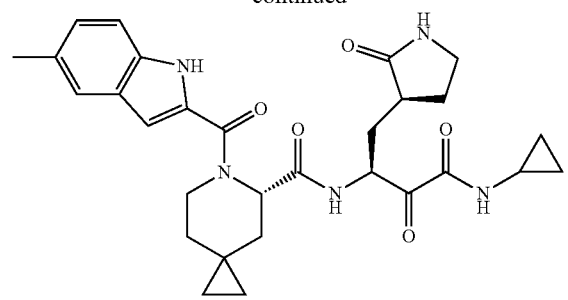
,
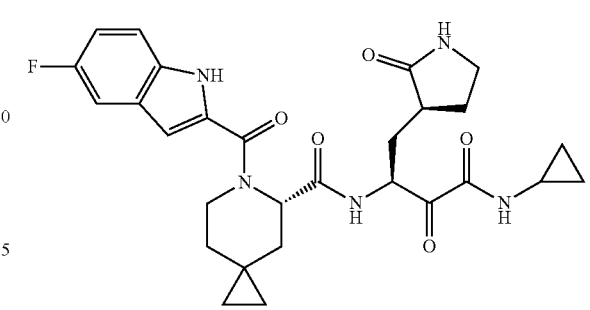
,
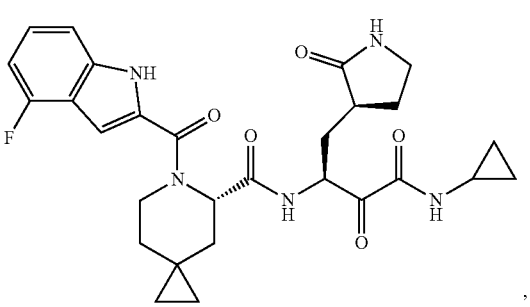
,
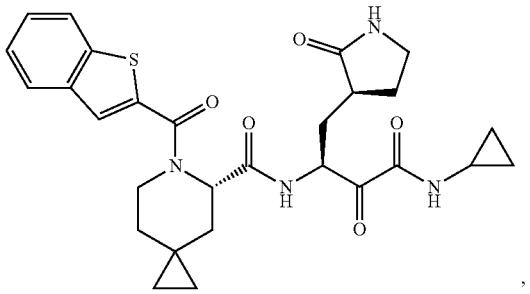
,
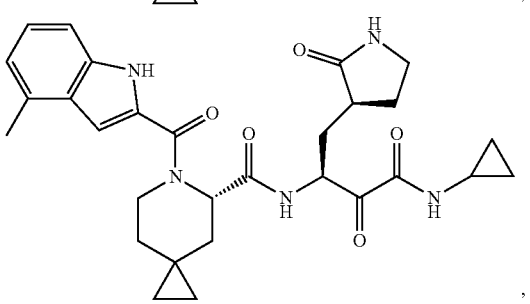
, -continued

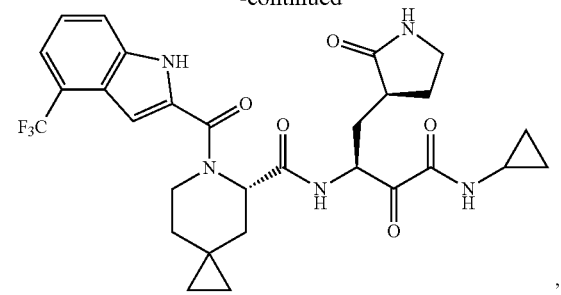

,

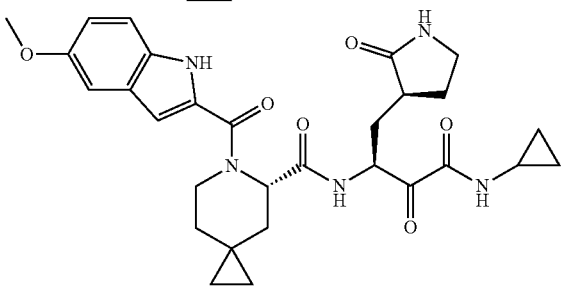

,

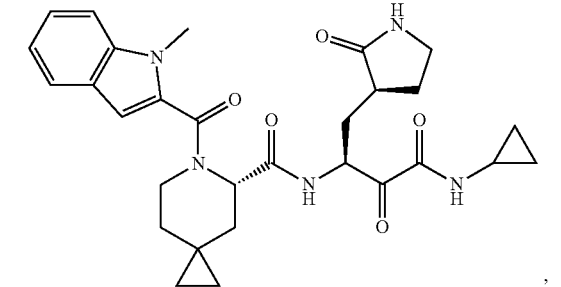

,

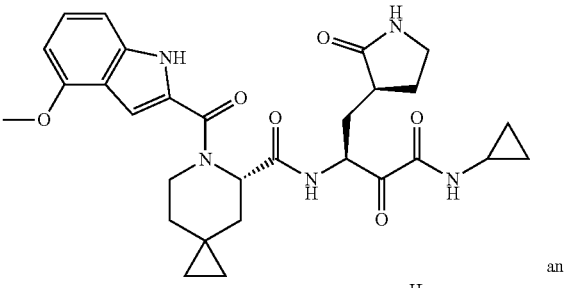

and

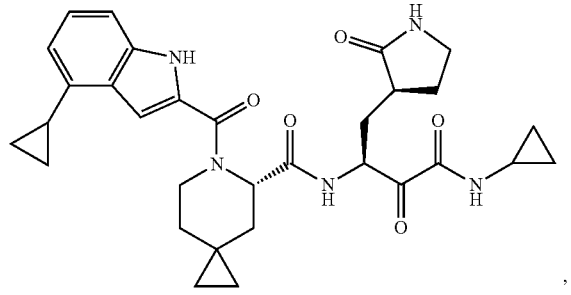

, or a pharmaceutically acceptable salt of any of the foregoing.

Synthesis

Compounds of Formula (I) along with those described herein may be prepared in various ways. General synthetic routes for preparing compounds of Formula (I) are shown and described herein along with some examples of starting materials used to synthesize compounds described herein. Additionally, for the purpose of the general synthetic routes, the structures depicted are appropriately protected, as known by one skilled in the art and the generic structures are meant to include these protecting groups. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

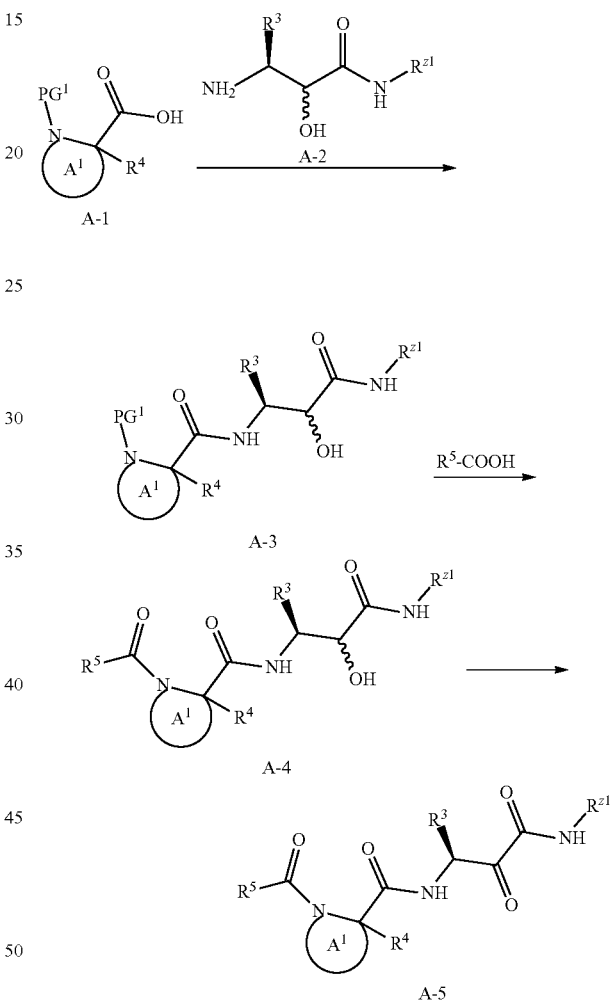

Scheme A describes the synthesis of compounds of general Formula (A-5). A protected amino acid of general Formula (A-1) (with $PG^1$ representing a suitable protecting group of a nitrogen, for example, -Boc) is coupled with an amine of general Formula (A-2) in presence of a coupling agent (such as EDC/HOAt and HATU) and a base (such as DIPEA) to provide a compound of general Formula (A-3). The protecting group can be removed, for example, by treatment with an acid when $PG^1$ is Boc, followed by the coupling with a carboxylic acid. The obtained α-hydroxyamide of general Formula (A-4) can be oxidized, providing a compound of general Formula (A-5). In Scheme A, $R^{z1}$ is part of the ketoamide described herein with respect to $R^1$.

Scheme B

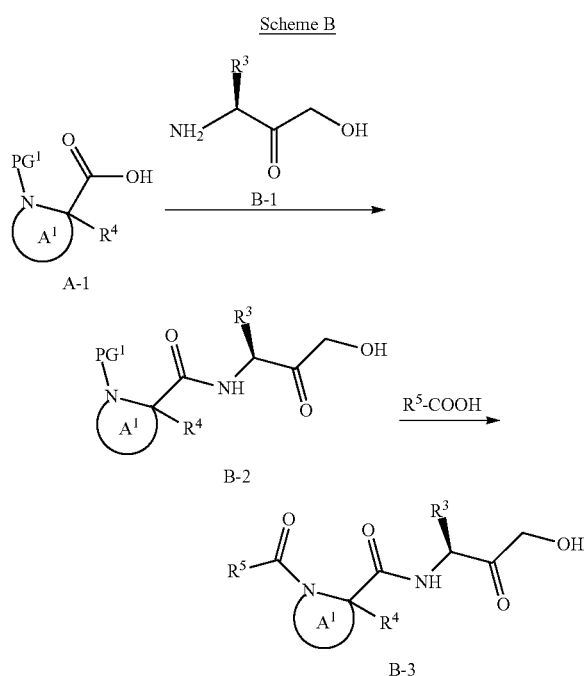

In Scheme B, a protected amino acid of general Formula (A-1) (with PG¹ representing a suitable protecting group of a nitrogen, for example, -Boc) can be coupled with an amino ketone of general Formula (B-1) under typical amide coupling conditions to provide a compound of general Formula (B-2). The protecting group can be then removed, for example, by treatment with an acid when PG¹ is Boc, followed by coupling with a carboxylic acid, resulting in the formation of a compound of general Formula (B-3).

Scheme C

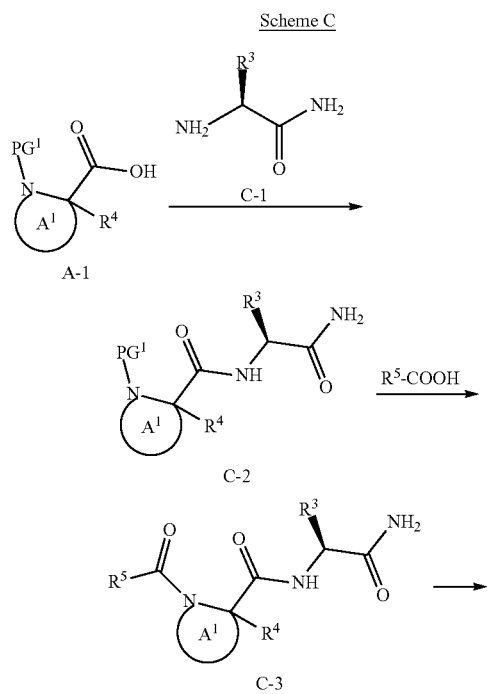

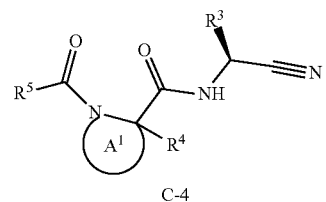

Scheme C describes the synthesis of compounds of general Formula (C-4). A protected amino acid of general Formula (A-1) (with PG¹ representing a suitable protecting group of a nitrogen, for example, -Boc) can be coupled with an amine of general Formula (C-1) under standard amide coupling conditions to provide a compound of general Formula (C-2). After the removal of protecting group PG¹ (for example, in acidic conditions for a Boc protecting group), coupling with a carboxylic acid can provide a compound of general Formula (C-3). Conversion of a compound of general Formula (C-3) to a compound of general Formula (C-4) can, for example, occur under the influence of trifluoroacetic anhydride (TFAA) and pyridine in $CH_2Cl_2$, or by the application of the Burgess reagent.

Scheme D

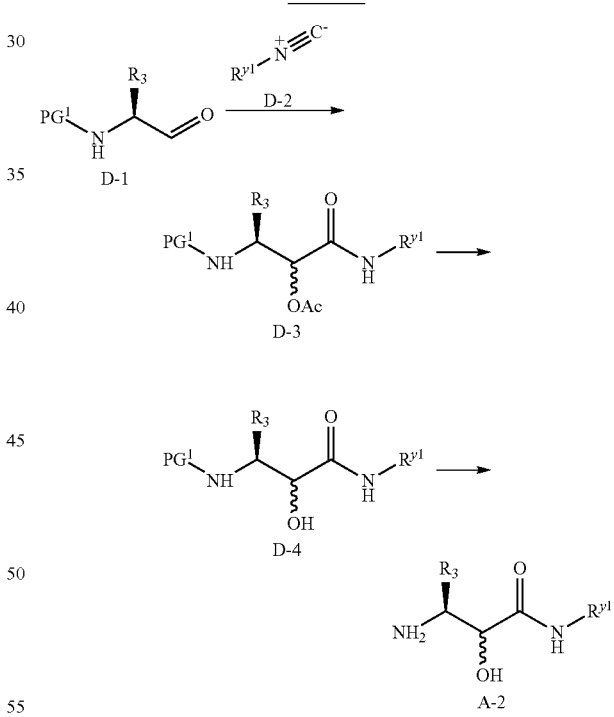

A compound of general Formula (A-2) can be prepared as outlined in Scheme D. An aldehyde of general Formula D-1 (with PG¹ representing a suitable protecting group of a nitrogen, for example, -Boc) and an isonitrile of general Formula (D-2), in the presence of a carboxylic acid (for example, acetic acid), can be condensed in a Passerini-like reaction to provide a compound of general Formula (D-3). After hydrolysis, a compound of general Formula (D-4) can be obtained. The PG¹ can be removed, for example, by treatment with HCl when PG¹ is Boc.

Scheme E

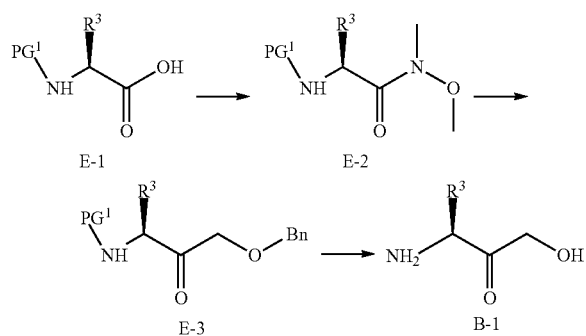

Scheme F

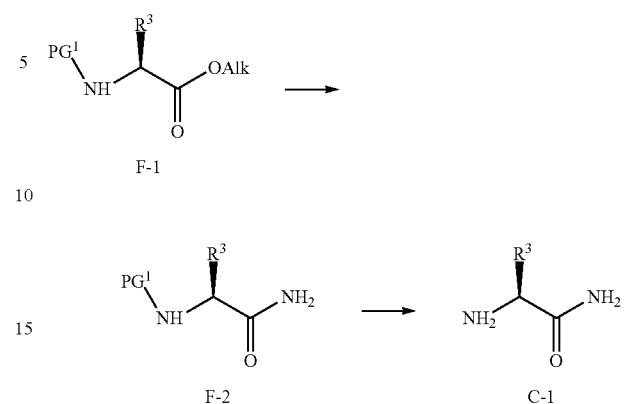

An amino ketone of general Formula (B-1), can be prepared as provided in Scheme E. A protected amino acid of general Formula (E-1) can be converted to its corresponding Weinreb amide under typical amide coupling conditions. Addition of an organometallic reagent (for example, prepared by mixing Mg, $HgCl_2$ and benzylchloromethyl ether) to the Weinreb amide, followed by work-up, can result in a ketone of general Formula (E-3). Benzyl group removal (for example, by palladium-catalyzed hydrogenation) and amine deprotection (for example, when $PG^1$ is Boc, by treatment with HCl) can provide an amino ketone of general Formula (B-1).

A compound of general Formula (C-1) can be prepared as outlined in Scheme F. A primary amide of general Formula (F-2) (with $PG^1$ representing a suitable protecting group of a nitrogen, for example, -Boc) can be prepared by aminolysis of an ester of general Formula (F-1) where Alk represents alkyl, for example, by stirring the ester in a methanolic ammonia solution at room temperature. The $PG^1$ can be removed, for example, by treatment with HCl when $PG^1$ is Boc, to provide a compound of general Formula (C-1).

Scheme G

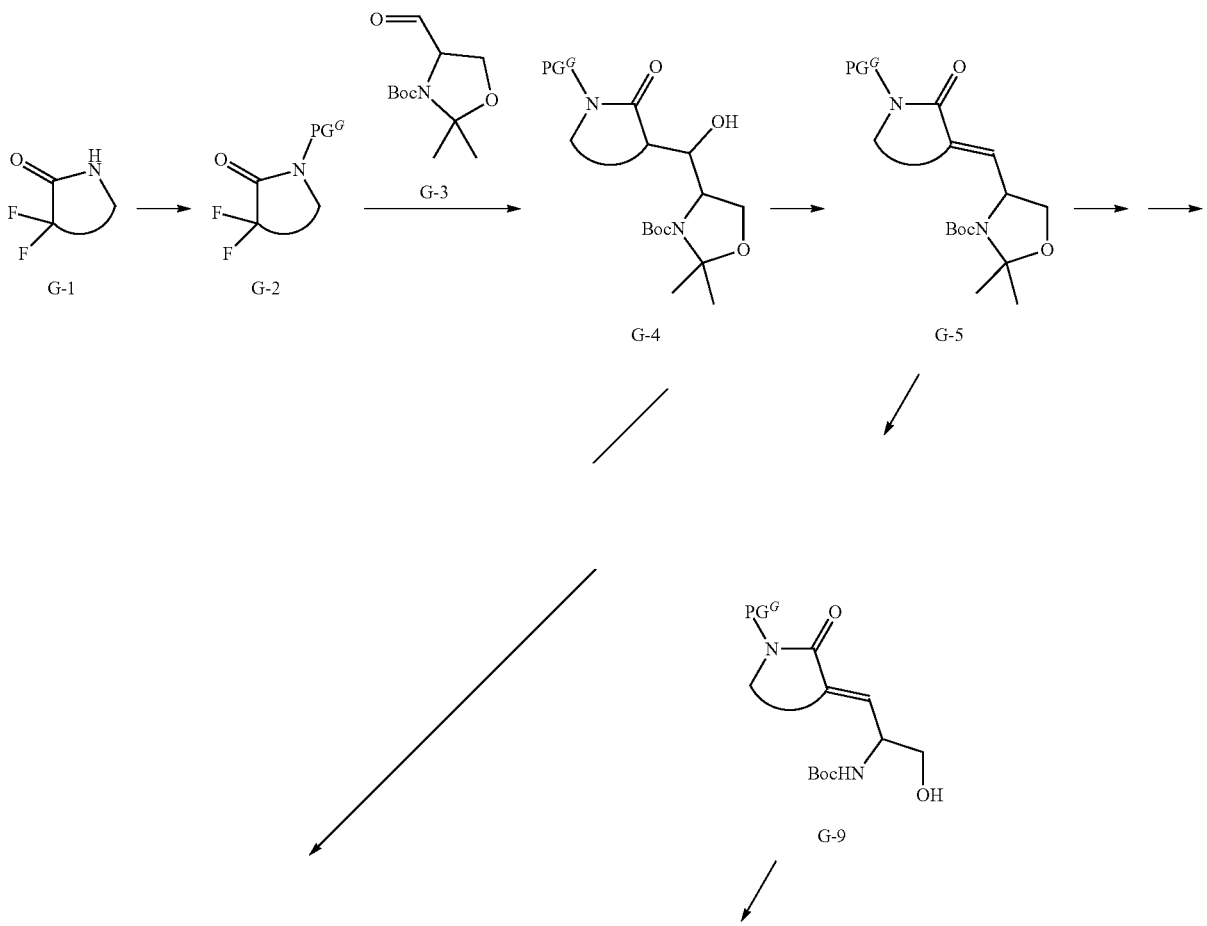

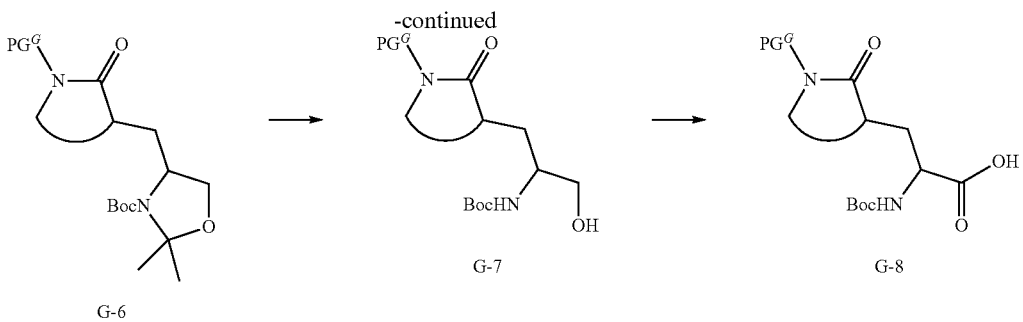

G-6 → G-7 → G-8

A method for preparing a subgroup of amino acids of general Formula (G-8) is described in Scheme G. A lactam of general Formula (G-1) can be protected with a suitable protecting group, $PG^G$. An example of such a $PG^G$ group is a Boc-group. For the purpose of Scheme G, this protecting group can be removed at any relevant stage; and therefore, $PG^G$ can be hydrogen for any of compounds of general Formulae (G-4), (G-5), (G-6), (G-7), (G-8) and/or (G-9). The lactam of general Formula (G-2) can be reacted with an aldehyde of general Formula (G-3) (S or R-Garner's aldehyde). The alcohol of general Formula (G-4) can be eliminated to provide an alkene compound of general Formula (G-5) (for example, by sequential conversion of the hydroxy to a corresponding mesylate, followed by elimination under basic conditions). The double bond can be reduced (for example, by hydrogenation, under influence of a homogeneous or a heterogenous catalyst, optionally diastereoselective) to provide a compound of general Formula (G-6). Removal of the acetonide of a compound of general Formula (G-6) to the Boc-protected amino alcohol of a compound of general Formula (G-7) can be followed by the oxidation to the carboxylic acid of a compound of general Formula (G-8). Alternatively, the acetonide can be deprotected in a compound of general Formula (G-5) to obtain a compound of general Formula (G-9). Reduction of the double bond of a compound of general Formula (G-9) (for example, by hydrogenation under influence of a homogeneous or a heterogenous catalyst, optionally diastereoselective) can be used to obtain a compound of general Formula (G-7). A compound of general Formula (G-4) can be deoxygenated, for example, by a Barton-type deoxygenation, to provide a compound of general Formula (G-6). A similar synthetic strategy can be used starting from a cyclic sulfonamide instead of a lactam of a compound of general Formula (G-1).

Scheme H

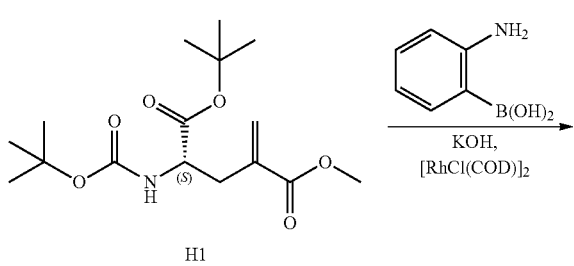

H1

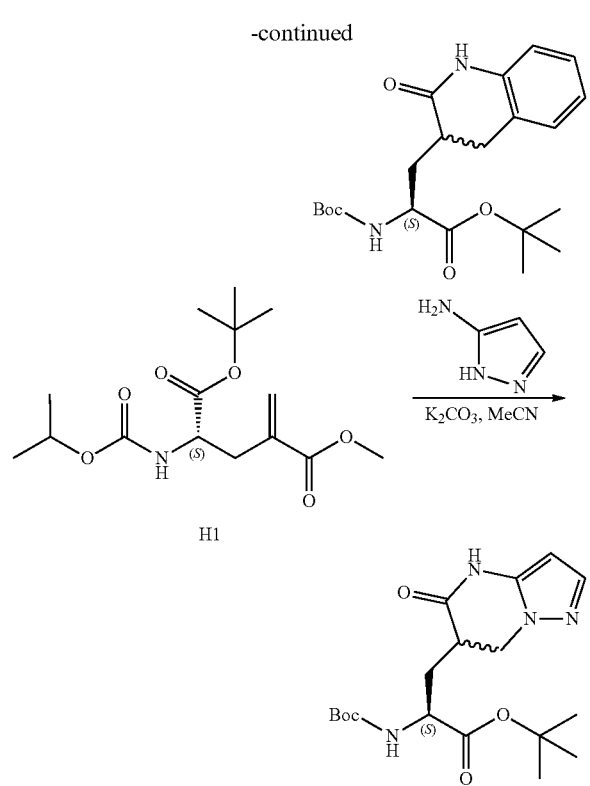

H1

An intermediate, compound H1 (J. Chem. Soc., Perkin Trans. 1, 1997, 3519-3530), can be used to prepare several examples of (or precursors to) amino acids of general Formulae (E-1) and (F-1), as described in Scheme H.

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection, inhalation and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a coronavirus infection that can include administering to a subject identified as suffering from the coronavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a coronavirus infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a coronavirus infection.

Some embodiments disclosed herein relate to a method of treating a coronavirus infection that can include contacting a cell infected with the coronavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a coronavirus infection. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating a coronavirus infection.

Some embodiments disclosed herein relate to a method of inhibiting replication of a coronavirus that can include contacting a cell infected with the coronavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of a coronavirus. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of a coronavirus.

In some embodiments, the coronavirus can be an α-coronavirus or a β-coronavirus. A compound described herein may be effective against one or more variants of a coronavirus. Examples of variants include, but are not limited to, alpha-variant (B.1.1.7), beta-variant (B.1.351), gamma variant (P.1), delta-variant (B.1.617.2) and omicron variant (B.1.1.529). In some embodiments, the coronavirus can be selected from CoV 229E, CoV NL63, CoV OC43, CoV HKU1, Middle East Respiratory Syndrome (MERS)-CoV, Severe Acute Respiratory Syndrome (SARS)-CoV, and SARS-CoV-2.

Some embodiments described herein relate to a method of treating a picornavirus infection that can include administering to a subject identified as suffering from the picornavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a picornavirus infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a picornavirus infection.

Some embodiments disclosed herein relate to a method of treating a picornavirus infection that can include contacting a cell infected with the picornavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a picornavirus infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a picornavirus infection.

Some embodiments disclosed herein relate to a method of inhibiting replication of a picornavirus that can include contacting a cell infected with the picornavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of a picornavirus. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of a picornavirus.

In some embodiments, the picornavirus can be a rhinovirus, including rhinovirus A, B and/or C. In some embodiments, a compound described herein, including a compound of Formula (I), or a pharmaceutically acceptable salt thereof, can be used to treat one or serotypes of a rhinovirus.

Some embodiments described herein relate to a method of treating a norovirus infection that can include administering to a subject identified as suffering from the norovirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a norovirus infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a norovirus infection.

Some embodiments disclosed herein relate to a method of treating a norovirus infection that can include contacting a cell infected with the norovirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a norovirus infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a norovirus infection.

Some embodiments disclosed herein relate to a method of inhibiting replication of a norovirus that can include contacting a cell infected with the norovirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of a norovirus. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of a norovirus.

Some embodiments disclosed herein relate to a method of treating a respiratory condition that is developed because of a coronavirus and/or a picornavirus infection that can include administering to a subject suffering from the respiratory condition and/or contacting a cell infected with the coronavirus and/or the picornavirus in a subject suffering from the respiratory condition with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a respiratory condition due to a coronavirus infection and/or a picornavirus infection with an effective amount of the compound, or a pharmaceutically acceptable salt thereof. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating a respiratory condition due to a coronavirus infection and/or a picornavirus infection.

A subject infected with a coronavirus can be asymptotic. A coronavirus infection can manifest itself via one or more symptoms. Examples of symptoms include, but are not limited to, coughing, sore throat, runny nose, sneezing, headache, fever, shortness of breath, myalgia, abdominal pain, fatigue, difficulty breathing, persistent chest pain or pressure, difficulty waking, loss of smell and taste, muscle or joint pain, chills, nausea or vomiting, nasal congestion, diarrhea, hemoptysis, conjunctival congestion, sputum production, chest tightness and/or palpitations. A coronavirus infection can cause complications. A non-limiting list of complications include, but are not limited to, sinusitis, otitis media, pneumonia, acute respiratory distress syndrome, disseminated intravascular coagulation, pericarditis and/or kidney failure.

As with a coronavirus, a subject infected with a picornavirus can be asymptotic. Alternatively, a subject can exhibit one or more of symptoms. Examples of symptoms of a picornavirus infection include, but are not limited to, aseptic meningitis, rash, conjunctivitis, runny nose a headache a cough a fever a sore throat, chest and/or abdominal pain and paralysis. As provided herein, subjects infected with a norovirus can exhibit one or more the symptoms including, but not limited to, nausea, non-bloody diarrhea, vomiting and abdominal pain. An example of a complication that can be attributed to a norovirus infection is dehydration, including severe dehydration.

Various indicators for determining the effectiveness of a method for treating a coronavirus, picornavirus and/or norovirus infection are also known to those skilled in the art. Examples of suitable indicators include, but are not limited to, a reduction in viral load indicated by reduction in coronavirus (or load) (e.g., reduction <$10^5$ copies/mL in serum), a reduction in plasma viral load, a reduction in viral replication, a reduction in time to seroconversion (virus undetectable in patient serum), an increase in the rate of sustained viral response to therapy a reduction of morbidity or mortality in clinical outcomes, reduction in the need for a ventilator and/or total time on a ventilator, reduction in hospitalization rates and/or reduction in time in an ICU (intensive care unit) and/or hospital.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, camels, non-human primates, such as monkeys, chimpanzees, and apes, and, in particular, humans. In some embodiments, the subject can be human, for example a human subject that is 60 years old or older.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, the subject can be asymptomatic, for example, the subject can be infected with coronavirus but does not exhibit any symptoms of the viral infection. In some embodiments, the subject can be have a pre-existing condition, such as asthma, hypertension, immunocompromised subjects (such as subjects with cancer, HIV and/or genetic immune deficiencies, bone marrow transplant subjects, solid organ transplant subjects, subjects who have had stem cells for cancer treatment and/or subjects who use oral or intravenous corticosteroids or other medicines called immunosuppressants), liver disease, subjects at risk for severe illness, chronic kidney disease being treated with dialysis, chronic lung disease, diabetes, hemoglobin disorders, serious heart conditions (for example, heart failure, coronary artery disease, congenital heart disease, cardiomyopathies, and pulmonary hypertension), severe obesity (such as subjects with a body mass index (BMI) of 40 or above) and people who live in a nursing home or long-term care facility. Additional examples and/or further information is provided by the CDC (https://www.cdc.gov/coronavirus/2019-ncov/need-extra-precautions/groups-at-higher-risk-.html).

A compound described herein, including a compound of Formula (I), or a pharmaceutically acceptable salt thereof, can be administered after a subject is infected with a coronavirus. In addition and/or alternatively, a compound described herein, including a compound of Formula (I), or a pharmaceutically acceptable salt thereof, can be administered prophylactically.

Examples of agents that have been used to treat a coronavirus infection include Remdesivir. However, there can be drawbacks associated with compounds being used to treat a coronavirus including, but not limited to, one or more adverse side effects, the need for subcutaneous administration and/or high cost. Potential advantages of a compound of Formula (I), or a pharmaceutically acceptable salt thereof, can be less adverse side effects, delay in the onset of an adverse side effect and/or reduction in the severity of an adverse side effect.

A coronavirus infection can be treated by inhibiting certain mechanisms. In some embodiments, a compound described herein (such as a compound of Formula (I), or a pharmaceutically acceptable salt thereof) can be selective for a coronavirus protease. For example, a compound of Formula (I), or a pharmaceutically acceptable salt thereof, can be selective for a coronavirus protease compared to a host protease, for example, one or more host proteases selected from Cathepsin L, Cathepsin B, Cathepsin D, Cathepsin K, Leukocyte Elastase, Chymotrypsin, Trypsin, Thrombin, Pepsin, Caspase 2, Elastase and Calpain. In some embodiments, the selectivity for a coronavirus protease over a host protease (such as those described herein) can be >2-fold. In some embodiments, the selectivity for a coronavirus protease over a host protease (such as those described herein) can be >10-fold. In some embodiments, the selectivity for a coronavirus protease over a host protease (such as those described herein) can be >100-fold.

Studies have shown that the entry of SARS-CoV-2 into the target cells is a process that can be mediated by multiple proteases including cysteine cathepsins L and/or transmembrane protease serine 2 (TMPRSS2) (Shang et al., PNAS (2020) 117:11727, and Hoffmann et al., Cell (2020) 181: 271-280). The cathepsin L inhibitor K117777, which lacks an inhibitory effect on the 3CLpro, can result in potent inhibition of SARS-CoV-2 in VeroE6, A549-ACE2 and/or HeLa-ACE2 (Mellott et al., bioRxiv (2020) 2020.2010.2023.347534). It has also been shown that the potent antiviral effect of K117777 is abolished when TMPRSS2 was expressed in A549-ACE2 (Steuten et al., bioRxiv (2020) 2020.2011.2021.392753). Off target activity of 3CLpro inhibitors, for example, on cathepsin L, may lead to an inaccurate assessment of the 3CLpro component of a compound's cellular potency. As an example, a compound described herein (such as a compound of Formula (I), or a pharmaceutically acceptable salt thereof) can have greater selectivity for a coronavirus protease over a host protease, such as cathepsin L. The selectivity can be determined by those skilled in the art, for example, using $IC_{50}$ and/or Ki values. In some embodiments, a compound described herein does not significantly inhibit cathepsin L (for example, $IC_{50} \geq 10000$ nM or >3.3 μM), but inhibits a coronavirus protease (for example, SARS-Cov-2 3Clpro).

A drawback with anti-viral treatment can be the development of resistance, including cross-resistance. Resistance can be a cause for treatment failure. The term "resistance" as used herein refers to a viral strain displaying a delayed, lessened and/or null response to an anti-viral agent. In some embodiments, a compound, or a pharmaceutically acceptable salt thereof, as described herein can be provided to a subject infected with a coronavirus strain that is resistant to one or more other anti-viral agents. In some embodiments, development of coronavirus resistant strains is delayed when a subject is treated with a compound, or a pharmaceutically acceptable salt thereof, as described herein compared to the development of a coronavirus resistant strain when treated with one or more other anti-viral agents.

Combination Therapies

In some embodiments, a compound, or a pharmaceutically acceptable salt thereof, as described herein can be used in combination with one or more additional agent(s) for treating and/or inhibiting replication a coronavirus. Additional agents include, but are not limited to, an ACE inhibitor, an anticoagulant, an anti-inflammatory, an ARB, an ASO, a Covid-19 convalescent plasma, an entry inhibitor, an $H_2$ pump antagonist, an H-conducting channel, an HIV protease inhibitor, an HMG-CoA reductase inhibitor, an immune globulin, an immunosuppressant, an immunotherapeutic agent, a monoclonal antibody, a neuraminidase inhibitor, a nucleoside inhibitor, a nucleoside analog inhibitor, a polymerase inhibitor, a protease inhibitor, an siRNA, a statin, a tissue plasminogen activator, an antibiotic, an antimicrobial and a vaccine. Examples of additional agents include Ascorbic acid, Anakin, Azithromycin, Baloxavir, Baricitinib, Chloroquine Phosphate, Colchicine, a corticosteroid, Epoprostenol, Famotidine, Favipiravir, an IGIV, an interferon (for example, recombinant interferon alpha 2b, IFN-α and/or PEG-IFN-α-2a), an IVIG, Ivermectin, γ-globulin, lopinavir, Methylprednisolone, Molnupiravir (MK-4482 or EIDD-2801), Niclosamide, Nitazoxanide, Nitric oxide, Oseltamivir, Peramivir, RANTES, ribavirin, Remdesivir, Ruxolitinib, Sarilumab, Siltuximab, Sirolimus, a statin, Tacrolimus, Tocilizumab, Umifenovir, Zanamivir, Casirivimab, imdevimab, bamlanivimab, etesevimab, paxlovid (PF-07321332), ritonavir and AT-527 (Good et al., Antimicrobial Agents and Chemotherapy (2021) 65(4): e02479-20).

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

Compounds

Compounds of Formula (I), along with pharmaceutically acceptable salts thereof, can be prepared in various ways, including those synthetic schemes shown and described herein, are provided below. Those skilled in the art will be able to recognize modifications of the disclosed syntheses and to devise routes based on the disclosures herein; all such modifications and alternate routes are within the scope of the claims.

Synthesis of Intermediates (3S)-3-amino-N-cyclopropyl-2-hydroxy-4-((S)-2-oxopyrrolidin-3-yl)butanamide To a stirred mixture of methyl (2S)-2-[(tert-butoxycarbonyl)amino]-3-[(3S)-2-oxopyrrolidin-3-yl]propanoate (3.0 g, 10.5 mmol, 1.0 eq.) in tetrahydrofuran (50 mL) was added lithium borohydride (26.2 mL, 52.4 mmol, 5.0 eq.) dropwise at 0° C. The mixture was stirred for 1 h at 0° C. and then concentrated under reduced pressure. The mixture was diluted with water (20 mL) and extracted with isopropanol: trichloromethane (1:5, 4×50 mL). The organic layers were combined, dried over anhydrous sodium sulfate, filtered and concentrated under reduced pressure. The residue was purified by silica gel column chromatography, eluted with dichloromethane:methanol (19:1) to afford tert-butyl N-[(2S)-1-hydroxy-3-[(3S)-2-oxopyrrolidin-3-yl]propan-2-yl]carbamate (2.6 g, crude) as a white solid. The crude product was precipitated by the addition of PE:EA (4:1, 40 mL) to afford tert-butyl N-[(2S)-1-hydroxy-3-[(3S)-2-oxopyrrolidin-3-yl]propan-2-yl]carbamate (2.4 g, 79%) as a white solid. LC-MS (ESI, m/z): 259 [M+H]$^+$.

To a stirred mixture of tert-butyl N-[(2S)-1-hydroxy-3-[(3S)-2-oxopyrrolidin-3-yl]propan-2-yl]carbamate (2.4 g, 9.29 mmol, 1.0 eq.) in dimethyl sulfoxide (40 mL) was added 2-iodoxybenzoic acid (7.80 g, 27.8 mmol, 3.0 eq.) in portions at room temperature (rt). The mixture was stirred for 3 h at rt, and then basified pH=8 with sat. sodium bicarbonate (aq.). The mixture was diluted with water (20 mL) and extracted with ethyl acetate (EA) (4×200 mL). The organic layers were combined, washed with brine (3×100 mL), dried over anhydrous sodium sulfate, filtered and concentrated under reduced pressure to afford tert-butyl N-[(2S)-1-oxo-3-[(3S)-2-oxopyrrolidin-3-yl]propan-2-yl]carbamate (1.5 g, 63%) as a yellow solid. LC-MS (ESI, m/z): 257 [M+H]$^+$.

To a stirred mixture of tert-butyl N-[(2S)-1-oxo-3-[(3S)-2-oxopyrrolidin-3-yl]propan-2-yl]carbamate (900 mg, 3.51 mmol, 1.0 eq.) in dichloromethane (10 mL) was added isocyanocyclopropane (471 mg, 7.02 mmol, 2.0 eq.) and acetic acid (633 mg, 10.5 mmol, 3.0 eq.) dropwise at 0° C. The mixture was stirred for 5 h at rt and concentrated under reduced pressure. The residue was purified by silica gel column chromatography, eluted with dichloromethane:methanol (49:1) to afford (2S)-2-[(tert-butoxycarbonyl)amino]-1-(cyclopropylcarbamoyl)-3-[(3S)-2-oxopyrrolidin-3-yl]propyl acetate (820 mg, 55%) as a yellow solid. LC-MS (ESI, m/z): 384 [M+H]$^+$.

To a stirred mixture of (2S)-2-[(tert-butoxycarbonyl)amino]-1-(cyclopropylcarbamoyl)-3-[(3S)-2-oxopyrrolidin-3-yl]propyl acetate (810 mg, 2.11 mmol, 1.0 eq.) in tetrahydrofuran (8 mL) was added lithium hydroxide (253 mg, 10.5 mmol, 5.0 eq., in water 8 mL) at 0° C. The mixture was stirred for 1 h at 0° C. The mixture was acidified to pH=6 with hydrochloric acid (2 M). The mixture was extracted with EA (4×60 mL). The organic layers were combined, dried over anhydrous sodium sulfate, filtered and concentrated under reduced pressure to afford tert-butyl N-[(2S)-1-(cyclopropylcarbamoyl)-1-hydroxy-3-[(3S)-2-oxopyrrolidin-3-yl]propan-2-yl]carbamate (680 mg, 94%) as a yellow solid. LCMS (ESI, m/z): 342 [M+H]$^+$.

To a solution of tert-butyl N-[(2S)-1-(cyclopropylcarbamoyl)-1-hydroxy-3-[(3S)-2-oxopyrrolidin-3-yl]propan-2-yl]carbamate (1.5 g, 4.39 mmol, 1.0 eq.) in DCM (15 mL) cooled at 0° C. was added 4N HCl in dioxane (5 mL, 20.0 mmol; 4.6 eq.). The mixture was stirred at rt for 2 h and then concentrated under reduced pressure to afford (3S)-3-amino-N-cyclopropyl-2-hydroxy-4-((S)-2-oxopyrrolidin-3-yl)butanamide hydrochloride as an off-white solid (1 g, 94%). LC-MS (ESI, m/z): 242 [M+H]$^+$.

Synthesis of (S)-3-((S)-2-amino-4-hydroxy-3-oxobutyl)pyrrolidin-2-one hydrochloride

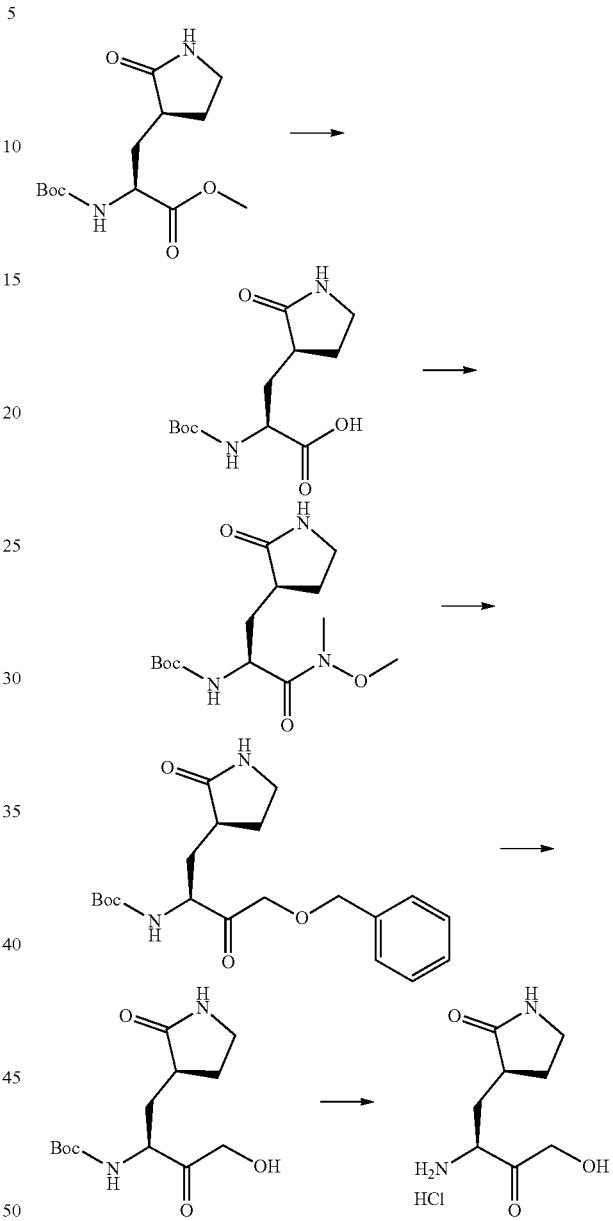

To a mixture of methyl (2S)-2-[(tert-butoxycarbonyl)amino]-3-[(3S)-2-oxopyrrolidin-3-yl]propanoate (4.00 g, 14.0 mmol, 1.0 eq.) in methanol (20 mL) was added sodium hydroxide (19 mL, 57.0 mmol, 4.0 eq., 3 M in water). The mixture was stirred for 1 h at 0° C. The mixture was concentrated under reduced pressure to remove the methanol, and the pH was adjusted to 6 with HCl (2 M). The mixture was extracted with EA (3×30 mL). The organic layers were combined, washed with brine (2×20 mL), dried over anhydrous sodium sulfate, filtered and concentrated under reduced pressure to provide (2S)-2-[(tert-butoxycarbonyl)amino]-3-[(3S)-2-oxopyrrolidin-3-yl]propanoic acid (3.56 g, 88%) as a light yellow solid.

To a mixture of (2S)-2-[(tert-butoxycarbonyl)amino]-3-[(3S)-2-oxopyrrolidin-3-yl]propanoic acid (3.56 g, 13.1 mmol, 1.0 eq.) in dichloromethane (50 mL) was added N,O-dimethylhydroxylamine hydrochloride (1.28 g, 13.1 mmol, 1.0 eq.), N-methylmorpholine (3.97 g, 39.0 mmol, 3.0 eq.), 1-hydroxybenzotriazole (1.77 g, 13.1 mmol, 1.0 eq.) and 1-(3-dimethylaminopropyl)-3-ethylcarbodiimide hydrochloride (2.76 g, 14.4 mmol, 1.1 eq.) at 0° C. The mixture was stirred for 2 h at 0° C. under $N_2$. The reaction was quenched with water (40 mL). The organic layers were washed with HCl (2×40 mL, 1 M), water (40 mL), sat. aq. sodium bicarbonate (2×40 mL) and brine (40 mL), dried over anhydrous sodium sulfate, filtered and concentrated under reduced pressure to provide tert-butyl N-[(1S)-1-[methoxy(methyl)carbamoyl]-2-[(3S)-2-oxopyrrolidin-3-yl]ethyl]carbamate (3.43 g, 81%) as a light yellow solid.

To a mixture of magnesium (2.36 g, 97.0 mmol, 9.0 eq.) and mercury dichloride (1.76 g, 6.47 mmol, 0.6 eq.) in THF (120 mL) was added benzylchloromethyl ether (15.2 g, 97.0 mmol, 9.0 eq.) at −45° C. under $N_2$. The mixture was stirred for 5 h from −45° C. to 5° C. The mixture was then cooled to −45° C., and tert-butyl N-[(1S)-1-[methoxy(methyl)carbamoyl]-2-[(3S)-2-oxopyrrolidin-3-yl]ethyl]carbamate (3.40 g, 10.8 mmol, 1.0 eq.) was added. The mixture was stirred overnight at rt under $N_2$. The reaction was quenched with sat. aq. ammonium chloride (200 mL). The mixture was extracted with EA (3×200 mL). The organic layers were combined, washed with brine (2×200 mL), dried over anhydrous sodium sulfate, filtered and concentrated under reduced pressure to afford the crude product. The crude product was diluted with dichloromethane (100 mL). A slurry was made with 100-200 silica gel mesh (10 g) and then loaded onto a column after removing the dichloromethane. The sample was purified by column chromatography (Column size 5×24 cm, column volume: 600 mL, silica gel size (100~ 200 mesh) quantity: 330 g) and eluted with methanol:dichloromethane (0%-5% over 20 min). The collected fractions: 3%-4% methanol:dichloromethane fractions were chosen as pure fractions. Those fractions were combined and concentrated under reduced pressure to provide tert-butyl N-[(2S)-4-(benzyloxy)-3-oxo-1-[(3S)-2-oxopyrrolidin-3-yl]butan-2-yl]carbamate (2.15 g, 45%) as a light yellow oil. $^1$H NMR (300 MHz, CDCl$_3$-d) δ 7.30-7.42 (m, 5H), 6.21 (s, 1H), 5.82 (d, J=7.9 Hz, 1H), 4.52-4.69 (m, 3H), 4.18-4.37 (m, 2H), 3.23-3.34 (m, 2H), 2.32-2.54 (m, 2H), 1.72-2.06 (m, 3H), 1.44 (s, 9H). LCMS (ESI, m/z): 277 [M-Boc+H]$^+$.

To a solution of tert-butyl N-[(2S)-4-(benzyloxy)-3-oxo-1-[(3S)-2-oxopyrrolidin-3-yl]butan-2-yl]carbamate (500 mg, 1.33 mmol, 1.0 eq.) in MeOH (5 mL) and EA (5 mL) was added 10% Pd/C (500 mg). The mixture was stirred at rt under hydrogen atmosphere for 24 h. The mixture was filtered through celite, and the solids were washed with DCM (20 mL). The filtrate was concentrated under reduced pressure. The residue was purified by flash chromatography on silica gel (24 g column) using a gradient of MeOH (3 to 5%) in DCM to afford tert-butyl ((S)-4-hydroxy-3-oxo-1-((S)-2-oxopyrrolidin-3-yl)butan-2-yl)carbamate (270 mg, 71%) as a colorless oil. LC-MS (ESI, m/z): 187 [M-Boc+2H]$^+$.

To a solution of tert-butyl ((S)-4-hydroxy-3-oxo-1-((S)-2-oxopyrrolidin-3-yl)butan-2-yl)carbamate (270 mg, 0.944 mmol, 1.0 eq.) in DCM (3 mL) cooled at 0° C. was added 4N HCl in dioxane (1.2 mL, 4.80 mmol; 4.8 eq.). The mixture was stirred at rt for 4 h and then concentrated under reduced pressure to afford (S)-3-((S)-2-amino-4-hydroxy-3-oxobutyl)pyrrolidin-2-one hydrochloride as an off-white solid (200 mg, 96%). LC-MS (ESI, m/z): 187 [M+H]$^+$.

(S)-2-amino-3-((S)-2-oxopyrrolidin-3-yl) propanamide Hydrochloride

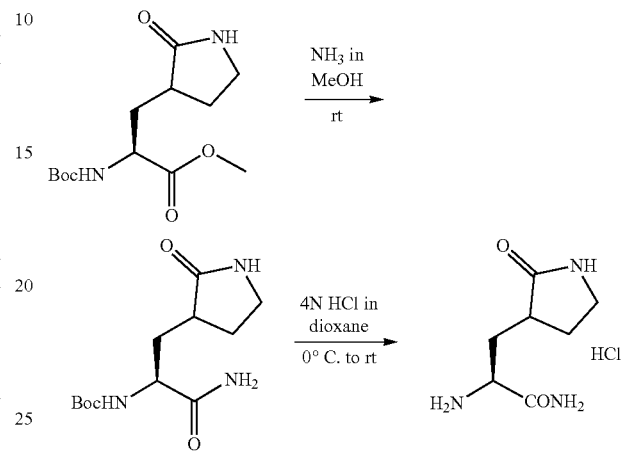

A solution of methyl (S)-2-((tert-butoxycarbonyl)amino)-3-((S)-2-oxopyrrolidin-3-yl)propanoate (500 mg, 1.75 mmol, 1.0 eq.) in 7 M NH$_3$ in MeOH (5 mL) was stirred at rt for 48 h and then concentrated under reduced pressure. The residue was purified by flash chromatography on silica gel (24 g column) using 10% MeOH in DCM as an eluent to afford tert-butyl ((S)-1-amino-1-oxo-3-((S)-2-oxopyrrolidin-3-yl)propan-2-yl)carbamate (350 mg, 73%) as an off-white solid. LC-MS (ESI, m/z): 272 [M+H]$^+$.

To a solution of tert-butyl ((S)-1-amino-1-oxo-3-((S)-2-oxopyrrolidin-3-yl)propan-2-yl)carbamate (300 mg, 1.11 mmol, 1.0 eq.) in DCM (3 mL) cooled at 0° C. was added 4N HCl in dioxane (1.5 mL, 6.00 mmol; 5.4 eq.). The mixture was stirred at rt for 2 h and then concentrated under reduced pressure to afford (S)-2-amino-3-((S)-2-oxopyrrolidin-3-yl)propanamide hydrochloride as an off-white solid (250 mg, 63%). LC-MS (ESI, m/z): 172 [M+H]$^+$.

(S)-3-((R*)-1-(tert-butoxycarbonyl)-5,5-dimethyl-2-oxopyrrolidin-3-yl)-2-((tert-butoxycarbonyl)amino) propanoic acid

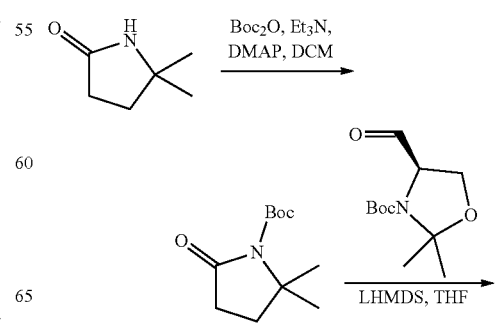

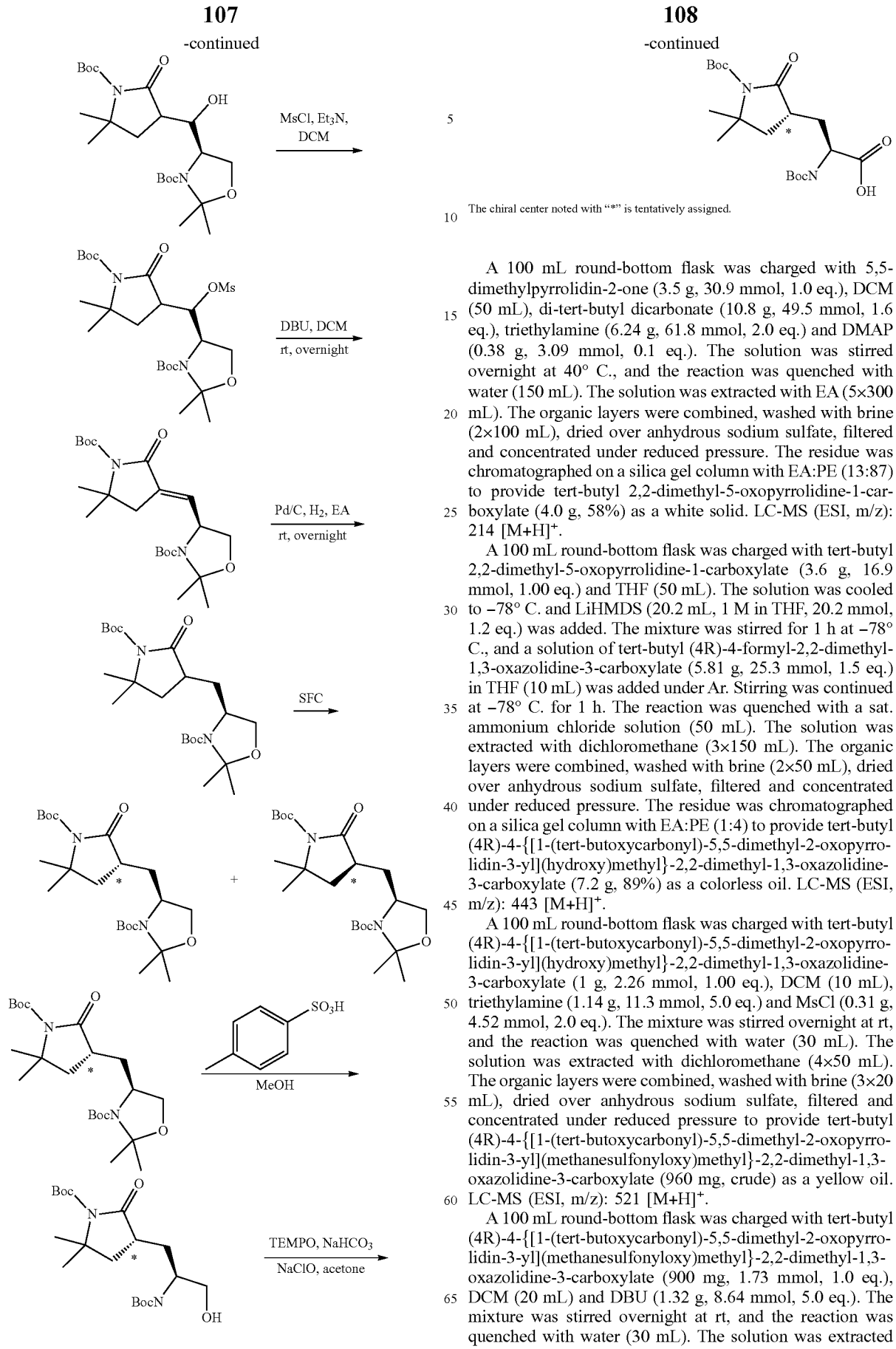

The chiral center noted with "*" is tentatively assigned.

A 100 mL round-bottom flask was charged with 5,5-dimethylpyrrolidin-2-one (3.5 g, 30.9 mmol, 1.0 eq.), DCM (50 mL), di-tert-butyl dicarbonate (10.8 g, 49.5 mmol, 1.6 eq.), triethylamine (6.24 g, 61.8 mmol, 2.0 eq.) and DMAP (0.38 g, 3.09 mmol, 0.1 eq.). The solution was stirred overnight at 40° C., and the reaction was quenched with water (150 mL). The solution was extracted with EA (5×300 mL). The organic layers were combined, washed with brine (2×100 mL), dried over anhydrous sodium sulfate, filtered and concentrated under reduced pressure. The residue was chromatographed on a silica gel column with EA:PE (13:87) to provide tert-butyl 2,2-dimethyl-5-oxopyrrolidine-1-carboxylate (4.0 g, 58%) as a white solid. LC-MS (ESI, m/z): 214 [M+H]$^+$.

A 100 mL round-bottom flask was charged with tert-butyl 2,2-dimethyl-5-oxopyrrolidine-1-carboxylate (3.6 g, 16.9 mmol, 1.00 eq.) and THF (50 mL). The solution was cooled to −78° C. and LiHMDS (20.2 mL, 1 M in THF, 20.2 mmol, 1.2 eq.) was added. The mixture was stirred for 1 h at −78° C., and a solution of tert-butyl (4R)-4-formyl-2,2-dimethyl-1,3-oxazolidine-3-carboxylate (5.81 g, 25.3 mmol, 1.5 eq.) in THF (10 mL) was added under Ar. Stirring was continued at −78° C. for 1 h. The reaction was quenched with a sat. ammonium chloride solution (50 mL). The solution was extracted with dichloromethane (3×150 mL). The organic layers were combined, washed with brine (2×50 mL), dried over anhydrous sodium sulfate, filtered and concentrated under reduced pressure. The residue was chromatographed on a silica gel column with EA:PE (1:4) to provide tert-butyl (4R)-4-{[1-(tert-butoxycarbonyl)-5,5-dimethyl-2-oxopyrrolidin-3-yl](hydroxy)methyl}-2,2-dimethyl-1,3-oxazolidine-3-carboxylate (7.2 g, 89%) as a colorless oil. LC-MS (ESI, m/z): 443 [M+H]$^+$.

A 100 mL round-bottom flask was charged with tert-butyl (4R)-4-{[1-(tert-butoxycarbonyl)-5,5-dimethyl-2-oxopyrrolidin-3-yl](hydroxy)methyl}-2,2-dimethyl-1,3-oxazolidine-3-carboxylate (1 g, 2.26 mmol, 1.00 eq.), DCM (10 mL), triethylamine (1.14 g, 11.3 mmol, 5.0 eq.) and MsCl (0.31 g, 4.52 mmol, 2.0 eq.). The mixture was stirred overnight at rt, and the reaction was quenched with water (30 mL). The solution was extracted with dichloromethane (4×50 mL). The organic layers were combined, washed with brine (3×20 mL), dried over anhydrous sodium sulfate, filtered and concentrated under reduced pressure to provide tert-butyl (4R)-4-{[1-(tert-butoxycarbonyl)-5,5-dimethyl-2-oxopyrrolidin-3-yl](methanesulfonyloxy)methyl}-2,2-dimethyl-1,3-oxazolidine-3-carboxylate (960 mg, crude) as a yellow oil. LC-MS (ESI, m/z): 521 [M+H]$^+$.

A 100 mL round-bottom flask was charged with tert-butyl (4R)-4-{[1-(tert-butoxycarbonyl)-5,5-dimethyl-2-oxopyrrolidin-3-yl](methanesulfonyloxy)methyl}-2,2-dimethyl-1,3-oxazolidine-3-carboxylate (900 mg, 1.73 mmol, 1.0 eq.), DCM (20 mL) and DBU (1.32 g, 8.64 mmol, 5.0 eq.). The mixture was stirred overnight at rt, and the reaction was quenched with water (30 mL). The solution was extracted with dichloromethane (3×80 mL). The organic layers were combined, washed with brine (2×30 mL), dried over anhydrous sodium sulfate, filtered and concentrated under reduced pressure. The residue was chromatographed on a silica gel column with EA:PE (1:4) to provide tert-butyl (4S)-4-{[1-(tert-butoxycarbonyl)-5,5-dimethyl-2-oxopyrrolidin-3-ylidene]methyl}-2,2-dimethyl-1,3-oxazolidine-3-carboxylate (635 mg, 82%) as a colorless oil. LC-MS (ESI, m/z): 425 [M+H]$^+$.

A 250 mL round-bottom flask was charged with tert-butyl (4S)-4-{[1-(tert-butoxycarbonyl)-5,5-dimethyl-2-oxopyrrolidin-3-ylidene]methyl}-2,2-dimethyl-1,3-oxazolidine-3-carboxylate (4.4 g, 10.4 mmol, 1.0 eq.), EA (50 mL) and 10% palladium on activated carbon (5.51 g). The contents of the flask were placed under an atmosphere of hydrogen (3 atm). The mixture was stirred overnight at rt. The solids were filtered off. The organic layer was concentrated under reduced pressure to provide tert-butyl (4S)-4-{[1-(tert-butoxycarbonyl)-5,5-dimethyl-2-oxopyrrolidin-3-yl]methyl}-2,2-dimethyl-1,3-oxazolidine-3-carboxylate (4.3 g, 78%) as a colorless oil. LC-MS (ESI, m/z): 427 [M+H]$^+$.

Tert-butyl (4S)-4-((1-(tert-butoxycarbonyl)-5,5-dimethyl-2-oxopyrrolidin-3-yl)methyl)-2,2-dimethyloxazolidine-3-carboxylate (3.6 g) was purified by prep-SFC using the following gradient conditions: Column: Lux Sum Cellulose-2, 3*25 cm, 5 m; Mobile Phase A: CO$_2$, Mobile Phase B: IPA (0.5% 2 M NH$_3$-MeOH); Flow rate: 60 mL/min; Gradient: isocratic 10% B; Column Temperature (° C.): 35; Back Pressure (bar): 100; Wave Length: 220 nm; RT1 (min): 4.81; RT2 (min): 6.43; Sample Solvent: MeOH—Preparative; Injection Volume: 1.5 mL; Number Of Runs: 27. Purification resulted in tert-butyl (S)-4-(((S*)-1-(tert-butoxycarbonyl)-5,5-dimethyl-2-oxopyrrolidin-3-yl)methyl)-2,2-dimethyloxazolidine-3-carboxylate (990 mg) as an off-white solid (Lux Cellulose-2 4.6*50 mm, 3 m, 35° C. Co-Solvent: IPA (0.1% DEA), 10% to 50% in 2.0 min, hold 1.0 min at 50%): Rt: 0.969 min), and tert-butyl (S)-4-(((R*)-1-(tert-butoxycarbonyl)-5,5-dimethyl-2-oxopyrrolidin-3-yl)methyl)-2,2-dimethyloxazolidine-3-carboxylate (1.6 g) as an off-white solid Lux Cellulose-2 4.6*50 mm, 3 m, 35° C. Co-Solvent: IPA (0.1% DEA), 10% to 50% in 2.0 min, hold 1.0 min at 50%): Rt: 1.411 min).

A 40 mL vial was charged with tert-butyl (S)-4-(((R*)-1-(tert-butoxycarbonyl)-5,5-dimethyl-2-oxopyrrolidin-3-yl)methyl)-2,2-dimethyloxazolidine-3-carboxylate (1.6 g, 3.75 mmol, 1.0 eq.), para-toluene sulfonate (64.6 mg, 0.375 mmol, 0.1 eq.) and MeOH (20 mL). The mixture was stirred overnight at rt. The reaction was quenched with water (20 mL). The solution was extracted with EA (3×30 mL). The organic layers were combined, washed with brine (50 mL), dried over anhydrous sodium sulfate, filtered and concentrated under reduced pressure to provide tert-butyl(S)-4-((S)-2-((tert-butoxycarbonyl)amino)-3-hydroxypropyl)-2,2-dimethyl-5-oxopyrrolidine-1-carboxylate (1.47 g, crude) as an off-white semi-solid. LC-MS (ESI, m/z): 387 [M+H]$^+$.

To a solution of tert-butyl (S)-4-((R*)-2-((tert-butoxycarbonyl)amino)-3-hydroxypropyl)-2,2-dimethyl-5-oxopyrrolidine-1-carboxylate (1.7 g, 4.40 mmol, 1.0 eq.) in acetone (22 mL) was added 5% sodium bicarbonate solution (22 mL, 13.1 mmol, 3.0 eq.) and 2,2,6,6-Tetramethylpiperidinooxy (0.14 g, 0.88 mmol, 0.2 eq.). Chlorosylsodium (1.15 g, 15.4 mmol, 3.5 eq.) was added dropwise at 0° C. The mixture was stirred at rt overnight, and the reaction was quenched with water (20 mL). The solution was washed with Et2O (2×20 mL). The pH value of the aqueous solution was adjusted to 2 with concentrated hydrochloric acid (1 mol/L). The solution was extracted with EtOAc (3×50 mL). The organic layers were combined, washed with brine (50 mL), dried over anhydrous sodium sulfate, filtered and concentrated under reduced pressure to provide (S)-3-((R*)-1-(tert-butoxycarbonyl)-5,5-dimethyl-2-oxopyrrolidin-3-yl)-2-((tert-butoxycarbonyl)amino)propanoic acid (1.2 g, 61%) as a white solid.

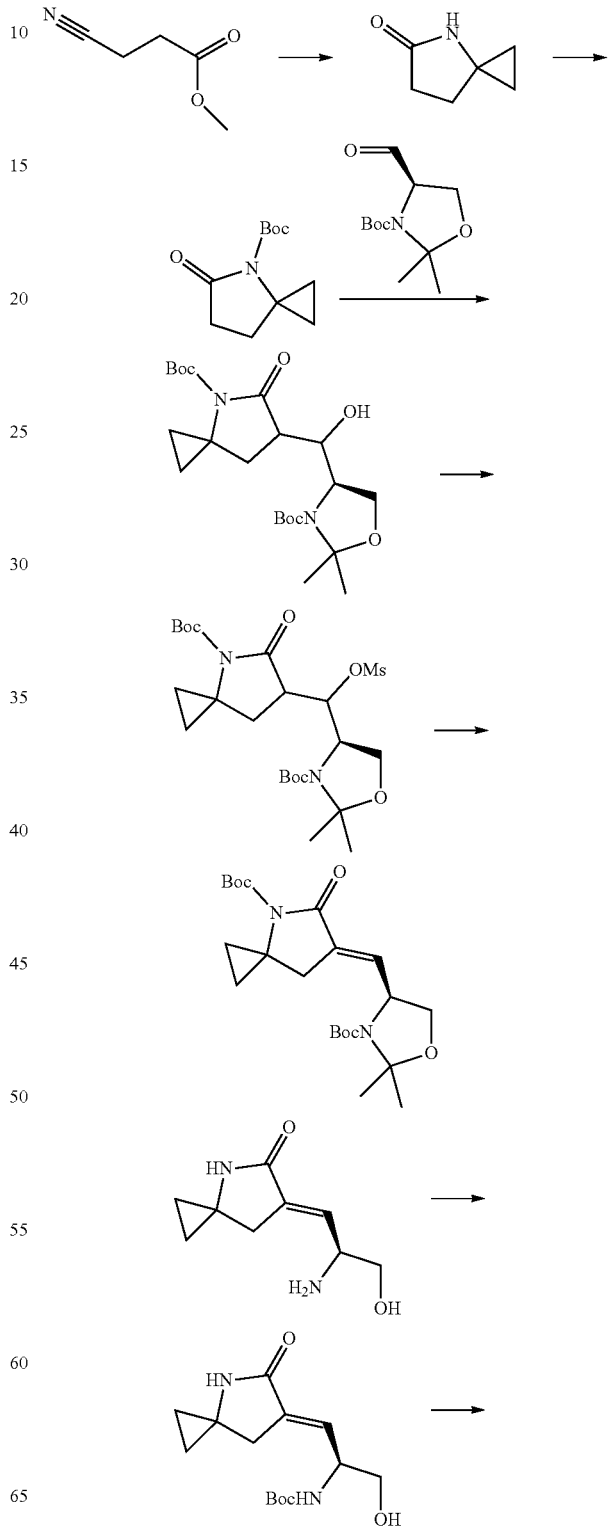

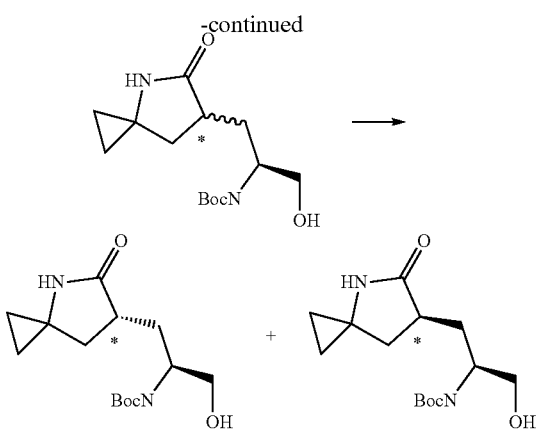

The absolute configuration of the chiral center noted with "*" is tentatively assigned.

To a solution of methyl 3-cyanopropanoate (10 g, 88.4 mmol, 1.0 eq.) in Et$_2$O (100 mL) was added Ti(O$^i$Pr)$_4$ (5.03 g, 17.7 mmol, 0.2 eq.). EtMgBr (194 mL, 1 M in THF, 194 mmol, 2.2 eq.) was then added dropwise under N$_2$. The mixture was stirred at rt for 2 h, and the reaction was quenched with water (20 mL). The mixture was extracted with EA (3×60 mL). The organic layers were combined, washed with brine (50 mL), dried over anhydrous sodium sulfate, filtered and concentrated under reduced pressure. The residue was chromatographed on a silica gel column with PE:MeOH (12:1) to provide 4-azaspiro[2.4]heptan-5-one (8.5 g, 69%) as a colorless oil. LC-MS (ESI, m/z): 112 [M+H]$^+$.

A 250 mL round-bottom flask was charged with 4-azaspiro[2.4]heptan-5-one (8.5 g, 76.5 mmol, 1.0 eq.), DCM (100 mL), di-tert-butyl dicarbonate (26.7 g, 122 mmol, 1.6 eq.), triethylamine (0.77 g, 7.65 mmol, 0.1 eq.) and DMAP (0.93 g, 7.65 mmol, 0.1 eq.). The resulting solution was stirred overnight at 40° C., and the reaction was quenched with water (70 mL). The solution was extracted with DCM (3×100 mL). The organic layers were combined, washed with brine (80 mL), dried over anhydrous sodium sulfate, filtered and concentrated under reduced pressure. The residue was chromatographed on a silica gel column with EA:PE (1:12) to provide tert-butyl 5-oxo-4-azaspiro[2.4]heptane-4-carboxylate (11 g, 58%) as a white solid. LC-MS (ESI, m/z): 212 [M+H]$^+$.

A 500 mL round-bottom flask was charged with tert-butyl 5-oxo-4-azaspiro[2.4]heptane-4-carboxylate (11 g, 52.1 mmol, 1.0 eq.) and THF (150 mL). The solution was cooled to −78° C. and LiHMDS (62.5 mL, 1 M in THF, 62.5 mmol, 1.2 eq.) was added. The mixture was stirred for 1 h at −78° C. and a solution of tert-butyl (4R)-4-formyl-2,2-dimethyl-1,3-oxazolidine-3-carboxylate (17.9 g, 78.1 mmol, 1.5 eq.) in THF (50 mL) under Ar was added. Stirring was continued at −78° C. for 1 h. The reaction was quenched with sat. ammonium chloride solution (100 mL). The solution was extracted with EA (3×200 mL). The organic layers were combined, washed with brine (200 mL), dried over anhydrous sodium sulfate, filtered and concentrated under reduced pressure. The residue was chromatographed on a silica gel column with EA:PE (1:8) to provide tert-butyl (4R)-4-((4-(tert-butoxycarbonyl)-5-oxo-4-azaspiro[2.4]heptan-6-yl)(hydroxy)methyl)-2,2-dimethyloxazolidine-3-carboxylate (19.7 g, 69%) as a colorless oil. LC-MS (ESI, m/z): 441 [M+H]$^+$.

A 500 mL round-bottom flask was charged with tert-butyl (4R)-4-((4-(tert-butoxycarbonyl)-5-oxo-4-azaspiro[2.4]heptan-6-yl)(hydroxy)methyl)-2,2-dimethyloxazolidine-3-carboxylate (19.7 g, 44.7 mmol, 1.0 eq.), DCM (250 mL), triethylamine (27.2 g, 268 mmol, 6.0 eq.) and MsCl (20.5 g, 179 mmol, 4.0 eq.). The mixture was stirred overnight at rt, and the reaction was quenched with water (100 mL). The solution was extracted with DCM (4×150 mL). The organic layers were combined, washed with brine (100 mL), dried over anhydrous sodium sulfate, filtered and concentrated under reduced pressure to provide tert-butyl (4R)-4-((4-(tert-butoxycarbonyl)-5-oxo-4-azaspiro[2.4]heptan-6-yl)((methylsulfonyl)oxy)methyl)-2,2-dimethyloxazolidine-3-carboxylate (22 g, crude) as an orange oil. LC-MS (ESI, m/z): 519 [M+H]$^+$.

A 500 mL round-bottom flask was charged with tert-butyl (4R)-4-((4-(tert-butoxycarbonyl)-5-oxo-4-azaspiro[2.4]heptan-6-yl)((methylsulfonyl)oxy)methyl)-2,2-dimethyloxazolidine-3-carboxylate (22 g, 42.4 mmol, 1.0 eq.), DCM (200 mL) and DBU (14.2 g, 93.3 mmol, 2.2 eq.). The mixture was stirred overnight at rt, and the reaction was quenched with water (80 mL). The solution was extracted with DCM (3×100 mL). The organic layers were combined, washed with brine (80 mL), dried over anhydrous sodium sulfate, filtered and concentrated under reduced pressure. The residue was chromatographed on a silica gel column with EA:PE (1:12) to provide tert-butyl 6-{[(4S)-3-(tert-butoxycarbonyl)-2,2-dimethyl-1,3-oxazolidin-4-yl]methylidene}-5-oxo-4-azaspiro[2.4]heptane-4-carboxylate (11.3 g, 57%) as a colorless oil. LC-MS (ESI, m/z): 423 [M+H]$^+$.

A 250 mL vial was charged with tert-butyl 6-{[(4S)-3-(tert-butoxycarbonyl)-2,2-dimethyl-1,3-oxazolidin-4-yl]methylidene}-5-oxo-4-azaspiro[2.4]heptane-4-carboxylate (11.3 g, 26.7 mmol, 1.0 eq.), 4-methylbenzenesulfonic acid (5.53 g, 32.1 mmol, 1.2 eq.) and MeOH (120 mL). The mixture was stirred overnight at rt, and then concentrated under reduced pressure to provide 6-[(2S)-2-amino-3-hydroxypropylidene]-4-azaspiro[2.4]heptan-5-one (5.8 g, crude) as an orange oil. LC-MS (ESI, m/z): 183 [M+H]$^+$.

To a solution of 6-[(2S)-2-amino-3-hydroxypropylidene]-4-azaspiro[2.4]heptan-5-one (5.8 g, 31.829 mmol, 1.00 eq.) in DCM (90 mL) was added triethylamine (25.8 g, 255 mmol, 8.0 eq.) and di-tert-butyl dicarbonate (20.8 g, 95.5 mmol, 3.0 eq.). The mixture was stirred at rt overnight, and the reaction was quenched with water (30 mL). The mixture was extracted with CDCl$_3$:isopropyl alcohol=3:1 (3×50 mL). The organic layers were combined, dried over anhydrous sodium sulfate, filtered and concentrated under reduced pressure. The residue was chromatographed on a silica gel column with MeOH:DCM (1:25) to provide tert-butyl N-[(2S)-1-hydroxy-3-[(6E)-5-oxo-4-azaspiro[2.4]heptan-6-ylidene]propan-2-yl]carbamate (3.9 g, 39%) as a brown yellow solid. LCMS (ESI, m/z): 283 [M+H]$^+$.

To a solution of tert-butyl N-[(2S)-1-hydroxy-3-[5-oxo-4-azaspiro[2.4]heptan-6-ylidene]propan-2-yl]carbamate (3.9 g, 13.8 mmol, 1.0 eq.) in THF (30 mL) and MeOH (90 mL) was added NiCl$_2$.6H$_2$O (23 g, 96.7 mmol, 7.0 eq.). NaBH$_4$ (11 g, 290 mmol, 21.0 eq.) was added in several portions at 0° C. The mixture was stirred at rt overnight, and the reaction was quenched with water (30 mL). The mixture was extracted with CDCl$_3$:isopropyl alcohol=3:1 (3×60 mL). The organic layers were combined, dried over anhydrous sodium sulfate, filtered and concentrated under reduced pressure. The residue was chromatographed on a C18 column with MeCN:H$_2$O (4:1) to provide tert-butyl N-[(2S)-1-hydroxy-3-{5-oxo-4-azaspiro[2.4]heptan-6- yl}propan-2-yl]carbamate (1.7 g, 39%) as a brown yellow solid. LCMS (ESI, m/z): 285 [M+H]+.

Tert-butyl N-[(2S)-1-hydroxy-3-{5-oxo-4-azaspiro[2.4]heptan-6-yl}propan-2-yl]carbamate (1.7 g) was purified by SFC using the following gradient conditions: Column: NB-Lux Sum i-Cellulose-5, 2.12*25 cm, 5 m; Mobile Phase A: $CO_2$, Mobile Phase B: MeOH (0.1% 2 M $NH_3$-MeOH); Flow rate: 100 mL/min; Gradient: isocratic 25% B; Column Temperature (° C.): 35; Back Pressure (bar): 100; Wave Length: 220 nm; RT1 (min): 3.37; RT2 (min): 4.02; Sample Solvent: MeOH—Preparative; Injection Volume: 1 mL; Number Of Runs: 40. Purification resulted in 590 mg of first eluding tert-butyl ((S)-1-hydroxy-3-((R*)-5-oxo-4-azaspiro[2.4]heptan-6-yl)propan-2-yl)carbamate as a brown yellow solid and 640 mg of last eluding tert-butyl ((S)-1-hydroxy-3-((S*)-5-oxo-4-azaspiro[2.4]heptan-6-yl)propan-2-yl)carbamate as a brown yellow solid.

Example 1

Compound 1

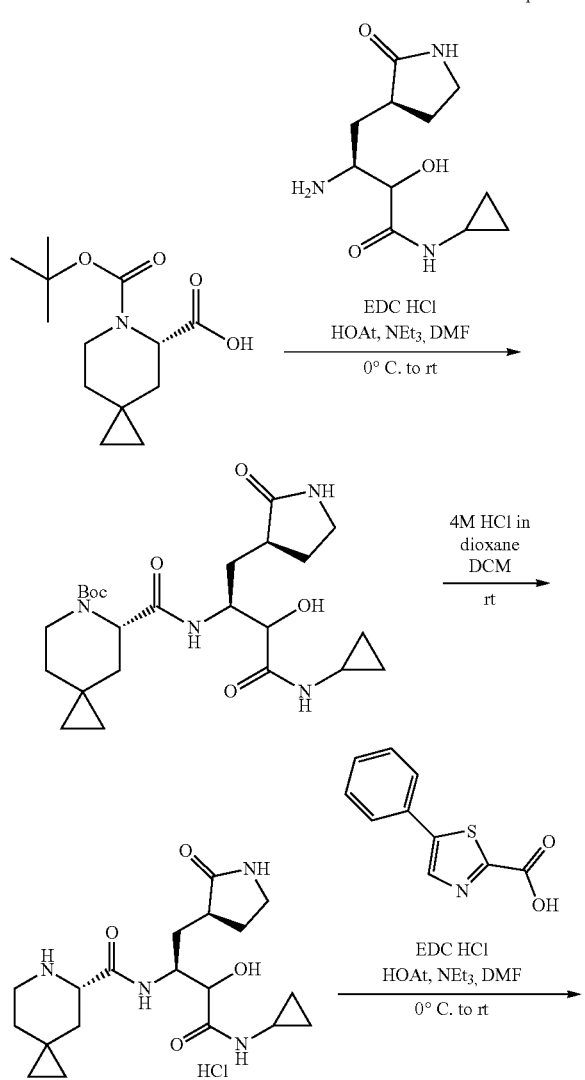

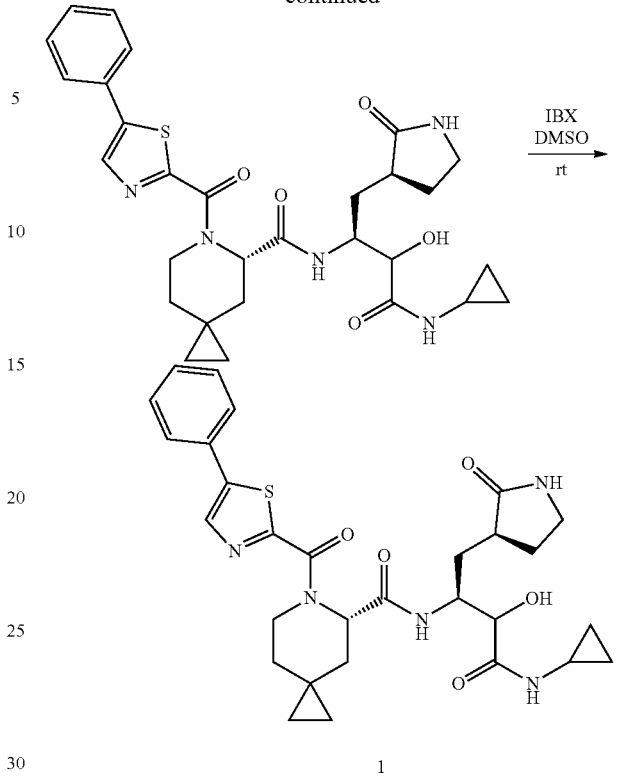

1

To a solution of (S)-6-(tert-butoxycarbonyl)-6-azaspiro[2.5]octane-5-carboxylic acid (1.79 g, 7.03 mmol, 1.0 eq.) in DMF (18 mL) cooled at 0° C. were added (3S)-3-amino-N-cyclopropyl-2-hydroxy-4-((S)-2-oxopyrrolidin-3-yl)butanamide hydrochloride (2.03 g, 8.44 mmol, 1.2 eq.), EDC·HCl (2.68 g, 14.1 mmol, 2.0 eq.), HOAt (956 mg, 7.03 mmol, 1.0 eq.) and $NEt_3$ (3.3 mL, 21.1 mmol, 3.0 eq.). The mixture was stirred at rt for 16 h. The mixture was diluted with water (20 mL) and extracted with EtOAc (5×20 mL). The organic phases were combined, washed with brine (30 mL), dried over $Na_2SO_4$, filtered and concentrated under reduced pressure. The residue was purified by flash chromatography on silica gel (40 g column) using 10% MeOH in DCM as the eluent to afford tert-butyl (5S)-5-(((2S)-4-(cyclopropylamino)-3-hydroxy-4-oxo-1-((S)-2-oxopyrrolidin-3-yl)butan-2-yl)carbamoyl)-6-azaspiro[2.5]octane-6-carboxylate (1.4 g, 38%) as an off-white solid. LC-MS (ESI, m/z): 479 [M+H]+.

To a solution of tert-butyl (5S)-5-(((2S)-4-(cyclopropylamino)-3-hydroxy-4-oxo-1-((S)-2-oxopyrrolidin-3-yl)butan-2-yl)carbamoyl)-6-azaspiro[2.5]octane-6-carboxylate (1.4 g, 2.92 mmol, 1.0 eq.) in DCM (14 mL) was added 4 M HCl in dioxane (7.0 mL, 28.0 mmol, 9.6 eq.). The mixture was stirred at rt for 5 h. The mixture was concentrated under reduced pressure and coevaporated with diethyl ether to afford (5S)—N-((2S)-4-(cyclopropylamino)-3-hydroxy-4-oxo-1-((S)-2-oxopyrrolidin-3-yl)butan-2-yl)-6-azaspiro[2.5]octane-5-carboxamide hydrochloride (1.35 g, crude) as an off-white solid. LC-MS (ESI, m/z): 379 [M+H]+.

To a solution of (5S)—N-((2S)-4-(cyclopropylamino)-3-hydroxy-4-oxo-1-((S)-2-oxopyrrolidin-3-yl)butan-2-yl)-6-azaspiro[2.5]octane-5-carboxamide hydrochloride (120 mg, 0.289 mmol, 1.0 eq.) in DMF (1.2 mL) cooled at 0° C. were added 5-phenylthiazole-2-carboxylic acid (71 mg, 0.347 mmol, 1.2 eq.), EDC·HCl (111 mg, 0.581 mmol, 2.0 eq.), HOAt (40 mg, 0.290 mmol, 1.0 eq.) and NEt₃ (0.12 mL, 0.871 mmol, 3.0 eq.). The mixture was stirred at rt for 16 h. The mixture was diluted with water (5 mL) and extracted with EA (3×10 mL). The organic phases were combined, washed with brine (3×5 mL), dried over Na₂SO₄, filtered and concentrated under reduced pressure. The residue was purified by flash chromatography on silica gel (12 g column) using a gradient of MeOH (1 to 10%) in DCM to afford (S)—N—((S)-4-(cyclopropylamino)-3,4-dioxo-1-((S)-2-oxopyrrolidin-3-yl)butan-2-yl)-6-(5-phenylthiazole-2-carbonyl)-6-azaspiro[2.5]octane-5-carboxamide (85 mg, 51%) as an off-white solid. LC-MS (ESI, m/z): 566 [M+H]⁺.

To a solution of (S)—N—((S)-4-(cyclopropylamino)-3,4-dioxo-1-((S)-2-oxopyrrolidin-3-yl)butan-2-yl)-6-(5-phenylthiazole-2-carbonyl)-6-azaspiro[2.5]octane-5-carboxamide (85 mg, 0.150 mmol, 1.0 eq.) in DMSO (1.7 mL) was added IBX (84 mg, 0.300 mmol, 2.0 eq.). The mixture was stirred at rt for 16 h. The mixture was diluted with EA, washed with sat. NaHCO₃ (3×5 mL) and brine (3×5 mL), dried over Na₂SO₄, filtered and concentrated under reduced pressure. The residue was purified by flash chromatography on silica gel (12 g column) using a gradient of MeOH (1 to 10%) in DCM and by prep-HPLC (Column: X-SELECT-C18, 19×250 mm Sum; Mobile Phase A: water, Mobile Phase B: ACN; Flow rate: 17 mL/min; Gradient: 10% B to 60% B in 8 min) to afford (S)—N—((S)-4-(cyclopropylamino)-3,4-dioxo-1-((S)-2-oxopyrrolidin-3-yl)butan-2-yl)-6-(5-phenylthiazole-2-carbonyl)-6-azaspiro[2.5]octane-5-carboxamide (40 mg, 47%) as an off-white solid. ¹H NMR (500 MHz, 363K, DMSO-d₆) δ 8.34 (m, 2H), 8.19 (brs, 1H), 7.69 (d, 2H), 7.39-7.50 (m, 3H), 7.34 (brs, 1H), 5.06 (m, 2H), 3.30-3.50 (m, 1H), 3.00-3.20 (m, 3H), 2.74 (m, 1H), 2.34 (m, 1H), 2.15 (m, 2H), 1.92 (m, 2H), 1.65-1.75 (m, 3H), 1.01 (d, 1H), 0.52-0.69 (m, 5H), 0.22-0.34 (m, 3H). LCMS (ESI, m/z): 564 [M+H]⁺.

Example 2

Compound 2

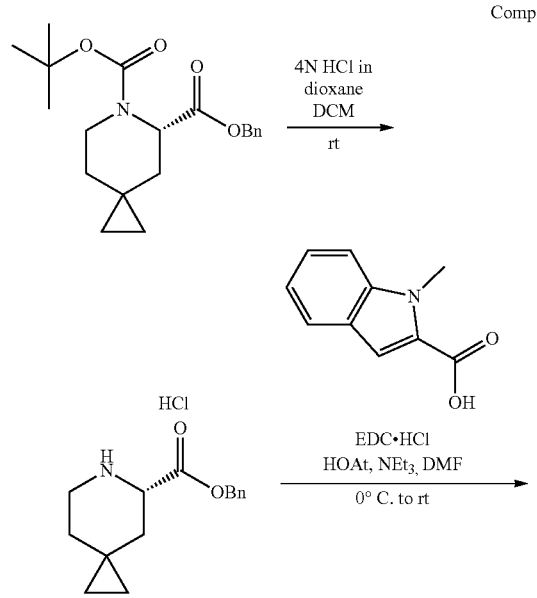

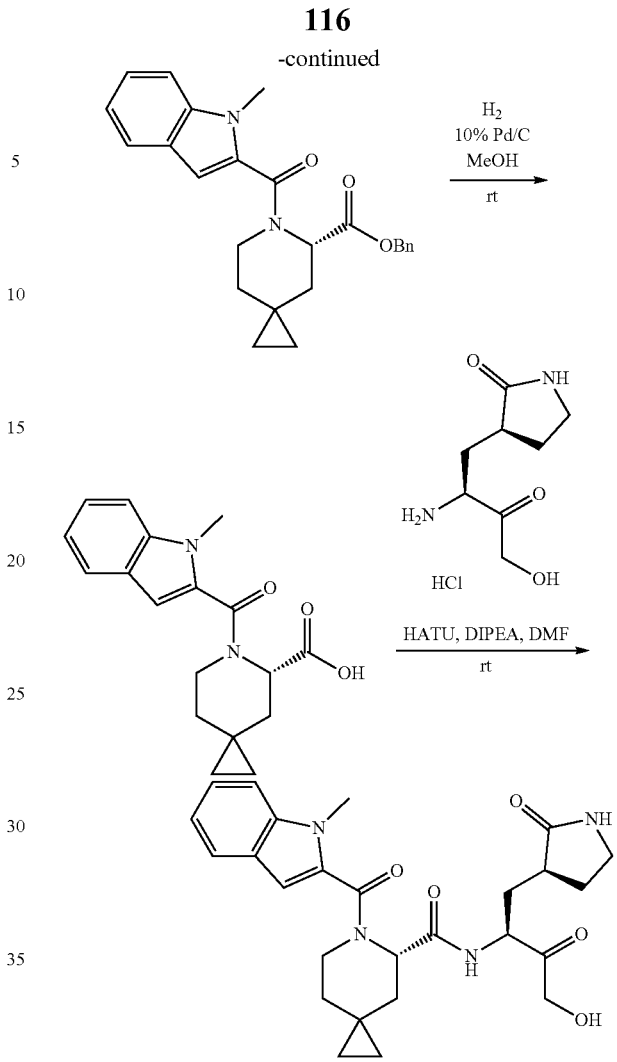

To a solution of 5-benzyl 6-(tert-butyl) (S)-6-azaspiro[2.5]octane-5,6-dicarboxylate (150 mg, 0.434 mmol, 1.0 eq.) in DCM (1.5 mL) cooled at 0° C. was added 4N HCl in dioxane (0.54 mL, 2.17 mmol, 5.0 eq.). The mixture was stirred at rt for 4 h and then concentrated under reduced pressure to afford 5-benzyl 6-(tert-butyl) (S)-6-azaspiro[2.5]octane-5,6-dicarboxylate hydrochloride (126 mg, 98%) as a brown oil. LCMS (ESI, m/z): 246 [M+H]⁺.

To a solution of 1-methyl-1H-indole-2-carboxylic acid (75 mg, 0.429 mmol, 1.0 eq.) and 5-benzyl 6-(tert-butyl) (S)-6-azaspiro[2.5]octane-5,6-dicarboxylate hydrochloride (126 mg, 0.305 mmol, 1.2 eq.) in DMF (2 mL) cooled at 0° C. were added EDC·HCl (162 mg, 0.845 mmol, 2.0 eq.), HOAt (58 mg, 0.426 mmol, 1.0 eq.) and NEt₃ (0.3 mL, 2.15 mmol, 5.0 eq.). The mixture was stirred at rt for 16 h. The mixture was diluted with water (10 mL) and extracted with EA (3×10 mL). The organic phases were combined, washed with brine (20 mL), dried over Na₂SO₄, filtered and concentrated under reduced pressure. The residue was purified by flash chromatography on silica gel (24 g column) using a gradient of EA (15 to 25%) in petroleum ether (PE) to afford benzyl (S)-6-(1-methyl-1H-indole-2-carbonyl)-6-azaspiro[2.5]octane-5-carboxylate (140 mg, 81%) as an off-white solid. LCMS (ESI, m/z): 403 [M+H]⁺.

To a solution of benzyl (S)-6-(1-methyl-1H-indole-2-carbonyl)-6-azaspiro[2.5]octane-5-carboxylate (180 mg, 0.447 mmol, 1.0 eq.) in MeOH (10 mL) was added 10% Pd/C (90 mg). The mixture was stirred at rt under hydrogen atmosphere for 16 h. The mixture was filtered through celite, and the solids were washed with DCM (20 mL). The filtrate was concentrated under reduced pressure to afford (S)-6-(1-methyl-1H-indole-2-carbonyl)-6-azaspiro[2.5]octane-5-carboxylic acid (130 mg, 93%) as an off-white solid. LCMS (ESI, m/z): 313 [M+H]+.

To a solution of (S)-6-(1-methyl-1H-indole-2-carbonyl)-6-azaspiro[2.5]octane-5-carboxylic acid (110 mg, 0.352 mmol, 1.0 eq.) and (S)-3-((S)-2-amino-4-hydroxy-3-oxobutyl)pyrrolidin-2-one hydrochloride (79 mg, 0.355 mmol, 1.0 eq.) in DMF (2 mL) cooled at 0° C. were added HATU (198 mg, 0.521 mmol, 1.5 eq.) and DIPEA (0.3 mL, 1.75 mmol, 5.0 eq.). The mixture was stirred at rt for 2 h. The mixture was diluted with water (5 mL) and extracted with EA (3×10 mL). The organic phases were combined, dried over Na2SO4, filtered and concentrated under reduced pressure. The residue was purified by prep-HPLC (Column: X-SELECT-C18, 19×250 mm 5 um; Mobile Phase A: 10 mM NH4HCO3 in water, Mobile Phase B: ACN; Flow rate: 17 mL/min; Gradient: 10% B to 60% B in 8 min) to afford (S)—N—((S)-4-hydroxy-3-oxo-1-((S)-2-oxopyrrolidin-3-yl)butan-2-yl)-6-(1-methyl-1H-indole-2-carbonyl)-6-azaspiro[2.5]octane-5-carboxamide (25 mg, 15%) as an off-white solid. LCMS (ESI, m/z): 481 [M+H]+.

Example 3

Compound 3

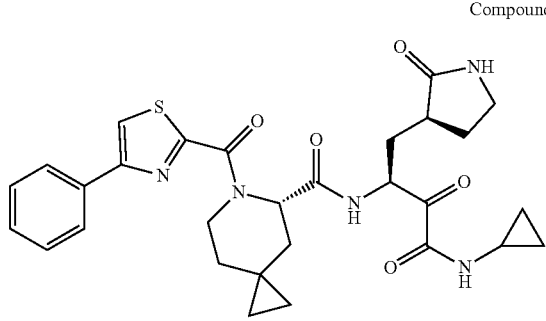

Compound 3 was prepared similarly as described for Compound 1 using 4-phenylthiazole-2-carboxylic acid in place of 5-phenylthiazole-2-carboxylic acid. 1H NMR (400 MHz, 362K, DMSO-d6) δ 8.37-8.46 (m, 1H), 8.30 (m, 1H), 8.24 (s, 1H), 7.92 (d, 2H), 7.43 (t, 2H), 7.35 (t, 1H), 7.27 (brs, 1H), 5.00-5.17 (m, 2H), 3.25-3.60 (m, 2H), 3.18 (m, 2H), 2.73 (m, 1H), 1.90-2.30 (m, 5H), 1.66-1.77 (m, 3H), 1.04 (d, 1H), 0.55-0.69 (m, 5H), 0.26-0.33 (m, 3H). LCMS (ESI, m/z): 564 [M+H]+.

Example 4

Compound 4

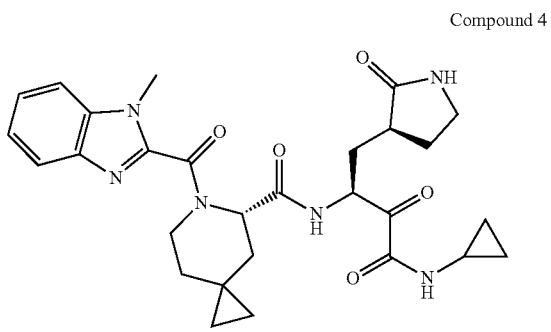 [SMILES: Cn1c(C(=O)N2CCC3(CC3)C[C@H]2C(=O)N[C@@H](C[C@@H]2CCNC2=O)C(=O)C(=O)NC2CC2)nc2ccccc21]

Compound 4 was prepared similarly as described for Compound 1 using 1-methyl-1H-benzo[d]imidazole-2-carboxylic acid in place of 5-phenylthiazole-2-carboxylic acid. LCMS (ESI, m/z): 533 [M−H]−.

Example 5

Compound 5

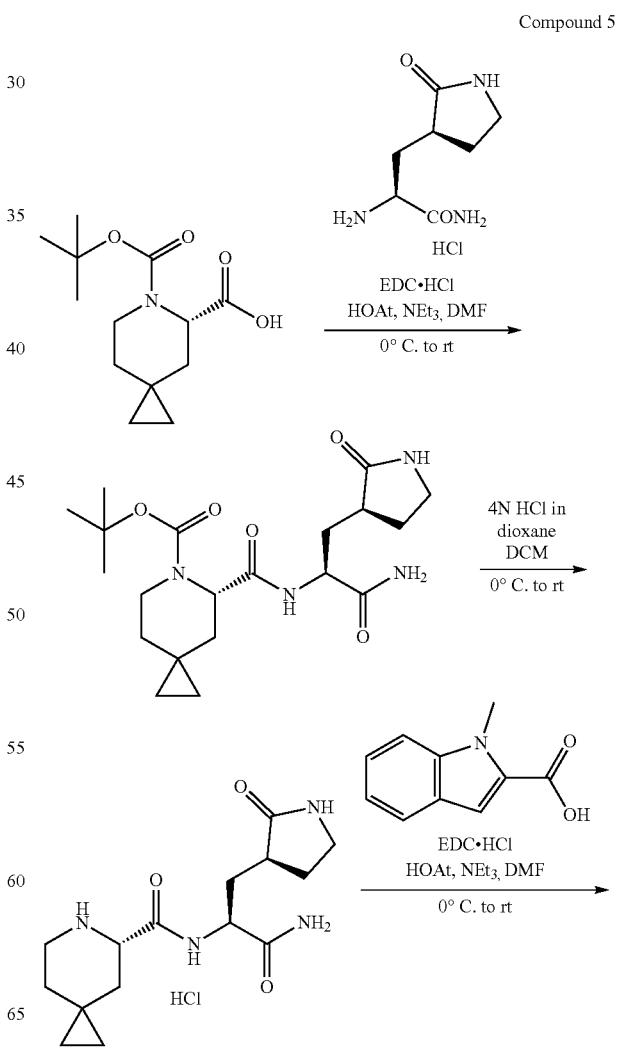

119

-continued

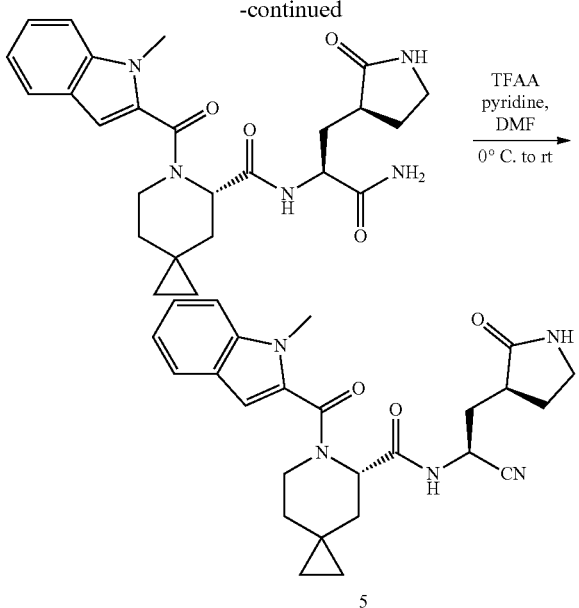

5

To a solution of (S)-6-(tert-butoxycarbonyl)-6-azaspiro[2.5]octane-5-carboxylic acid (260 mg, 1.02 mmol, 1.0 eq.) in DMF (3 mL) cooled at 0° C. were added (S)-2-amino-3-((S)-2-oxopyrrolidin-3-yl)propanamide hydrochloride (209 mg, 1.22 mmol, 1.1 eq.), EDC·HCl (309 mg, 2.04 mmol, 2.0 eq.), HOAt (139 mg, 1.02 mmol, 1.0 eq.) and NEt₃ (0.4 mL, 3.06 mmol, 3.0 eq.). The mixture was stirred at rt for 16 h. The mixture was diluted with water (10 mL) and extracted with DCM (3×10 mL). The organic phases were combined, washed with brine (30 mL), dried over Na₂SO₄, filtered and concentrated under reduced pressure. The residue was purified by flash chromatography on silica gel (24 g column) using a gradient of MeOH (1 to 5%) in DCM as the eluent to afford tert-butyl (S)-5-(((S)-1-amino-1-oxo-3-((S)-2-oxopyrrolidin-3-yl)propan-2-yl)carbamoyl)-6-azaspiro[2.5]octane-6-carboxylate (250 mg, 60%) as an off-white solid. LC-MS (ESI, m/z): 409 [M+H]⁺.

To a solution of tert-butyl (S)-5-(((S)-1-amino-1-oxo-3-((S)-2-oxopyrrolidin-3-yl)propan-2-yl)carbamoyl)-6-azaspiro[2.5]octane-6-carboxylate (200 mg, 0.490 mmol, 1.0 eq.) in DCM (14 mL) cooled at 0° C. was added 4N HCl in dioxane (1.0 mL, 4.00 mmol, 8.2 eq.). The mixture was stirred at rt for 16 h and then concentrated under reduced pressure to afford (S)—N—((S)-1-amino-1-oxo-3-((S)-2-oxopyrrolidin-3-yl)propan-2-yl)-6-azaspiro[2.5]octane-5-carboxamide (200 mg, 75%) as an off-white solid. LC-MS (ESI, m/z): 309 [M+H]⁺.

To a solution of (S)—N—((S)-1-amino-1-oxo-3-((S)-2-oxopyrrolidin-3-yl)propan-2-yl)-6-azaspiro[2.5]octane-5-carboxamide hydrochloride (200 mg, 0.649 mmol, 1.0 eq.) in DMF (4 mL) cooled at 0° C. were added 1-methyl-1H-indole-2-carboxylic acid (136 mg, 1.17 mmol, 1.2 eq.), EDC·HCl (248 mg, 1.30 mmol, 2.0 eq.), HOAt (88 mg, 0.649 mmol, 1.0 eq.) and NEt₃ (0.28 mL, 1.95 mmol, 3.0 eq.). The mixture was stirred at rt for 16 h. The mixture was diluted with water (10 mL) and extracted with DCM (3×10 mL). The organic phases were combined, washed with brine (20 mL), dried over Na₂SO₄, filtered and concentrated under reduced pressure. The residue was purified by flash chromatography on silica gel (24 g column) using a gradient of MeOH (1 to 5%) in DCM to afford (S)—N—((S)-1-amino-1-oxo-3-((S)-2-oxopyrrolidin-3-yl)propan-2-yl)-6-(1-

120 methyl-1H-indole-2-carbonyl)-6-azaspiro[2.5]octane-5-carboxamide (200 mg, 66%) as an off-white solid. LC-MS (ESI, m/z): 466 [M+H]⁺.

To a solution of (S)—N—((S)-1-amino-1-oxo-3-((S)-2-oxopyrrolidin-3-yl)propan-2-yl)-6-(1-methyl-1H-indole-2-carbonyl)-6-azaspiro[2.5]octane-5-carboxamide (150 mg, 0.322 mmol, 1.0 eq.) in DMF (3 mL) cooled at 0° C. were added pyridine (70 mg, 0.806 mmol, 2.5 eq.) and a solution of TFAA (0.02 mL, 0.322 mmol, 1.0 eq.) in DMF (1 mL). The mixture was stirred at rt for 45 min. The mixture was diluted with water and then extracted with EA (2×20 mL). The organic phases were combined, dried over Na₂SO₄, filtered and concentrated under reduced pressure. The residue was purified by preparative TLC using 5% MeOH in DCM and by prep-HPLC (Column: X-SELECT-C18, 19×250 mm 5 um; Mobile Phase A: 10 mM NH₄HCO₃ in water, Mobile Phase B: ACN; Flow rate: 17 mL/min; Gradient: 10% B to 60% B in 8 min) to afford (S)—N—((S)-1-cyano-2-((S)-2-oxopyrrolidin-3-yl)ethyl)-6-(1-methyl-1H-indole-2-carbonyl)-6-azaspiro[2.5]octane-5-carboxamide (58 mg, 44%) as an off-white solid. ¹H NMR (400 MHz, 372K, DMSO-d₆) δ 8.50 (d, 1H), 7.55 (d, 1H), 7.44 (d, 1H), 7.33 (s, 1H), 7.22 (t, 1H), 7.06 (t, 1H), 6.56 (s, 1H), 5.00 (m, 2H), 4.16 (d, 1H), 3.75 (s, 3H), 3.46 (t, 1H), 3.16 (m, 2H), 2.11-2.32 (m, 4H), 1.87 (m, 2H), 1.74 (m, 1H), 1.63 (d, 1H), 0.98 (d, 1H), 0.31-0.47 (m, 4H). LCMS (ESI, m/z): 446 [M−H]⁻.

Example 6

Compound 6

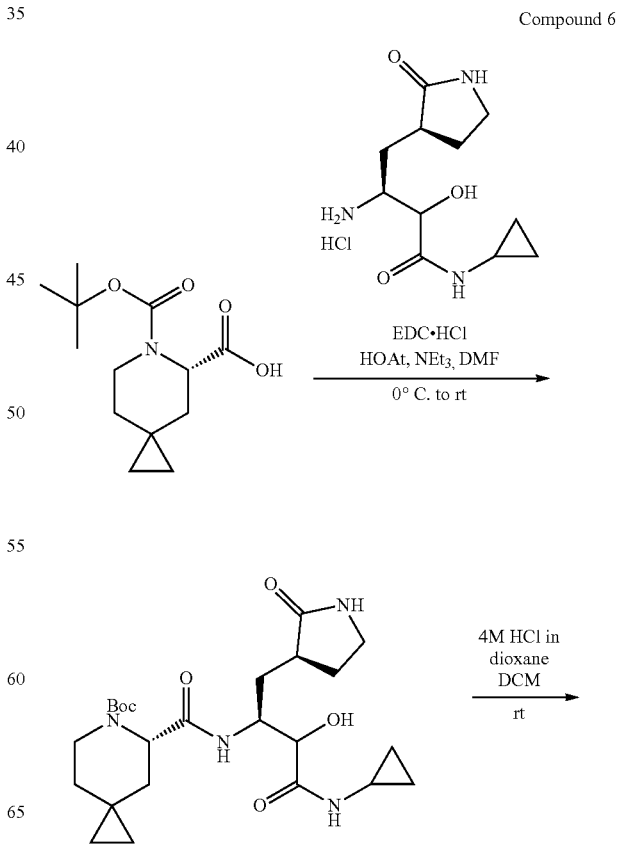

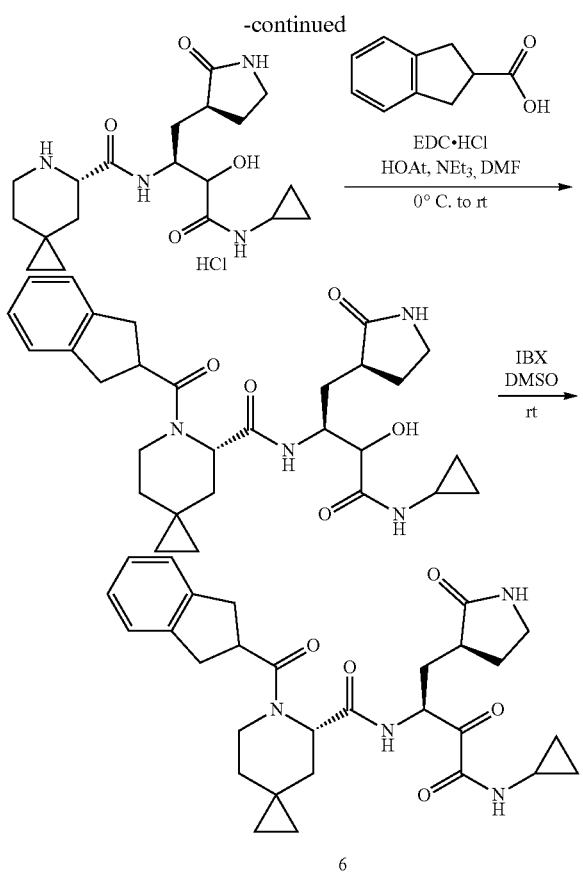

To a solution of (S)-6-(tert-butoxycarbonyl)-6-azaspiro[2.5]octane-5-carboxylic acid (1.79 g, 7.03 mmol, 1.0 eq.) in DMF (18 mL) cooled at 0° C. were added (3S)-3-amino-N-cyclopropyl-2-hydroxy-4-((S)-2-oxopyrrolidin-3-yl)butanamide hydrochloride (2.03 g, 8.44 mmol, 1.2 eq.), EDC·HCl (2.68 g, 14.1 mmol, 2.0 eq.), HOAt (956 mg, 7.03 mmol, 1.0 eq.) and NEt₃ (3.3 mL, 21.1 mmol, 3.0 eq.). The mixture was stirred at rt for 16 h. The mixture was diluted with water (20 mL) and extracted with EtOAc (5×20 mL). The organic phases were combined, washed with brine (30 mL), dried over Na₂SO₄, filtered and concentrated under reduced pressure. The residue was purified by flash chromatography on silica gel (40 g column) using 10% MeOH in DCM as the eluent to afford tert-butyl (5S)-5-(((2S)-4-(cyclopropylamino)-3-hydroxy-4-oxo-1-((S)-2-oxopyrrolidin-3-yl)butan-2-yl)carbamoyl)-6-azaspiro[2.5]octane-6-carboxylate (1.4 g, 38%) as an off-white solid. LC-MS (ESI, m/z): 479 [M+H]⁺.

To a solution of tert-butyl (5S)-5-(((2S)-4-(cyclopropylamino)-3-hydroxy-4-oxo-1-((S)-2-oxopyrrolidin-3-yl)butan-2-yl)carbamoyl)-6-azaspiro[2.5]octane-6-carboxylate (1.4 g, 2.92 mmol, 1.0 eq.) in DCM (14 mL) was added 4 M HCl in dioxane (7.0 mL, 28.0 mmol, 9.6 eq.). The mixture was stirred at rt for 5 h. The mixture was concentrated under reduced pressure and coevaporated with diethyl ether to afford (5S)—N-((2S)-4-(cyclopropylamino)-3-hydroxy-4-oxo-1-((S)-2-oxopyrrolidin-3-yl)butan-2-yl)-6-azaspiro[2.5]octane-5-carboxamide hydrochloride (1.35 g, crude) as an off-white solid. LC-MS (ESI, m/z): 379 [M+H]⁺.

To a solution of (5S)—N-((2S)-4-(cyclopropylamino)-3-hydroxy-4-oxo-1-((S)-2-oxopyrrolidin-3-yl)butan-2-yl)-6-azaspiro[2.5]octane-5-carboxamide hydrochloride (120 mg, 0.289 mmol, 1.0 eq.) in DMF (1.2 mL) cooled at 0° C. were added 2,3-dihydro-1H-indene-2-carboxylic acid (52 mg, 0.321 mmol, 1.1 eq.), EDC·HCl (111 mg, 0.581 mmol, 2.0 eq.), HOAt (39 mg, 0.290 mmol, 1.0 eq.) and NEt₃ (0.12 mL, 0.871 mmol, 3.0 eq.). The mixture was stirred at rt for 16 h. The mixture was diluted with water (10 mL) and extracted with EA (3×10 mL). The organic phases were combined, washed with brine (3×5 mL), dried over Na₂SO₄, filtered and concentrated under reduced pressure. The residue was purified by flash chromatography on silica gel (12 g column) using a gradient of MeOH (1 to 10%) in DCM to afford (5S)—N-((2S)-4-(cyclopropylamino)-3-hydroxy-4-oxo-1-((S)-2-oxopyrrolidin-3-yl)butan-2-yl)-6-(2,3-dihydro-1H-indene-2-carbonyl)-6-azaspiro[2.5]octane-5-carboxamide (76 mg, 50%) as an off-white solid. LC-MS (ESI, m/z): 523 [M+H]⁺.

To a solution of (5S)—N-((2S)-4-(cyclopropylamino)-3-hydroxy-4-oxo-1-((S)-2-oxopyrrolidin-3-yl)butan-2-yl)-6-(2,3-dihydro-1H-indene-2-carbonyl)-6-azaspiro[2.5]octane-5-carboxamide (76 mg, 0.145 mmol, 1.0 eq.) in DMSO (1.5 mL) was added IBX (82 mg, 0.293 mmol, 2.0 eq.). The mixture was stirred at rt for 24 h. The mixture was diluted with EA (10 mL), washed with sat. NaHCO₃ (3×5 mL) and brine (3×5 mL), dried over Na₂SO₄, filtered and concentrated under reduced pressure. The residue was purified by flash chromatography on silica gel (12 g column) using a gradient of MeOH (1 to 10%) in DCM to afford (S)—N—((S)-4-(cyclopropylamino)-3,4-dioxo-1-((S)-2-oxopyrrolidin-3-yl)butan-2-yl)-6-(2,3-dihydro-1H-indene-2-carbonyl)-6-azaspiro[2.5]octane-5-carboxamide (38 mg, 50%) as an off-white solid. ¹H NMR (400 MHz, 363K, DMSO-d₆) δ 8.15-8.30 (m, 2H), 7.32 (brs, 1H), 7.05-7.18 (m, 4H), 5.06 (m, 2H), 3.90-4.25 (m, 1H), 3.36-3.70 (m, 2H), 3.02-3.24 (m, 6H), 2.74 (m, 1H), 2.33 (m, 1H), 2.23 (m, 1H), 1.89-2.04 (m, 2H), 1.61-1.83 (m, 4H), 0.96 (d, 1H), 0.59-0.70 (m, 4H), 0.51 (m, 1H), 0.20-0.30 (m, 3H). LCMS (ESI, m/z): 521 [M+H]⁺.

Example 7

Compound 7

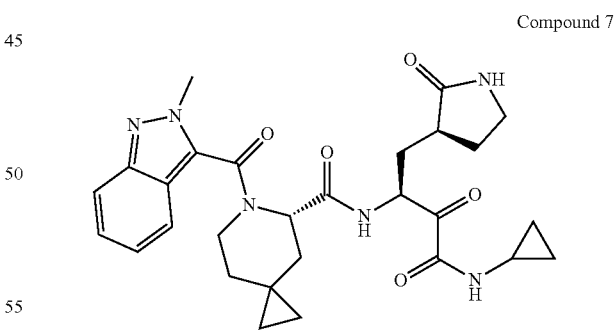

Compound 7 was prepared similarly as described for Compound 6 using 2-methyl-2H-indazole-3-carboxylic acid in place of 2,3-dihydro-1H-indene-2-carboxylic acid. ¹H NMR (400 MHz, 363K, DMSO-d₆) δ 8.40 (m, 1H), 8.28 (m, 1H), 7.63 (m, 2H), 7.36 (brs, 1H), 7.27 (t, 1H), 7.14 (t, 1H), 5.08 (m, 1H), 4.89 (brs, 1H), 4.13 (s, 3H), 3.90 (brs, 1H), 3.53 (m, 1H), 3.08-3.20 (m, 2H), 2.74 (m, 1H), 2.10-2.26 (m, 3H), 1.80-1.95 (m, 2H), 1.60-1.75 (m, 3H), 0.93 (d, 1H), 0.50-0.72 (m, 5H), 0.20-0.35 (m, 3H). LCMS (ESI, m/z): 535 [M+H]⁺.

Example 8

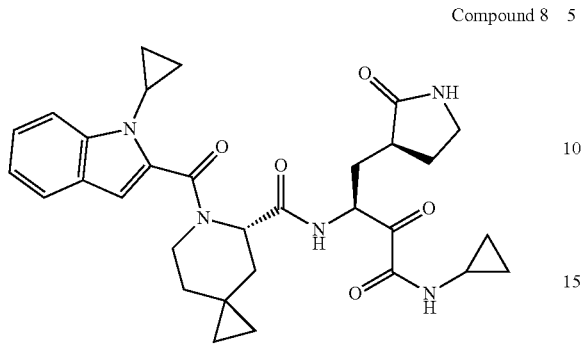

Compound 8

Compound 8 was prepared similarly as described for Compound 6 using 1-cyclopropyl-1H-indole-2-carboxylic acid in place of 2,3-dihydro-1H-indene-2-carboxylic acid. $^1$H NMR (400 MHz, 363K, DMSO-d$_6$) δ 8.26-8.39 (m, 2H), 7.55 (m, 2H), 7.40-7.38 (m, 1H), 7.21 (t, 1H), 7.06 (t, 1H), 6.52 (m, 1H), 5.13 (m, 2H), 3.38-3.50 (m, 2H), 3.35 (m, 1H), 3.10-3.22 (m, 2H), 2.76 (m, 1H), 2.05-2.31 (m, 3H), 1.58-1.88 (m, 5H), 1.03-1.07 (m, 2H), 0.88-0.98 (m, 3H), 0.42-0.70 (m, 5H), 0.29 (m, 3H). LCMS (ESI, m/z): 558 [M–H]$^-$.

1-Cyclopropyl-1H-indole-2-carboxylic acid: To a solution of methyl 1H-indole-2-carboxylate (250 mg, 1.42 mmol, 1.0 eq.) in DCE (4 mL) were added cyclopropylboronic acid (245 mg, 2.85 mmol, 2.0 eq.), copper(II) acetate (257 mg, 1.42 mmol, 1.0 eq.), 2,2'-bipyridyl (221 mg, 1.42 mmol, 1.0 eq.) and sodium carbonate (299 mg, 2.85 mmol, 2.0 eq.). The mixture was heated at 70° C. for 19 h. Cyclopropylboronic acid (245 mg, 2.85 mmol, 2.0 eq.) and sodium carbonate (299 mg, 2.85 mmol, 2.0 eq.) were added, and the mixture was heated at 70° C. for 8 h. Cyclopropylboronic acid (245 mg, 2.85 mmol, 2.0 eq.), sodium carbonate (299 mg, 2.85 mmol, 2.0 eq.), copper (II) acetate (257 mg, 1.42 mmol, 1.0 eq.), and 2,2'-bipyridyl (221 mg, 1.42 mmol, 1.0 eq.) were added, and the mixture was heated at 70° C. for 16 h. After cooling to rt, the mixture was diluted with sat. NH$_4$Cl and extracted with EA (2×25 mL). The organic phases were combined, washed with brine (2×20 mL), dried over Na$_2$SO$_4$, filtered and concentrated under reduced pressure. The residue was purified by flash chromatography on silica gel (24 g column) using a gradient of EA (5 to 15%) in PE to afford methyl 1-cyclopropyl-1H-indole-2-carboxylate (220 mg, 72%) as an off-white solid. LC-MS (ESI, m/z): 216 [M+H]$^+$.

To a solution of methyl 1-cyclopropyl-1H-indole-2-carboxylate (220 mg, 1.02 mmol, 1.0 eq.) in THF (1.1 mL) and water (1.1 mL) was added LiOH (82 mg, 2.04 mmol, 2.0 eq.). The mixture was stirred at rt for 16 h and then concentrated under reduced pressure. The residue was taken up with 1N HCl and extracted with EA (2×10 mL). The organic phases were combined, dried over Na$_2$SO$_4$, filtered and concentrated under reduced pressure to afford 1-cyclopropyl-1H-indole-2-carboxylic acid (168 mg, 82%) as an off-white solid. LC-MS (ESI, m/z): 202 [M+H]$^+$.

Example 9

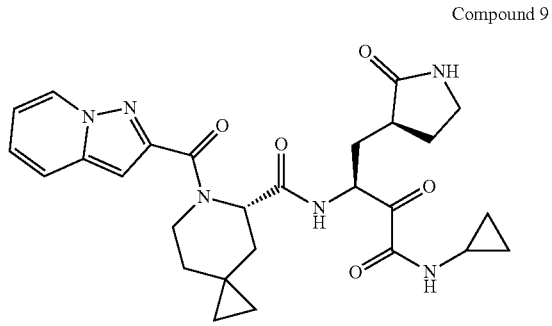 [SMILES: O=C(NC1CC1)C(=O)[C@H](C[C@@H]1CCNC1=O)NC(=O)[C@@H]1CC2(CCN1C(=O)c1cc3ccccn3n1)CC2]

Compound 9

Compound 9 was prepared similarly as described for Compound 6 using pyrazolo[1,5-a]pyridine-2-carboxylic acid in place of 2,3-dihydro-1H-indene-2-carboxylic acid. LCMS (ESI, m/z): 521 [M+H]$^+$.

Example 10

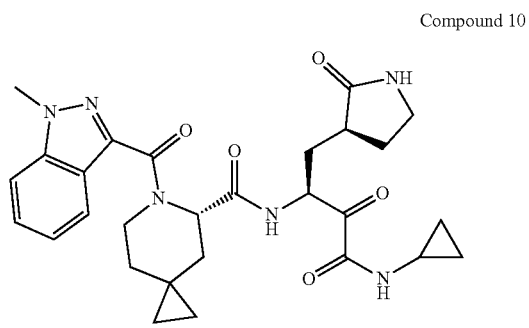 [SMILES: Cn1nc(C(=O)N2CCC3(CC3)C[C@H]2C(=O)N[C@@H](C[C@@H]2CCNC2=O)C(=O)C(=O)NC2CC2)c2ccccc21]

Compound 10

Compound 10 was prepared similarly as described for Compound 6 using 1-methyl-1H-indazole-3-carboxylic acid in place of 2,3-dihydro-1H-indene-2-carboxylic acid. LCMS (ESI, m/z): 533 [M–H]$^-$.

Example 11

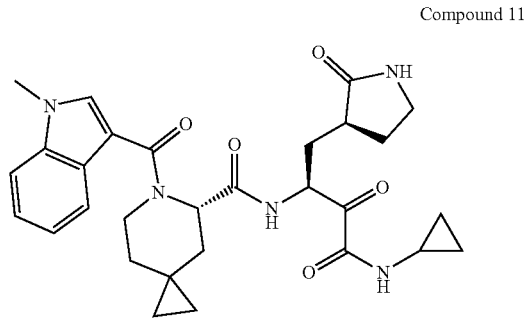 [SMILES: Cn1cc(C(=O)N2CCC3(CC3)C[C@H]2C(=O)N[C@@H](C[C@@H]2CCNC2=O)C(=O)C(=O)NC2CC2)c2ccccc21]

Compound 11

Compound 11 was prepared similarly as described for Compound 6 using 1-methyl-1H-indole-3-carboxylic acid in place of 2,3-dihydro-1H-indene-2-carboxylic acid. LCMS (ESI, m/z): 532 [M–H]$^-$.

Example 12

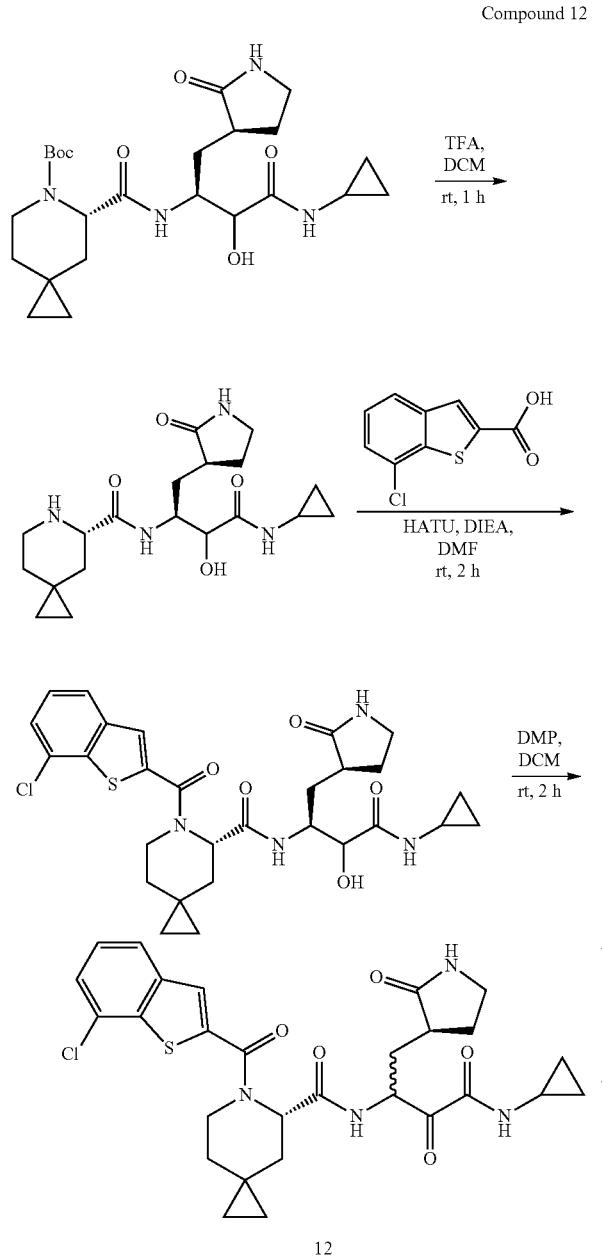

12

A 8 mL vial was charged with tert-butyl (5S)-5-(((2S)-4-(cyclopropylamino)-3-hydroxy-4-oxo-1-((S)-2-oxopyrrolidin-3-yl)butan-2-yl)carbamoyl)-6-azaspiro[2.5]octane-6-carboxylate (110 mg, 0.230 mmol, 1.0 eq.) in DCM (3 mL). Trifluoroacetic acid (1 mL) was added, and the mixture was stirred for 1 h at room temperature (rt). The mixture was concentrated under reduced pressure to provide (5S)—N-((2S)-4-(cyclopropylamino)-3-hydroxy-4-oxo-1-((S)-2-oxopyrrolidin-3-yl)butan-2-yl)-6-azaspiro[2.5]octane-5-carboxamide (95 mg, 97%) as a yellow solid. LC-MS (ESI, m/z): 379 [M+H]⁺.

A 40 mL vial was charged with 7-chloro-1-benzothiophene-2-carboxylic acid (48.76 mg, 0.229 mmol, 1.1 eq.) in DMF (5 mL). N,N,N',N'-tetramethyl-O-(7-azabenzotriazol-1-yl)uronium hexafluorophosphate (87.2 mg, 0.229 mmol, 1.1 eq.) and N,N-diisopropylethylamine (0.11 mL, 0.624 mmol, 3.0 eq.) were added. The mixture was stirred for 30 min at rt. (5S)—N-((2S)-4-(cyclopropylamino)-3-hydroxy-4-oxo-1-((S)-2-oxopyrrolidin-3-yl)butan-2-yl)-6-azaspiro[2.5]octane-5-carboxamide (78.9 mg, 0.208 mmol, 1.0 eq.) was added. The mixture was stirred for 1 h at rt, and then diluted with water (10 mL). The mixture was extracted with ethyl acetate (3×20 mL). The organic layers were combined, washed with brine (2×20 mL), dried over anhydrous sodium sulfate, filtered and concentrated under reduced pressure. The residue was chromatographed on a silica gel column with DCM:MeOH (9:1) to provide (5S)-6-(7-chlorobenzo[b]thiophene-2-carbonyl)-N-((2S)-4-(cyclopropylamino)-3-hydroxy-4-oxo-1-((S)-2-oxopyrrolidin-3-yl)butan-2-yl)-6-azaspiro[2.5]octane-5-carboxamide (90 mg, 67%) as a yellow solid. LC-MS (ESI, m/z): 573 [M+H]⁺.

A 8 mL vial was charged with (5S)-6-(7-chlorobenzo[b]thiophene-2-carbonyl)-N-((2S)-4-(cyclopropylamino)-3-hydroxy-4-oxo-1-((S)-2-oxopyrrolidin-3-yl)butan-2-yl)-6-azaspiro[2.5]octane-5-carboxamide (80 mg, 0.140 mmol, 1.0 eq.) in DCM (5 mL). Dess-Martin periodinane (118 mg, 0.280 mmol, 2.0 eq.) was added at 0° C., and the mixture stirred for 30 min at 0° C. The mixture was stirred for 2 h at rt. The reaction was quenched with sodium thiosulfate (1 M) and sat. sodium bicarbonate solution. The solution was extracted with dichloromethane (3×20 mL). The organic layers were combined, washed with brine (2×10 mL), dried over anhydrous sodium sulfate, filtered and concentrated under reduced pressure. The residue was purified by pre-TLC with DCM:MeOH (9:1) to provide (5S)-6-(7-chlorobenzo[b]thiophene-2-carbonyl)-N-(4-(cyclopropylamino)-3,4-dioxo-1-((S)-2-oxopyrrolidin-3-yl)butan-2-yl)-6-azaspiro[2.5]octane-5-carboxamide (31.1 mg, 38%) as a white solid. LC-MS (ESI, m/z): 571 [M+H]⁺.

Example 13

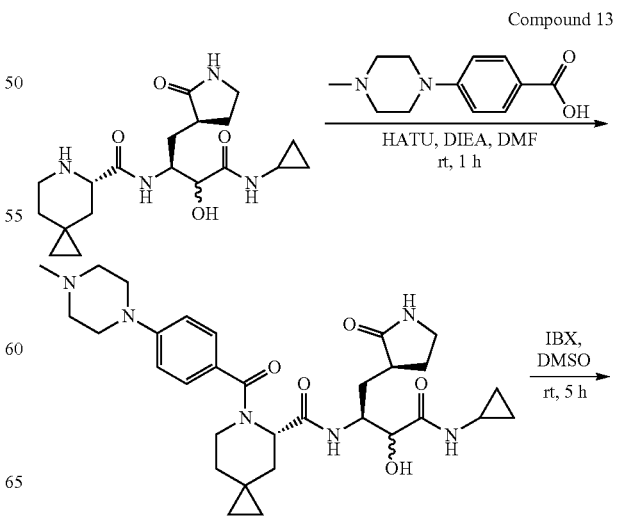

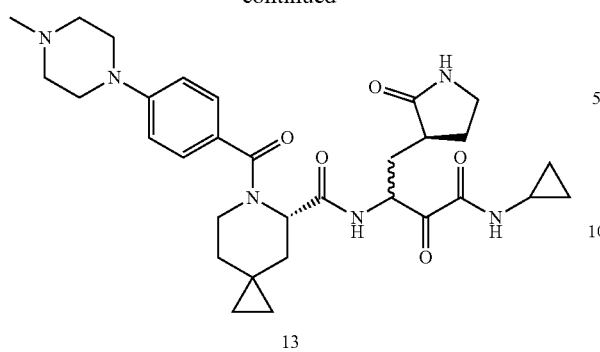

13

To a solution of (3S)-3-[(5S)-6-azaspiro[2.5]octan-5-yl-formamido]-N-cyclopropyl-2-hydroxy-4-[(3S)-2-oxopyrrolidin-3-yl]butanamide (79.1 mg, 0.209 mmol, 1.0 eq.) in DMF (2 mL) was added 4-(4-methylpiperazin-1-yl)benzoic acid (46.0 mg, 0.209 mmol, 1.0 eq.), o-(7-azabenzotriazol-1-yl)-N,N,N',N'-tetramethyluronium hexafluorophosphate (95.3 mg, 0.251 mmol, 1.2 eq.) and N-ethyl-N-isopropylpropan-2-amine (162 mg, 1.25 mmol, 6.0 eq.) stirred at 0° C. The mixture was stirred for 1 h at rt, and then purified by C18 column with CH$_3$CN:Water (0.05% TFA). The fraction was concentrated under reduced pressure to afford (3S)—N-cyclopropyl-2-hydroxy-3-{[(5S)-6-[4-(4-methylpiperazin-1-yl)benzoyl]-6-azaspiro[2.5]octan-5-yl]formamido}-4-[(3S)-2-oxopyrrolidin-3-yl]butanamide (55 mg, 45%). LCMS (ESI, m/z): 581 [M+H]$^+$.

To a solution of (3S)—N-cyclopropyl-2-hydroxy-3-{[(5S)-6-[4-(4-methylpiperazin-1-yl)benzoyl]-6-azaspiro[2.5]octan-5-yl]formamido}-4-[(3S)-2-oxopyrrolidin-3-yl]butanamide (55.0 mg, 0.095 mmol, 1.0 eq.) in DMSO (2 mL) was added 2-iodoxybenzoic acid (79.6 mg, 0.285 mmol, 3.0 eq.) at rt. The mixture was stirred for 5 h at rt, and the reaction was quenched with sat. aq. sodium bicarbonate (5 mL). The mixture was extracted with ethyl acetate (3×10 mL). The organic layers were combined, washed with water (3×20 mL) and brine (2×20 mL), dried over anhydrous sodium sulfate, filtered and concentrated under reduced pressure to afford the crude product. The crude product was purified by TLC (Mobile phase: EtOAc, Rf=0.1; detection: UV) to provide (3S)—N-cyclopropyl-3-{[(5S)-6-[4-(4-methylpiperazin-1-yl)benzoyl]-6-azaspiro[2.5]octan-5-yl]formamido}-2-oxo-4-[(3S)-2-oxopyrrolidin-3-yl]butanamide (4.2 mg, 7%). LCMS (ESI, m/z): 579 [M+H]$^+$.

Example 14

Compound 14

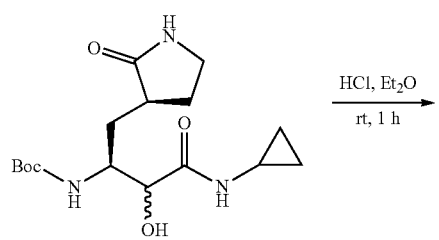

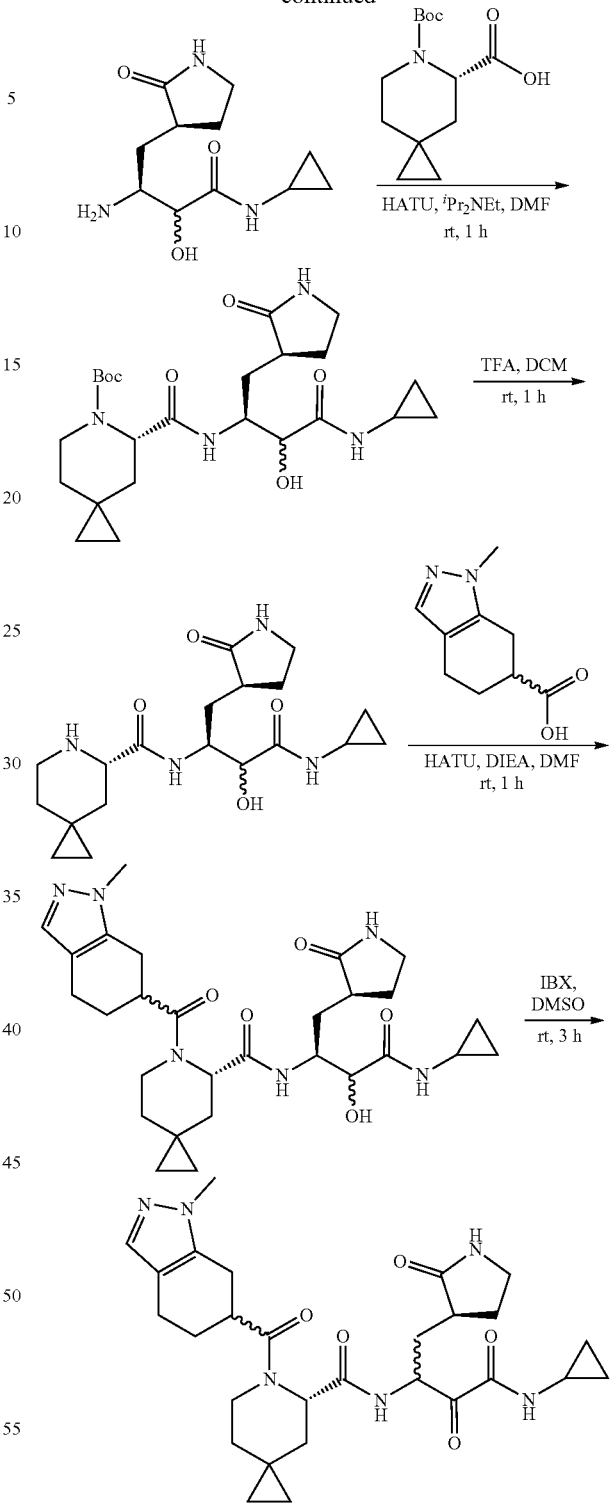

14

To a stirred mixture of tert-butyl (5S)-5-{[(2S)-1-(cyclopropylcarbamoyl)-1-hydroxy-3-[(3S)-2-oxopyrrolidin-3-yl]propan-2-yl]carbamoyl}-6-azaspiro[2.5]octane-6-carboxylate (800 mg, 1.67 mmol, 1.0 eq.) in DCM (4 mL) was added hydrochloric acid (8 mL, 2 M in Et$_2$O). The mixture was stirred for 1 h at rt, and then concentrated under reduced pressure to afford (3S)-3-[(5S)-6-azaspiro[2.5]octan-5-yl-formamido]-N-cyclopropyl-2-hydroxy-4-[(3S)-2-oxopyrrolidin-3-yl]butanamide (650 mg, crude) as a light yellow solid. LC-MS (ESI, m/z): 242 [M+H]⁺.

To a stirred mixture of (5S)-6-(tert-butoxycarbonyl)-6-azaspiro[2.5]octane-5-carboxylic acid (690 mg, 2.70 mmol, 1.0 eq.) and (3S)-3-amino-N-cyclopropyl-2-hydroxy-4-[(3S)-2-oxopyrrolidin-3-yl]butanamide (717 mg, 2.97 mmol, 1.1 eq.) in DMF (10 mL) was added o-(7-Azabenzotriazol-1-yl)-N,N,N',N'-tetramethyluronium hexafluorophosphate (1.23 g, 3.24 mmol, 1.2 eq.) and N-ethyl-N-isopropylpropan-2-amine (2.10 g, 16.2 mmol, 6.0 eq.). The mixture was stirred for 1 h at rt. The reaction was quenched with water (50 mL). The mixture was extracted with ethyl acetate (3×50 mL). The organic layers were combined, washed with brine (2×50 mL), dried over anhydrous sodium sulfate, filtered and concentrated under reduced pressure to afford the crude product. The crude product was diluted with dichloromethane (20 mL) and made into a slurry with 100-200 silica gel mesh (3 g). The mixture was loaded onto a column after removing the dichloromethane. The sample was purified by column chromatography (Column size 5×24 cm, column volume: 300 mL, silica gel size (100~ 200 mesh) quantity: 120 g) and eluted with methanol:dichloromethane (0%-12% over 30 min). The collected fractions (8%-9%) were chosen as the pure fractions, and those fractions were combined and concentrated under reduced pressure to provide tert-butyl (5S)-5-{[(2S)-1-(cyclopropylcarbamoyl)-1-hydroxy-3-[(3S)-2-oxopyrrolidin-3-yl]propan-2-yl]carbamoyl}-6-azaspiro[2.5]octane-6-carboxylate (740 mg, 53%) as a light yellow solid. ¹H NMR (400 MHz, DMSO-d₆) δ 7.09-8.11 (m, 3H), 5.53-5.90 (m, 2H), 4.45-4.69 (m, 1H), 3.77-4.26 (m, 3H), 3.30-3.32 (m, 1H), 2.96-3.28 (m, 3H), 2.60-2.79 (m, 1H), 1.85-2.35 (m, 4H), 1.56-1.82 (m, 2H), 1.13-1.55 (m, 10H), 0.06-1.05 (m, 8H). LC-MS (ESI, m/z): 479 [M+H]⁺.

To a solution of (3S)-3-[(5S)-6-azaspiro[2.5]octan-5-yl-formamido]-N-cyclopropyl-2-hydroxy-4-[(3S)-2-oxopyrrolidin-3-yl]butanamide (71.2 mg, 0.188 mmol, 1.0 eq.) in DMF (2 mL) was added 1-methyl-4,5,6,7-tetrahydroindazole-6-carboxylic acid (33.9 mg, 0.188 mmol, 1.0 eq.), o-(7-azabenzotriazol-1-yl)-N,N,N',N'-tetramethyluronium hexafluorophosphate (85.8 mg, 0.226 mmol, 1.2 eq.) and N-ethyl-N-isopropylpropan-2-amine (146 mg, 1.13 mmol, 6.0 eq.) stirred at 0° C. The mixture was stirred for 1 h at rt. The mixture was purified by C18 column with CH₃CN: Water (0.05% TFA), and the fraction was concentrated under reduced pressure to provide (3S)—N-cyclopropyl-2-hydroxy-3-{[(5S)-6-(1-methyl-4,5,6,7-tetrahydroindazole-6-carbonyl)-6-azaspiro[2.5]octan-5-yl]formamido}-4-[(3S)-2-oxopyrrolidin-3-yl]butanamide (65.0 mg, 63%). LCMS (ESI, m/z): 541 [M+H]⁺.

To a solution of (3S)—N-cyclopropyl-2-hydroxy-3-{[(5S)-6-(1-methyl-4,5,6,7-tetrahydroindazole-6-carbonyl)-6-azaspiro[2.5]octan-5-yl]formamido}-4-[(3S)-2-oxopyrrolidin-3-yl]butanamide (65.0 mg, 0.120 mmol, 1.0 eq.) in DMSO (1.5 mL) was added 2-iodoxybenzoic acid (101 mg, 0.360 mmol, 3.0 eq.) at rt. The mixture was stirred for 3 h at rt, and the reaction was quenched with sat. aq. sodium bicarbonate (5 mL). The mixture was extracted with ethyl acetate (5×10 mL). The organic layers were combined, washed with brine (3×20 mL), dried over anhydrous sodium sulfate, filtered and concentrated under reduced pressure to afford the crude product. The crude product was purified by prep-HPLC (Column: XSelect CSH Prep C18 OBD Column, 5 um, 19*150 mm; Mobile Phase A: Water (10 mmol/L NH₄HCO₃), Mobile Phase B: ACN; Flow rate: 25 mL/min; Gradient: 25% B to 70% B in 7 min; 254 nm; Rt: 5.30 min) to provide (5S)—N-(4-(cyclopropylamino)-3,4-dioxo-1-((S)-2-oxopyrrolidin-3-yl)butan-2-yl)-6-(1-methyl-4,5,6,7-tetrahydro-1H-indazole-6-carbonyl)-6-azaspiro[2.5]octane-5-carboxamide (13.0 mg, 18%). LCMS (ESI, m/z): 539 [M+H]⁺.

Example 15

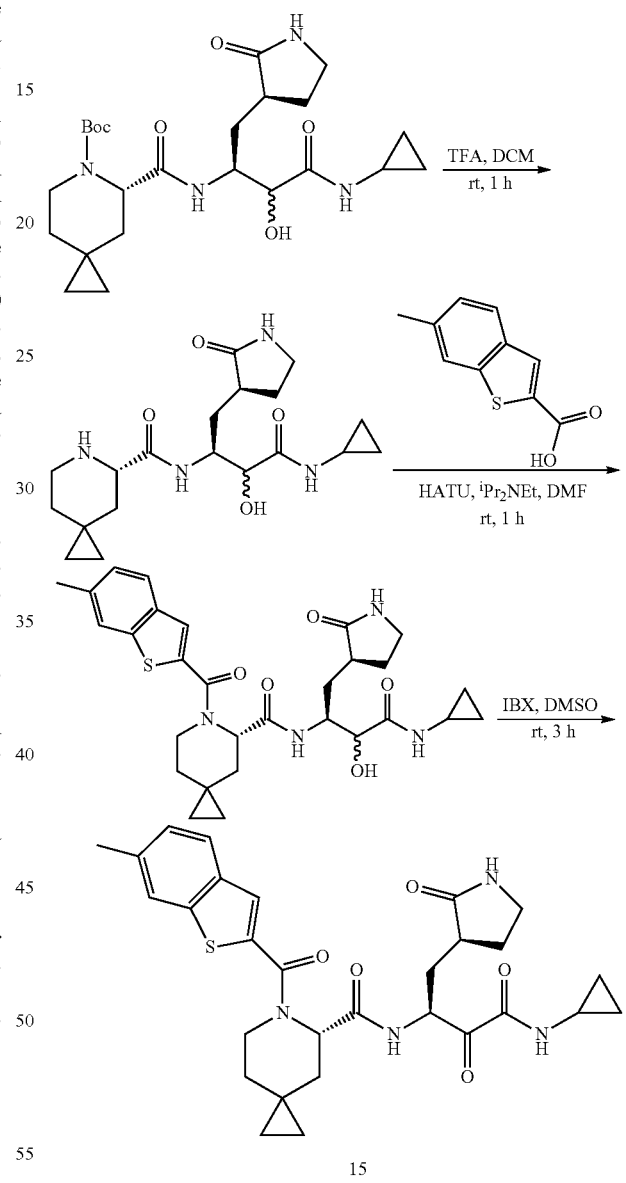

Compound 15

15

To a mixture of tert-butyl (5S)-5-{[(2S)-1-(cyclopropylcarbamoyl)-1-hydroxy-3-[(3S)-2-oxopyrrolidin-3-yl]propan-2-yl]carbamoyl}-6-azaspiro[2.5]octane-6-carboxylate (640 mg, 1.34 mmol, 1.0 eq.) in DCM (15 mL) was added trifluoroacetic acid (5 mL). The mixture was stirred for 1 h at rt, and then concentrated under reduced pressure to afford (3S)-3-[(5S)-6-azaspiro[2.5]octan-5-yl formamido]-N-cyclopropyl-2-hydroxy-4-[(3S)-2-oxopyrrolidin-3-yl]butanamide (510 mg, crude) as a yellow semi-solid. LC-MS (ESI, m/z): 379 [M+H]⁺.

To a mixture of (3S)-3-[(5S)-6-azaspiro[2.5]octan-5-yl-formamido]-N-cyclopropyl-2-hydroxy-4-[(3S)-2-oxopyrrolidin-3-yl]butanamide (79.0 mg, 0.209 mmol, 1.0 eq.), 6-methyl-1-benzothiophene-2-carboxylic acid (40.0 mg, 0.209 mmol, 1.0 eq.) and o-(7-azabenzotriazol-1-yl)-N,N,N',N'-tetramethyluronium hexafluorophosphate (95.0 mg, 0.251 mmol, 1.2 eq.) in DMF (2 mL) was added N-ethyl-N-isopropylpropan-2-amine (108 mg, 0.836 mmol, 4.0 eq.) at 0° C. The mixture was stirred for 1 h at rt, and the reaction was quenched with water (5 mL). The mixture was extracted with EtOAc (3×5 mL). The organic layers were combined, washed with brine (2×5 mL), dried over anhydrous sodium sulfate, filtered and concentrated under reduced pressure to afford the crude product. The crude product was purified by TLC (Mobile phase: MeOH:DCM (1:12); Rf=0.4; detection: UV) to provide (3S)—N-cyclopropyl-2-hydroxy-3-{[(5S)-6-(6-methyl-1-benzothiophene-2-carbonyl)-6-azaspiro[2.5]octan-5-yl]formamido}-4-[(3S)-2-oxopyrrolidin-3-yl]butanamide (30.0 mg, 21%) as a light yellow solid. LC-MS (ESI, m/z): 553 [M+H]$^+$.

To a mixture of (3S)—N-cyclopropyl-2-hydroxy-3-{[(5S)-6-(6-methyl-1-benzothiophene-2-carbonyl)-6-azaspiro[2.5]octan-5-yl]formamido}-4-[(3S)-2-oxopyrrolidin-3-yl]butanamide (30.0 mg, 0.054 mmol, 1.0 eq.) in DMSO (1 mL) was added 2-Iodoxybenzoic acid (46.0 mg, 0.162 mmol, 3.0 eq.). The mixture was stirred for 3 h at rt, and the reaction was quenched with sat. aq. sodium bicarbonate (3 mL). The mixture was extracted with EtOAc (3×3 mL). The organic layers were combined, washed with brine (2×3 mL), dried over anhydrous sodium sulfate, filtered and concentrated under reduced pressure to afford the crude product. The crude product was purified by TLC (Mobile phase: methanol:dichloromethane (1:11); Rf=0.4; detection: UV) to provide (3S)—N-cyclopropyl-3-{[(5S)-6-(6-methyl-1-benzothiophene-2-carbonyl)-6-azaspiro[2.5]octan-5-yl]formamido}-2-oxo-4-[(3S)-2-oxopyrrolidin-3-yl]butanamide (6.5 mg, 21%) as a white solid. $^1$H NMR (400 MHz, 80° C., DMSO-d$_6$) δ 8.35-8.68 (m, 2H), 7.73-7.90 (m, 2H), 7.20-7.72 (m, 3H), 5.05-5.20 (m, 1H), 4.85-5.04 (m, 1H), 4.10-4.40 (m, 1H), 3.28-3.60 (m, 1H), 3.10-3.27 (m, 2H), 2.70-2.83 (m, 1H), 2.49 (s, 3H), 2.02-2.40 (m, 3H), 1.40-2.00 (m, 5H), 0.88-1.00 (m, 1H), 0.12-0.75 (m, 8H). LC-MS (ESI, m/z): 551 [M+H]$^+$.

Example 16

Compound 16

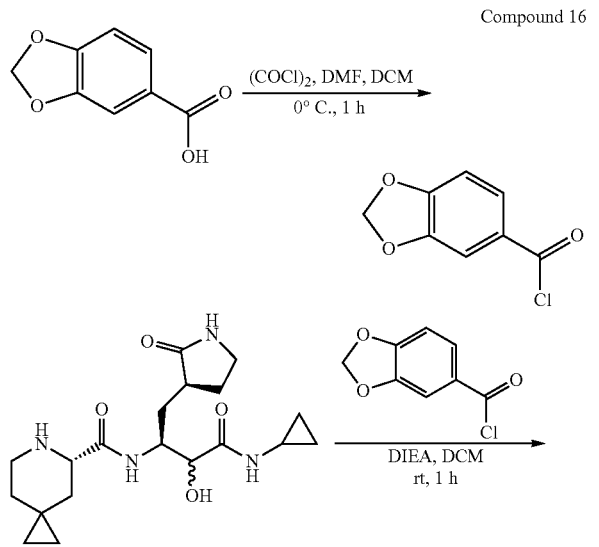

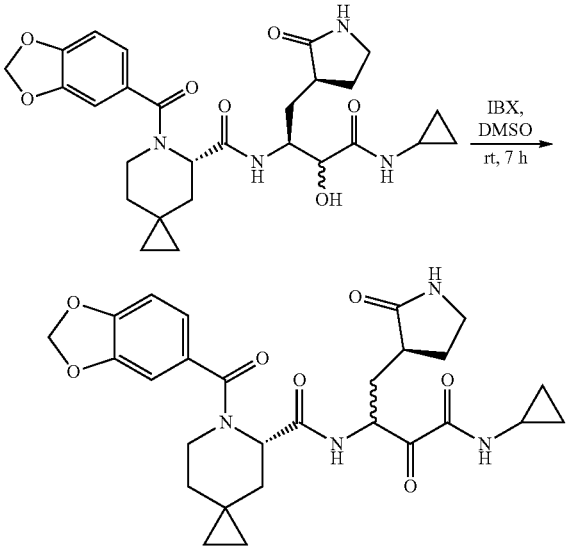

16

To a solution of 2H-1,3-benzodioxole-5-carboxylic acid (57.3 mg, 0.345 mmol, 1.0 eq.) in DCM (0.6 mL) was added oxalyl dichloride (65.7 mg, 0.517 mmol, 1.5 eq.) and DMF (0.01 mL) at 0° C. The mixture was stirred for 1 h at 0° C. and used into next step directly.

To a solution of (3S)-3-[(5S)-6-azaspiro[2.5]octan-5-yl-formamido]-N-cyclopropyl-2-hydroxy-4-[(3S)-2-oxopyrrolidin-3-yl]butanamide (87.0 mg, 0.230 mmol, 1.0 eq.) in DCM (2 mL) was added 2H-1,3-benzodioxole-5-carbonyl chloride (63.6 mg, 0.345 mmol, 1.5 eq.) and N-ethyl-N-isopropylpropan-2-amine (178 mg, 1.38 mmol, 6.0 eq.) stirred at 0° C. The mixture was stirred for 1 h at rt, and the reaction was quenched with water (5 mL). The mixture was extracted with ethyl acetate (3×10 mL). The organic layers were combined, dried over anhydrous sodium sulfate, filtered and concentrated under reduced pressure to afford the crude product. The crude product was purified by TLC (Mobile phase: MeOH:DCM (1:15); Rf=0.3; detection: UV) to afford (3S)-3-{[(5S)-6-(2H-1,3-benzodioxole-5-carbonyl)-6-azaspiro[2.5]octan-5-yl]formamido}-N-cyclopropyl-2-hydroxy-4-[(3S)-2-oxopyrrolidin-3-yl]butanamide (23 mg, 19%). LCMS (ESI, m/z): 527 [M+H]$^+$.

To a solution of (3S)-3-{[(5S)-6-(2H-1,3-benzodioxole-5-carbonyl)-6-azaspiro[2.5]octan-5-yl]formamido}-N-cyclopropyl-2-hydroxy-4-[(3S)-2-oxopyrrolidin-3-yl]butanamide (23.0 mg, 0.044 mmol, 1.0 eq.) in DMSO (2 mL) was added 2-iodoxybenzoic acid (36.7 mg, 0.132 mmol, 3.0 eq.) at rt. The mixture was stirred for 7 h at rt, and the reaction was quenched with sat. aq. sodium bicarbonate (5 mL). The mixture was extracted with ethyl acetate (3×10 mL). The organic layers were combined, washed with water (3×20 mL) and brine (2×20 mL), dried over anhydrous sodium sulfate, filtered and concentrated under reduced pressure to afford the crude product. The crude product was purified by TLC (Mobile phase: MeOH:DCM (1:11); Rf=0.4; detection: UV) to provide (3S)-3-{[(5S)-6-(2H-1,3-benzodioxole-5-carbonyl)-6-azaspiro[2.5]octan-5-yl]formamido}-N-cyclopropyl-2-oxo-4-[(3S)-2-oxopyrrolidin-3-yl]butanamide (6.8 mg, 28%). LCMS (ESI, m/z): 525 [M+H]$^+$.

Example 17

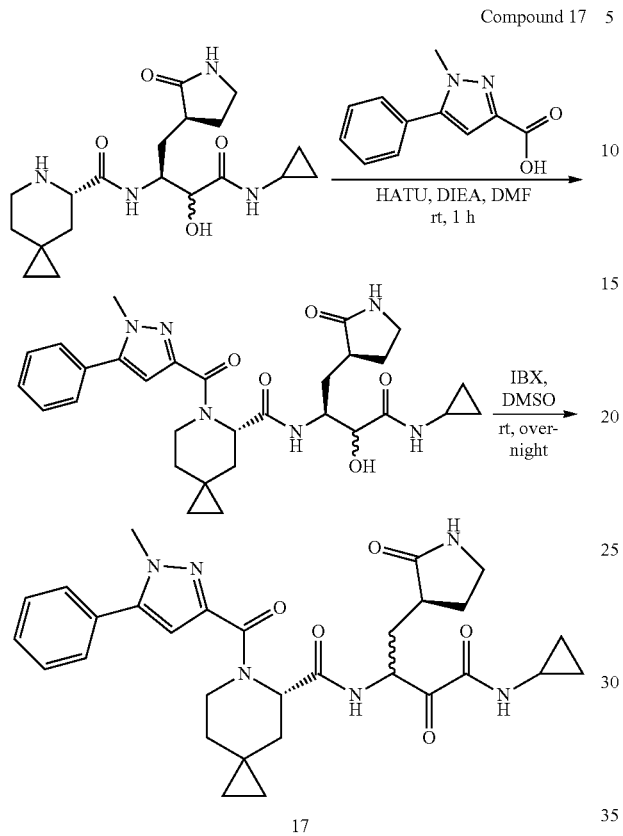

To a solution of (3S)-3-[(5S)-6-azaspiro[2.5]octan-5-yl-formamido]-N-cyclopropyl-2-hydroxy-4-[(3S)-2-oxopyrrolidin-3-yl]butanamide (119 mg, 0.313 mmol, 1.0 eq.) in DMF (2 mL) was added 1-methyl-5-phenylpyrazole-3-carboxylic acid (63.4 mg, 0.313 mmol, 1.0 eq.), o-(7-azabenzotriazol-1-yl)-N,N,N',N'-tetramethyluronium hexafluorophosphate (143 mg, 0.376 mmol, 1.2 eq.) and N-ethyl-N-isopropylpropan-2-amine (243 mg, 1.88 mmol, 6.0 eq.) at 0° C. The mixture was stirred for 1 h at rt, and the reaction was quenched with water (5 mL). The mixture was extracted with ethyl acetate (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH:DCM (1:15); Rf=0.3; detection: UV) to provide (3S)—N-cyclopropyl-2-hydroxy-3-{[(5S)-6-(1-methyl-5-phenylpyrazole-3-carbonyl)-6-azaspiro[2.5]octan-5-yl]formamido}-4-[(3S)-2-oxopyrrolidin-3-yl]butanamide (70 mg, 39%). LCMS (ESI, m/z): 563 [M+H]$^+$.

To a solution of (3S)—N-cyclopropyl-2-hydroxy-3-{[(5S)-6-(1-methyl-5-phenylpyrazole-3-carbonyl)-6-azaspiro[2.5]octan-5-yl]formamido}-4-[(3S)-2-oxopyrrolidin-3-yl]butanamide (70.0 mg, 0.124 mmol, 1.0 eq.) in DMSO (1.5 mL) was added 2-iodoxybenzoic acid (105 mg, 0.372 mmol, 3.0 eq.) at rt. The mixture was stirred overnight at rt, and the reaction was quenched with sat. aq. sodium bicarbonate (5 mL). The mixture was extracted with ethyl acetate (3×10 mL). The organic layers were combined, washed with water (3×20 mL) and brine (3×20 mL), dried over anhydrous sodium sulfate, filtered and concentrated under reduced pressure to afford the crude product. The crude product was purified by TLC (Mobile phase: MeOH:DCM (1:13); Rf=0.3; detection: UV) to provide (5S)—N-(4-(cyclopropylamino)-3,4-dioxo-1-((S)-2-oxopyrrolidin-3-yl)butan-2-yl)-6-(1-methyl-5-phenyl-1H-pyrazole-3-carbonyl)-6-azaspiro[2.5]octane-5-carboxamide (27.0 mg, 37%). LCMS (ESI, m/z): 561 [M+H]$^+$.

Example 18

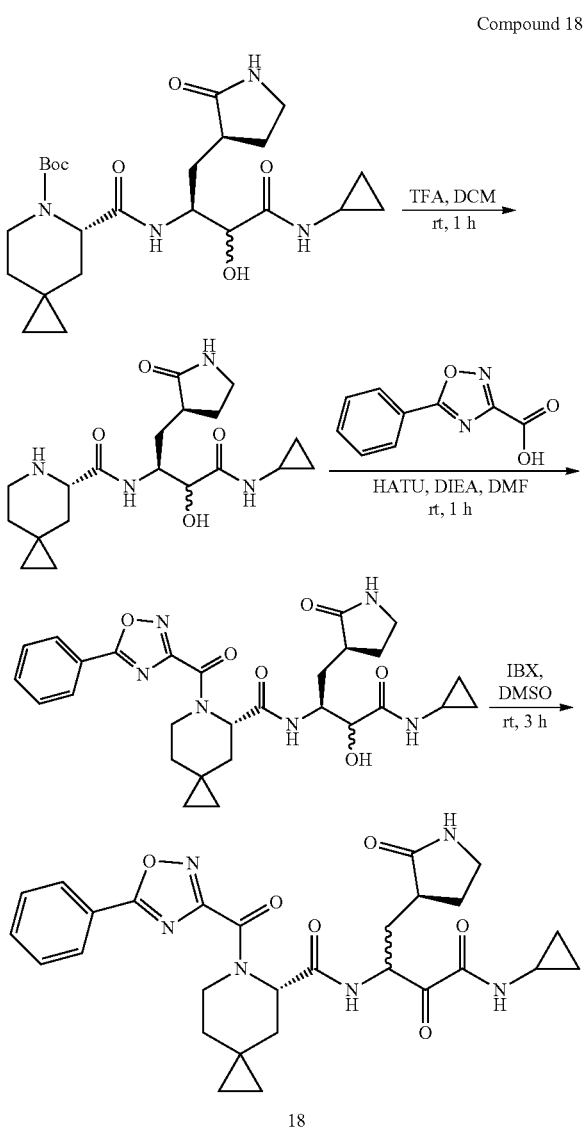

To a mixture of tert-butyl (5S)-5-{[(2S)-1-(cyclopropylcarbamoyl)-1-hydroxy-3-[(3S)-2-oxopyrrolidin-3-yl]propan-2-yl]carbamoyl}-6-azaspiro[2.5]octane-6-carboxylate (440 mg, 0.920 mmol, 1.0 eq.) in DCM (9 mL) was added trifluoroacetic acid (3 mL). The mixture was stirred for 1 h at rt and then concentrated under reduced pressure to afford (3S)-3-[(5S)-6-azaspiro[2.5]octan-5-ylformamido]-N-cyclopropyl-2-hydroxy-4-[(3S)-2-oxopyrrolidin-3-yl]butanamide (340 mg, crude) as a yellow semi-solid. LC-MS (ESI, m/z): 379 [M+H]$^+$.

To a mixture of (3S)—N-cyclopropyl-2-hydroxy-4-[(3S)-2-oxopyrrolidin-3-yl]-3-{[(5S)-6-(5-phenyl-1,2,4-oxadiazole-3-carbonyl)-6-azaspiro[2.5]octan-5-yl]formamido}butanamide (79.0 mg, 0.143 mmol, 1.0 eq.), 5-phenyl-1,2,4-oxadiazole-3-carboxylic acid (40.0 mg, 0.209 mmol, 1.0 eq.) and o-(7-azabenzotriazol-1-yl)-N,N,N′,N′-tetramethyluronium hexafluorophosphate (95.0 mg, 0.251 mmol, 1.2 eq.) in DMF (2 mL) was added N-ethyl-N-isopropylpropan-2-amine (216 mg, 1.67 mmol, 8.0 eq.) at 0° C. The mixture was stirred for 1 h at rt, and the reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH:DCM (1:11); Rf=0.4; detection: UV) to provide (3S)—N-cyclopropyl-2-hydroxy-4-[(3S)-2-oxopyrrolidin-3-yl]-3-{[(5S)-6-(5-phenyl-1,2,4-oxadiazole-3-carbonyl)-6-azaspiro[2.5]octan-5-yl]formamido}butanamide (40.0 mg, 33%) as an off-white solid. LC-MS (ESI, m/z): 551 [M+H]⁺.

To a mixture of (3S)—N-cyclopropyl-2-hydroxy-4-[(3S)-2-oxopyrrolidin-3-yl]-3-{[(5S)-6-(5-phenyl-1,2,4-oxadiazole-3-carbonyl)-6-azaspiro[2.5]octan-5-yl]formamido}butanamide (40.0 mg, 0.073 mmol, 1.0 eq.) in DMSO (1 mL) was added 2-iodoxybenzoic acid (61.0 mg, 0.219 mmol, 3.0 eq.). The mixture was stirred for 3 h at rt, and the reaction was quenched with sat. aq. sodium bicarbonate (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH:DCM (1:11); Rf=0.4; detection: UV) to provide N-cyclopropyl-2-oxo-4-[(3S)-2-oxopyrrolidin-3-yl]-3-{[(5S)-6-(5-phenyl-1,2,4-oxadiazole-3-carbonyl)-6-azaspiro[2.5]octan-5-yl]formamido}butanamide (23.7 mg, 58%) as a white solid. ¹H NMR (400 MHz, 80° C., DMSO-d₆) δ 8.05-8.70 (m, 4H), 7.75-7.90 (m, 1H), 7.60-7.74 (m, 2H), 7.10-7.59 (m, 1H), 5.02-5.35 (m, 1H), 4.45-4.80 (m, 1H), 3.60-3.90 (m, 1H), 3.35-3.59 (m, 1H), 3.15-3.34 (m, 2H), 2.63-2.89 (m, 1H), 1.45-2.50 (m, 8H), 0.95-1.15 (m, 1H), 0.20-0.80 (m, 8H). LC-MS (ESI, m/z): 549 [M+H]⁺.

Example 19

Compound 19

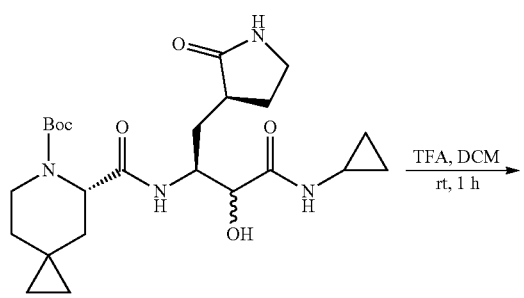

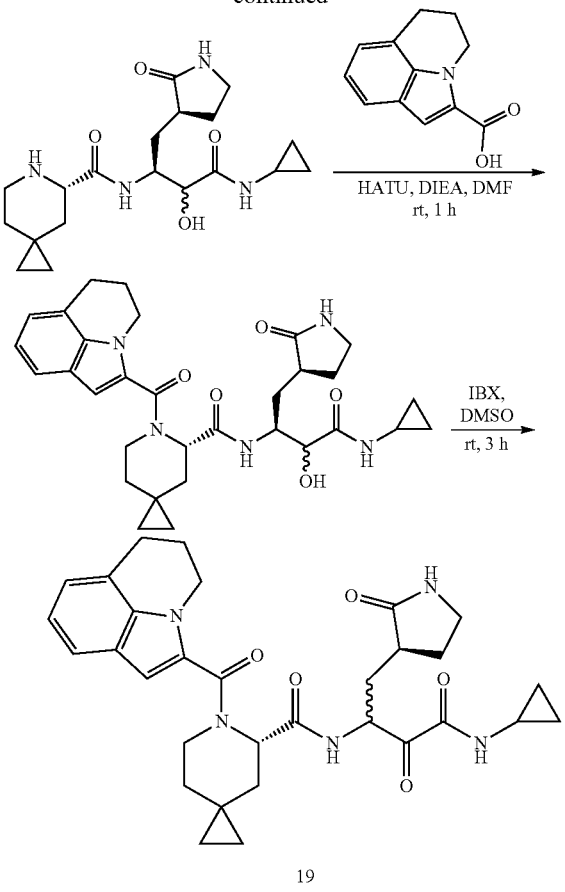

To a mixture of tert-butyl (5S)-5-{[(2S)-1-(cyclopropylcarbamoyl)-1-hydroxy-3-[(3S)-2-oxopyrrolidin-3-yl]propan-2-yl]carbamoyl}-6-azaspiro[2.5]octane-6-carboxylate (100 mg, 0.209 mmol, 1.0 eq.) in DCM (3 mL) was added trifluoroacetic acid (1 mL). The mixture was stirred for 1 h at rt, and then concentrated under reduced pressure to afford (3S)-3-[(5S)-6-azaspiro[2.5]octan-5-ylformamido]-N-cyclopropyl-2-hydroxy-4-[(3S)-2-oxopyrrolidin-3-yl]butanamide (79.0 mg, crude) as a yellow semi-solid. LC-MS (ESI, m/z): 379 [M+H]⁺.

To a mixture of (3S)-3-[(5S)-6-azaspiro[2.5]octan-5-ylformamido]-N-cyclopropyl-2-hydroxy-4-[(3S)-2-oxopyrrolidin-3-yl]butanamide (79.0 mg, 0.209 mmol, 1.0 eq.), 1-azatricyclo[6.3.1.0^{4,12}]dodeca-2,4(12),5,7-tetraene-2-carboxylic acid (42.0 mg, 0.209 mmol, 1.0 eq.) and o-(7-azabenzotriazol-1-yl)-N,N,N′,N′-tetramethyluronium hexafluorophosphate (95.0 mg, 0.251 mmol, 1.2 eq.) in DMF (2 mL) was added N-ethyl-N-isopropylpropan-2-amine (108 mg, 0.836 mmol, 4.0 eq.) at 0° C. The mixture was stirred for 1 h at rt, and the reaction was quenched with water (5 mL). The mixture was extracted with EtOAc (3×5 mL). The organic layers were combined, washed with brine (2×5 mL), dried over anhydrous sodium sulfate, filtered and concentrated under reduced pressure to afford crude product. The crude product was purified by TLC (Mobile phase: MeOH:DCM (1:12); Rf=0.4; detection: UV) to provide (3S)-3-{[(5S)-6-{1-azatricyclo[6.3.1.0^{4,12}]dodeca-2,4(12),5,7-tetraene-2-carbonyl}-6-azaspiro[2.5]octan-5-yl]formamido}-N-cyclopropyl-2-hydroxy-4-[(3S)-2-oxopyrrolidin-3-yl]butanamide (50.0 mg, 34%) as a yellow solid. LC-MS (ESI, m/z): 562 [M+H]⁺.

To a mixture of (3S)-3-{[(5S)-6-{1-azatricyclo[6.3.1.0^{4,12}]dodeca-2,4(12),5,7-tetraene-2-carbonyl}-6-azaspiro[2.5]octan-5-yl]formamido}-N-cyclopropyl-2-hydroxy-4-[(3S)-2-oxopyrrolidin-3-yl]butanamide (50.0 mg, 0.089 mmol, 1.0 eq.) in DMSO (1 mL) was added 2-iodoxybenzoic acid (75.0 mg, 0.267 mmol, 3.0 eq.). The mixture was stirred for 3 h at rt, and the reaction was quenched with sat. aq. sodium bicarbonate (5 mL). The mixture was extracted with EtOAc (3×5 mL). The organic layers were combined, washed with brine (2×5 mL), dried over anhydrous sodium sulfate, filtered and concentrated under reduced pressure to afford the crude product. The crude product was purified by TLC (Mobile phase: methanol:dichloromethane (1:11); Rf=0.3; detection: UV) to provide 3-{[(5S)-6-{1-azatricyclo[6.3.1.0^{4,12}]dodeca-2,4(12),5,7-tetraene-2-carbonyl}-6-azaspiro[2.5]octan-5-yl]formamido}-N-cyclopropyl-2-oxo-4-[(3S)-2-oxopyrrolidin-3-yl]butanamide (20.6 mg, 39%) as an off-white solid. LC-MS (ESI, m/z): 560 [M+H]+.

Example 20

Compound 20

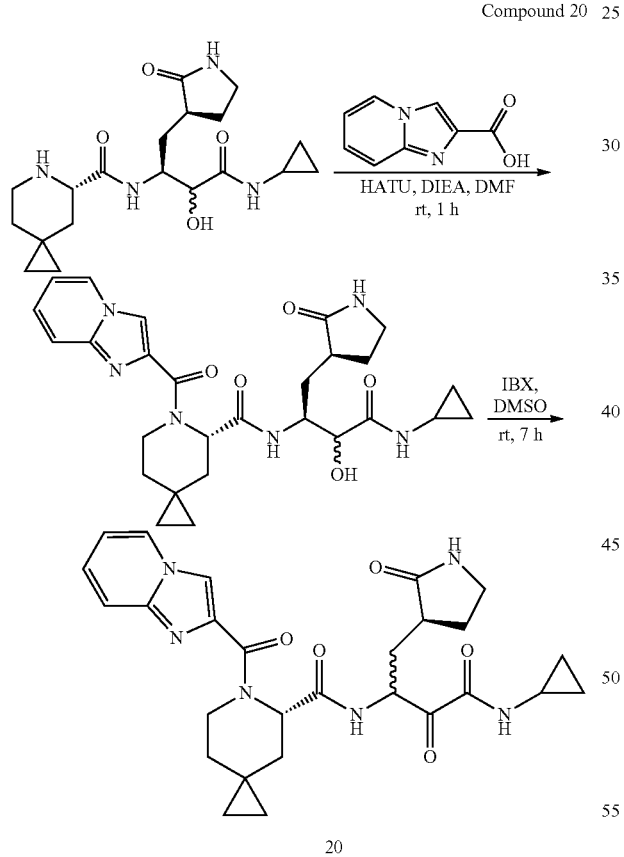

To a solution of (3S)-3-[(5S)-6-azaspiro[2.5]octan-5-yl-formamido]-N-cyclopropyl-2-hydroxy-4-[(3S)-2-oxopyrrolidin-3-yl]butanamide (79.1 mg, 0.209 mmol, 1.0 eq.) in DMF (2 mL) was added imidazo[1,2-a]pyridine-2-carboxylic acid (33.9 mg, 0.209 mmol, 1.0 eq.), o-(7-azabenzotriazol-1-yl)-N,N,N',N'-tetramethyluronium hexafluorophosphate (95.3 mg, 0.251 mmol, 1.2 eq.) and N-ethyl-N-isopropylpropan-2-amine (162 mg, 1.25 mmol, 6.0 eq.) stirred at 0° C. The mixture was stirred for 1 h at rt, and then purified by C18 column with CH3CN:Water (0.05% TFA). The fraction was concentrated under reduced pressure to afford (3S)—N-cyclopropyl-2-hydroxy-3-{[(5S)-6-{imidazo[1,2-a]pyridine-2-carbonyl}-6-azaspiro[2.5]octan-5-yl]formamido}-4-[(3S)-2-oxopyrrolidin-3-yl]butanamide (40 mg, 36%). LCMS (ESI, m/z): 523 [M+H]+.

To a solution of (3S)—N-cyclopropyl-2-hydroxy-3-{[(5S)-6-{imidazo[1,2-a]pyridine-2-carbonyl}-6-azaspiro[2.5]octan-5-yl]formamido}-4-[(3S)-2-oxopyrrolidin-3-yl]butanamide (40.0 mg, 0.077 mmol, 1.0 eq.) in DMSO (2 mL) was added 2-iodoxybenzoic acid (64.3 mg, 0.231 mmol, 3.0 eq.) at rt. The mixture was stirred for 7 h at rt, and the reaction was quenched with sat. aq. sodium bicarbonate (5 mL). The mixture was extracted with ethyl acetate (3×10 mL). The organic layers were combined, dried over anhydrous sodium sulfate, filtered and concentrated under reduced pressure to afford the crude product. The crude product was purified by prep-HPLC (Column: XBridge Prep Phenyl OBD Column, 19*150 mm, 5 m; Mobile Phase A: Water (10 mmol/L NH4HCO3+0.1% NH3·H2O), Mobile Phase B: ACN; Flow rate: 25 mL/min; Gradient: 20% B to 33% B in 10 min, 33% B; Wave Length: 220 nm; RT1 (min): 5.33) to provide (3S)—N-cyclopropyl-3-{[(5S)-6-{imidazo[1,2-a]pyridine-2-carbonyl}-6-azaspiro[2.5]octan-5-yl]formamido}-2-oxo-4-[(3S)-2-oxopyrrolidin-3-yl]butanamide (13.6 mg, 33%). 1H NMR (400 MHz, 80° C., DMSO-d6) δ 8.47-8.53 (m, 1H), 8.36-8.42 (m, 1H), 8.26-8.34 (m, 1H), 8.22-8.25 (m, 1H), 7.47-7.56 (m, 1H), 7.33-7.40 (m, 1H), 7.20-7.30 (m, 1H), 6.86-6.94 (m, 1H), 4.49-5.95 (m, 2H), 3.08-3.52 (m, 4H), 2.65-2.76 (m, 1H), 1.57-2.40 (m, 8H), 0.85-0.95 (m, 1H), 0.17-0.68 (m, 8H). LCMS (ESI, m/z): 521 [M+H]+.

Example 21

Compound 21

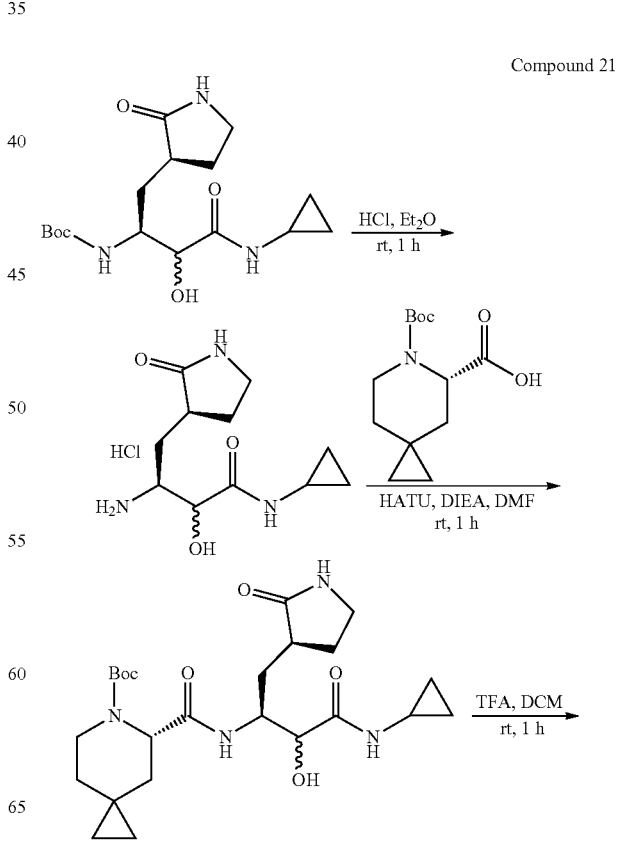

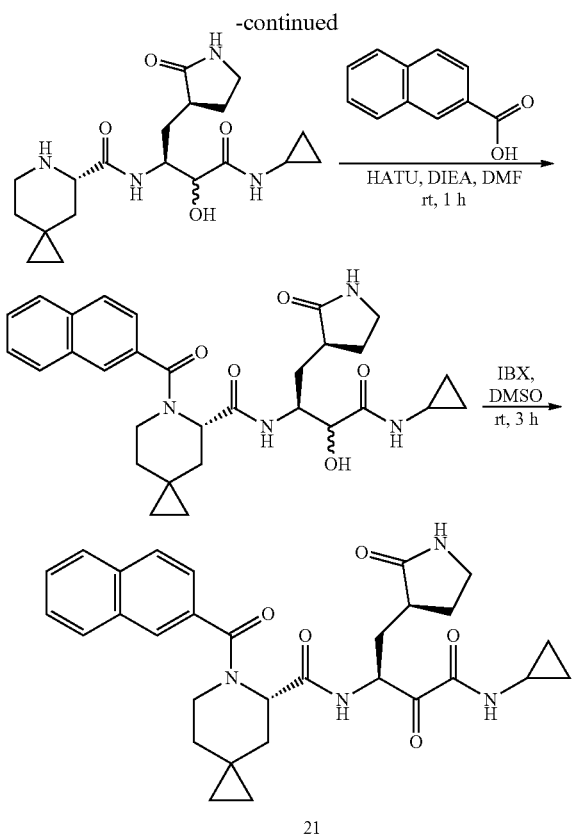

21

A mixture of tert-butyl ((2S)-4-(cyclopropylamino)-3-hydroxy-4-oxo-1-((S)-2-oxopyrrolidin-3-yl)butan-2-yl)carbamate (500 mg, 1.47 mmol, 1.0 eq.) in hydrogen chloride (10 mL, 2 M in Et₂O) was stirred for 1 h at rt. The mixture was concentrated under reduced pressure to afford (3S)-3-amino-N-cyclopropyl-2-hydroxy-4-oxo-1-((S)-2-oxopyrrolidin-3-yl)butanamide hydrochloride (406 mg, crude) as a white solid. LC-MS (ESI, m/z): 243 [M+H]⁺.

To a stirred solution of (3S)-3-amino-N-cyclopropyl-2-hydroxy-4-((S)-2-oxopyrrolidin-3-yl)butanamide hydrochloride (406 mg, 1.46 mmol, 1.0 eq.), o-(7-azabenzotriazol-1-yl)-N,N,N',N'-tetramethyluronium hexafluorophosphate (667 mg, 1.75 mmol, 1.2 eq.) and (5S)-6-(tert-butoxycarbonyl)-6-azaspiro[2.5]octane-5-carboxylic acid (373 mg, 1.46 mmol, 1.0 eq.) in DMF (8 mL) was added N-ethyl-N-isopropylpropan-2-amine (1.32 g, 10.2 mmol, 7.0 eq.) at 0° C. The mixture was stirred for 1 h at rt, and the reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was diluted with DCM (20 mL) and made into a slurry with 100-200 silica gel mesh (2 g). The slurry was loaded to a column after removing the DCM. The sample was purified by column chromatography (Column size 4×24 cm, column volume: 200 mL, silica gel size (100~200 mesh) (quantity: 80 g) and eluted with MeOH:DCM (0%-15% over 30 min). The collected fractions: 7%-9% MeOH:DCM fractions were chosen as the pure fractions, and those fractions were combined and concentrated under reduced pressure to provide tert-butyl (5S)-5-(((2S)-4-(cyclopropylamino)-3-hydroxy-4-oxo-1-((S)-2-oxopyrrolidin-3-yl)butan-2-yl)carbamoyl)-6-azaspiro[2.5]octane-6-carboxylate (214 mg, 30%) as a white solid.

To a stirred mixture of tert-butyl (5S)-5-(((2S)-4-(cyclopropylamino)-3-hydroxy-4-oxo-1-((S)-2-oxopyrrolidin-3-yl)butan-2-yl)carbamoyl)-6-azaspiro[2.5]octane-6-carboxylate (100 mg, 0.210 mmol, 1.0 eq.) in DCM (3 mL) was added trifluoroacetic acid (1 mL). The mixture was stirred for 1 h at rt. and then concentrated under reduced pressure to afford (5S)—N-((2S)-4-(cyclopropylamino)-3-hydroxy-4-oxo-1-((S)-2-oxopyrrolidin-3-yl)butan-2-yl)-6-azaspiro[2.5]octane-5-carboxamide (79.0 mg, crude) as a white solid. LC-MS (ESI, m/z): 379 [M+H]⁺.

To a stirred mixture of (5S)—N-((2S)-4-(cyclopropylamino)-3-hydroxy-4-oxo-1-((S)-2-oxopyrrolidin-3-yl)butan-2-yl)-6-azaspiro[2.5]octane-5-carboxamide (79.0 mg, 0.209 mmol, 1.0 eq.), β-naphthoic acid (35.9 mg, 0.209 mmol, 1.0 eq.) and o-(7-azabenzotriazol-1-yl)-N,N,N',N'-tetramethyluronium hexafluorophosphate (95.2 mg, 0.251 mmol, 1.2 eq.) in dimethylformamide (2 mL) was added N-ethyl-N-isopropylpropan-2-amine (216 mg, 1.67 mmol, 8.0 eq.) at 0° C. The mixture was stirred for 1 h at rt, and the reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH:DCM=1:11; Rf=0.3; detection: UV) to provide (5S)-6-(2-naphthoyl)-N-((2S)-4-(cyclopropylamino)-3-hydroxy-4-oxo-1-((S)-2-oxopyrrolidin-3-yl)butan-2-yl)-6-azaspiro[2.5]octane-5-carboxamide as a white solid. LC-MS (ESI, m/z): 533 [M+H]⁺.

To a mixture of (5S)-6-(2-naphthoyl)-N-((2S)-4-(cyclopropylamino)-3-hydroxy-4-oxo-1-((S)-2-oxopyrrolidin-3-yl)butan-2-yl)-6-azaspiro[2.5]octane-5-carboxamide (80.0 mg, 0.150 mmol, 1.0 eq.) in DMSO (4 mL) was added 2-iodoxybenzoic acid (126 mg, 0.450 mmol, 3.0 eq.). The mixture was stirred for 3 h at rt, and the reaction was quenched with sat. aq. sodium bicarbonate (10 mL). The mixture was extracted with EtOAc (3×10 mL). The organic layers were combined, washed with brine (3×10 mL), dried over anhydrous sodium sulfate, filtered and concentrated under reduced pressure to afford the crude product. The crude product was purified by TLC (Mobile phase: MeOH:DCM=1:11; Rf=0.3; detection: UV) to provide (S)-6-(2-naphthoyl)-N—((S)-4-(cyclopropylamino)-3,4-dioxo-1-((S)-2-oxopyrrolidin-3-yl)butan-2-yl)-6-azaspiro[2.5]octane-5-carboxamide (39.7 mg, 49%). LC-MS (ESI, m/z): 531 [M+H]⁺.

Example 22

Compound 22

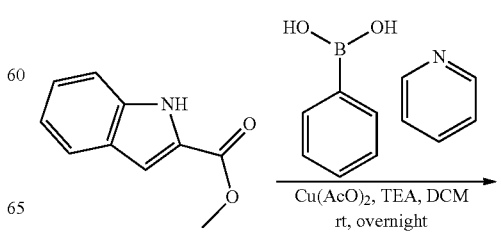

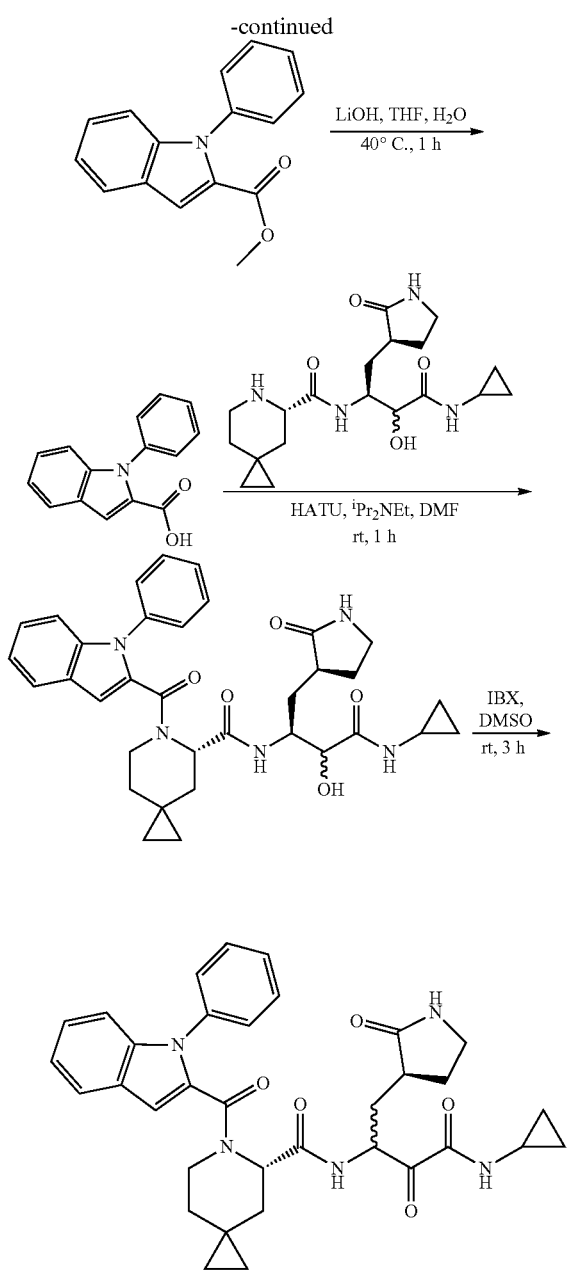

22

To a stirred mixture of methyl 1H-indole-2-carboxylate (5.00 g, 28.5 mmol, 1.0 eq.), phenyl boronic acid (4.52 g, 37.1 mmol, 1.3 eq.), pyridine (4.52 g, 57.1 mmol, 2.0 eq.) and triethylamine (5.78 g, 57.0 mmol, 2.0 eq.) in DCM (100 mL) was added cupric acetate (10.4 g, 57.1 mmol, 2.0 eq.). The mixture was stirred overnight at rt under nitrogen, and the reaction was quenched with sat. aq. sodium bicarbonate (150 mL). The mixture was extracted with DCM (3×150 mL). The organic layers were combined, washed with brine (2×150 mL), dried over anhydrous sodium sulfate, filtered and concentrated under reduced pressure to afford the crude product. The residue was purified by silica gel column chromatography with EtOAc:PE (7:93) to afford methyl 1-phenylindole-2-carboxylate (1.26 g, 16%) as a white solid.

$^1$H NMR (400 MHz, DMSO-d$_6$) δ 7.71-7.80 (m, 1H), 7.45-7.55 (m, 4H), 7.30-7.40 (m, 3H), 7.10-7.25 (m, 2H), 3.77 (s, 1H). LC-MS (ESI, m/z): 252 [M+H]$^+$.

To a mixture of methyl 1-phenylindole-2-carboxylate (300 mg, 1.19 mmol, 1.0 eq.), in tetrahydrofuran (3 mL) was added lithium hydroxide (143 mg, 5.97 mmol, 5.0 eq., in water 3 mL) at rt. The mixture was stirred for 1 h at 40° C. The mixture was acidified to pH=6 with hydrochloric acid (1 M). The mixture was extracted with ethyl acetate (3×10 mL). The organic layers were combined, washed with brine (2×10 mL), dried over anhydrous sodium sulfate, filtered and concentrated under reduced pressure to afford 1-phenylindole-2-carboxylic acid (237 mg, 71%, crude) as a white solid. $^1$H NMR (400 MHz, DMSO-d$_6$) δ 7.70-7.81 (m, 1H), 7.46-7.55 (m, 3H), 7.37-7.45 (m, 3H), 7.10-7.35 (m, 2H), 6.95-7.08 (m, 1H). LC-MS (ESI, m/z): 238 [M+H]$^+$.

To a mixture of 1-phenylindole-2-carboxylic acid (59.4 mg, 0.251 mmol, 1.2 eq.) and o-(7-azabenzotriazol-1-yl)-N,N,N',N'-tetramethyluronium hexafluorophosphate (75.4 mg, 0.31 mmol, 1.5 eq.) in dimethylformamide (2 mL) was added N-ethyl-N-isopropylpropan-2-amine (216 mg, 1.67 mmol, 8.0 eq.). The mixture was stirred for 0.5 h at 0° C. (3S)-3-[(5S)-6-azaspiro[2.5]octan-5-ylformamido]-N-cyclopropyl-2-hydroxy-4-[(3S)-2-oxopyrrolidin-3-yl]butanamide (79.0 mg, 0.210 mmol, 1.0 eq.) was then added. The mixture was stirred for 1 h at rt, and the reaction was quenched with water (10 mL). The mixture was extracted with EtOAc (3×10 mL). The organic layers were combined, washed with brine (3×10 mL), dried over anhydrous sodium sulfate, filtered and concentrated under reduced pressure to afford the crude product. The crude product was purified by TLC (Mobile phase: MeOH:DCM (ethyl acetate:petroleum ether)=1:11; Rf=0.3; detection: UV) to provide (3S)—N-cyclopropyl-2-hydroxy-4-[(3S)-2-oxopyrrolidin-3-yl]-3-{[(5S)-6-(1-phenylindole-2-carbonyl)-6-azaspiro[2.5]octan-5-yl]formamido}butanamide (40.2 mg, 27%) as a white solid. LC-MS (ESI, m/z): 598 [M+H]$^+$.

To a stirred mixture of (3S)—N-cyclopropyl-2-hydroxy-4-[(3S)-2-oxopyrrolidin-3-yl]-3-{[(5S)-6-(1-phenylindole-2-carbonyl)-6-azaspiro[2.5]octan-5-yl]formamido}butanamide (40.0 mg, 0.067 mmol, 1.0 eq.) in DMSO (2 mL) was added 2-iodoxybenzoic acid (56.2 mg, 0.201 mmol, 3.0 eq.). The mixture was stirred for 3 h at rt, and the reaction was quenched with sat. aq. sodium bicarbonate (10 mL). The mixture was extracted with EtOAc (3×10 mL). The organic layers were combined, washed with brine (3×10 mL), dried over anhydrous sodium sulfate, filtered and concentrated under reduced pressure to afford the crude product. The crude product was purified by TLC (Mobile phase: MeOH:DCM=1:11; Rf=0.3; detection: UV) to provide N-cyclopropyl-2-oxo-4-[(3S)-2-oxopyrrolidin-3-yl]-3-{[(5S)-6-(1-phenylindole-2-carbonyl)-6-azaspiro[2.5]octan-5-yl]formamido}butanamide (15.5 mg, 37%) as a white solid. $^1$H NMR (400 MHz, 80° C., DMSO-d$_6$) δ 8.20-8.49 (m, 2H), 6.71-7.77 (m, 11H), 4.65-5.18 (m, 2H), 3.91-4.29 (m, 1H), 3.30-3.47 (m, 1H), 3.19-3.22 (m, 2H), 2.71-2.79 (m, 1H), 2.12-2.30 (m, 3H), 1.50-1.95 (m, 5H), 0.79-0.88 (m, 1H), 0.14-0.61 (m, 8H). LC-MS (ESI, m/z): 596 [M+H]$^+$.

Example 23

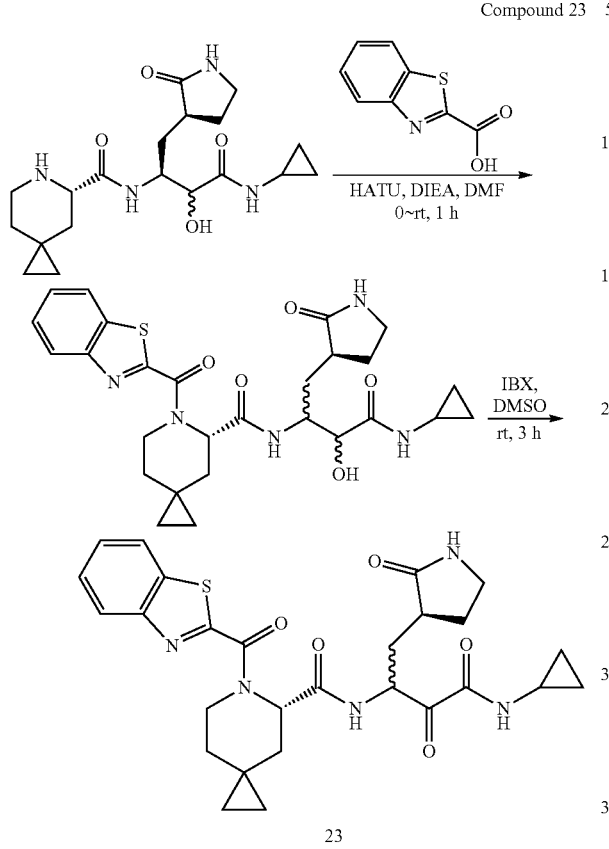

Compound 23

To a stirred mixture of 3-[(5S)-6-azaspiro[2.5]octan-5-ylformamido]-N-cyclopropyl-2-hydroxy-4-[(3S)-2-oxopyrrolidin-3-yl]butanamide (86.9 mg, 0.230 mmol, 1.0 eq.), 1,3-benzothiazole-2-carboxylic acid (41.1 mg, 0.230 mmol, 1.0 eq.) and o-(7-azabenzotriazol-1-yl)-N,N,N',N'-tetramethyluronium hexafluorophosphate (105 mg, 0.276 mmol, 1.2 eq.) in DMF (2 mL) was added N-ethyl-N-isopropylpropan-2-amine (237 mg, 1.84 mmol, 8.0 eq.) at 0° C. The mixture was stirred for 1 h at rt, and the reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH:DCM=1:11; Rf=0.3; detection: UV) to provide 3-{[(5S)-6-(1,3-benzothiazole-2-carbonyl)-6-azaspiro[2.5]octan-5-yl]formamido}-N-cyclopropyl-2-hydroxy-4-[(3S)-2-oxopyrrolidin-3-yl]butanamide (53.0 mg, 40%) as a yellow solid. LC-MS (ESI, m/z): 540 [M+H]$^+$.

To a stirred mixture of 3-{[(5S)-6-(1,3-benzothiazole-2-carbonyl)-6-azaspiro[2.5]octan-5-yl]formamido}-N-cyclopropyl-2-hydroxy-4-[(3S)-2-oxopyrrolidin-3-yl]butanamide (50.0 mg, 0.093 mmol, 1.0 eq.) in DMSO (2.5 mL) was added 2-iodoxybenzoic acid (77.8 mg, 0.279 mmol, 3.0 eq.). The mixture was stirred for 3 h at rt, and the reaction was quenched with sat. aq. sodium bicarbonate (10 mL). The mixture was extracted with EtOAc (3×10 mL). The organic layers were combined, washed with brine (3×10 mL), dried over anhydrous sodium sulfate, filtered and concentrated under reduced pressure to afford the crude product. The crude product was purified by TLC (Mobile phase: MeOH:DCM=1:11; Rf=0.4; detection: UV) to provide 3-{[(5S)-6-(1,3-benzothiazole-2-carbonyl)-6-azaspiro[2.5]octan-5-yl]formamido}-N-cyclopropyl-2-oxo-4-[(3S)-2-oxopyrrolidin-3-yl]butanamide (25.4 mg, 50%) as a white solid. LC-MS (ESI, m/z): 538 [M+H]$^+$.

Example 24

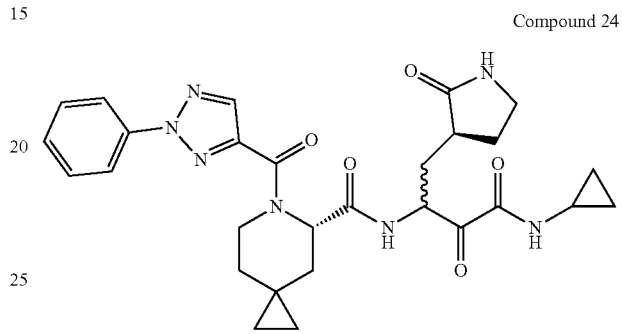

Compound 24

Compound 24 was prepared similarly as described for Compound 23, using 2-phenyl-1,2,3-triazole-4-carboxylic acid in place of 1,3-benzothiazole-2-carboxylic acid. LC-MS (ESI, m/z): 548 [M+H]$^+$.

Example 25

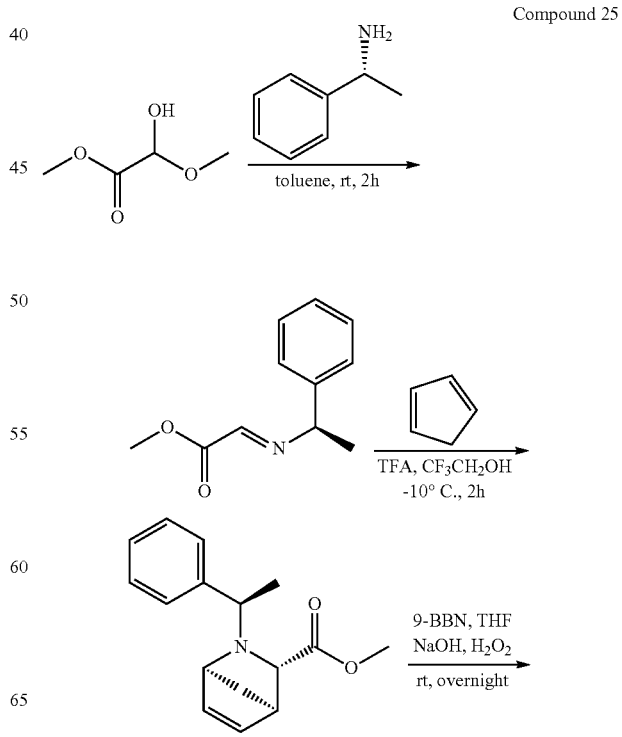

Compound 25

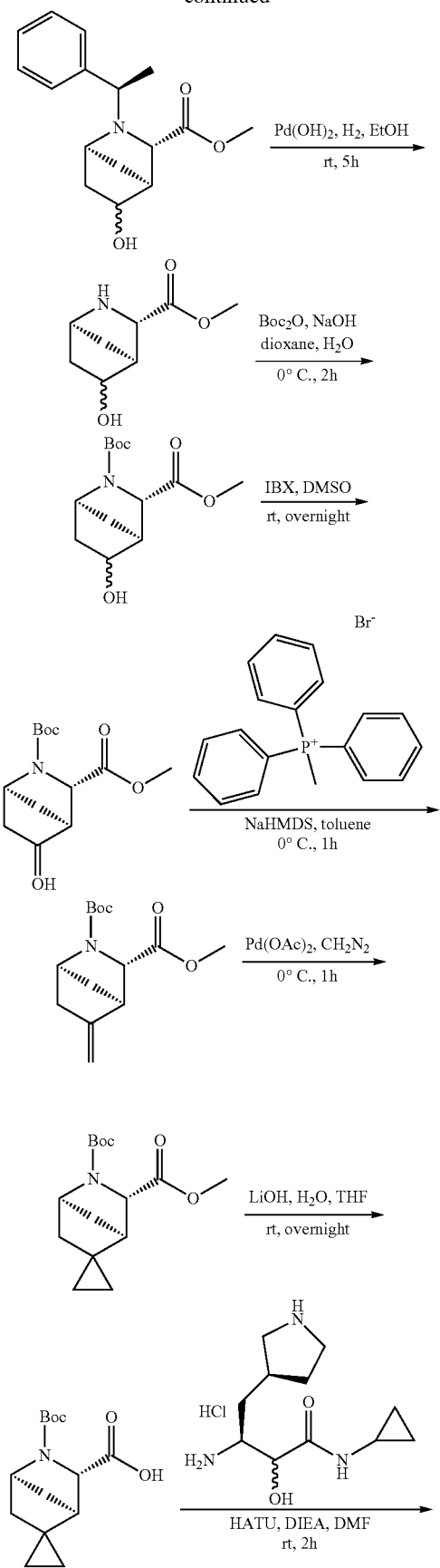
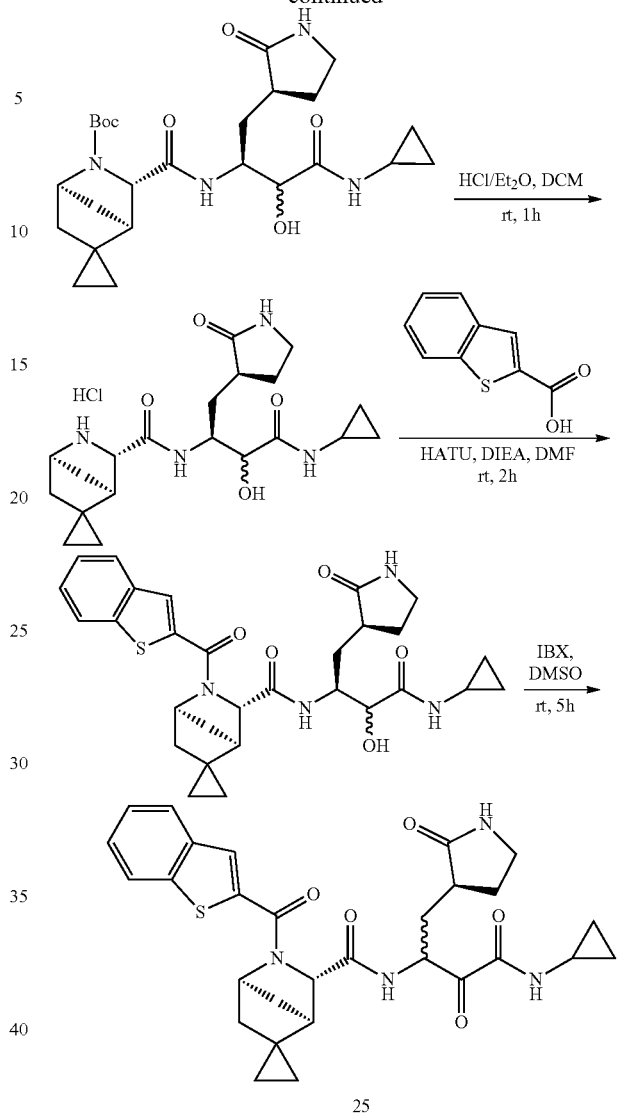

To a stirred mixture of methyl 2-hydroxy-2-methoxyacetate (50.0 g, 416 mmol, 1.0 eq.) in toluene (200 mL) was added (R)-1-phenylethan-1-amine (50.5 g, 416 mmol, 1.0 eq.) dropwise at 0° C. The mixture was stirred for 2 h at rt. The reaction was quenched with water at rt. The mixture was extracted with ethyl acetate (3×500 mL). The organic layers were combined, washed with brine (2×200 mL), dried over anhydrous sodium sulfate, filtered and concentrated under reduced pressure to afford methyl (2E)-2-{[(1R)-1-phenylethyl]imino}acetate (79 g, crude) as a yellow oil. LC-MS (ESI, m/z): 192 [M+H]$^+$.

To a stirred mixture of methyl (2E)-2-{[(1R)-1-phenylethyl]imino}acetate (40.0 g, 209 mmol, 1.0 eq.) in 2,2,2-trifluoroethanol (200 mL) was added trifluoroacetic acid (23.8 g, 209 mmol, 1.0 eq.) dropwise at −10° C. The mixture was stirred for 1 h at −10° C., then cyclopentadiene (15.2 g, 230 mmol, 1.1 eq.) was added. The mixture was stirred for 1 h at −10° C. The reaction was quenched with sat. sodium carbonate (100 mL) at 0° C. The mixture was extracted with dichloromethane (3×500 mL). The organic layers were combined, washed with brine (2×300 mL), dried over anhydrous sodium sulfate, filtered and concentrated under reduced pressure. The residue was purified by silica gel column chromatography, eluted with petroleum ether:ethyl acetate (14:1) to afford methyl (1S,3S,4R)-2-[(1R)-1-phenylethyl]-2-azabicyclo[2.2.1]hept-5-ene-3-carboxylate (18 g, 31%) as a yellow oil. $^1$H NMR (400 MHz, Chloroform-d) δ 7.19-7.35 (m, 4H), 7.13-7.21 (m, 1H), 6.40-6.45 (m, 1H), 6.25-6.29 (m, 1H), 4.31 (s, 1H), 3.35 (s, 3H), 3.01-3.06 (m, 1H), 2.91 (s, 1H), 2.22 (s, 1H), 2.05-2.15 (m, 1H), 1.39-1.44 (m, 4H). LC-MS (ESI, m/z): 258 [M+H]$^+$.

To a stirred mixture of methyl (1S,3S,4R)-2-[(1R)-1-phenylethyl]-2-azabicyclo[2.2.1]hept-5-ene-3-carboxylate (30.0 g, 117 mmol, 1.0 eq.) in tetrahydrofuran (300 mL) were added 9-borabicyclo[3.3.1]nonane (466 mL, 175 mmol, 2.0 eq., 0.5 M in THF) dropwise at 0° C. The mixture was stirred for overnight at rt. The reaction was quenched with sodium hydroxide (204 mL, 408 mmol, 3.5 eq.) and hydrogen peroxide (66 g, 583 mmol, 5.0 eq., 30%) at 0° C. The mixture was extracted with ethyl acetate (3×500 mL). The organic layers were combined, washed with brine (2×200 mL), dried over anhydrous sodium sulfate, filtered and concentrated under reduced pressure. The residue was purified by silica gel column chromatography with petroleum ether:ethyl acetate (3:2) to afford methyl (1S,3S,4S)-5-hydroxy-2-[(1R)-1-phenylethyl]-2-azabicyclo[2.2.1]heptane-3-carboxylate as a yellow solid. The residue was purified by trituration with diethyl ether (30 mL) to afford methyl (1S,3S,4S)-5-hydroxy-2-[(1R)-1-phenylethyl]-2-azabicyclo[2.2.1]heptane-3-carboxylate (5.0 g, 15%) as a white solid. $^1$H NMR (400 MHz, Chloroform-d) δ 7.16-7.30 (m, 5H), 3.89-3.94 (m, 1H), 3.77 (s, 1H), 3.27-3.35 (m, 4H), 2.36-2.47 (m, 2H), 2.25 (s, 1H), 2.02-2.06 (m, 1H), 1.63-1.73 (m, 2H), 1.27-1.36 (m, 4H). LC-MS (ESI, m/z): 276 [M+H]$^+$.

To a stirred mixture of methyl (1S,3S,4S)-5-hydroxy-2-[(1R)-1-phenylethyl]-2-azabicyclo[2.2.1]heptane-3-carboxylate (3.30 g, 11.9 mmol, 1.0 eq.) in ethanol (50 mL) was added palladium hydroxide (0.66 g) under hydrogen at rt. The mixture was stirred for 5 h at rt. The mixture was filtered, and the filter cake was washed with ethanol (3×20 mL). The filtrate was concentrated under reduced pressure to afford methyl (1S,3S,4S)-5-hydroxy-2-azabicyclo[2.2.1]heptane-3-carboxylate (2.0 g, crude) as a colorless oil. LC-MS (ESI, m/z): 172 [M+H]$^+$.

To a stirred mixture of methyl (1S,3S,4S)-5-hydroxy-2-azabicyclo[2.2.1]heptane-3-carboxylate (2.10 g, 12.3 mmol, 1.0 eq.) in dioxane (15 mL) and water (3 mL) was added sodium hydroxide (0.490 g, 12.267 mmol, 1.0 eq.) and di-tert-butyl dicarbonate (2.68 g, 12.3 mmol, 1.0 eq.) dropwise at 0° C. The mixture was stirred for 2 h at 0° C. and then diluted with water (20 mL) at 0° C. The mixture was extracted with ethyl acetate (3×150 mL). The organic layers were combined, washed with brine (2×60 mL), dried over anhydrous sodium sulfate, filtered and concentrated under reduced pressure. The residue was purified by silica gel column chromatography with petroleum ether:ethyl acetate (2:3) to afford 2-tert-butyl 3-methyl (1S,3S,4S)-5-hydroxy-2-azabicyclo[2.2.1]heptane-2,3-dicarboxylate (1.23 g, 35%) as a colorless oil. LC-MS (ESI, m/z): 216 [M+H-56]$^+$.

To a stirred mixture of 2-tert-butyl 3-methyl (1S,3S,4S)-5-hydroxy-2-azabicyclo[2.2.1]heptane-2,3-dicarboxylate (1.20 g, 4.42 mmol, 1.0 eq.) in dimethyl sulfoxide (10 mL) was added 2-iodoxybenzoic acid (3.72 g, 13.3 mmol, 3.0 eq.) in portions at rt. The mixture was stirred for overnight at rt, and the reaction was quenched with sat. sodium bicarbonate (20 mL) at rt. The mixture was extracted with ethyl acetate (3×100 mL). The organic layers were combined, washed with brine (3×50 mL), dried over anhydrous sodium sulfate, filtered and concentrated under reduced pressure. The residue was purified by silica gel column chromatography, eluted with petroleum ether:ethyl acetate (8:1) to afford 2-tert-butyl 3-methyl (1S,3S,4S)-5-oxo-2-azabicyclo[2.2.1]heptane-2,3-dicarboxylate (1.06 g, 85%) as a yellow oil. $^1$H NMR (400 MHz, Chloroform-d) δ 4.57-4.74 (m, 1H), 4.03-4.22 (m, 1H), 3.76 (s, 1H), 3.00-3.03 (m, 1H), 2.18-2.46 (m, 3H), 1.80-1.86 (m, 1H), 1.37-1.51 (m, 9H). LC-MS (ESI, m/z): 214 [M+H-56]$^+$.

To a stirred mixture of methyltriphenylphosphonium bromide (1.02 g, 2.86 mmol, 1.1 eq.) in toluene (12 mL) was added sodium bis(trimethylsilyl)amide (1.43 mL, 2.86 mmol, 1.1 eq., 1 M in THF) dropwise at 0° C. under nitrogen. The mixture was stirred for 1 h at 0° C., and then 2-tert-butyl 3-methyl (1S,3S,4S)-5-oxo-2-azabicyclo[2.2.1]heptane-2,3-dicarboxylate (700 mg, 2.60 mmol, 1.0 eq.) was added. The mixture was stirred for 1 h at 0° C. The reaction was quenched with sat. ammonium chloride (20 mL) at 0° C. The mixture was extracted with ethyl acetate (3×50 mL). The organic layers were combined, washed with brine (2×30 mL), dried over anhydrous sodium sulfate, filtered and concentrated under reduced pressure. The residue was purified by silica gel column chromatography, eluted with petroleum ether:ethyl acetate (15:1) to afford 2-tert-butyl 3-methyl (1S,3S,4R)-5-methylidene-2-azabicyclo[2.2.1]heptane-2,3-dicarboxylate (540 mg, 74%) as a yellow oil. $^1$H NMR (400 MHz, Chloroform-d) δ 5.15-5.18 (m, 1H), 4.85-4.89 (m, 1H), 4.32-4.45 (m, 1H), 3.86-3.99 (m, 1H), 3.73-3.75 (m, 3H), 3.09-3.12 (m, 1H), 2.23-2.44 (m, 2H), 2.03-2.08 (m, 1H), 1.38-1.49 (m, 10H). LC-MS (ESI, m/z): 212 [M+H-56]$^+$.

To a stirred mixture of 2-tert-butyl 3-methyl (1S,3S,4R)-5-methylidene-2-azabicyclo[2.2.1]heptane-2,3-dicarboxylate (520 mg, 1.94 mmol, 1.0 eq.) in diethyl ether (20 mL) was added diazomethane (2.45 g, 58.3 mmol, 30.0 eq.) and palladium acetate (186 mg, 0.389 mmol, 0.2 eq.) at −30° C. The mixture was stirred for 1 h at −30° C. The mixture was filtered, and the filter cake was washed with diethyl ether (3×20 mL). The filtrate was concentrated under reduced pressure. The residue was purified by silica gel column chromatography with petroleum ether:ethyl acetate (9:1) to afford 5-tert-butyl 6-methyl (1R,4S,6S)-5-azaspiro[bicyclo[2.2.1]heptane-2,1'-cyclopropane]-5,6-dicarboxylate (420 mg, 66%) as a yellow oil. $^1$H NMR (400 MHz, Chloroform-d) δ 4.28-4.42 (m, 1H), 4.01-4.17 (m, 1H), 3.69-3.72 (m, 3H), 1.86-2.02 (m, 2H), 1.69-1.76 (m, 2H), 1.57-1.60 (m, 1H), 1.40-1.50 (m, 9H), 0.41-0.74 (m, 4H). LC-MS (ESI, m/z): 226 [M+H-56]$^+$.

To a stirred mixture of 5-tert-butyl 6-methyl (1R,4S,6S)-5-azaspiro[bicyclo[2.2.1]heptane-2,1'-cyclopropane]-5,6-dicarboxylate (400 mg, 1.42 mmol, 1.0 eq.) in tetrahydrofuran (10 mL) and water (2 mL) was added lithium hydroxide (170 mg, 7.11 mmol, 5.0 eq.) dropwise at rt. The mixture was stirred for overnight at rt. The mixture was extracted with ethyl acetate (30 mL). The layers were acidified to pH=3 with hydrochloric acid (2 M). The mixture was extracted with ethyl acetate (3×30 mL). The organic layers were combined, washed with brine (2×20 mL), dried over anhydrous sodium sulfate, filtered and concentrated under reduced pressure to afford (1R,4S,6S)-5-(tert-butoxycarbonyl)-5-azaspiro[bicyclo[2.2.1]heptane-2,1'-cyclopropane]-6-carboxylic acid (380 mg) as a yellow oil. LC-MS (ESI, m/z): 212 [M+H-56]$^+$.

To a stirred mixture of (1R,4S,6S)-5-(tert-butoxycarbonyl)-5-azaspiro[bicyclo[2.2.1]heptane-2,1'-cyclopropane]-6-carboxylic acid (380 mg, 1.42 mmol, 1.0 eq.) and (3S)-3-amino-N-cyclopropyl-2-hydroxy-4-[(3S)-pyrrolidin-3-yl]

butanamide hydrochloride (375 mg, 1.42 mmol, 1.0 eq.) in N,N-dimethylformamide (8 mL) was added O-(7-Aza-1H-benzotriazol-1-yl)-N,N,N',N'-tetramethyluronium hexafluorophosphate (703 mg, 1.85 mmol, 1.3 eq.) and N,N-diisopropylethylamine (735 mg, 5.68 mmol, 4.0 eq.) dropwise at 0° C. The mixture was stirred for 2 h at rt. The reaction was quenched with water (15 mL) at rt. The mixture was extracted with ethyl acetate (3×40 mL). The organic layers were combined, washed with brine (3×30 mL), dried over anhydrous sodium sulfate, filtered and concentrated under reduced pressure. The residue was purified by silica gel column chromatography with dichloromethane:methanol (16:1) to afford tert-butyl (1R,4S,6S)-6-{[(2S)-1-(cyclopropylcarbamoyl)-1-hydroxy-3-[(3S)-2-oxopyrrolidin-3-yl]propan-2-yl]carbamoyl}-5-azaspiro[bicyclo[2.2.1]heptane-2,1'-cyclopropane]-5-carboxylate (370 mg, 48%) as a white solid. LC-MS (ESI, m/z): 491 [M+H]⁺.

To a stirred mixture of tert-butyl (1R,4S,6S)-6-{[(2S)-1-(cyclopropylcarbamoyl)-1-hydroxy-3-[(3S)-2-oxopyrrolidin-3-yl]propan-2-yl]carbamoyl}-5-azaspiro[bicyclo[2.2.1]heptane-2,1'-cyclopropane]-5-carboxylate (100 mg, 0.204 mmol, 1.0 eq.) in dichloromethane (1 mL) was added hydrochloric acid (4 mL, 2 M) dropwise at rt. The mixture was stirred for 1.5 h at rt and concentrated under reduced pressure to afford (3S)-3-[(1R,4S,6S)-5-azaspiro[bicyclo[2.2.1]heptane-2,1'-cyclopropan]-6-ylformamido]-N-cyclopropyl-2-hydroxy-4-[(3S)-2-oxopyrrolidin-3-yl]butanamide hydrochloride (87 mg, crude) as a white solid. LC-MS (ESI, m/z): 391 [M+H]⁺.

To a stirred mixture of 1-benzothiophene-2-carboxylic acid (36.0 mg, 0.202 mmol, 1.0 eq.) and N,N-diisopropylethylamine (104 mg, 0.808 mmol, 4.0 eq.) in N,N-dimethylformamide (8 mL) were added O-(7-Aza-1H-benzotriazol-1-yl)-N,N,N',N'-tetramethyluronium hexafluorophosphate (99.8 mg, 0.263 mmol, 1.3 eq.) at 0° C. The mixture was stirred for 10 min at 0° C., then (3S)-3-[(1R,4S,6S)-5-azaspiro[bicyclo[2.2.1]heptane-2,1'-cyclopropan]-6-ylformamido]-N-cyclopropyl-2-hydroxy-4-[(3S)-2-oxopyrrolidin-3-yl]butanamide hydrochloride (86.3 mg, 0.202 mmol, 1.0 eq.) was added. The mixture was stirred for 2 h at rt. The reaction was quenched with water (15 mL) at rt. The mixture was extracted with ethyl acetate (3×40 mL). The organic layers were combined, washed with brine (3×30 mL), dried over anhydrous sodium sulfate, filtered and concentrated under reduced pressure. The residue was purified by TLC (dichloromethane:methanol (1:10)) to afford (3S)-3-[(1R,4S,6S)-5-(1-benzothiophene-2-carbonyl)-5-azaspiro[bicyclo[2.2.1]heptane-2,1'-cyclopropan]-6-ylformamido]-N-cyclopropyl-2-hydroxy-4-[(3S)-2-oxopyrrolidin-3-yl]butanamide (70.0 mg, 59%) as a white solid. LC-MS (ESI, m/z): 551 [M+H]⁺.

To a stirred mixture of (3S)-3-[(1R,4S,6S)-5-(1-benzothiophene-2-carbonyl)-5-azaspiro[bicyclo[2.2.1]heptane-2,1'-cyclopropan]-6-ylformamido]-N-cyclopropyl-2-hydroxy-4-[(3S)-2-oxopyrrolidin-3-yl]butanamide (60.0 mg, 0.109 mmol, 1.0 eq.) in dimethyl sulfoxide (8 mL) was added 2-iodoxybenzoic acid (91.5 mg, 0.327 mmol, 3.0 eq.) at rt. The mixture was stirred for 5 h at rt. The reaction was quenched with sat. sodium bicarbonate (15 mL) at rt. The mixture was extracted with ethyl acetate (3×40 mL). The combined organic layers were washed with brine (3×30 mL), dried over anhydrous sodium sulfate, filtered and concentrated under reduced pressure. The residue was purified by TLC (dichloromethane:methanol (11:1)) to afford 3-[(1R,4S,6S)-5-(1-benzothiophene-2-carbonyl)-5-azaspiro[bicyclo[2.2.1]heptane-2,1'-cyclopropan]-6-ylformamido]-N-cyclopropyl-2-oxo-4-[(3S)-2-oxopyrrolidin-3-yl]butanamide (15.4 mg, 25%) as a white solid. LC-MS (ESI, m/z): 549 [M+H]⁺.

Example 26

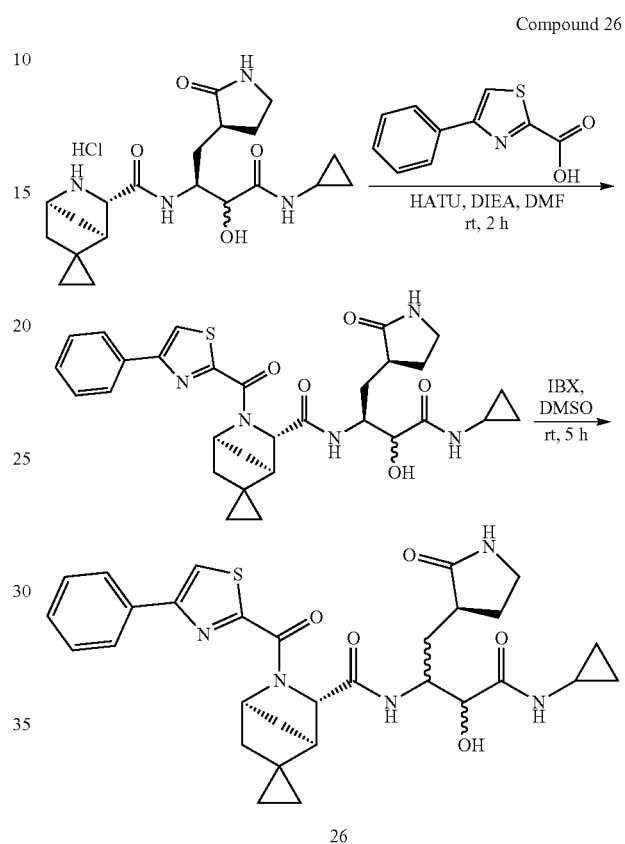

Compound 26

26

To a stirred mixture of 4-phenyl-1,3-thiazole-2-carboxylic acid (42.0 mg, 0.205 mmol, 1.0 eq.) and O-(7-Aza-1H-benzotriazol-1-yl)-N,N,N',N'-tetramethyluronium hexafluorophosphate (101 mg, 0.267 mmol, 1.3 eq.) in DMF (8 mL) was added N,N-diisopropylethylamine (132 mg, 1.03 mmol, 5.0 eq.) at 0° C. The mixture was stirred for 10 min at 0° C., and then (3S)-3-[(1R,4S,6S)-5-azaspiro[bicyclo[2.2.1]heptane-2,1'-cyclopropan]-6-ylformamido]-N-cyclopropyl-2-hydroxy-4-[(3S)-2-oxopyrrolidin-3-yl]butanamide hydrochloride (87.4 mg, 0.205 mmol, 1.0 eq.) was added. The mixture was stirred for 2 h at rt. The reaction was quenched with water (15 mL) at rt. The mixture was extracted with ethyl acetate (3×40 mL). The organic layers were combined, washed with brine (3×30 mL), dried over anhydrous sodium sulfate, filtered and concentrated under reduced pressure. The residue was purified by TLC (dichloromethane:methanol (12:1)) to afford (3S)—N-cyclopropyl-2-hydroxy-4-[(3S)-2-oxopyrrolidin-3-yl]-3-[(1R,4S,6S)-5-(4-phenyl-1,3-thiazole-2-carbonyl)-5-azaspiro[bicyclo[2.2.1]heptane-2,1'-cyclopropan]-6-ylformamido]butanamide (70.0 mg, 58%) as a brown solid. ¹H NMR (400 MHz, DMSO-$d_6$) δ 8.30-8.42 (m, 1H), 7.67-8.05 (m, 3H), 7.14-7.66 (m, 5H), 5.48-5.60 (m, 1H), 4.82-5.31 (m, 1H), 4.03-4.37 (m, 1H), 3.63-3.90 (m, 1H), 3.22-3.44 (m, 1H), 2.96-3.22 (m, 2H), 2.60-2.83 (m, 1H), 2.02-2.42 (m, 3H), 1.50-2.01 (m, 5H), 0.98-1.22 (m, 2H), 0.37-1.01 (m, 8H). LC-MS (ESI, m/z): 578 [M+H]⁺.

To a stirred mixture of (3S)—N-cyclopropyl-2-hydroxy-4-[(3S)-2-oxopyrrolidin-3-yl]-3-[(1R,4S,6S)-5-(4-phenyl-1,3-thiazole-2-carbonyl)-5-azaspiro[bicyclo[2.2.1]heptane-2,1'-cyclopropan]-6-ylformamido]butanamide (62.0 mg, 0.107 mmol, 1.0 eq.) in dimethyl sulfoxide (6 mL) was added 2-iodoxybenzoic acid (90.2 mg, 0.321 mmol, 3.0 eq.) at rt. The mixture was stirred for 5 h at rt. The reaction was quenched with sat. sodium bicarbonate (15 mL) at rt. The mixture was extracted with ethyl acetate (3×40 mL). The organic layers were combined, washed with brine (3×30 mL), dried over anhydrous sodium sulfate, filtered and concentrated under reduced pressure. The residue was purified by TLC (dichloromethane:methanol (11:1)) to afford N-cyclopropyl-2-oxo-4-[(3S)-2-oxopyrrolidin-3-yl]-3-[(1R,4S,6S)-5-(4-phenyl-1,3-thiazole-2-carbonyl)-5-azaspiro[bicyclo[2.2.1]heptane-2,1'-cyclopropan]-6-ylformamido]butanamide (38.7 mg, 62%) as a white solid. LC-MS (ESI, m/z): 576 [M+H]$^+$.

Example 27

Compound 27

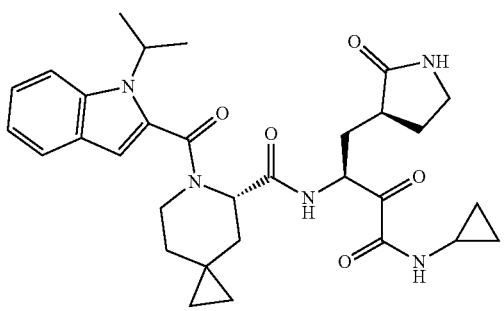

Compound 27 was prepared similarly as described for Compound 1 using 1-isopropyl-1H-indole-2-carboxylic acid in place of 5-phenylthiazole-2-carboxylic acid. $^1$H NMR (400 MHz, 363K, DMSO-d$_6$) δ ppm 8.36 (brs, 1H), 8.27 (d, 1H), 7.57 (d, 1H), 7.52 (m, 1H), 7.35 (brs, 1H), 7.14 (t, 1H), 7.03 (t, 1H), 6.50 (s, 1H), 5.12 (m, 1H), 4.90 (brs, 1H), 4.75-(m, 1H), 4.20 (brs, 1H), 3.42 (brs, 1H), 3.19 (m, 2H), 2.77 (m, 1H), 2.20-2.40 (m, 2H), 2.07 (m, 1H), 1.68-1.95 (m, 4H), 1.50-1.60 (m, 7H), 0.94 (d, 1H), 0.58-0.70 (m, 4H), 0.52 (m, 1H), 0.20-0.32 (m, 3H). LCMS (ESI, m/z): 560 [M−H]$^-$.

1-Isopropyl-1H-indole-2-carboxylic acid: To a suspension of NaH (91 mg, 2.28 mmol, 2.0 eq.) in DMF (2.0 mL) cooled at 0° C. was added methyl 1H-indole-2-carboxylate (200 mg, 1.14 mmol, 1.0 eq.). The mixture was stirred at rt for 30 min. After cooling to 0° C., a solution of 2-iodopropane (0.17 mL, 1.71 mmol, 1.5 eq.) in DMF (0.5 mL) was added. The mixture was stirred at rt for 24 h. The mixture was diluted with ice/water (10 mL) and then extracted with EA (3×10 mL). The organic phases were combined, washed with water and brine, dried over Na$_2$SO$_4$, filtered and concentrated under reduced pressure. The residue was purified by flash chromatography on silica gel (12 g column) using a gradient of EA (0 to 3%) in PE to afford methyl 1-isopropyl-1H-indole-2-carboxylate (130 mg, 52%) as a colorless liquid. LC-MS (ESI, m/z): 218 [M+H]$^+$.

To a solution of methyl 1-isopropyl-1H-indole-2-carboxylate (130 mg, 0.598 mmol, 1.0 eq.) in EtOH (3.8 mL) was added 2 M NaOH (3.8 mL, 7.60 mmol, 12.7 eq.). The mixture was refluxed for 1 h. After cooling to rt, the mixture was concentrated under reduced pressure. The residue was taken up with ice/water and extracted with Et$_2$O. The aqueous phase was acidified with conc. HCl and then extracted with EA (3×10 mL). The organic phases were combined, dried over Na$_2$SO$_4$, filtered and concentrated under reduced pressure to afford 1-isopropyl-1H-indole-2-carboxylic acid 2 (100 mg, 82%) as an off-white solid. LC-MS (ESI, m/z): 204 [M+H]$^+$.

Example 28

Compound 28

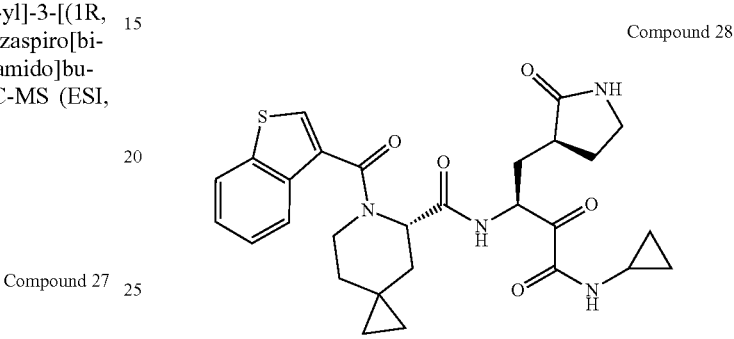

Compound 28 was prepared similarly as described for Compound 1 using benzo[b]thiophene-3-carboxylic acid in place of 5-phenylthiazole-2-carboxylic acid. $^1$H NMR (400 MHz, 362K, DMSO-d$_6$) δ ppm 8.30-8.40 (m, 2H), 7.99 (dd, 1H), 7.84 (m, 2H), 7.34-7.45 (m, 3H), 5.07 (m, 1H), 4.84 (brs, 1H), 4.00 (brs, 1H), 3.40 (m, 1H), 3.21-3.10 (m, 2H), 2.76 (m, 1H), 2.15-2.30 (m, 2H), 2.10 (m, 1H), 1.78-1.96 (m, 2H), 1.68-1.74 (m, 2H), 1.61 (d, 1H), 0.89 (d, 1H), 0.58-0.67 (m, 4H), 0.51 (m, 1H), 0.20-0.30 (m, 3H). LCMS (ESI, m/z): 535 [M−H]$^-$.

Example 29

Compound 29

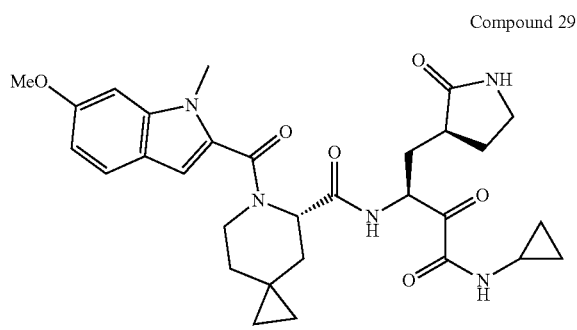 [SMILES: COc1ccc2cc(C(=O)N3CCC4(CC4)C[C@H]3C(=O)N[C@@H](C[C@@H]3CCNC3=O)C(=O)C(=O)NC3CC3)n(C)c2c1]

Compound 29 was prepared similarly as described for Compound 1 using 6-methoxy-1-methyl-1H-indole-2-carboxylic acid in place of 5-phenylthiazole-2-carboxylic acid. $^1$H NMR (400 MHz, 362K, DMSO-d$_6$) δ ppm 8.30-8.40 (m, 2H), 7.34-7.48 (m, 2H), 6.96 (d, 1H), 6.70-6.75 (m, 1H), 6.56 (s, 1H), 4.95-5.20 (m, 2H), 4.23 (m, 1H), 3.82 (s, 3H), 3.71 (s, 3H), 3.32-3.50 (m, 1H), 3.10-3.22 (m, 2H), 2.75 (m, 1H), 2.04-2.38 (m, 3H), 1.60-1.96 (m, 5H), 0.93 (m, 1H), 0.58-0.70 (m, 4H), 0.43 (m, 1H), 0.22-0.35 (m, 3H). LCMS (ESI, m/z): 562 [M−H]$^-$.

Example 30

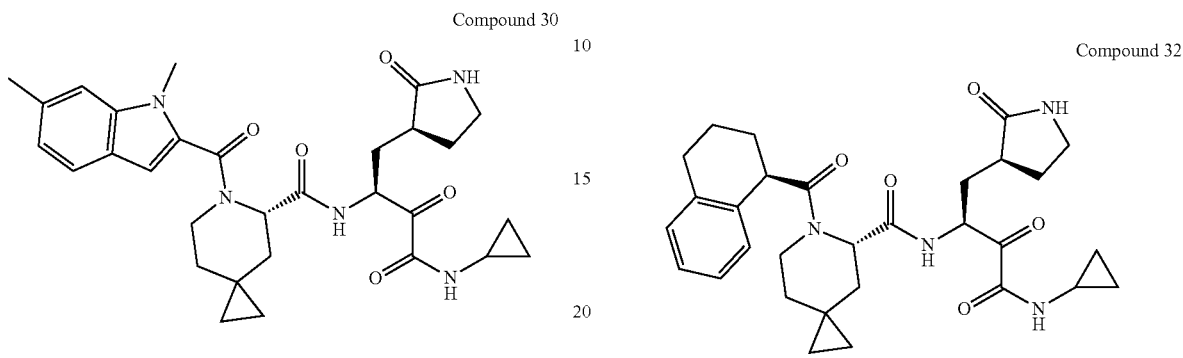

Compound 30

Compound 30 was prepared similarly as described for Compound 1 using 1,6-dimethyl-1H-indole-2-carboxylic acid in place of 5-phenylthiazole-2-carboxylic acid. $^1$H NMR (400 MHz, 360K, DMSO-$d_6$) δ ppm 8.30-8.40 (m, 2H), 7.45 (d, 1H), 7.36 (brs, 1H), 7.24 (s, 1H), 6.90 (d, 1H), 6.56 (s, 1H), 5.10 (m, 1H), 4.96 (m, 1H), 4.21 (brs, 1H), 3.71 (s, 3H), 3.39 (m, 1H), 3.07-3.23 (m, 2H), 2.76 (m, 1H), 2.44 (s, 3H), 2.18-2.35 (m, 2H), 2.05-2.14 (m, 1H), 1.82-1.96 (m, 2H), 1.72 (m, 2H), 1.63 (d, 1H), 0.94 (d, 1H), 0.56-0.71 (m, 4H), 0.52 (m, 1H), 0.32-0.20 (m, 3H). LCMS (ESI, m/z): 546 [M−H]$^-$.

Example 31

Compound 31

Compound 31 was prepared similarly as described for Compound 1 using 6-chloro-1-methyl-1H-indole-2-carboxylic acid in place of 5-phenylthiazole-2-carboxylic acid. $^1$H NMR (400 MHz, 360K, DMSO-$d_6$) δ ppm 8.30-8.40 (m, 2H), 7.54-7.60 (m, 2H), 7.35 (brs, 1H), 7.06 (m, 1H), 6.65 (s, 1H), 5.07 (m, 1H), 4.94 (brs, 1H), 4.18 (brs, 1H), 3.73 (s, 3H), 3.39 (m, 1H), 3.09-3.19 (m, 2H), 2.75 (m, 1H), 2.07-2.33 (m, 3H), 1.82-1.96 (m, 2H), 1.60-1.78 (m, 3H), 0.95 (m, 1H), 0.58-0.69 (m, 4H), 0.52 (m, 1H), 0.22-0.36 (m, 3H). LCMS (ESI, m/z): 568 [M+H]$^+$.

Example 32

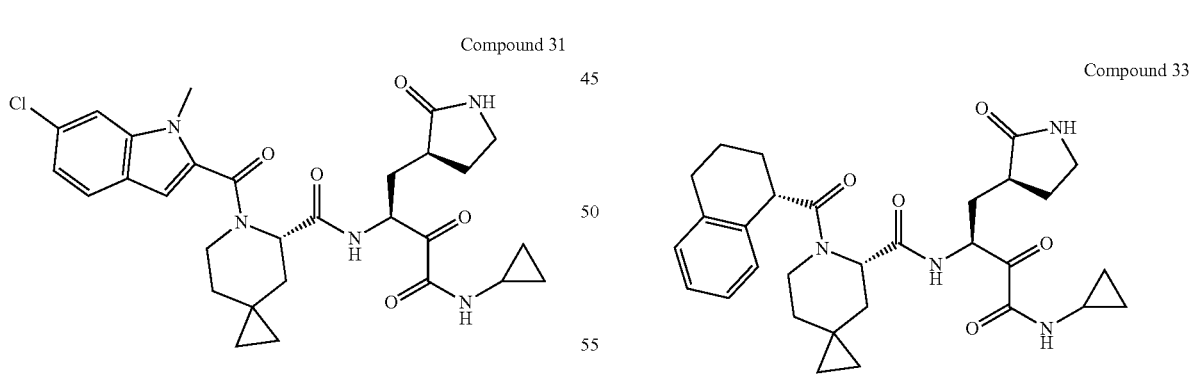

Compound 32

Compound 32 was prepared similarly as described for Compound 1 using (R)-1,2,3,4-tetrahydronaphthalene-1-carboxylic acid in place of 5-phenylthiazole-2-carboxylic acid. $^1$H NMR (400 MHz, 363K, DMSO-$d_6$) δ ppm 8.05-8.40 (m, 2H), 7.29-7.35 (m, 1H), 6.93-7.10 (m, 4H), 5.07 (m, 2H), 4.13 (brs, 2H), 3.42 (brs, 1H), 3.04-3.19 (m, 2H), 2.63-2.79 (m, 3H), 2.11-2.39 (m, 2H), 1.59-2.03 (m, 10H), 0.97 (d, 1H), 0.56-0.70 (m, 4H), 0.42-0.52 (m, 1H), 0.20-0.35 (m, 3H). LCMS (ESI, m/z): 535 [M+H]$^+$.

Example 33

Compound 33

Compound 33 was prepared similarly as described for Compound 1 using (S)-1,2,3,4-tetrahydronaphthalene-1-carboxylic acid in place of 5-phenylthiazole-2-carboxylic acid. $^1$H NMR (400 MHz, 363K, DMSO-$d_6$) δ ppm 8.00-8.42 (m, 2H), 7.24-7.43 (m, 1H), 6.93-7.14 (m, 4H), 5.08 (m, 2H), 4.14 (brs, 2H), 3.37 (brs, 1H), 3.00-3.20 (m, 2H), 2.65-2.82 (m, 3H), 2.11-2.37 (m, 2H), 1.58-2.09 (m, 10H), 0.97 (d, 1H), 0.57-0.70 (m, 4H), 0.39-0.55 (m, 1H), 0.21-0.34 (m, 3H). LCMS (ESI, m/z): 535 [M+H]$^+$.

Example 34
Compounds 34A and 34B
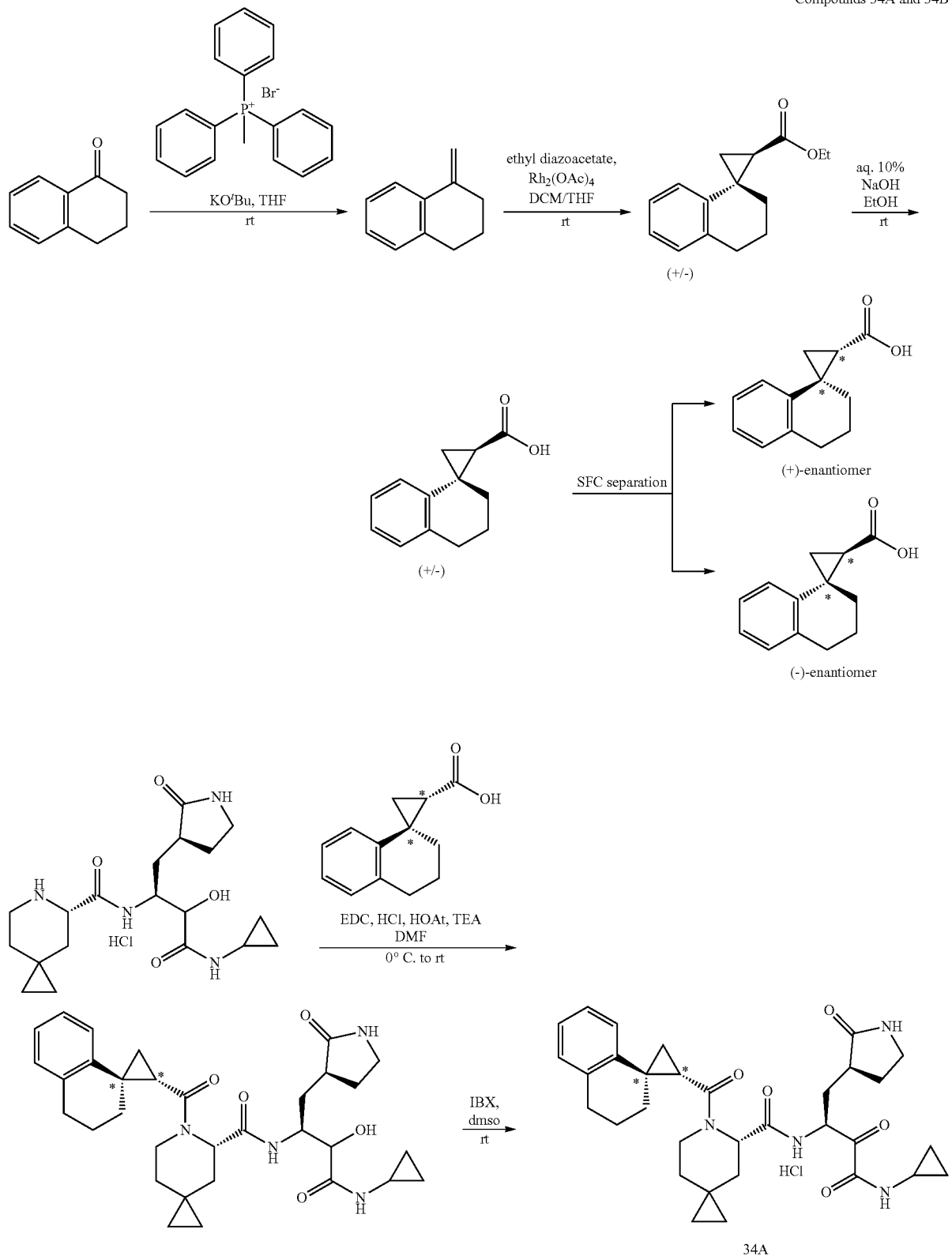

The chiral centers noted with "*" are tentatively assigned.

To a suspension of 3,4-dihydronaphthalen-1(2H)-one (4.0 g, 27.4 mmol, 1 eq.) and methyltriphenylphosphonium bromide (19.6 g, 54.7 mmol, 2 eq.) in THF (104 mL) was added dropwise a solution of tBuOK (6.1 g, 54.7 mmol, 2 eq.) in THF (54 mL) over a period of 2 h. The mixture was stirred at rt for 3 h and then concentrated under reduced pressure. The residue was taken up in hexane. The mixture was filtered through a silica-gel plug and rinsed with hexane to obtain 1-methylene-1,2,3,4-tetrahydronaphthalene (3.8 g, 96%) as a pale brown liquid.

To a solution of 1-methylene-1,2,3,4-tetrahydronaphthalene (1 g, 6.93 mmol, 1 eq.) and Rh$_2$(OAc)$_4$ (31 mg, 0.070 mmol, 0.01 eq.) in DCM (4.2 mL) was added a solution of ethyl diazoacetate (1.46 mL, 3.87 mmol, 2 eq.) in THF (2 mL) over a period of 1 h. The mixture was stirred at rt for 1 h and then concentrated under reduced pressure. The residue was purified by flash chromatography on silica gel using a gradient of EA (0 to 1%) in PE to afford trans ethyl-3',4'-dihydro-2'H-spiro[cyclopropane-1,1'-naphthalene]-2-carboxylate (525 mg, 33%) as a colorless oil. $^1$H NMR (400 MHz, CDCl$_3$) δ 7.06-7.15 (m, 3H), 6.69-6.74 (m, 1H), 4.11-4.20 (m, 2H), 2.87 (t, 2H), 1.92-2.00 (m, 3H), 1.82-1.91 (m, 1H), 1.68-1.78 (m, 1H), 1.52-1.62 (m, 2H), 1.25 (t, 3H). LC-MS (ESI, m/z): 231 [M+H]$^+$. Additionally, cis ethyl-3',4'-dihydro-2'H-spiro[cyclopropane-1,1'-naphthalene]-2-carboxylate (395 mg) was also obtained.

To a solution of trans ethyl-3',4'-dihydro-2'H-spiro[cyclopropane-1,1'-naphthalene]-2-carboxylate (250 mg, 1.09 mmol, 1 eq.) in EtOH (2.7 mL) was added 10% NaOH aqueous solution (2.7 mL, 4.50 mmol, 4 eq.). The reaction mixture was stirred at rt for 18 h. The reaction mixture was diluted with cold water (5 mL) and acidified with 1 M HCl until pH 2. The precipitated solid was collected by filtration and washed with water and hexane to afford trans 3',4'-dihydro-2'H-spiro[cyclopropane-1,1'-naphthalene]-2-carboxylic acid (180 mg, 82%) as a white solid. LC-MS (ESI, m/z): 203 [M+H]$^+$.

Trans 3',4'-Dihydro-2'H-spiro[cyclopropane-1,1'-naphthalene]-2-carboxylic acid (250 mg) was purified by prep-SFC using the following conditions: Column: (R, R) Whelk-01, 3*25 cm, 5 m; Mobile Phase A: CO$_2$, Mobile Phase B: MeOH; Flow rate: 60 g/min; Gradient: isocratic 15% B; Column Temperature: 30° C.; Back Pressure: 100 bar. Purification provided (1S*,2S*)-3',4'-dihydro-2'H-spiro[cyclopropane-1,1'-naphthalene]-2-carboxylic acid (80 mg) and (1R*,2R*)-3',4'-dihydro-2'H-spiro[cyclopropane-1,1'-naphthalene]-2-carboxylic acid (90 mg).

(1S*,2S*)-3',4'-Dihydro-2'H-spiro[cyclopropane-1,1'-naphthalene]-2-carboxylic acid: $^1$H NMR (400 MHz, CDCl$_3$) δ 7.07-7.14 (m, 3H), 6.70-6.75 (m, 1H), 2.88 (t, 2H), 1.75-2.08 (m, 5H), 1.65-1.70 (m, 1H), 1.55-1.60 (m, 1H). [α]$^{25}_D$: +389.5° (c 0.1, MeOH). SFC: (R, R) Whelk-01, 4.6*250 mm, 5 m, 30° C., co-Solvent: MeOH, hold 6 min at 10%, Rt: 1.78 min.

(1R*,2R*)-3',4'-Dihydro-2'H-spiro[cyclopropane-1,1'-naphthalene]-2-carboxylic acid: $^1$H NMR (400 MHz, CDCl$_3$) δ 7.07-7.14 (m, 3H), 6.70-6.75 (m, 1H), 2.88 (t, 2H), 1.75-2.08 (m, 5H), 1.65-1.70 (m, 1H), 1.55-1.60 (m, 1H). [α]25$_D$: -375.3° (c 0.1, MeOH). SFC: (R, R) Whelk-01 4.6*250 mm, 5 m, 30° C. Co-Solvent: MeOH, hold 6 min at 10%; Rt: 2.31 min.

To a solution of (5S)—N-((2S)-4-(cyclopropylamino)-3-hydroxy-4-oxo-1-((S)-2-oxopyrrolidin-3-yl)butan-2-yl)-6-azaspiro[2.5]octane-5-carboxamide hydrochloride (100 mg, 0.242 mmol, 1.0 eq.) in DMF (1.2 mL) cooled at 0° C. were added (1S*,2S*)-3',4'-dihydro-2'H-spiro[cyclopropane-1,1'-naphthalene]-2-carboxylic acid (54 mg, 0.265 mmol, 1.1 eq.), EDC·HCl (92 mg, 0.480 mmol, 2.0 eq.), HOAt (33 mg, 0.242 mmol, 1.0 eq.) and NEt$_3$ (0.10 mL, 0.721 mmol, 3.0 eq.). The mixture was stirred at rt for 16 h. The mixture was diluted with water (10 mL) and extracted with 10% MeOH in DCM (3×10 mL). The organic phases were combined, washed with brine (5 mL), dried over Na$_2$SO$_4$, filtered and concentrated under reduced pressure. The residue was purified by flash chromatography on silica gel (24 g column) using a gradient of MeOH (2 to 4%) in DCM to afford (5S)—N-((2S)-4-(cyclopropylamino)-3-hydroxy-4-oxo-1-((S)-2-oxopyrrolidin-3-yl)butan-2-yl)-6-((1S*,2S*)-3',4'-dihydro-2'H-spiro[cyclopropane-1,1'-naphthalene]-2-carbonyl)-6-azaspiro[2.5]octane-5-carboxamide (80 mg, 59%) as an off-white solid. LC-MS (ESI, m/z): 563 [M+H]$^+$.

To a solution of (5S)—N-((2S)-4-(cyclopropylamino)-3-hydroxy-4-oxo-1-((S)-2-oxopyrrolidin-3-yl)butan-2-yl)-6-((1S*,2S*)-3',4'-dihydro-2'H-spiro[cyclopropane-1,1'-naphthalene]-2-carbonyl)-6-azaspiro[2.5]octane-5-carboxamide (75 mg, 0.133 mmol, 1.0 eq.) in DMSO (1 mL) was added IBX (75 mg, 0.268 mmol, 2.0 eq.). The mixture was stirred at rt for 24 h. The mixture was diluted with 10% MeOH in DCM and washed with sat. NaHCO$_3$ (5 mL). The phases were separated. The organic phase was washed with brine (5 mL), dried over Na$_2$SO$_4$, filtered and concentrated under reduced pressure. The residue was purified by flash chromatography on silica gel (12 g column) using a gradient of MeOH (1 to 10%) in DCM and by prep-HPLC (Column: X-BRIDGE-C18, 30×150 mm Sum; Mobile Phase A: 10 mM NH$_4$HCO$_3$ in water, Mobile Phase B: ACN; Flow rate: 17 mL/min; Gradient: 10% B to 70% B in 8 min) to afford (S)—N—((S)-4-(cyclopropylamino)-3,4-dioxo-1-((S)-2-oxopyrrolidin-3-yl)butan-2-yl)-6-((1S*,2S*)-3',4'-dihydro-2'H-spiro[cyclopropane-1,1'-naphthalene]-2-carbonyl)-6-azaspiro[2.5]octane-5-carboxamide (18 mg, 24%) as a white solid. $^1$H NMR (400 MHz, 362K, DMSO-d$_6$) δ 8.33 (m, 1H), 7.80 (brs, 1H), 7.32 (m, 1H), 7.02-7.12 (m, 3H), 6.87-6.76 (m, 1H), 5.07 (m, 1H), 4.45 (brs, 1H), 3.74 (m, 1H), 3.46 (m, 1H), 3.10-3.26 (m, 3H), 2.85-2.70 (m, 3H), 2.30-2.10 (m, 2H), 1.40-2.02 (m, 11H), 1.26 (m, 1H), 0.82-0.92 (m, 1H), 0.53-0.69 (m, 4H), 0.34-0.50 (m, 1H), 0.15-0.28 (m, 3H). LCMS (ESI, m/z): 561 [M+H]$^+$.

34B

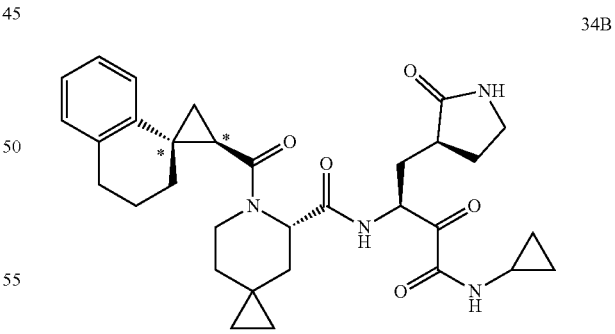

Compound 34B was prepared similarly as described for Compound 34A using (1R*,2R*)-3',4'-dihydro-2'H-spiro[cyclopropane-1,1'-naphthalene]-2-carboxylic acid in place of (1S*,2S*)-3',4'-dihydro-2'H-spiro[cyclopropane-1,1'-naphthalene]-2-carboxylic acid. $^1$H NMR (400 MHz, 362K, DMSO-d$_6$) δ 8.28 (m, 1H), 8.20 (m, 1H), 7.31-7.42 (m, 1H), 7.02-7.12 (m, 3H), 6.84-6.88 (m, 1H), 4.90-5.28 (m, 2H), 3.73 (brs, 1H), 3.30-3.54 (m, 1H), 3.16 (m, 3H), 2.70-2.82 (m, 3H), 2.10-2.40 (m, 3H), 2.00-1.84 (m, 1H), 1.58-1.82

(m, 7H), 1.45 (m, 1H), 1.25 (m, 2H), 0.80-0.88 (m, 1H), 0.58-0.70 (m, 4H), 0.46 (m, 1H), 0.15-0.30 (m, 3H). LCMS (ESI, m/z): 561 [M+H]⁺.

Example 35

Compound 35

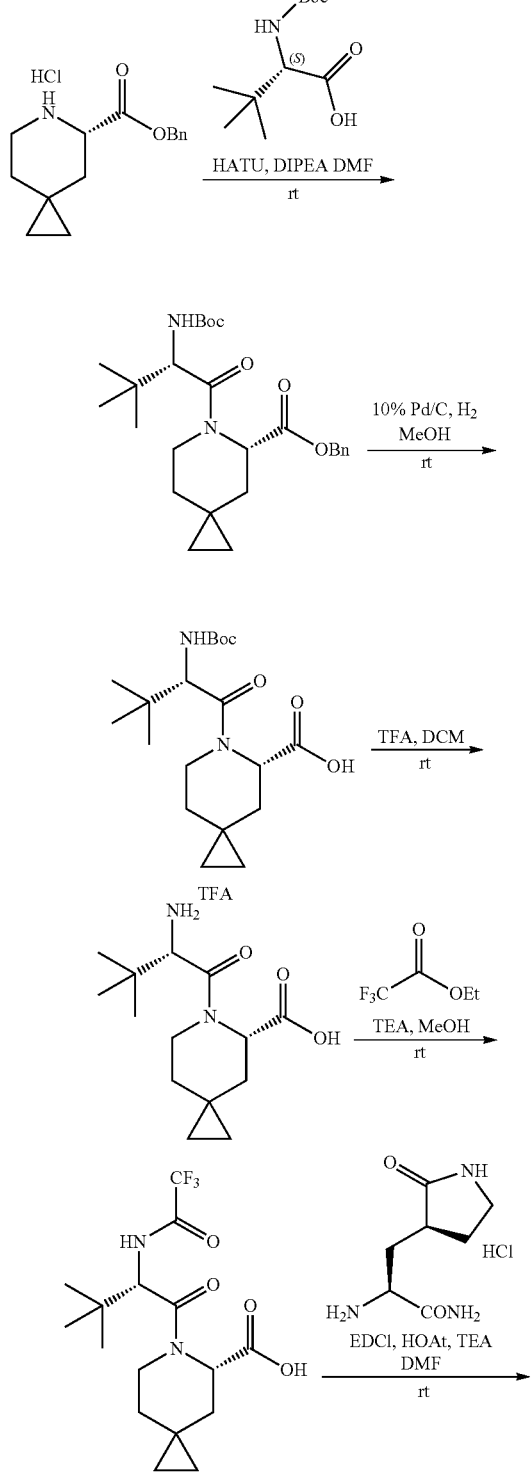

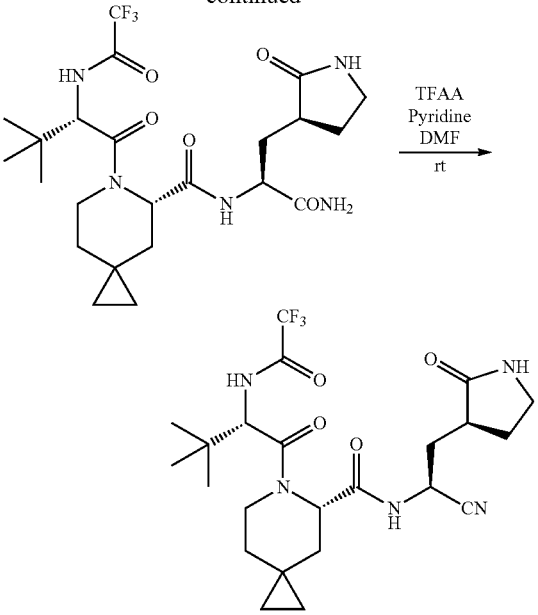

To a solution of benzyl (S)-6-azaspiro[2.5]octane-5-carboxylate hydrochloride (300 mg, 1.22 mmol, 1.0 eq.) and (S)-2-((tert-butoxycarbonyl)amino)-3,3-dimethylbutanoic acid (424 mg, 1.83 mmol, 1.5 eq.) in DMF (3 mL) cooled at 0° C. were added HATU (697 mg, 1.83 mmol, 1.5 eq.) and DIPEA (0.64 mL, 3.67 mmol, 3.0 eq.). The mixture was stirred at rt for 5 h. The mixture was diluted with water (10 mL) and extracted with EA (2×10 mL). The organic phases were combined, washed with brine (2×10 mL), dried over Na₂SO₄, filtered and concentrated under reduced pressure. The residue was purified by flash chromatography on silica gel (24 g column) using a gradient of EA (30 to 60%) in PE to afford benzyl (S)-6-((S)-2-((tert-butoxycarbonyl)amino)-3,3-dimethylbutanoyl)-6-azaspiro[2.5]octane-5-carboxylate (400 mg, 71%) as a colorless oil. LCMS (ESI, m/z): 459 [M+H]⁺.

To a solution of benzyl (S)-6-((S)-2-((tert-butoxycarbonyl)amino)-3,3-dimethylbutanoyl)-6-azaspiro[2.5]octane-5-carboxylate (300 mg, 0.655 mmol, 1.0 eq.) in MeOH (5 mL) was added 10% Pd/C (30 mg). The mixture was stirred at rt under hydrogen (bladder pressure) for 3 h. The mixture was filtered through celite. The filtrate was concentrated under reduced pressure to afford (S)-6-((S)-2-((tert-butoxycarbonyl)amino)-3,3-dimethylbutanoyl)-6-azaspiro[2.5]octane-5-carboxylic acid (220 mg, 91%) as an off-white solid. LCMS (ESI, m/z): 369 [M+H]⁺.

To a solution of (S)-6-((S)-2-((tert-butoxycarbonyl)amino)-3,3-dimethylbutanoyl)-6-azaspiro[2.5]octane-5-carboxylic acid (100 mg, 0.271 mmol, 1.0 eq.) in DCM (5 mL) cooled at 0° C. was added TFA (0.51 mL, 6.79 mmol, 5.0 eq.). The mixture was stirred at rt for 3 h and then concentrated under reduced pressure to afford ((S)-6-((S)-2-amino-3,3-dimethylbutanoyl)-6-azaspiro[2.5]octane-5-carboxylic acid trifluoroacetic acid salt as a pale brown liquid.

To a solution of (S)-6-((S)-2-amino-3,3-dimethylbutanoyl)-6-azaspiro[2.5]octane-5-carboxylic acid trifluoroacetic acid salt (70 mg, 0.261 mmol, 1.0 eq.) in MeOH (1 mL) were added ethyl 2,2,2-trifluoroacetate (0.038 mL, 0.522 mmol, 2.0 eq.) and NEt₃ (0.100 mL, 0.721 mmol, 3.0 eq.). The mixture was stirred at rt for 16 h and then concentrated under reduced pressure. The residue was purified by flash chromatography on C18 column with CH₃CN:water (0.01% TFA). The fractions containing the desired compound were combined and partially concentrated under reduced pressure to remove CH₃CN. The residue was extracted with EA (2×10 mL). The organic phases were combined, dried over Na₂SO₄, filtered and concentrated under reduced pressure to afford (S)-6-((S)-3,3-dimethyl-2-(2,2,2-trifluoroacetamido)butanoyl)-6-azaspiro[2.5]octane-5-carboxylic acid (50 mg, 51% over two steps) as a white solid. LCMS (ESI, m/z): 365 [M+H]⁺.

To a solution of (S)-6-((S)-3,3-dimethyl-2-(2,2,2-trifluoroacetamido)butanoyl)-6-azaspiro[2.5]octane-5-carboxylic acid (50 mg, 0.137 mmol, 1.0 eq.) in DMF (0.5 mL) cooled at 0° C. were added (S)-2-amino-3-((S)-2-oxopyrrolidin-3-yl)propanamide hydrochloride (34 mg, 0.164 mmol, 1.2 eq.), EDC·HCl (52 mg, 0.274 mmol, 2.0 eq.), HOAt (18 mg, 0.137 mmol, 1.0 eq.) and NEt₃ (0.050 mL, 0.411 mmol, 3.0 eq.). The mixture was stirred at rt for 16 h. The mixture was diluted with water (5 mL) and extracted with EA (2×5 mL). The organic phases were combined, washed with brine (2×5 mL), dried over Na₂SO₄, filtered and concentrated under reduced pressure. The residue was purified by flash chromatography on C18 column with CH₃CN:water (0.01% TFA). The fractions containing the desired compound were combined and partially concentrated under reduced pressure to remove CH₃CN. The residue was extracted with EA (2×10 mL). The organic phases were combined, dried over Na₂SO₄, filtered and concentrated under reduced pressure to afford (S)—N—((S)-1-amino-1-oxo-3-((S)-2-oxopyrrolidin-3-yl)propan-2-yl)-6-((S)-3,3-dimethyl-2-(2,2,2-trifluoroacetamido)butanoyl)-6-azaspiro[2.5]octane-5-carboxamide (40 mg, 56%) as a white solid. LCMS (ESI, m/z): 518 [M+H]⁺.

To a solution of (S)—N—((S)-1-amino-1-oxo-3-((S)-2-oxopyrrolidin-3-yl)propan-2-yl)-6-((S)-3,3-dimethyl-2-(2,2,2-trifluoroacetamido)butanoyl)-6-azaspiro[2.5]octane-5-carboxamide (30 mg, 0.058 mmol, 1.0 eq.) in DMF (0.3 mL) were added pyridine (0.014 mL, 0.174 mmol, 3.0 eq.) and TFAA (0.016 mL, 0.116 mmol, 2.0 eq.). The mixture was stirred at rt for 30 min. The mixture was diluted with water (5 mL) and extracted with EA (2×5 mL). The organic phases were combined, washed with brine (2×5 mL), dried over Na₂SO₄, filtered and concentrated under reduced pressure. The residue was purified by flash chromatography on C18 column with CH₃CN:water (0.01% NH₄HCO₃) to afford (S)—N—((S)-1-cyano-2-((S)-2-oxopyrrolidin-3-yl)ethyl)-6-((S)-3,3-dimethyl-2-(2,2,2-trifluoroacetamido)butanoyl)-6-azaspiro[2.5]octane-5-carboxamide (17 mg, 61%) as a white solid. ¹H NMR (400 MHz, DMSO-d₆, 362K) δ 8.35-8.50 (brs, 2H), 7.20-7.45 (m, 1H), 4.45-5.19 (m, 3H), 3.78-4.08 (m, 1H), 3.63 (brs, 1H), 3.11-3.22 (m, 2H), 2.07-2.29 (m, 3H), 1.55-2.05 (m, 5H), 0.90-1.10 (m, 10H), 0.10-0.50 (m, 4H). LC-MS (ESI, m/z): 498 [M−H]⁻.

Example 36

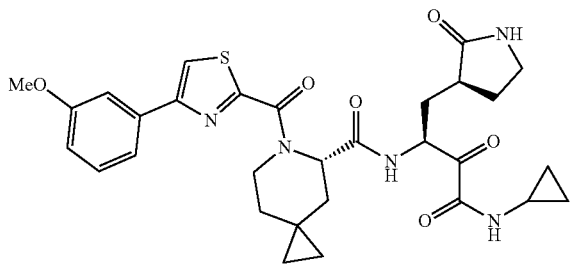

Compound 36

Compound 36 was prepared similarly as described for Compound 1 using 4-(3-methoxyphenyl)thiazole-2-carboxylic acid in place of 5-phenylthiazole-2-carboxylic acid. ¹H NMR (400 MHz, 362K, DMSO-d₆) δ 8.24-8.50 (m, 3H), 7.44-7.54 (d, 2H), 7.34 (m, 1H), 7.28 (br. s., 1H), 6.93 (d, 1H), 5.02-5.18 (m, 2H), 3.81 (s, 3H), 3.25-3.60 (m, 2H), 3.02-3.18 (m, 2H), 2.73 (m, 1H), 2.05-2.48 (m, 4H), 1.94 (m, 1H), 1.55-1.80 (m, 3H), 1.04 (d, 1H), 0.55-0.68 (m, 5H), 0.27-0.35 (m, 3H). LCMS (ESI, m/z): 594 [M+H]⁺.

4-(3-Methoxyphenyl)thiazole-2-carboxylic acid: To a solution of 2-bromo-1-(3-methoxyphenyl)ethan-1-one (500 mg, 2.18 mmol, 1.0 eq.) in EtOH (5 mL) was added ethyl 2-amino-2-thioxoacetate (436 mg, 3.27 mmol, 1.5 eq.). The mixture was heated at 70° C. for 5 h. The mixture was concentrated under reduced pressure. The residue was purified by flash chromatography on silica gel using a gradient of EA (10 to 20%) in PE to afford ethyl 4-(3-methoxyphenyl)thiazole-2-carboxylate 1 (260 mg, 45%) as a colorless liquid. LC-MS (ESI, m/z): 264 [M+H]⁺.

To a solution of ethyl 4-(3-methoxyphenyl)thiazole-2-carboxylate (200 mg, 0.760 mmol, 1.0 eq.) in EtOH (2 mL) was added 2 M NaOH (0.95 mL, 1.90 mmol, 2.5 eq.). The mixture was stirred at overnight. The mixture was diluted with water (3 mL) and extracted with Et₂O (2×2 mL). The aqueous phase was acidified with 1N HCl and extracted with EA (3×5 mL). The organic phases were combined, dried over Na₂SO₄, filtered and concentrated under reduced pressure. The residue was purified by flash chromatography on silica gel using a gradient of MeOH (2 to 3%) in DCM to afford 4-(3-methoxyphenyl)thiazole-2-carboxylic acid (100 mg, 56%) as an off-white solid. LC-MS (ESI, m/z): 236 [M+H]⁺.

Example 37

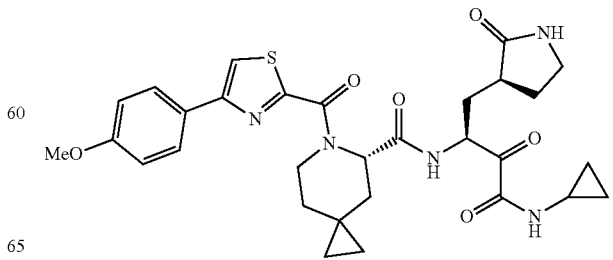

Compound 37

Compound 37 was prepared similarly as described for Compound 1 using 4-(4-methoxyphenyl)thiazole-2-carboxylic acid in place of 5-phenylthiazole-2-carboxylic acid. ¹H NMR (400 MHz, 362K, DMSO-d₆) δ 8.25-8.49 (m, 2H), 8.07 (m, 1H), 7.85 (m, 2H), 7.29 (br. s., 1H), 7.00 (m, 2H), 5.02-5.20 (m, 2H), 3.81 (s, 3H), 3.36-3.56 (m, 2H), 3.04-3.18 (m, 2H), 2.73 (m, 1H), 2.05-2.39 (m, 4H), 1.93 (m, 1H), 1.56-1.89 (m, 3H), 1.04 (d, 1H), 0.54-0.69 (m, 5H), 0.24-0.39 (m, 3H). LCMS (ESI, m/z): 594 [M+H]⁺.

Example 38

Compound 38

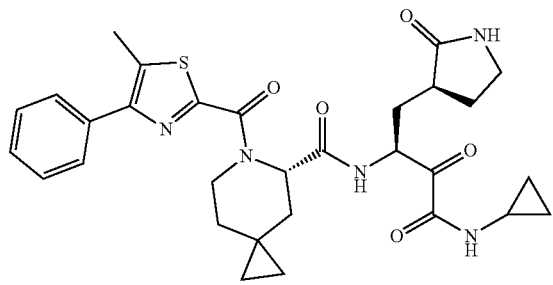

Compound 38 was prepared similarly as described for Compound 1 using 5-methyl-4-phenylthiazole-2-carboxylic acid in place of 5-phenylthiazole-2-carboxylic acid. ¹H NMR (400 MHz, 363K, DMSO-d₆) δ 8.21-8.45 (m, 2H), 7.66 (m, 2H), 7.45 (m, 2H), 7.36 (m, 1H), 7.29 (br. s., 1H), 4.99-5.16 (m, 2H), 3.26-3.58 (m, 2H), 3.02-3.21 (m, 2H), 2.73 (m, 1H), 2.59 (s, 3H), 2.03-2.33 (m, 4H), 1.90 (m, 1H), 1.56-1.77 (m, 3H), 1.00 (d, 1H), 0.54-0.69 (m, 4H), 0.46 (m, 1H), 0.21-0.36 (m, 3H). LCMS (ESI, m/z): 578 [M+H]⁺.

5-Methyl-4-phenylthiazole-2-carboxylic acid: to a solution of 2-bromo-1-phenylpropan-1-one of (500 mg, 2.35 mmol, 1.0 eq.) in EtOH (5 mL) was added ethyl 2-amino-2-thioxoacetate (470 mg, 3.53 mmol, 1.5 eq.). The mixture was refluxed overnight and then concentrated under reduced pressure. The residue was partitioned between EA and water. The phases were separated. The aqueous phase was extracted with EA. The organic phases were combined, washed with brine, dried over Na₂SO₄, filtered and concentrated under reduced pressure. The residue was purified by flash chromatography on silica gel using a gradient of EA (2 to 3%) in hexane to afford ethyl 5-methyl-4-phenylthiazole-2-carboxylate (350 mg, 60%). LC-MS (ESI, m/z): 248 [M+H]⁺.

To a solution of ethyl 5-methyl-4-phenylthiazole-2-carboxylate (350 mg, 1.41 mmol, 1.0 eq.) in EtOH (3.5 mL) was added 2 M NaOH (1.7 mL, 3.52 mmol, 2.5 eq.). The mixture was stirred at overnight, and then partially concentrated to remove EtOH. The residue was acidified with 4N HCl. The precipitate was filtered and dried under high vacuum to afford 5-methyl-4-phenylthiazole-2-carboxylic acid (250 mg, 81%). LC-MS (ESI, m/z): 220 [M+H]⁺.

Example 39

Compound 39

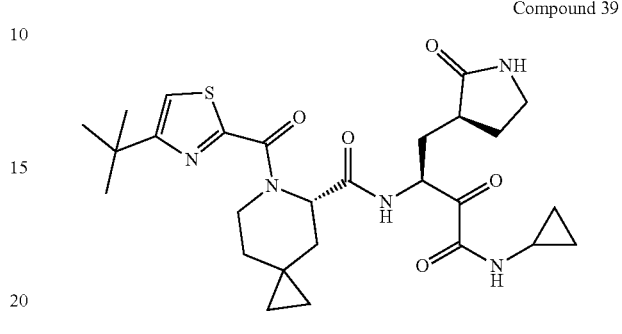

Compound 39 was prepared similarly as described for Compound 1 using 4-(tert-butyl)thiazole-2-carboxylic acid in place of 5-phenylthiazole-2-carboxylic acid. ¹H NMR (400 MHz, 362K, DMSO-d₆) δ 8.25-8.42 (m, 2H), 7.47 (m, 1H), 7.32 (br. s., 1H), 5.00-5.16 (m, 2H), 3.25-3.55 (m, 2H), 3.07-3.23 (m, 2H), 2.73 (m, 1H), 2.03-2.38 (m, 4H), 1.91 (m, 1H), 1.64-1.78 (m, 3H), 1.30 (s, 9H), 0.99 (d, 1H), 0.55-0.68 (m, 4H), 0.45 (m, 1H), 0.23-0.34 (m, 3H). LCMS (ESI, m/z): 544 [M+H]⁺.

Example 40

Compound 40

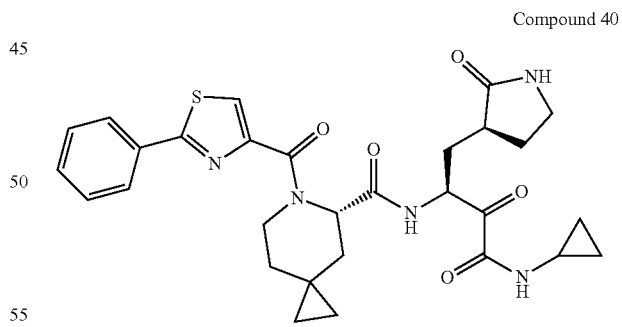

Compound 40 was prepared similarly as described for Compound 1 using 2-phenylthiazole-4-carboxylic acid in place of 5-phenylthiazole-2-carboxylic acid. ¹H NMR (500 MHz, 363K, DMSO-d₆) δ 8.21-8.39 (m, 2H), 8.05 (m, 1H), 7.89-7.95 (m, 2H), 7.46-7.57 (m, 3H), 7.31 (br. s., 1H), 5.03-5.22 (m, 2H), 4.33 (m, 1H), 3.40 (m, 1H), 3.05-3.22 (m, 2H), 2.73 (m, 1H), 2.04-2.35 (m, 4H), 1.91 (m, 1H), 1.59-1.98 (m, 3H), 0.96 (d, 1H), 0.51-0.69 (m, 4H), 0.45 (m, 1H), 0.22-0.33 (m, 3H). LCMS (ESI, m/z): 564 [M+H]⁺.

Example 41

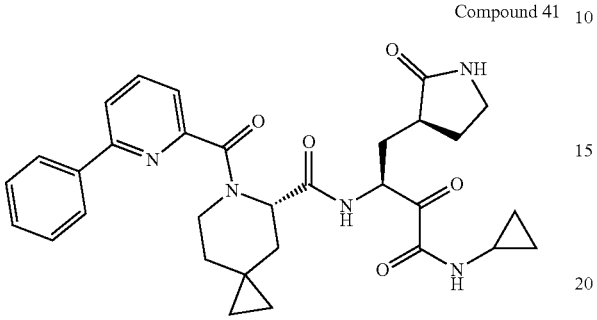

Compound 41

Compound 41 was prepared similarly as described for Compound 1 using 6-phenylpicolinic acid in place of 5-phenylthiazole-2-carboxylic acid. LCMS (ESI, m/z): 558 [M+H]+.

Example 42

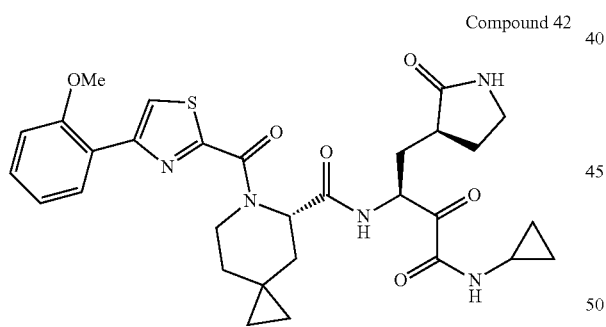

Compound 42

Compound 42 was prepared similarly as described for Compound 1 using 4-(2-methoxyphenyl)thiazole-2-carboxylic acid in place of 5-phenylthiazole-2-carboxylic acid. $^1$H NMR (400 MHz, 362K, DMSO-d$_6$) δ 8.19-8.52 (m, 3H), 8.01 (m, 1H), 7.32 (m, 2H), 7.14 (m, 1H), 7.03 (m, 1H), 5.02-5.18 (m, 2H), 3.93 (s, 3H), 3.28-3.66 (m, 2H), 3.02-3.20 (m, 2H), 2.73 (m, 1H), 2.05-2.39 (m, 4H), 1.94 (m, 1H), 1.55-1.82 (m, 3H), 1.04 (d, 1H), 0.42-0.72 (m, 5H), 0.24-0.40 (m, 3H). LCMS (ESI, m/z): 594 [M+H]+.

4-(2-Methoxyphenyl)thiazole-2-carboxylic acid was prepared similarly as described for 4-(3-methoxyphenyl)thiazole-2-carboxylic acid using 2-bromo-1-(2-methoxyphenyl)ethan-1-one in place of 2-bromo-1-(3-methoxyphenyl)ethan-1-one. LC-MS (ESI, m/z): 236 [M+H]+.

Example 43

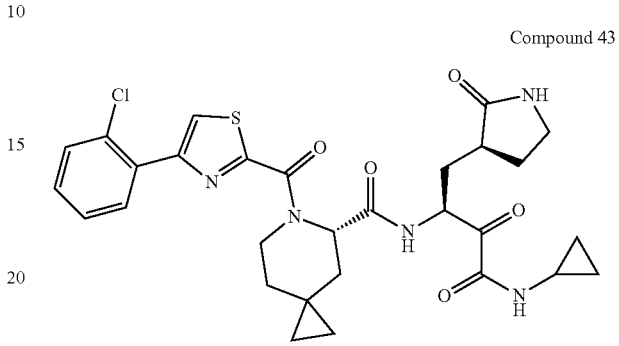

Compound 43

Compound 43 was prepared similarly as described for Compound 1 using 4-(2-chlorophenyl)thiazole-2-carboxylic acid in place of 5-phenylthiazole-2-carboxylic acid. $^1$H NMR (400 MHz, 361K, DMSO-d$_6$) δ 8.27-8.52 (m, 2H), 8.24 (d, 1H), 7.79-7.86 (m, 1H), 7.53 (m, 1H), 7.36-7.47 (m, 2H), 7.30 (br. s., 1H), 5.00-5.17 (m, 2H), 3.33-3.60 (m, 2H), 3.05-3.22 (m, 2H), 2.73 (m, 1H), 2.02-2.29 (m, 3H), 1.92 (m, 2H), 1.50-1.77 (m, 3H), 1.00 (d, 1H), 0.42-0.68 (m, 5H), 0.24-0.37 (m, 3H). LCMS (ESI, m/z): 598 [M+H]+.

Example 44

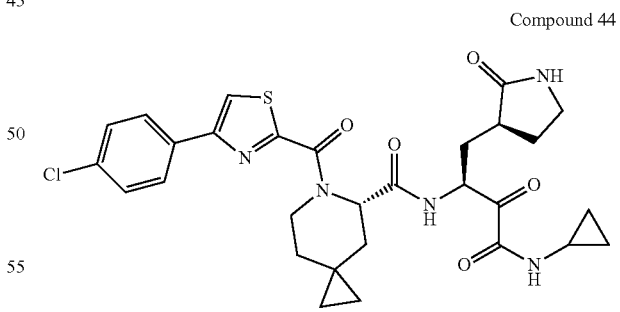

Compound 44

Compound 44 was prepared similarly as described for Compound 1 using 4-(4-chlorophenyl)thiazole-2-carboxylic acid in place of 5-phenylthiazole-2-carboxylic acid. $^1$H NMR (400 MHz, 367K, DMSO-d$_6$) δ 8.24-8.40 (m, 3H), 7.94 (d, 2H), 7.47 (m, 2H), 7.27 (br. s., 1H), 5.05 (m, 2H), 3.32-3.64 (m, 2H), 3.00-3.16 (m, 2H), 2.72 (m, 1H), 2.02-2.36 (m, 3H), 1.93 (m, 2H), 1.58-1.78 (m, 3H), 1.04 (d, 1H), 0.54-0.69 (m, 5H), 0.24-0.35 (m, 3H). LCMS (ESI, m/z): 598 [M+H]+.

Example 45

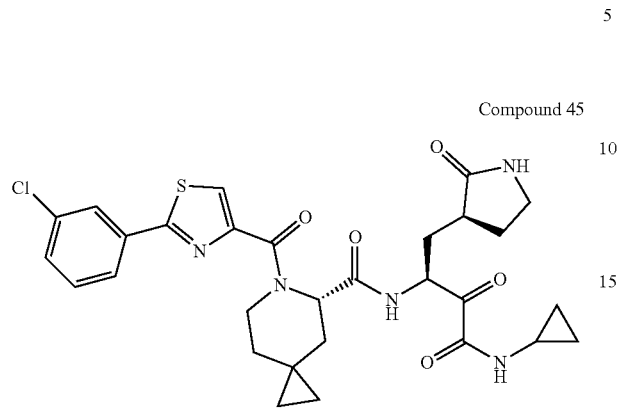

Compound 45

Compound 45 was prepared similarly as described for Compound 1 using 4-(3-chlorophenyl)thiazole-2-carboxylic acid in place of 5-phenylthiazole-2-carboxylic acid. $^1$H NMR (400 MHz, 363K, DMSO-$d_6$) δ 8.24-8.53 (m, 3H), 7.86-7.98 (m, 2H), 7.37-7.48 (m, 2H), 7.28 (br. s., 1H), 5.02-5.18 (m, 2H), 3.32-3.60 (m, 2H), 3.01-3.21 (m, 2H), 2.73 (m, 1H), 2.02-2.38 (m, 3H), 1.94 (m, 2H), 1.58-1.78 (m, 3H), 1.04 (d, 1H), 0.54-0.68 (m, 5H), 0.25-0.37 (m, 3H). LCMS (ESI, m/z): 598 [M+H]$^+$.

Example 46

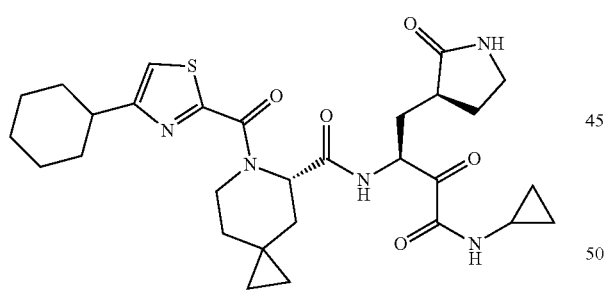

Compound 46

Compound 46 was prepared similarly as described for Compound 1 using 4-cyclohexylthiazole-2-carboxylic acid in place of 5-phenylthiazole-2-carboxylic acid. $^1$H NMR (400 MHz, 362K, DMSO-$d_6$) δ ppm 8.24-8.42 (m, 2H), 7.46 (m, 1H), 7.33 (br. s., 1H), 5.03-5.17 (m, 2H), 3.27-3.60 (m, 2H), 3.07-3.23 (m, 2H), 2.76 (m, 1H), 2.05-2.38 (m, 4H), 1.83-2.04 (m, 4H), 1.62-1.81 (m, 6H), 1.18-1.52 (m, 5H), 1.00 (d, 1H), 0.55-0.71 (m, 4H), 0.47 (m, 1H), 0.22-0.35 (m, 3H). LCMS (ESI, m/z): 570 [M+H]$^+$.

4-Cyclohexylthiazole-2-carboxylic acid was prepared similarly as described for 4-(3-methoxyphenyl)thiazole-2-carboxylic acid using 2-bromo-1-cyclohexylethan-1-one in place of 2-bromo-1-(3-methoxyphenyl)ethan-1-one. LC-MS (ESI, m/z): 212 [M+H]$^+$.

Example 47

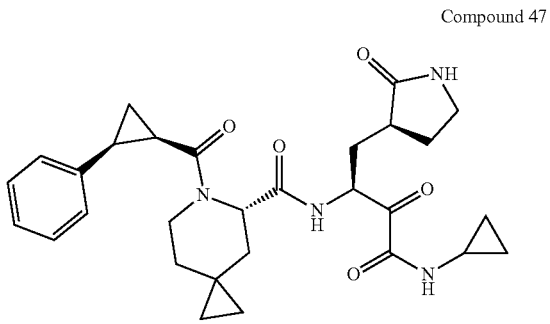 [SMILES: O=C(NC1CC1)C(=O)[C@H](C[C@@H]1CCNC1=O)NC(=O)[C@@H]1CC2(CCN1C(=O)[C@@H]1C[C@@H]1c1ccccc1)CC2]

Compound 47

Compound 47 was prepared similarly as described for Compound 1 using cis-2-phenylcyclopropanecarboxylic acid in place of 5-phenylthiazole-2-carboxylic acid. LCMS (ESI, m/z): 521 [M+H]$^+$.

Example 48

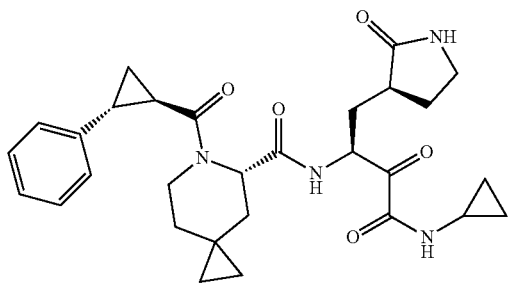

Compound 48

Compound 48 was prepared similarly as described for Compound 1 using trans-2-phenylcyclopropanecarboxylic acid in place of 5-phenylthiazole-2-carboxylic acid. LCMS (ESI, m/z): 521 [M+H]$^+$.

Example 49

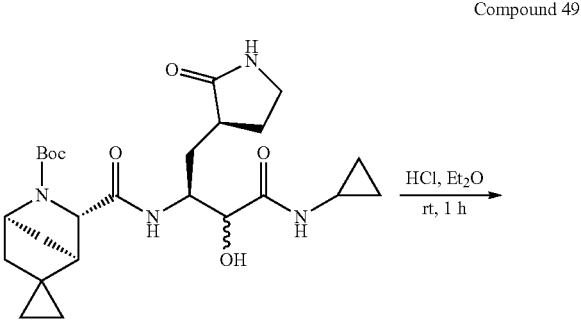

Compound 49

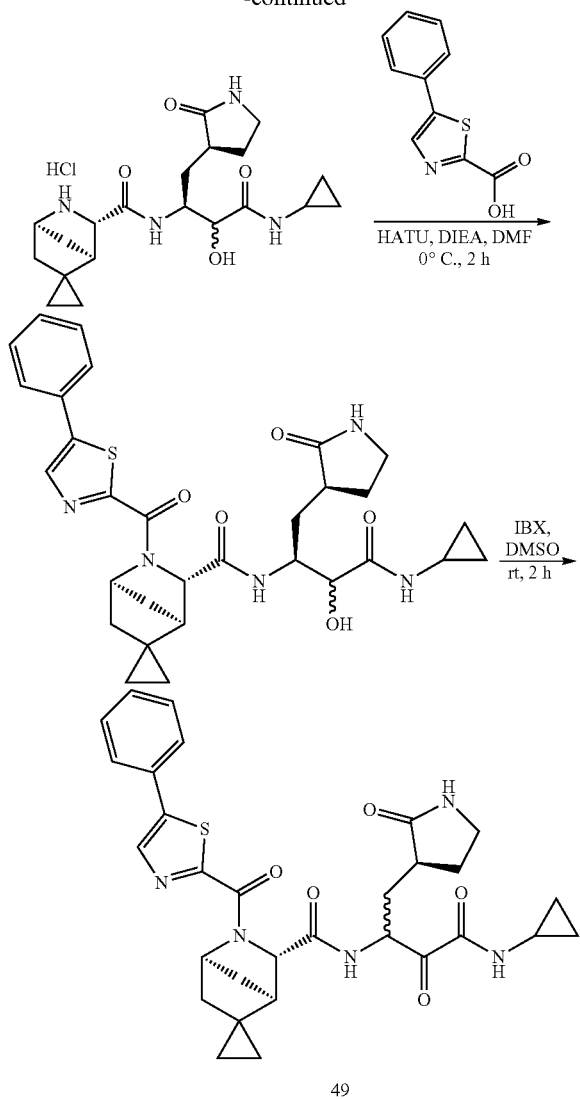

49

A mixture of tert-butyl (1R,4S,6S)-6-{[(2S)-1-(cyclopropylcarbamoyl)-1-hydroxy-3-[(3S)-2-oxopyrrolidin-3-yl]propan-2-yl]carbamoyl}-5-azaspiro[bicyclo[2.2.1]heptane-2,1'-cyclopropane]-5-carboxylate (20.0 mg, 0.041 mmol, 1.0 eq.) in hydrogen chloride (2 mL, 2 M in Et$_2$O) was stirred for 1 h at rt. The mixture was concentrated under reduced pressure to afford (3S)-3-[(1R,4S,6S)-5-azaspiro[bicyclo[2.2.1]heptane-2,1'-cyclopropan]-6-ylformamido]-N-cyclopropyl-2-hydroxy-4-[(3S)-2-oxopyrrolidin-3-yl]butanamide hydrochloride (75 mg, crude) as a yellow oil. LC-MS (ESI, m/z): 391 [M+H]$^+$.

To a mixture of 5-phenyl-1,3-thiazole-2-carboxylic acid (36.05 mg, 0.176 mmol, 1.0 eq.) in N,N-dimethylformamide (2 mL) was added o-(7-azabenzotriazol-1-yl)-N,N,N',N'-tetramethyluronium hexafluorophosphate (80.1 mg, 0.211 mmol, 1.2 eq.) and N-ethyl-N-isopropylpropan-2-amine (136 mg, 1.05 mmol, 6.0 eq.) at 0° C. The mixture was stirred for 20 min at 0° C., and then (3S)-3-[(1R,4S,6S)-5-azaspiro[bicyclo[2.2.1]heptane-2,1'-cyclopropan]-6-ylformamido]-N-cyclopropyl-2-hydroxy-4-[(3S)-2-oxopyrrolidin-3-yl]butanamide hydrochloride (75.0 mg, 0.176 mmol, 1.0 eq.) was added. The mixture was stirred for 2 h at 0° C. The reaction was quenched with water (30 mL). The mixture was extracted with EA (3×50 mL). The organic layers were combined, washed with brine (3×30 mL), dried over anhydrous sodium sulfate, filtered and concentrated under reduced pressure. The residue was purified by TLC (dichloromethane:methanol, 15:1) to afford (3S)—N-cyclopropyl-2-hydroxy-4-[(3S)-2-oxopyrrolidin-3-yl]-3-[(1R,4S,6S)-5-(5-phenyl-1,3-thiazole-2-carbonyl)-5-azaspiro[bicyclo[2.2.1]heptane-2,1'-cyclopropan]-6-ylformamido]butanamide (60.0 mg, 59%) as a yellow solid. LC-MS (ESI, m/z): 578 [M+H]$^+$.

To a stirred mixture of (3S)—N-cyclopropyl-2-hydroxy-4-[(3S)-2-oxopyrrolidin-3-yl]-3-[(1R,4S,6S)-5-(5-phenyl-1,3-thiazole-2-carbonyl)-5-azaspiro[bicyclo[2.2.1]heptane-2,1'-cyclopropan]-6-ylformamido]butanamide (60.0 mg, 0.104 mmol, 1.0 eq.) in DMSO (2 mL) was added 2-iodoxybenzoic acid (87.2 mg, 0.312 mmol, 3.0 eq.). The mixture was stirred for overnight at rt. The reaction was quenched with sat. sodium bicarbonate (10 mL). The mixture was extracted with EtOAc (3×20 mL). The organic layers were combined, washed with brine (3×20 mL), dried over anhydrous sodium sulfate, filtered and concentrated under reduced pressure. The residue was purified by TLC (dichloromethane:methanol, 16:1) to afford N-cyclopropyl-2-oxo-4-[(3S)-2-oxopyrrolidin-3-yl]-3-[(1R,4S,6S)-5-(5-phenyl-1,3-thiazole-2-carbonyl)-5-azaspiro[bicyclo[2.2.1]heptane-2,1'-cyclopropan]-6-ylformamido]butanamide (13.2 mg, 21%) as a white solid. LC-MS (ESI, m/z): 576 [M+H]$^+$.

Example 50

Compound 50

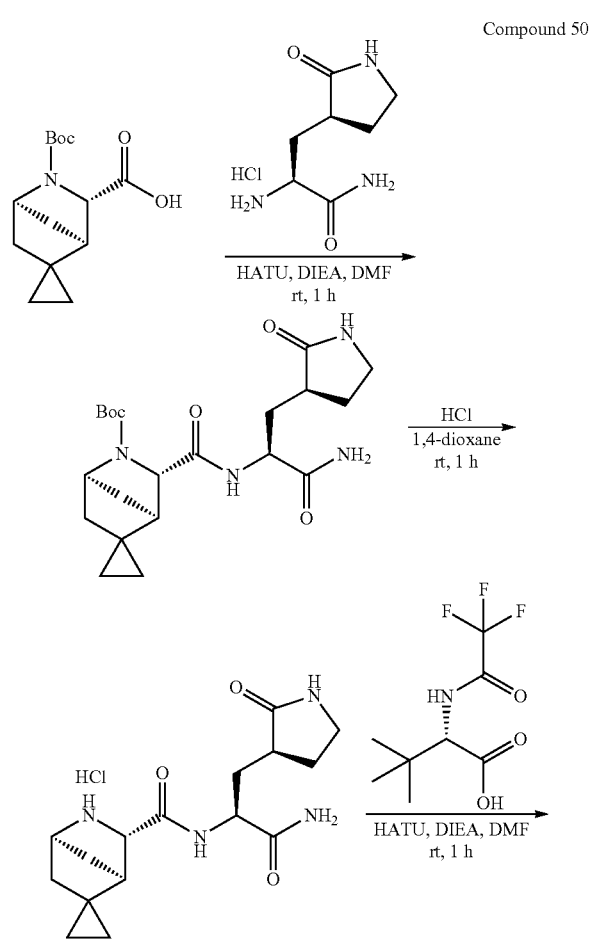

171
-continued

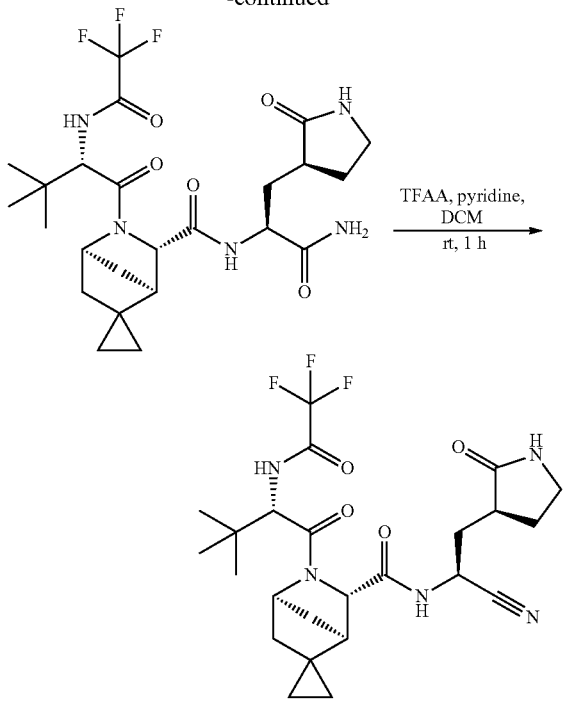

To a stirred mixture of (1R,4S,6S)-5-(tert-butoxycarbonyl)-5-azaspiro[bicyclo[2.2.1]heptane-2,1'-cyclopropane]-6-carboxylic acid (120 mg, 0.449 mmol, 1.0 eq.) and o-(7-Azabenzotriazol-1-yl)-N,N,N',N'-tetramethyluronium hexafluorophosphate (204 mg, 0.539 mmol, 1.2 eq.) in DMF (2 mL) was added N-ethyl-N-isopropylpropan-2-amine (348 mg, 2.69 mmol, 6.0 eq.). The mixture was stirred for 10 min at 0° C., and then (2S)-2-amino-3-[(3S)-2-oxopyrrolidin-3-yl]propanamide hydrochloride (102 mg, 0.494 mmol, 1.1 eq.) was added. The mixture was stirred for 1 h at rt. The crude product was purified by C18 column with CH₃CN: Water (0.05% FA). The desired fractions were concentrated under reduced pressure to provide tert-butyl (1R,4S,6S)-6-{[(1S)-1-carbamoyl-2-[(3S)-2-oxopyrrolidin-3-yl]ethyl]carbamoyl}-5-azaspiro[bicyclo[2.2.1]heptane-2,1'-cyclopropane]-5-carboxylate (120 mg, 60%) as a white solid. LC-MS (ESI, m/z): 421 [M+H]⁺.

To a stirred mixture of tert-butyl (1R,4S,6S)-6-{[(1S)-1-carbamoyl-2-[(3S)-2-oxopyrrolidin-3-yl]ethyl]carbamoyl}-5-azaspiro[bicyclo[2.2.1]heptane-2,1'-cyclopropane]-5-carboxylate (140 mg, 0.333 mmol, 1.0 eq.) in DCM (1 mL) was added hydrogen chloride (3 mL, 2 M in Et₂O). The mixture was stirred for 1 h at rt, and then concentrated under reduced pressure to afford (2S)-2-[(1R,4S,6S)-5-azaspiro[bicyclo[2.2.1]heptane-2,1'-cyclopropan]-6-ylformamido]-3-[(3S)-2-oxopyrrolidin-3-yl]propanamide hydrochloride (110 mg, crude) as a white solid. LC-MS (ESI, m/z): 321 [M+H]⁺.

To a stirred mixture of (2S)-3,3-dimethyl-2-(2,2,2-trifluoroacetamido)butanoic acid (70.7 mg, 0.311 mmol, 1.1 eq.) and o-(7-Azabenzotriazol-1-yl)-N,N,N',N'-tetramethyluronium hexafluorophosphate (129 mg, 0.340 mmol, 1.2 eq.) in DMF (2 mL) were added N-ethyl-N-isopropylpropan-2-amine (219 mg, 1.69 mmol, 6.0 eq.). The mixture was stirred for 10 min at 0° C., and then (2S)-2-[(1R,4S,6S)-5-azaspiro[bicyclo[2.2.1]heptane-2,1'-cyclopropan]-6-ylformamido]-3-[(3S)-2-oxopyrrolidin-3-yl]propanamide hydrochloride (101 mg, 0.283 mmol, 1.0 eq.) was added. The mixture was stirred for 1 h at rt and purified by C18 column with

172

CH₃CN/Water (0.05% FA). The desired fractions were concentrated under reduced pressure to provide (2S)-2-[(1R,4S,6S)-5-[(2S)-3,3-dimethyl-2-(2,2,2-trifluoroacetamido)butanoyl]-5-azaspiro[bicyclo[2.2.1]heptane-2,1'-cyclopropan]-6-ylformamido]-3-[(3S)-2-oxopyrrolidin-3-yl]propanamide (90.0 mg, 57%) as a white solid. LC-MS (ESI, m/z): 530 [M+H]⁺.

To a stirred mixture of (2S)-2-[(1R,4S,6S)-5-[(2S)-3,3-dimethyl-2-(2,2,2-trifluoroacetamido)butanoyl]-5-azaspiro[bicyclo[2.2.1]heptane-2,1'-cyclopropan]-6-ylformamido]-3-[(3S)-2-oxopyrrolidin-3-yl]propanamide (90.0 mg, 0.170 mmol, 1.0 eq.) and pyridine (53.7 mg, 0.680 mmol, 4.0 eq.) in DCM (2 mL) was added trifluoroacetic anhydride (64.2 mg, 0.306 mmol, 1.8 eq.). The mixture was stirred for 1 h at rt. The reaction was quenched with water (10 mL). The mixture was extracted with dichloromethane (3×10 mL). The organic layers were combined, washed with brine (2×10 mL), dried over anhydrous sodium sulfate, filtered and concentrated under reduced pressure to afford the crude product. The crude product was purified by prep-HPLC with the following conditions (Column: XBridge Shield RP18 OBD Column, 19*250 mm, 10 m; Mobile Phase A: Water (0.1% FA), Mobile Phase B: ACN; Flow rate: 25 mL/min; Gradient: 38% B to 68% B in 7 min, 68% B; Wave Length: 254 nm; RT1 (min): 5.07) to afford (1R,4S,6S)—N-[(1S)-1-cyano-2-[(3S)-2-oxopyrrolidin-3-yl]ethyl]-5-[(2S)-3,3-dimethyl-2-(2,2,2-trifluoroacetamido)butanoyl]-5-azaspiro[bicyclo[2.2.1]heptane-2,1'-cyclopropane]-6-carboxamide (18.2 mg, 20%) as a white solid. ¹H NMR (400 MHz, 80° C., DMSO-d₆) δ 9.08-9.65 (m, 1H), 8.45-9.03 (m, 1H), 7.30-7.65 (m, 1H), 4.80-4.98 (m, 1H), 4.42-4.76 (m, 2H), 4.02-4.18 (m, 1H), 3.10-3.30 (m, 2H), 2.30-2.44 (m, 1H), 1.97-2.25 (m, 3H), 1.59-1.97 (m, 5H), 1.40-1.58 (m, 1H), 0.90-1.06 (m, 9H), 0.61-0.83 (m, 2H), 0.21-0.54 (m, 2H). LC-MS (ESI, m/z): 512 [M+H]⁺.

Example 51

Compound 51

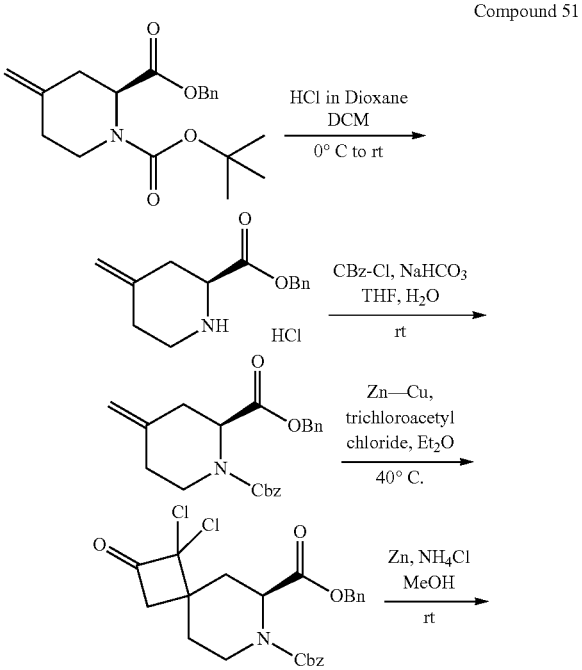

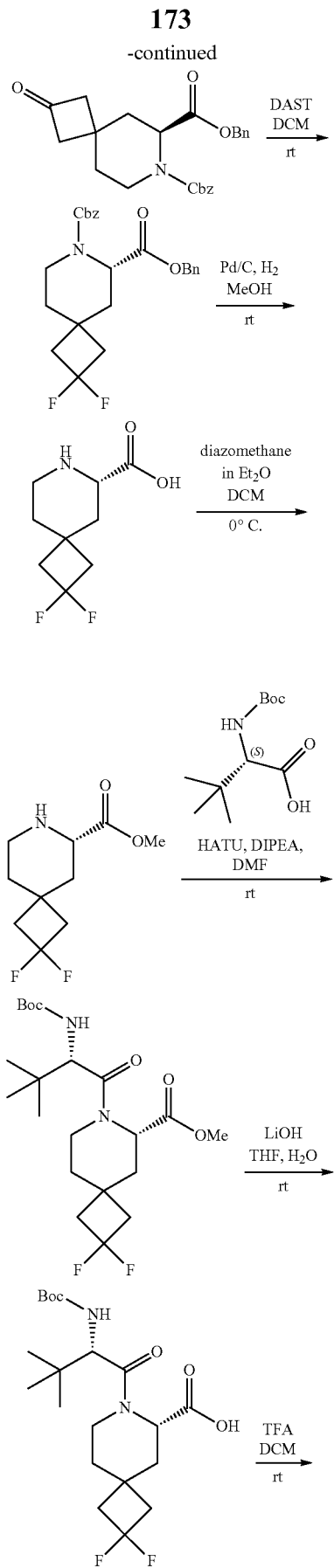
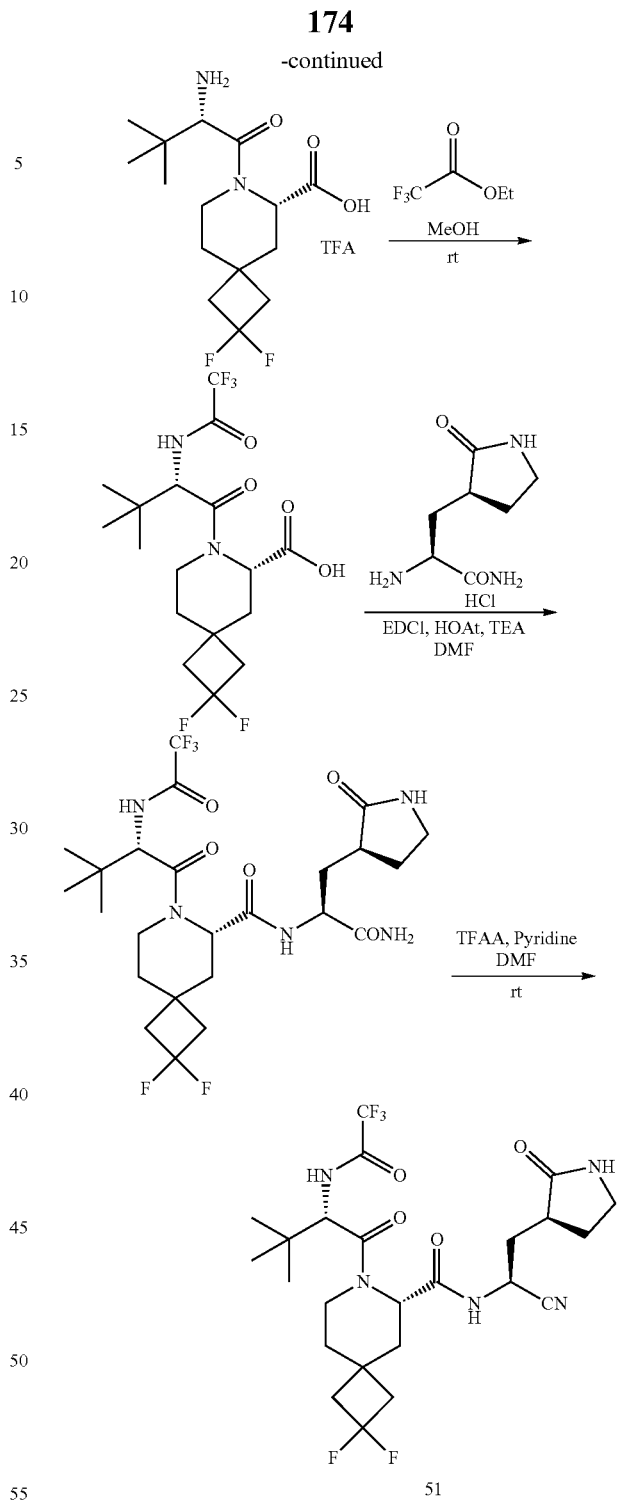

To a solution of 2-benzyl 1-(tert-butyl) (S)-4-methylenepiperidine-1,2-dicarboxylate (3.5 g, 10.6 mmol, 1.0 eq.) in DCM (35 mL) cooled at 0° C. was added 4N HCl in dioxane (10.5 mL, 42.0 mmol, 4.0 eq.). The mixture was stirred at rt for 3 h and then concentrated under reduced pressure to afford benzyl (S)-4-methylenepiperidine-2-carboxylate hydrochloride (2.6 g, 93%) as a white solid. LC-MS (ESI, m/z): 232 [M+H]$^+$.

To a solution of benzyl (S)-4-methylenepiperidine-2-carboxylate hydrochloride (2.4 g, 9.02 mmol, 1.0 eq.) in THF (20 mL) and water (2.5 mL) were added NaHCO$_3$ (2.27 g, 27.1 mmol, 3.0 eq.) and Cbz-Cl (3.0 mL, 10.8 mmol, 1.2 eq.). The mixture was stirred at rt overnight. The mixture was diluted with water (20 mL) and extracted with EA (3×20 mL). The organic phases were combined, washed with brine, dried over Na$_2$SO$_4$, filtered and concentrated under reduced pressure. The residue was purified by flash chromatography on silica gel using a gradient of EA (10 to 30%) in PE to afford dibenzyl (S)-4-methylenepiperidine-1,2-dicarboxylate (3.0 g, 94%) as a colorless oil. LC-MS (ESI, m/z): 366 [M+H]$^+$.

To a solution of Zn—Cu (8.0 g, 63.4 mmol, 7.0 eq.) in Et$_2$O (30 mL) were added trichloacetyl chloride (4.06 g, 36.2 mmol, 4.0 eq.) and a solution of dibenzyl (S)-4-methylenepiperidine-1,2-dicarboxylate (3.0 g, 9.06 mmol, 1.0 eq.) in Et$_2$O (20 mL). The mixture was at 40° C. for 5 h. After cooling to rt, the mixture was washed with sat. NaHCO$_3$ (30 mL), and the phases were separated. The aqueous phase was extracted with Et$_2$O (2×30 mL). The organic phases were combined, dried over Na$_2$SO$_4$, filtered and concentrated under reduced pressure. The residue was purified by flash chromatography on silica gel using a gradient of EA (10 to 30%) in PE to afford dibenzyl (6S)-1,1-dichloro-2-oxo-7-azaspiro[3.5]nonane-6,7-dicarboxylate (3.2 g, 84%) as a colorless liquid.

To a solution of dibenzyl (6S)-1,1-dichloro-2-oxo-7-azaspiro[3.5]nonane-6,7-dicarboxylate (3.0 g, 6.31 mmol, 1.0 eq.) in MeOH (30 mL) were added NH$_4$Cl (3.37 g, 63.1 mmol, 10.0 eq.) and Zn (4.0 g, 63.1 mmol, 10.0 eq.). The mixture was stirred at rt for 2 h, and then filtered through celite. The filtrate was concentrated under reduced pressure. The residue was purified by flash chromatography on silica gel using a gradient of EA (10 to 30%) in PE to afford dibenzyl (S)-2-oxo-7-azaspiro[3.5]nonane-6,7-dicarboxylate (2.4 g, 88%) as a colorless liquid. LC-MS (ESI, m/z): 408 [M+H]$^+$.

To a solution of dibenzyl (S)-2-oxo-7-azaspiro[3.5]nonane-6,7-dicarboxylate (1.8 g, 4.42 mmol, 1.0 eq.) in DCM (20 mL) cooled at 0° C. was added DAST (2.92 mL, 22.1 mmol, 5.0 eq.). The mixture was stirred at rt overnight. After cooling to 0° C., ice/water (20 mL) was added, and the mixture was extracted with EtOAc (2×20 mL). The organic phases were combined, washed with sat. NaHCO$_3$ (30 mL), dried over Na$_2$SO$_4$, filtered and concentrated under reduced pressure. The residue was purified by flash chromatography on silica gel using a gradient of EA (10 to 30%) in PE to afford dibenzyl (S)-2,2-difluoro-7-azaspiro[3.5]nonane-6,7-dicarboxylate (1.5 g, 80%) as a white solid. LC-MS (ESI, m/z): 430 [M+H]$^+$.

To a solution of dibenzyl (S)-2,2-difluoro-7-azaspiro[3.5]nonane-6,7-dicarboxylate (1.5 g, 3.49 mmol, 1.0 eq.) in MeOH (15 mL) was added 10% Pd/C (700 mg). The mixture was stirred overnight under hydrogen (bladder pressure). The mixture was filtered through celite, and the filtrate was concentrated under reduced pressure to afford (S)-2,2-difluoro-7-azaspiro[3.5]nonane-6-carboxylic acid (600 mg, 84%) as a colorless liquid. LC-MS (ESI, m/z): 206 [M+H]$^+$.

To a solution of (S)-2,2-difluoro-7-azaspiro[3.5]nonane-6-carboxylic acid (200 mg, 0.975 mmol, 1.0 eq.) in DCM (5 mL) cooled at 0° C. was added 2 M diazomethane solution in Et$_2$O (6.0 mL, 12.0 mmol, 12.3 eq.) over 30 min. The mixture was stirred at rt for 2 h. The mixture was concentrated under reduced pressure to afford methyl (S)-2,2-difluoro-7-azaspiro[3.5]nonane-6-carboxylate (200 mg, 94%) as a pale yellow liquid. LC-MS (ESI, m/z): 220 [M+H]$^+$.

To a solution of methyl (S)-2,2-difluoro-7-azaspiro[3.5]nonane-6-carboxylate (200 mg, 0.913 mmol, 1.0 eq.) in DMF (2 mL) cooled at 0° C. were added (S)-2-((tert-butoxycarbonyl)amino)-3,3-dimethylbutanoic acid (253 mg, 1.10 mmol, 1.2 eq.), HATU (416 mg, 1.010 mmol, 1.2 eq.) and DIPEA (0.398 mL, 2.28 mmol, 2.5 eq.). The mixture was stirred at rt for 5 h. The mixture was diluted with water (10 mL) and extracted with EA (2×10 mL). The organic phases were combined, washed with sat. NaHCO$_3$ (30 mL), dried over Na$_2$SO$_4$, filtered and concentrated under reduced pressure. The residue was purified by flash chromatography on silica gel using a gradient of EA (30 to 60%) in PE to afford methyl (S)-7-((S)-2-((tert-butoxycarbonyl)amino)-3,3-dimethylbutanoyl)-2,2-difluoro-7-azaspiro[3.5]nonane-6-carboxylate (350 mg, 88%) as a colorless oil. LC-MS (ESI, m/z): 433 [M+H]$^+$.

To a stirred solution of methyl (S)-7-((S)-2-((tert-butoxycarbonyl)amino)-3,3-dimethylbutanoyl)-2,2-difluoro-7-azaspiro[3.5]nonane-6-carboxylate (300 mg, 0.694 mmol, 1.0 eq.) in THF (1.5 mL) and water (1.5 mL) was added LiOH (43 mg, 1.04 mmol, 1.5 eq.). The mixture was stirred at rt for 2 h and then partially concentrated under reduced pressure to remove THF. The residue was acidified with 1N HCl until pH 4 and extracted with EA (2×10 mL). The organic phases were combined, dried over Na$_2$SO$_4$, filtered and concentrated under reduced pressure to afford (S)-7-((S)-2-((tert-butoxycarbonyl)amino)-3,3-dimethylbutanoyl)-2,2-difluoro-7-azaspiro[3.5]nonane-6-carboxylic acid (270 mg, 93%) as an off-white solid. LC-MS (ESI, m/z): 419 [M+H]$^+$.

To a solution of (S)-7-((S)-2-((tert-butoxycarbonyl)amino)-3,3-dimethylbutanoyl)-2,2-difluoro-7-azaspiro[3.5]nonane-6-carboxylic acid (270 mg, 0.645 mmol, 1.0 eq.) in DCM (2.7 mL) cooled at 0° C. was added TFA (0.24 mL, 3.22 mmol, 5.0 eq.). The mixture was stirred at rt for 3 h and then concentrated under reduced pressure to afford quantitatively (S)-7-((S)-2-amino-3,3-dimethylbutanoyl)-2,2-difluoro-7-azaspiro[3.5]nonane-6-carboxylic acid as a trifluoroacetic acid salt. LC-MS (ESI, m/z): 319 [M+H]$^+$.

To a solution of (S)-7-((S)-2-amino-3,3-dimethylbutanoyl)-2,2-difluoro-7-azaspiro[3.5]nonane-6-carboxylic acid trifluoroacetic acid salt (200 mg, 0.628 mmol, 1.0 eq.) in MeOH (2 mL) were added ethyl 2,2,2-trifluoroacetate (0.23 mL, 3.14 mmol, 5.0 eq.) and NEt$_3$ (0.44 mL, 3.14 mmol, 5.0 eq.). The mixture was stirred at rt overnight and then concentrated under reduced pressure. The residue was purified by flash chromatography on C18 gel using 0.01% TFA in ACN to afford (S)-7-((S)-3,3-dimethyl-2-(2,2,2-trifluoroacetamido)butanoyl)-2,2-difluoro-7-azaspiro[3.5]nonane-6-carboxylic acid (150 mg, 56%) as a white solid. LC-MS (ESI, m/z): 415 [M+H]$^+$.

To a solution of (S)-7-((S)-3,3-dimethyl-2-(2,2,2-trifluoroacetamido)butanoyl)-2,2-difluoro-7-azaspiro[3.5]nonane-6-carboxylic acid (100 mg, 0.241 mmol, 1.0 eq.) in DMF (1 mL) cooled at 0° C. were added (S)-2-amino-3-((S)-2-oxopyrrolidin-3-yl)propanamide hydrochloride (59 mg, 0.289 mmol, 1.2 eq.), EDC·HCl (92 mg, 0.482 mmol, 2.0 eq.), HOAt (32 mg, 0.241 mmol, 1.0 eq.) and NEt$_3$ (0.10 mL, 0.723 mmol, 3.0 eq.). The mixture was stirred at rt overnight. The mixture was diluted with water (5 mL) and extracted with EA (2×5 mL). The organic phases were combined, washed with brine, dried over Na$_2$SO$_4$, filtered and concentrated under reduced pressure. The residue was purified by flash chromatography on C18 gel using 0.01% FA in acetonitrile to afford to afford (S)—N—((S)-1-amino-1-oxo-3-((S)-2-oxopyrrolidin-3-yl)propan-2-yl)-7-((S)-3,3-dimethyl-2-(2,2,2-trifluoroacetamido)butanoyl)-2,2-difluoro-7-azaspiro[3.5]nonane-6-carboxamide (100 mg, 73%) as a white solid. LC-MS (ESI, m/z): 568 [M+H]$^+$.

To a solution of (S)—N—((S)-1-amino-1-oxo-3-((S)-2-oxopyrrolidin-3-yl)propan-2-yl)-7-((S)-3,3-dimethyl-2-(2,2,2-trifluoroacetamido)butanoyl)-2,2-difluoro-7-aza spiro[3.5]nonane-6-carboxamide (100 mg, 0.176 mmol, 1.0 eq.) in DMF (1 mL) were added pyridine (0.042 mL, 0.529 mmol, 3.0 eq.) and TFAA (0.049 mL, 0.352 mmol, 2.0 eq.). The mixture was stirred at rt for 30 min. The mixture was diluted with water (5 mL) and extracted with EA (2×5 mL). The organic phases were combined, washed with brine, dried over $Na_2SO_4$, filtered and concentrated under reduced pressure. The residue was purified by prep-HPLC (Column: X-SELECT-C18, 19×150 mm 5 um; Mobile Phase A: 0.1% FA in water, Mobile Phase B: ACN; Flow rate: 17 mL/min; gradient: 20% B to 70% B in 8 min) to afford (S)—N—((S)-1-cyano-2-((S)-2-oxopyrrolidin-3-yl)ethyl)-7-((S)-3,3-dimethyl-2-(2,2,2-trifluoroacetamido)butanoyl)-2,2-difluoro-7-azaspiro[3.5]nonane-6-carboxamide (90 mg, 93%) as a white solid. $^1$H NMR (500 MHz, 363K, DMSO-$d_6$) δ 8.58-8.84 (m, 2H), 7.39 (s, 1H), 4.75-5.08 (m, 3H), 3.94 (m, 1H), 3.52 (m, 1H), 3.16 (m, 2H), 2.30-2.42 (m, 5H), 2.19 (m, 3H), 1.85 (m, 2H), 1.75 (m, 2H), 1.60 (m, 1H), 0.98 (s, 9H). LCMS (ESI, m/z): 548 [M−H]$^−$.

Example 52

Compound 52

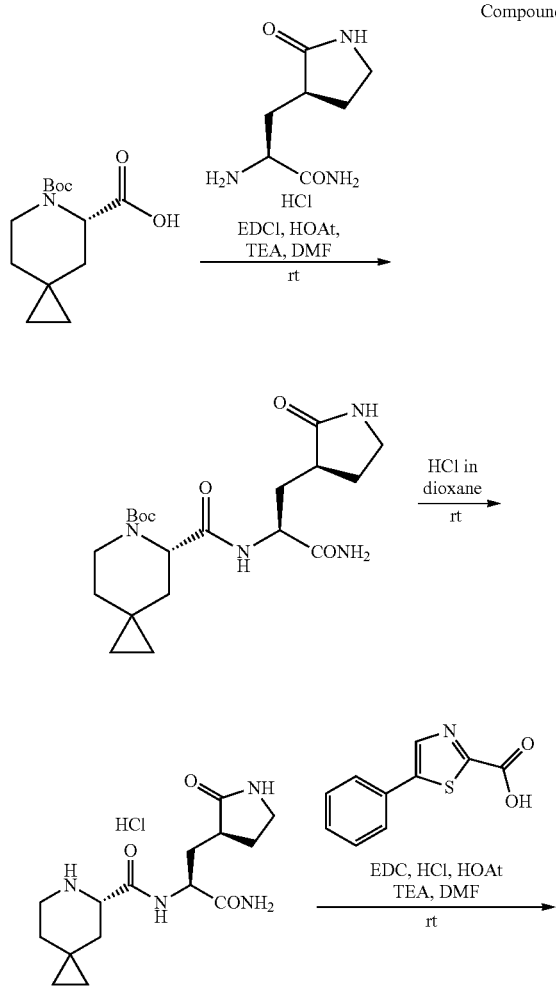

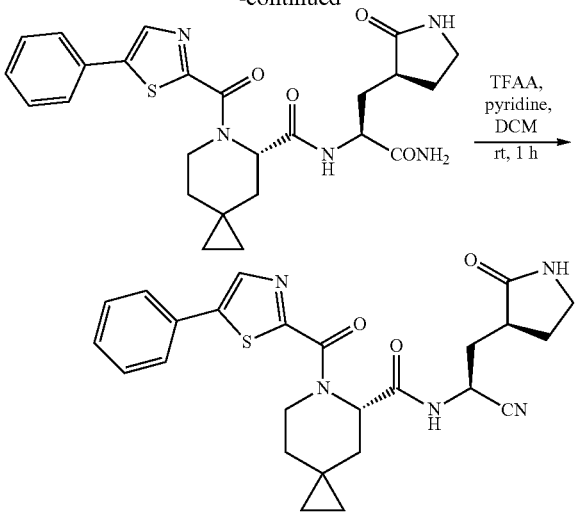

52

To a solution of (S)-2-amino-3-((S)-2-oxopyrrolidin-3-yl)propanamide hydrochloride (121 mg, 0.588 mmol, 1.0 eq.) in DMF (1.5 mL) cooled at 0° C. were added (S)-6-(tert-butoxycarbonyl)-6-azaspiro[2.5]octane-5-carboxylic acid (150 mg, 0.588 mmol, 1.0 eq.), EDC·HCl (224 mg, 1.18 mmol, 2.0 eq.), HOAt (80 mg, 0.588 mmol, 1.0 eq.) and TEA (0.300 mL, 2.35 mmol, 4.0 eq.). The mixture was stirred at rt for 16 h. The mixture was diluted with water (5 ml) and extracted with EA (3×10 mL). The organic phases were combined, dried over $Na_2SO_4$, filtered and concentrated under reduced pressure. The residue was purified by flash chromatography on silica gel using a gradient of MeOH (1 to 10%) in DCM to afford tert-butyl (S)-5-(((S)-1-amino-1-oxo-3-((S)-2-oxopyrrolidin-3-yl)propan-2-yl)carbamoyl)-6-azaspiro[2.5]octane-6-carboxylate (150 mg, 62%) as a white solid. LC-MS (ESI, m/z): 409 [M+H]$^+$.

To a solution of tert-butyl (S)-5-(((S)-1-amino-1-oxo-3-((S)-2-oxopyrrolidin-3-yl)propan-2-yl)carbamoyl)-6-azaspiro[2.5]octane-6-carboxylate (150 mg, 0.367 mmol, 1.0 eq.) in DCM (2 mL) was added 4N HCl in dioxane (0.500 mL, 2.00 mmol, 5.4 eq.). The mixture was stirred at rt for 4 h and then concentrated under reduced pressure to afford (S)—N—((S)-1-amino-1-oxo-3-((S)-2-oxopyrrolidin-3-yl)propan-2-yl)-6-azaspiro[2.5]octane-5-carboxamide hydrochloride salt (0.150 g, 90%) as an off-white solid. LC-MS (ESI, m/z): 309 [M+H]$^+$.

To a solution of (S)—N—((S)-1-amino-1-oxo-3-((S)-2-oxopyrrolidin-3-yl)propan-2-yl)-6-azaspiro[2.5]octane-5-carboxamide hydrochloride salt (150 mg, 0.436 mmol, 1.0 eq.) in DMF (1.0 mL) cooled at 0° C. were added 5-phenylthiazole-2-carboxylic acid (89 mg, 0.436 mmol, 1.0 eq.), EDC·HCl (166 mg, 0.872 mmol, 2.0 eq.), HOAt (59 mg, 0.436 mmol, 1.0 eq.) and TEA (0.24 mL, 1.74 mmol, 4.0 eq.). The mixture was stirred at rt for 16 h. The mixture was diluted with water (20 mL) and extracted with EA (3×10 mL). The organic phases were combined, dried over $Na_2SO_4$, filtered and concentrated under reduced pressure. The residue was purified by flash chromatography on silica gel using a gradient of MeOH (1 to 10%) in DCM to afford (S)—N—((S)-1-amino-1-oxo-3-((S)-2-oxopyrrolidin-3-yl)propan-2-yl)-6-(5-phenylthiazole-2-carbonyl)-6-azaspiro[2.5]octane-5-carboxamide (150 mg, 69%) as a white solid. LC-MS (ESI, m/z): 496 [M+H]$^+$.

To a stirred solution of (S)—N—((S)-1-amino-1-oxo-3-((S)-2-oxopyrrolidin-3-yl)propan-2-yl)-6-(5-phenylthiazole-2-carbonyl)-6-azaspiro[2.5]octane-5-carboxamide (100 mg, 0.202 mmol, 1.0 eq.) in DMF (1 mL) were added pyridine (0.050 mL, 0.606 mmol, 3.0 eq.) and TFAA (0.056 mL, 0.404 mmol, 2.0 eq.). The mixture was stirred at rt for 1 h. The mixture was diluted with water (10 mL) and extracted with EA (3×10 mL). The organic phases were combined, dried over $Na_2SO_4$, filtered and concentrated under reduced pressure. The residue was purified by prep-HPLC (Column: X-SELECT-C18, 19×250 mm, 5 um; Mobile Phase A: 10 mM ammonium bicarbonate in water, Mobile Phase B: ACN; Flow rate: 22 mL/min; Gradient: 35% B to 75% B in 8 min) to afford (S)—N—((S)-1-cyano-2-((S)-2-oxopyrrolidin-3-yl)ethyl)-6-(5-phenylthiazole-2-carbonyl)-6-azaspiro[2.5]octane-5-carboxamide (24 mg, 25%) as a white solid. $^1$H NMR (500 MHz, 363K, DMSO-$d_6$) δ 8.61 (d, 1H), 8.21 (s, 1H), 7.69 (d, 2H), 7.48-7.37 (m, 4H), 4.99 (m, 2H), 3.38 (m, 2H), 3.16 (m, 2H), 2.33 (m, 1H), 2.20-2.14 (m, 3H), 1.86 (m, 2H), 1.73 (m, 2H), 1.02 (d, 1H), 0.44 (m, 1H), 0.33 (in, 3H). LC-MS (ESI, m/z): 478 $[M+H]^+$.

Example 52

LC-MS Methods

| Compound No. | Rt (min) | $[M + H]^+$ or $[M - H]^-$ | LCMS Method |
|---|---|---|---|
| 1 | 2.195 | $[M + H]^+ = 564$ | A |
| 2 | 2.037 | $[M + H]^+ = 481$ | A |
| 3 | 2.193 | $[M + H]^+ = 564$ | A |
| 4 | 2.001 | $[M - H]^- = 533$ | A |
| 5 | 2.019 | $[M - H]^- = 446$ | A |
| 6 | 2.155 | $[M + H]^+ = 521$ | A |
| 7 | 2.022 | $[M + H]^+ = 535$ | A |
| 8 | 2.198 | $[M - H]^- = 558$ | A |
| 9 | 1.982 | $[M + H]^+ = 521$ | A |
| 10 | 2.053 | $[M - H]^- = 533$ | A |
| 11 | 1.969 | $[M - H]^- = 532$ | A |
| 12 | 1.218, 1.299 | $[M + H]^+ = 571$ | 48 |
| 13 | 1.303, 1.348, 1.365, 1.431 | $[M + H]^+ = 579$ | 55 |
| 14 | 1.217, 1.263, 1.281, 1.359 | $[M + H]^+ = 539$ | 53 |
| 15 | 1.210, 1.287 | $[M + H]^+ = 551$ | 48 |
| 16 | 1.327, 1.342, 1.420 | $[M + H]^+ = 525$ | 54 |
| 17 | 0.939, 1.028 | $[M + H]^+ = 561$ | 48 |
| 18 | 1.017, 1.100 | $[M + H]^+ = 549$ | 48 |
| 19 | 1.133, 1.212 | $[M + H]^+ = 560$ | 48 |
| 20 | 1.269, 1.354 | $[M + H]^+ = 521$ | 56 |
| 21 | 1.055, 1.138 | $[M + H]^+ = 531$ | 48 |
| 22 | 1.310, 1.377 | $[M + H]^+ = 596$ | 48 |
| 23 | 1.000, 1.123 | $[M + H]^+ = 538$ | 48 |
| 24 | 1.284, 1.348 | $[M + H]^+ = 548$ | 47 |
| 25 | 0.909, 1.084 | $[M + H]^+ = 549$ | 48 |
| 26 | 1.115 | $[M + H]^+ = 576$ | 48 |
| 27 | 2.157 | $[M - H]^- = 560$ | A |
| 28 | 2.046 | $[M - H]^- = 535$ | A |
| 29 | 2.069 | $[M - H]^- = 562$ | A |
| 30 | 2.145 | $[M - H]^- = 546$ | A |
| 31 | 2.170 | $[M - H]^- = 568$ | A |
| 32 | 2.088 | $[M + H]^+ = 535$ | A |
| 33 | 2.089 | $[M + H]^+ = 535$ | A |
| 34A | 2.155 | $[M + H]^+ = 561$ | A |
| 34B | 2.169 | $[M + H]^+ = 561$ | A |
| 35 | 2.077 | $[M - H]^- = 498$ | A |
| 36 | 2.118 | $[M + H]^+ = 594$ | A |
| 37 | 2.112 | $[M + H]^+ = 594$ | A |
| 38 | 2.159 | $[M + H]^+ = 578$ | A |
| 39 | 2.163 | $[M + H]^+ = 544$ | A |
| 40 | 2.073 | $[M + H]^+ = 564$ | A |
| 41 | 2.063 | $[M + H]^+ = 558$ | A |
| 42 | 2.143 | $[M + H]^+ = 594$ | A |
| 43 | 2.163 | $[M + H]^+ = 598$ | A |
| 44 | 2.183 | $[M + H]^+ = 598$ | A |
| 45 | 2.145, 2.243 | $[M + H]^+ = 598$ | A |
| 46 | 2.186, 2.284 | $[M + H]^+ = 570$ | A |
| 47 | 1.995 | $[M + H]^+ = 521$ | A |
| 48 | 2.028 | $[M + H]^+ = 521$ | A |
| 49 | 1.020 | $[M + H]+ = 576$ | 63 |
| 50 | 0.939 | $[M + H]+ = 512$ | 11 |
| 51 | 2.151 | $[M - H]^- = 548$ | A |
| 52 | 2.180 | $[M + H]^+ = 478$ | A |

Final compounds can be obtained in some cases as a mixture with a corresponding stereoisomer. Retention times of the main isomers are depicted in the table above.

Description of LC-MS Methods

| LC Method | Instrument | Column | Mobile Phase | Gradient | Flow | Col T | Run Time |
|---|---|---|---|---|---|---|---|
| A | Agilent 6150 SQ Mass Spectrometer coupled to an Agilent 1290 Infinity LC System | Acquity UPLC BEH C18 (1.7 μm, 2.1*50 mm) | A: 0.1% FA in Water, B: 0.1% FA in Acetonitrile | 98% A held for 0.2 min, to 2% A in 1.3 min, held for 1.8 min, to 98% A in 0.1 min, held for 0.4 min | 0.6 mL/min | 70 | 3.8 min |
| 11 | Shimadzu LCMS-2020 | HALO 2.0 μm C18 90A (2.0 μm, 3.0*30 mm) | A: Water/0.1% FA B: Acetonitrile/ 0.1% FA | From 95% A to 0% A in 1.09 min, held for 0.6 min, to 95% A in 0.05 min, held for 0.10 min | 1.5 mL/min | 40 | 1.85 min |
| 47 | Shimadzu LCMS-2020 | Shim-pack Scepter SP-C18 (3 μm, 3.0*33 mm) | A: Water/6.5 mM $NH_4HCO_3$ + Ammonia Hydroxide (pH = 10) B: Acetonitrile | From 80% A to 5% A in 1.99 min, held for 0.7 min, to 90% A in 0.05 min, held for 0.25 min | 1.2 mL/min | 40 | 3 min |
| 48 | Shimadzu LCMS-2020 | Shim-pack Scepter SP-C18 (3 μm, 3.0*33 mm) | A: Water/6.5 mM $NH_4HCO_3$ + Ammonia Hydroxide (pH = 10) B: Acetonitrile | From 70% A to 5% A in 1.99 min, held for 0.7 min, to 90% A in 0.05 min, held for 0.25 min | 1.2 mL/min | 40 | 3 min |
| 53 | Shimadzu LCMS-2020 | Shim-Pack C18 (3 μm, 3.0*33 mm) | A: Water/0.1% FA B: ACN/0.1% FA | From 95% A to 35% A in 1.69 min, to 5% A in 0.6 min, held for 0.5 min, to 90% A in 0.03 min, held for 0.17 min | 1.2 mL/min | 40 | 3 min |

| LC Method | Instrument | Column | Mobile Phase | Gradient | Flow | Col T | Run Time |
|---|---|---|---|---|---|---|---|
| 54 | Shimadzu LCMS-2020 | Shim-Pack C18 (3 µm, 3.0*33 mm) | A: Water/6.5 mM NH$_4$HCO$_3$ + Ammonia Hydroxide (pH = 10) B: Acetonitrile | From 90% A to 30% A in 1.69 min, to 5% A in 0.6 min, held for 0.5 min, to 90% A in 0.03 min, held for 0.17 min | 1.2 mL/min | 40 | 3 min |
| 55 | Shimadzu LCMS-2020 | Shim-Pack C18 (3 µm, 3.0*33 mm) | A: Water/6.5 mM NH$_4$HCO$_3$ + Ammonia Hydroxide (pH = 10) B: Acetonitrile | From 90% A to 35% A in 1.69 min, to 5% A in 0.6 min, held for 0.5 min, to 90% A in 0.03 min, held for 0.17 min | 1.2 mL/min | 40 | 3 min |
| 56 | Shimadzu LCMS-2020 | Shim-Pack C18 (3 µm, 3.0*33 mm) | A: Water/6.5 mM NH$_4$HCO$_3$ + Ammonia Hydroxide (pH = 10) B: Acetonitrile | From 90% A to 40% A in 1.69 min, to 5% A in 0.6 min, held for 0.5 min, to 90% A in 0.03 min, held for 0.17 min | 1.2 mL/min | 40 | 3 min |
| 63 | Shimadzu LCMS-2020 | Shim-Pack C18 (3 µm, 3.0*33 mm) | A: Water/6.5 mM NH$_4$HCO$_3$ + Ammonia Hydroxide (pH = 10) B: Acetonitrile | From 90% A to 5% A in 1.19 min, held for 0.6 min, to 90% A in 0.02 min, held for 0.18 min | 1.5 mL/min | 40 | 2 min |

Example 53

Additional Compounds

Additional compounds of Formula (I) can be prepared using similar materials and methods described herein, such as those described below.

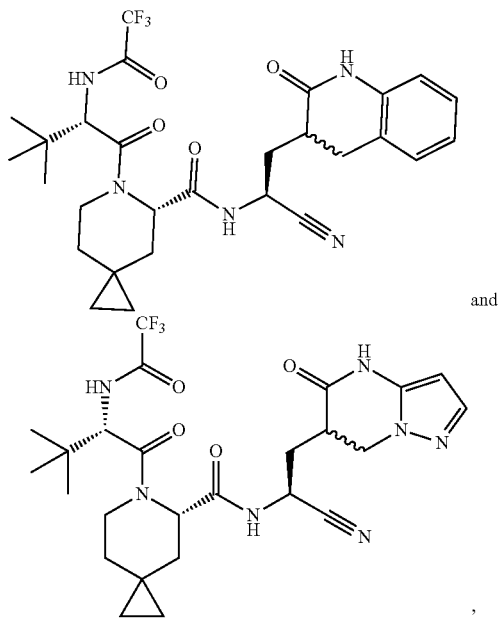

including pharmaceutically acceptable salts thereof.

Example A

SARS-Cov-2 3CLpro and HRV3C Duplex Assay

Protease assays were performed in 384-well low volume polypropylene microtiter plates at ambient temperature. For the duplex assay, 3CLpro and HRV3C was added using a Multidrop Combi (Thermo Scientific; Waltham, MA) and preincubated for 30 mins with small molecules. The reactions were initiated by the addition of the two peptide substrates. The reactions were incubated for 30 mins and quenched by the addition of 0.5% formic acid (final) with subsequent neutralization using 1% sodium bicarbonate (final). Internal standard peptides were added in 20 mM Hepes pH 8.0 for quantitation of the protease products. For SAMDI-MS analysis, 2 µL of each reaction mixture was transferred using a 384-channel automated liquid handler to SAMDI biochip arrays functionalized with a neutravidin-presenting self-assembled monolayer. The SAMDI arrays were incubated for 1 h in a humidified chamber to allow the specific immobilization of the biotinylated peptide substrates, cleaved products and internal standards. The samples were purified by washing the SAMDI arrays with deionized ultrafiltered water and dried with compressed air. A matrix comprising alpha-cyano cinnamic acid in 80% acetonitrile: 20% aqueous ammonium citrate was applied in an automated format by dispensing 50 nL to each spot in the array. SAMDI-MS was performed using reflector-positive mode on an AB Sciex TOF-TOF 5800 System (AB Sciex, Framingham, MA) with 400 shots/spot analyzed in a random raster sampling. For data analysis, area under the curves (peaks) (AUCs) for the product and internal standard were calculated using the TOF/TOF Series Explorer (AB Sciex), and the amount of product formed was calculated using the equation (AUC product/AUC internal standard). The amount of product generated was calculated using the ratio of product area under the curve (AUC) divided by the AUC of the internal standard. Negative controls were pre-quenched with 0.5% formic acid final. Assay robustness was determined by Z-Factor. The IC$_{50}$s were determined by fitting the curves using a four-parameter equation in Graphpad Prism 8.

Table 1 indicates related IC$_{50}$ values for the tested compounds where 'A' indicates an EC$_{50}$<20 nM, 'B' indicates an IC$_{50}$ of ≥20 nM and <200 nM, 'C' indicates an IC$_{50}$≥200 nM and <2000 nM and 'D' indicates an IC$_{50}$≥2000 nM and <20000 nM. '>10 indicates an IC$_{50}$>10000 nM. As shown by the data in Table 1, compounds described herein (including pharmaceutically acceptable salts thereof) can effectively inhibit and be used to treat a coronavirus and rhinovirus.

TABLE 1

| Compound | SARS-Cov-2 | HRV |
|---|---|---|
| 1 | B | C |
| 2 | B | >10 |
| 3 | B | D |
| 4 | B | D |
| 5 | C | >10 |
| 6 | B | C |
| 7 | A | C |
| 8 | A | D |
| 9 | C | D |
| 10 | B | C |
| 11 | B | A |
| 12 | A | B |
| 13 | C | >10 |
| 14 | B | C |
| 15 | A | D |
| 16 | B | D |
| 17 | C | D |
| 18 | B | C |
| 19 | A | C |
| 20 | C | >10 |
| 21 | A | C |
| 22 | A | C |
| 23 | B | D |
| 24 | C | C |
| 25 | B | C |
| 26 | C | C |
| 27 | A | C |
| 28 | A | B |
| 29 | A | D |
| 30 | B | >10 |
| 31 | A | D |
| 32 | B | C |
| 33 | B | C |
| 34A | C | >10 |
| 34B | B | D |
| 35 | A | >10 |
| 36 | C | D |
| 37 | C | C |
| 38 | C | D |
| 39 | C | D |
| 40 | C | C |
| 41 | C | C |
| 42 | C | >10 |
| 43 | C | >10 |
| 44 | C | >10 |
| 45 | B | D |
| 46 | C | >10 |
| 47 | D | C |
| 48 | B | C |
| 49 | B | D |
| 50 | A | >10 |
| 51 | C | >10 |
| 52 | C | >10 |

Example B

Coronavirus Assay
OC43 Coronavirus Assay in HeLa Cells

The human beta-coronavirus OC43 was purchased from ATCC (Manassas, VA) and propagated using HCT-8 human colorectal epithelial cells (ATCC). HeLa human cervical epithelial cells (ATCC) were used as susceptible host cell lines and were cultured using EMEM media, supplemented with 10% fetal bovine serum (FBS), 1% (v/v) penicillin/streptomycin (P/S), 1% (v/v) HEPES and 1% (v/v) cellgro Glutagro™ supplement (all Corning, Manassas, VA) at 37° C. For the OC43 antiviral assay, $1.5 \times 10^4$ HeLa cells per well were plated in 100 µL complete media in white 96-well plates with clear bottoms at 37° C. for up to 24 h to facilitate attachment and allow cells to recover from seeding stresses. Next day, the cell culture medium was removed. Serially diluted compounds in 100 µL assay media (EMEM, 2% FBS, 1% P/S, 1% cellgro Glutagro™ supplement, 1% HEPES) were added to the cells and incubated for 4H at 37° C. in a humidified 5% $CO_2$ incubator. 100 µL of OC43 virus stock was diluted to a concentration known to produce optimal cytopathic effect, inducing 80-90% reduction in cell viability. 96-well plates were incubated for 6 (HeLa) days at 33° C.; each plate contains uninfected control wells as well as virus-infected wells that were not treated with compound. Cytotoxicity plates without the addition of OC43 virus were carried out in parallel. At the end of the incubation period, 100 µL cell culture supernatant was replaced with 100 µL cell-titer-glo reagent (Promega, Madison, WI) and incubated for at least 10 min at rt prior to measuring luminescence. Luminescence was measured on a Perkin Elmer (Waltham, MA) Envision plate reader. Antiviral % inhibition was calculated as follows: [(Compound treated cells infected sample)−(no compound infected control)]/[(Uninfected control)−(no compound infected control)]*100; Using Graph-Pad (San Diego, CA) prism software version 8.3.1, the antiviral dose-response plot was generated as a sigmoidal fit, log(inhibitor) vs response-variable slope (four parameters) model and the $EC_{50}$ was calculated which is the predicted compound concentration corresponding to a 50% inhibition of the viral cytopathic effect.

Table 2 indicates related $EC_{50}$ and $CC_{50}$ values for the tested compounds 'A' indicates an $EC_{50}$<100 nM, 'B' indicates an $EC_{50}$ of ≥100 nM and <1000 nM, 'C' indicates an $EC_{50}$≥1000 nM and <10000 nM and 'D' indicates an $EC_{50}$≥10000 nM and <100000 nM. For $CC_{50}$, 'A' indicates a $CC_{50}$≥100000 nM, 'B' indicates an $CC_{50}$ of ≥10000 nM and <100000 nM and 'C' indicates an $CC_{50}$<10000 nM.

TABLE 2

| Compound | $EC_{50}$ | $CC_{50}$ |
|---|---|---|
| 1 | B | B |
| 2 | C | A |
| 3 | B | B |
| 4 | C | A |
| 5 | C | A |
| 6 | B | A |
| 7 | B | A |
| 8 | B | A |
| 9 | C | A |
| 10 | C | A |
| 11 | C | A |
| 12 | B | B |
| 13 | >10 | A |
| 14 | >10 | A |
| 15 | B | A |
| 16 | C | A |
| 17 | C | A |
| 18 | C | A |
| 19 | C | A |
| 20 | >10 | A |
| 21 | B | A |
| 22 | B | B |
| 23 | B | A |
| 24 | C | A |
| 25 | C | A |
| 26 | B | A |
| 27 | B | A |
| 28 | C | A |
| 29 | B | A |
| 30 | B | A |
| 31 | B | A |
| 32 | C | A |
| 33 | C | A |
| 34A | B | A |
| 34B | B | B |
| 35 | B | A |
| 36 | B | >100 |
| 37 | B | >100 |

TABLE 2-continued

| Compound | EC$_{50}$ | CC$_{50}$ |
|---|---|---|
| 38 | B | >100 |
| 39 | B | >100 |
| 40 | B | >100 |
| 41 | B | >100 |
| 42 | B | >100 |
| 43 | B | >100 |
| 44 | B | B |
| 45 | B | B |
| 46 | B | >100 |
| 47 | >10 | >100 |
| 48 | B | >100 |
| 49 | B | >100 |
| 50 | A | >100 |
| 51 | C | >100 |
| 52 | >10 | >100 |

SARS-CoV-2 Infection Model in VeroE6 Cells

The SARS-CoV-2 antiviral assay is derived from the previously established SARS-CoV assay (PMID: 15961169). In this assay, fluorescence of Vero E6-eGFP cells declines after infection with SARS-CoV-2 due to the cytopathogenic effect of the virus. In the presence of an antiviral compound, the cytopathogenicity is inhibited and the fluorescent signal rescued. On day −1, the test compounds were serially diluted in assay medium (DMEM supplemented with 2% v/v FCS). The plates were incubated (37° C., 5% CO$_2$ and 95% relative humidity) overnight. On day 0, the diluted compounds were mixed with Vero E6-eGFP cells (25,000 cells/well), SARS-CoV-2-GHB-03021/2020 (20 TCID$_{50}$/well) and the MDR1-inhibitor CP-100356 (final concentration 0.5 µM) in 96-well blackview plates (Greiner Bio-One, Vilvoorde, Belgium). The plates were incubated in a humidified incubator at 37° C. and 5% CO$_2$. At 4 days p.i., the wells were examined for eGFP expression using an argon laser-scanning microscope. The microscope settings were excitation at 488 nm and emission at 510 nm and the fluorescence images of the wells were converted into signal values. The results were expressed as EC$_{50}$ values defined as the concentration of compound achieving 50% rescue from the virus-reduced eGFP signals as compared to the untreated virus-infected control cells. Toxicity of compounds in the absence of virus was evaluated in a standard MTS-assay as described previously (PMID: 22575574).

Table 3 indicates related EC$_{50}$ and CC$_{50}$ values for the tested compounds 'A' indicates an EC$_{50}$<1000 nM, 'B' indicates an EC$_{50}$ of ≥1000 nM and <10000 nM, 'C' indicates an EC$_{50}$≥10000 nM and <100000 nM. For CC$_{50}$, 'A' indicates a CC$_{50}$≥10000 nM, 'B' indicates an CC$_{50}$ of ≥1000 nM and <10000 nM, 'C' indicates an CC$_{50}$<1000 nM. >100 refers to >100 µM, >50 refers to >50 µM.

TABLE 3

| Compound | VeroE6 + CP (EC$_{50}$) | VeroE6 + CP (CC$_{50}$) |
|---|---|---|
| 1 | A | >50 |
| 2 | B | >50 |
| 3 | B | >50 |
| 4 | B | >50 |
| 5 | B | >50 |
| 6 | A | >100 |
| 7 | B | >50 |
| 8 | A | >50 |
| 9 | B | >50 |
| 10 | B | >50 |
| 11 | B | >50 |
| 12 | A | >100 |
| 13 | >50 | >50 |
| 14 | C | >50 |
| 15 | A | >50 |
| 16 | B | >50 |
| 17 | B | >50 |
| 18 | B | >50 |
| 19 | A | >100 |
| 20 | >50 | >50 |
| 21 | A | >50 |
| 22 | A | >50 |
| 23 | B | >50 |
| 24 | B | >50 |
| 25 | B | >50 |
| 26 | B | >50 |
| 27 | A | >50 |
| 28 | A | >50 |
| 29 | A | >50 |
| 30 | A | >50 |
| 31 | A | >50 |
| 32 | A | >50 |
| 33 | A | >50 |
| 34A | B | >50 |
| 34B | A | >50 |
| 35 | A | >50 |
| 36 | B | >50 |
| 37 | B | >50 |
| 38 | B | >50 |
| 39 | B | >50 |
| 40 | B | >50 |
| 41 | B | >50 |
| 42 | B | >50 |
| 43 | B | >50 |
| 44 | B | >50 |
| 45 | A | A |
| 46 | B | >50 |
| 47 | >50 | >50 |
| 48 | B | >50 |
| 49 | A | >50 |
| 50 | A | >50 |
| 51 | B | >50 |
| 52 | C | >50 |

Tables 2 and 3 demonstrate that compounds described herein (including pharmaceutically acceptable salts thereof) can effectively inhibit and treat a coronavirus.

Example C

Picornavirus & Norovirus Assays

Compounds of Formula (I), including pharmaceutically acceptable salts thereof, are tested following a protocol similar to the protocol described in one of the following articles: Kim et al., Journal of Virology (2012) 86(21): 11754-11762, Zhang et al, JACS (2020) (https://dx.doi.org/10.1021/acs.jmedchem.9b01828), and U.S. Pat. No. 9,603,864.

The protocols of Kim et al., and Zhang et al., can be used to test for activity against a coronavirus.

Example D

For the cathepsin L assay, 10 pM of human cathepsin L (R&D Systems; Minneapolis, MN) was preincubated for 30 mins with test compounds. Reactions were initiated by the addition of a peptide substrate Z-FR-AMC (final concentration 2 µM, Anaspec; Fremont, CA). Fluorescence was measured at 2-minute intervals for 30 mins using a 355/460 excitation/emission filter module on an Envision plate reader (Perkin Elmer; Waltham, MA). The IC$_{50}$ values were calculated for each assay by fitting the curves using a four-parameter equation in GraphPad Prism.

Table 4 indicates related IC$_{50}$ values for the tested compounds where 'A' indicates an IC$_{50}$≥10000 nM, 'B' indicates an IC$_{50}$ of ≥1000 nM and <10000 nM, 'C' indicates an IC$_{50}$≥100 nM and <1000 nM, 'D' indicates an IC$_{50}$<100 nM.

TABLE 4

| Compound | Cathepsin L IC$_{50}$ |
|---|---|
| 1 | A |
| 2 | A |
| 3 | A |
| 4 | A |
| 5 | A |
| 6 | A |
| 7 | B |
| 8 | A |
| 9 | A |
| 10 | A |
| 11 | B |
| 12 | B |
| 13 | B |
| 14 | A |
| 15 | B |
| 16 | A |
| 17 | A |
| 18 | A |
| 19 | B |
| 20 | A |
| 21 | B |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34A | B |
| 34B | B |
| 35 | A |
| 36 | A |
| 37 | A |
| 38 | A |
| 39 | B |
| 40 | A |
| 41 | A |
| 42 | A |
| 43 | A |
| 44 | A |
| 45 | A |
| 46 | B |
| 47 | A |
| 48 | B |
| 49 | A |
| 50 | A |
| 51 | A |
| 52 | A |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the present disclosure.

What is claimed is:

1. A compound of Formula (I), or a pharmaceutically acceptable salt thereof, having the structure:

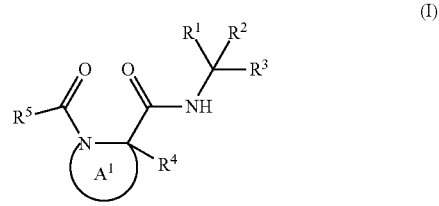

(I)

wherein:
Ring A$^1$ is

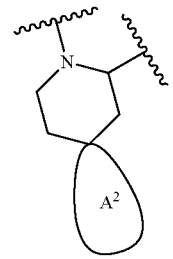

;

Ring A$^2$ is an unsubstituted or a substituted monocyclic C$_{3-6}$ cycloalkyl;

R$^1$ is selected from the group consisting of cyano, an unsubstituted or a substituted C$_{2-5}$ alkynyl, an unsubstituted or a substituted ketoamide, —CH(OH)—(S(=O)$_2$—O$^-$), —CH(OH)((P=O)(OR$^6$)$_2$) and —C(=O)CH$_2$—O—((P=O)(OR$^7$)$_2$), R$^2$ is hydrogen, deuterium or halogen;

R$^3$ is an unsubstituted or a substituted C-amido(C$_{1-4}$ alkyl), an unsubstituted or a substituted monocyclic nitrogen-containing heteroaryl(C$_{1-4}$ alkyl), an unsubstituted or a substituted monocyclic nitrogen-containing heterocyclyl(C$_{1-4}$ alkyl), an unsubstituted or a substituted bicyclic nitrogen-containing heteroaryl(C$_{1-4}$ alkyl) or an unsubstituted or a substituted bicyclic nitrogen-containing heterocyclyl(C$_{1-4}$ alkyl);

R$^4$ is hydrogen, deuterium or halogen;

R$^5$ is 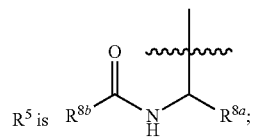;

R$^{8a}$ is selected from the group consisting of an unsubstituted or a substituted C$_{2-6}$ alkyl, an unsubstituted or a substituted C$_{2-6}$ alkenyl, an unsubstituted or a substituted C$_{2-6}$ alkynyl, an unsubstituted or a substituted monocyclic C$_{3-6}$ cycloalkyl, an unsubstituted or a substituted bicyclic C$_{5-8}$ cycloalkyl and an unsubstituted or a substituted monocyclic 4- to 6-membered heterocyclyl, wherein when the C$_{2-6}$ alkyl is substituted, the C$_{2-6}$ alkyl is substituted 1, 2, 3 or 4 times with a substituent independently selected from the group consisting of halogen, cyano, an unsubstituted or a substituted monocyclic C$_{3-6}$ cycloalkyl, an unsubstituted C$_{1-4}$ alkoxy and an unsubstituted $C_{1-4}$ haloalkoxy, or the $C_{2-6}$ alkyl is substituted 1 to 13 times with deuterium;

wherein when the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted, the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted 1, 2, 3 or 4 times with a substituent independently selected from the group consisting of halogen, an unsubstituted $C_{1-4}$ alkyl, an unsubstituted $C_{2-4}$ alkenyl, an unsubstituted $C_{2-4}$ alkynyl, an unsubstituted $C_{1-6}$ haloalkyl, an unsubstituted or a substituted monocyclic $C_{3-6}$ cycloalkyl and an unsubstituted $C_{1-4}$ alkoxy; and $R^{8b}$ is selected from the group consisting of an unsubstituted or a substituted $C_{1-6}$ alkyl, an unsubstituted or a substituted $C_{1-6}$ haloalkyl, an unsubstituted or a substituted monocyclic $C_{3-6}$ cycloalkyl, an unsubstituted or a substituted bicyclic $C_{5-6}$ cycloalkyl, an unsubstituted or a substituted monocyclic heteroaryl and an unsubstituted or a substituted monocyclic heterocyclyl, wherein the substituted $C_{1-6}$ alkyl is substituted 1 or 2 times with an unsubstituted $C_{1-4}$ alkoxy, wherein the substituted monocyclic $C_{3-6}$ cycloalkyl is substituted 1, 2, 3 or 4 times with a substituent independently selected from the group consisting of halogen, an unsubstituted $C_{1-4}$ alkyl, an unsubstituted $C_{2-4}$ alkenyl, an unsubstituted $C_{1-4}$ alkoxy, an unsubstituted $C_{1-4}$ haloalkyl and an unsubstituted monocyclic $C_{3-6}$ cycloalkyl, and wherein the substituted $C_{1-6}$ haloalkyl is substituted 1 or 2 times with an unsubstituted $C_{1-4}$ alkoxy; and each $R^6$ and each $R^7$ are independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl).

2. The compound of claim 1, wherein Ring $A^2$ is an unsubstituted monocyclic $C_{3-6}$ cycloalkyl.

3. The compound of claim 2, wherein $R^{8a}$ is an unsubstituted $C_{2-6}$ alkyl; and $R^{8b}$ is an unsubstituted $C_{1-6}$ haloalkyl.

4. The compound of claim 2, wherein $R^5$ is selected from the group consisting of:

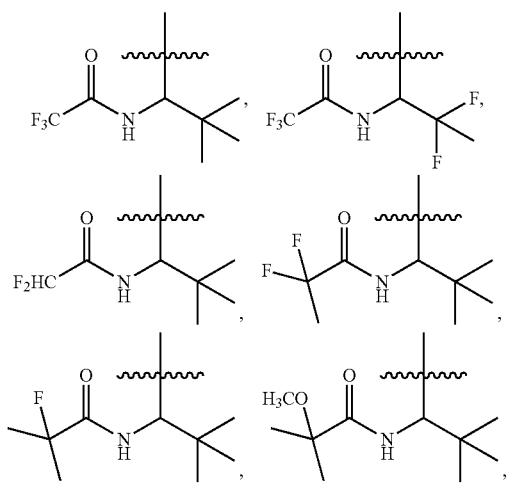

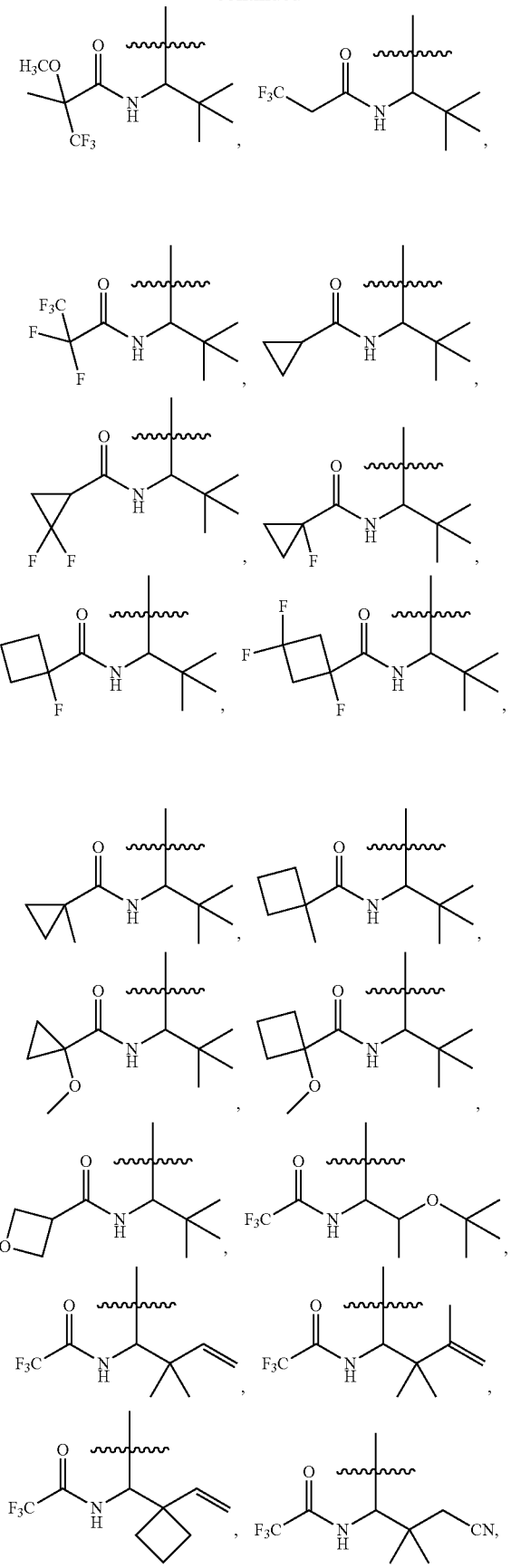

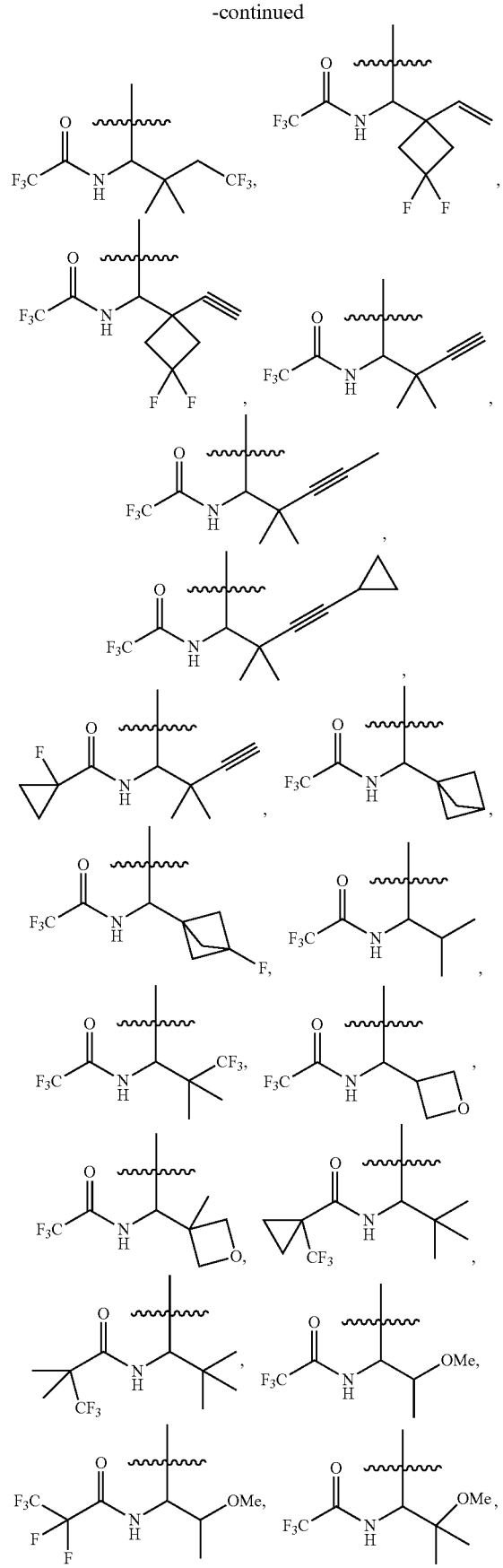
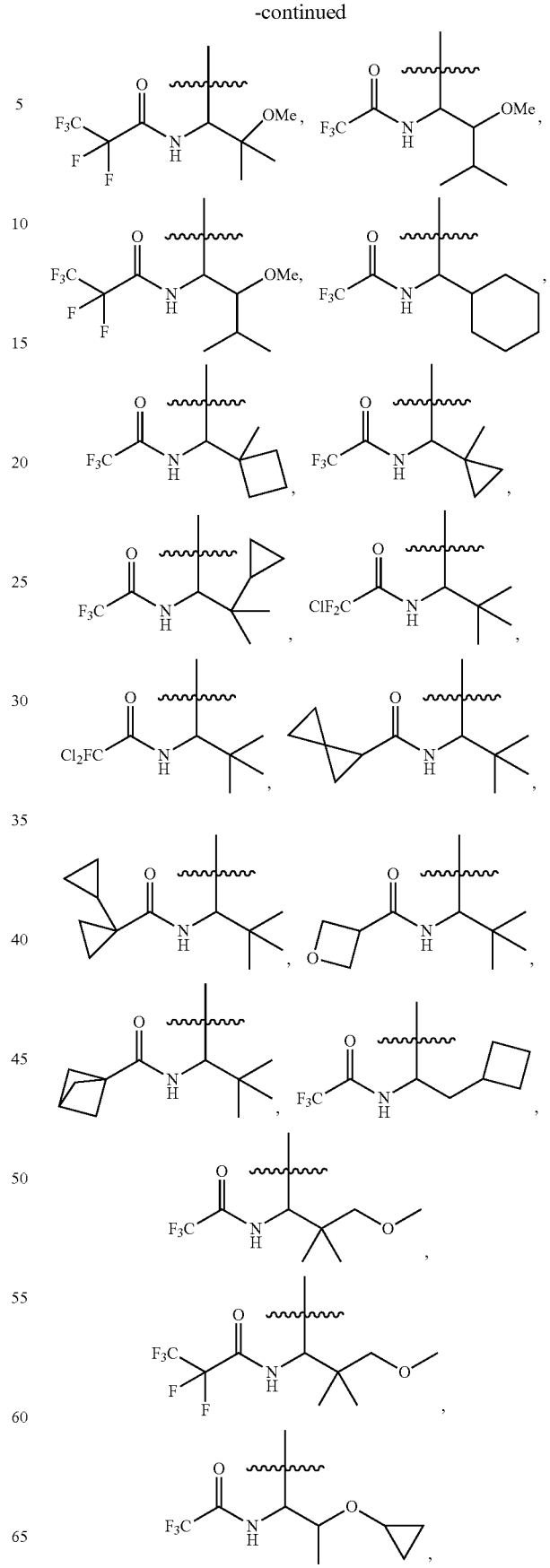

-continued

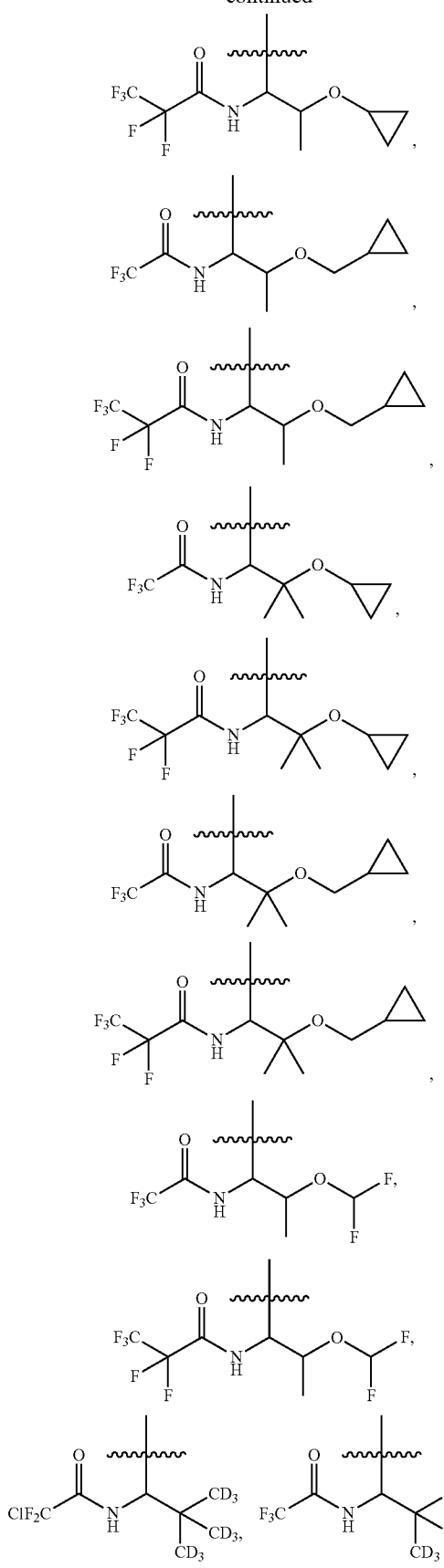

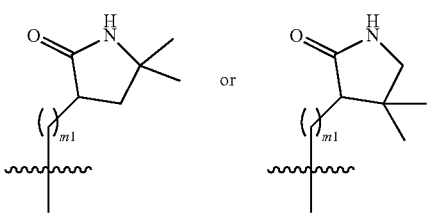

5. The compound of claim 1, wherein $R^1$ is cyano.

6. The compound of claim 1, wherein $R^3$ is an unsubstituted or a substituted monocyclic nitrogen-containing heterocyclyl($C_{1-4}$ alkyl).

7. The compound of claim 6, wherein the monocyclic nitrogen-containing heterocyclyl($C_{1-4}$ alkyl) is azepan-2-one($C_{1-4}$ alkyl), imidazolidin-2-one($C_{1-4}$ alkyl), tetrahydropyrimidin-2-one($C_{1-4}$ alkyl), pyrrolidin-2-one($C_{1-4}$ alkyl), piperidin-2-one($C_{1-4}$ alkyl), pyrazolidin-3-one($C_{1-4}$ alkyl), oxazolidin-4-one($C_{1-4}$ alkyl) 1,4-oxazepan-3-one($C_{1-4}$ alkyl) or morpholin-3-one($C_{1-4}$ alkyl).

8. The compound of claim 1, wherein $R^3$ is

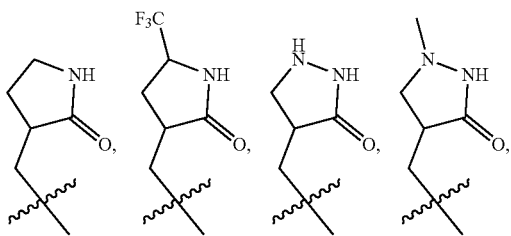

9. The compound of claim 1, wherein $R^3$ is selected from the group consisting of:

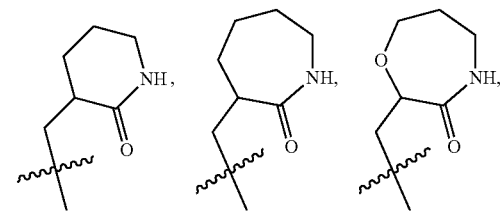

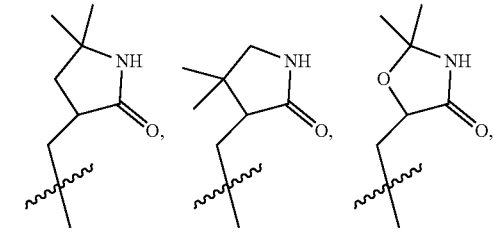

-continued
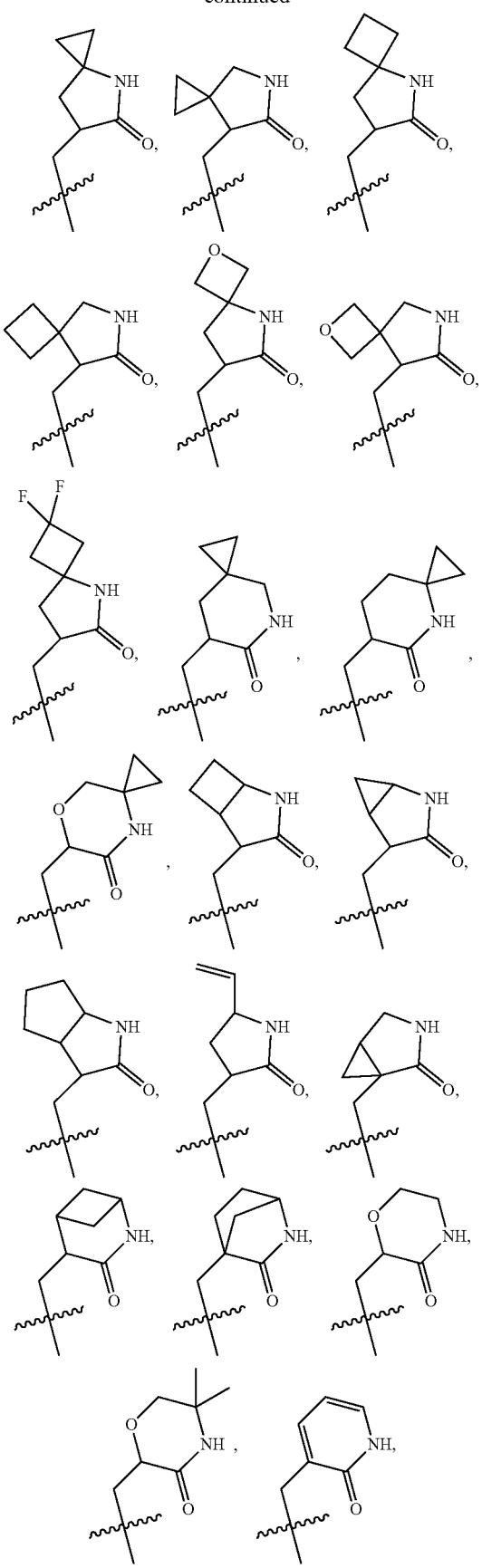
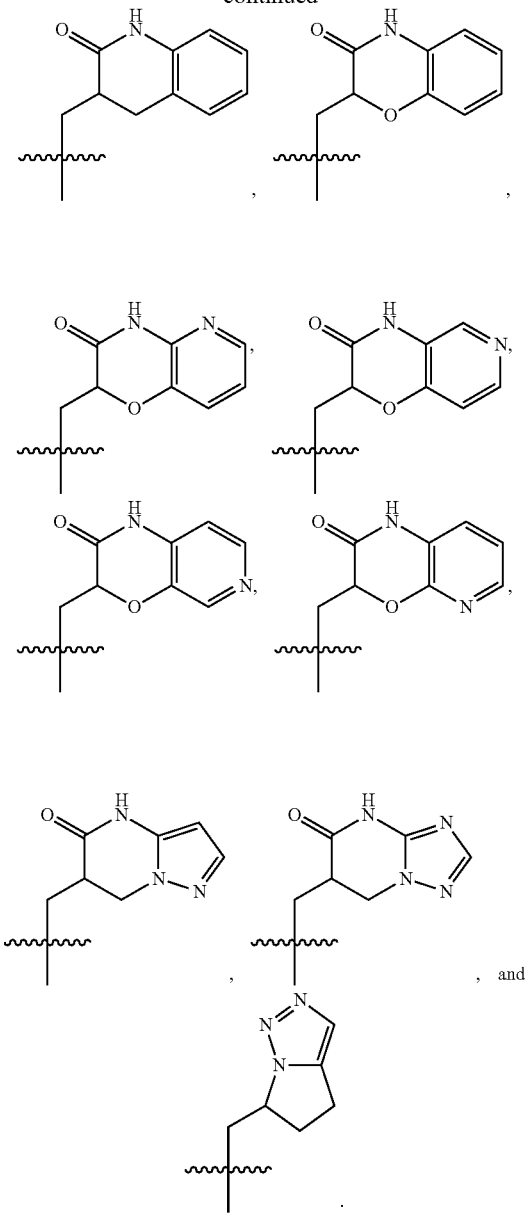
10. The compound of claim 1, wherein $R^2$ is hydrogen; and $R^4$ is hydrogen.
11. The compound of claim 1, wherein the compound is selected from the group consisting of:
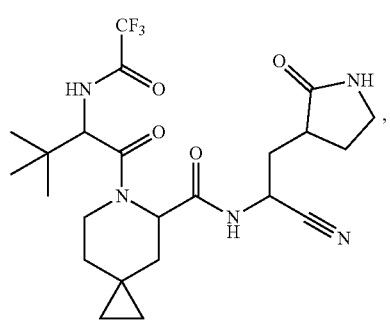

-continued

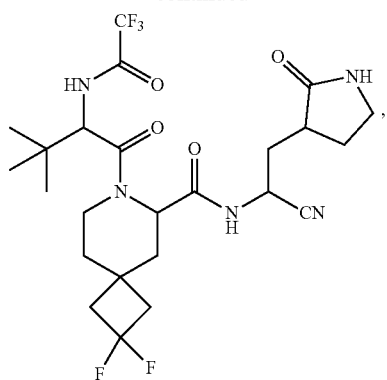

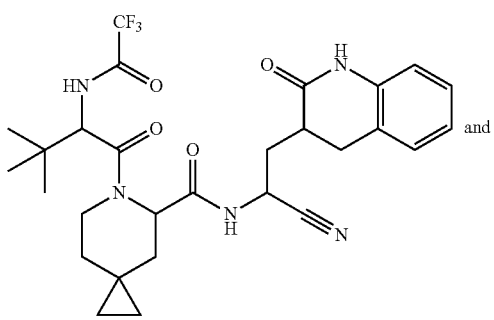

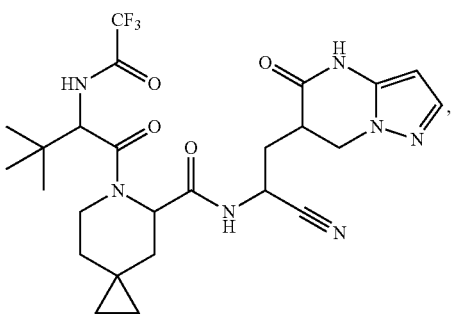

or pharmaceutically acceptable salt of any of the foregoing.

12. The compound of claim 1, wherein the compound is selected from the group consisting of:

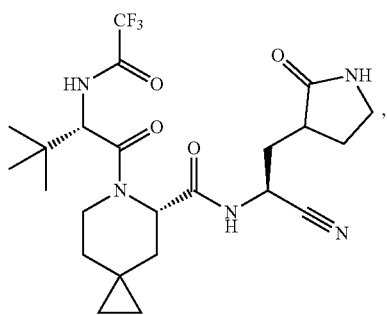

-continued

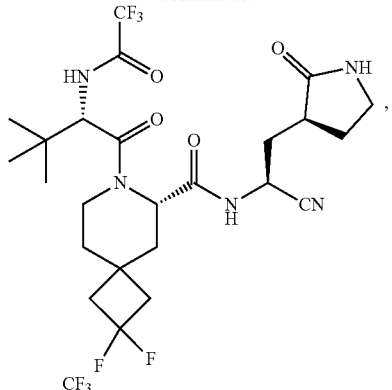

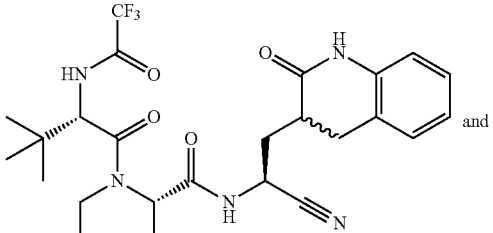

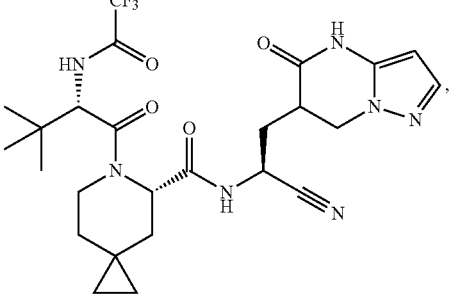

or pharmaceutically acceptable salt of any of the foregoing.

13. A pharmaceutical composition comprising an effective amount of a compound of claim 1, or a pharmaceutically acceptable salt thereof, and excipient.

14. A method for treating a coronavirus infection in a subject comprising administering to the subject in need thereof an effective amount of a compound of claim 1, or a pharmaceutically acceptable salt thereof.

15. The method of claim 14, further comprising administering an additional agent selected from the group consisting of an ACE inhibitor, an anticoagulant, an anti-inflammatory, an ARB, an ASO, a Covid-19 convalescent plasma, an entry inhibitor, an $H_2$ pump antagonist, an H-conducting channel, an HIV protease inhibitor, an HMG-CoA reductase inhibitor, an immune globulin, an immunosuppressant, an immunotherapeutic agent, a neuraminidase inhibitor, a nucleoside inhibitor, a nucleoside analog inhibitor, a polymerase inhibitor, a protease inhibitor, an siRNA, a statin, a tissue plasminogen activator, an antibiotic, an antimicrobial and a vaccine.

16. A method for inhibiting a coronavirus protease comprising contacting a cell infected with a coronavirus with an effective amount of a compound of claim 1, or a pharmaceutically acceptable salt thereof, wherein the compound selectively inhibits the coronavirus protease of the coronavirus compared to Cathepsin L.

17. The compound of claim 2, wherein the unsubstituted monocyclic $C_{3-6}$ cycloalkyl is an unsubstituted cyclopropyl.

18. The compound of claim 9, wherein R³ is selected from the group consisting of:
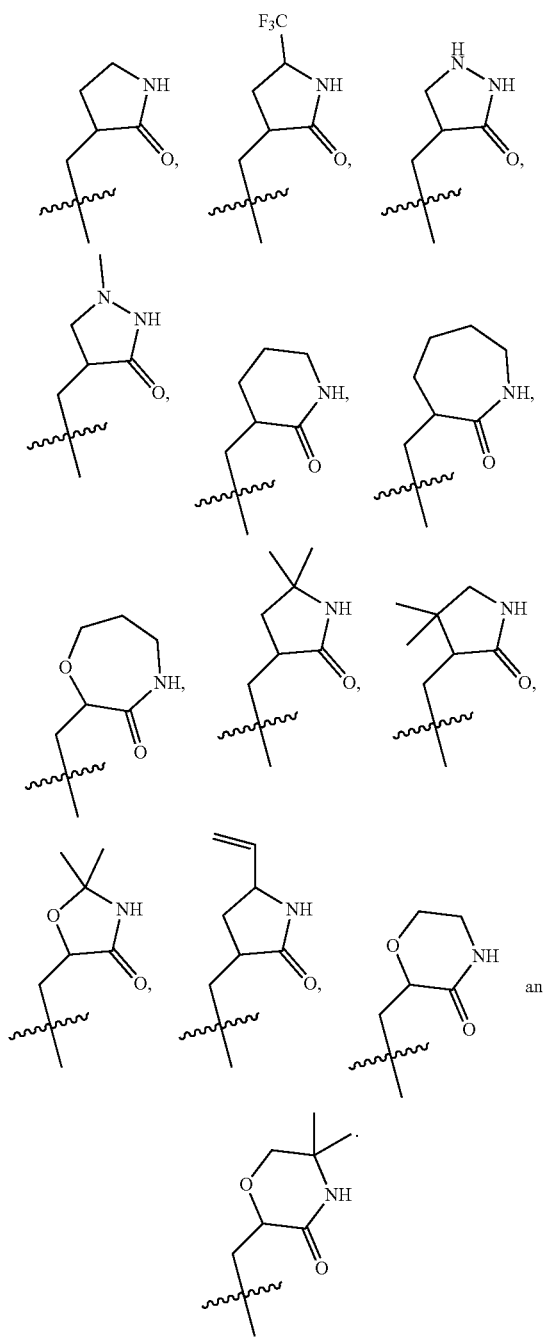
19. The compound of claim 4, wherein R⁵ is selected from the group consisting of:
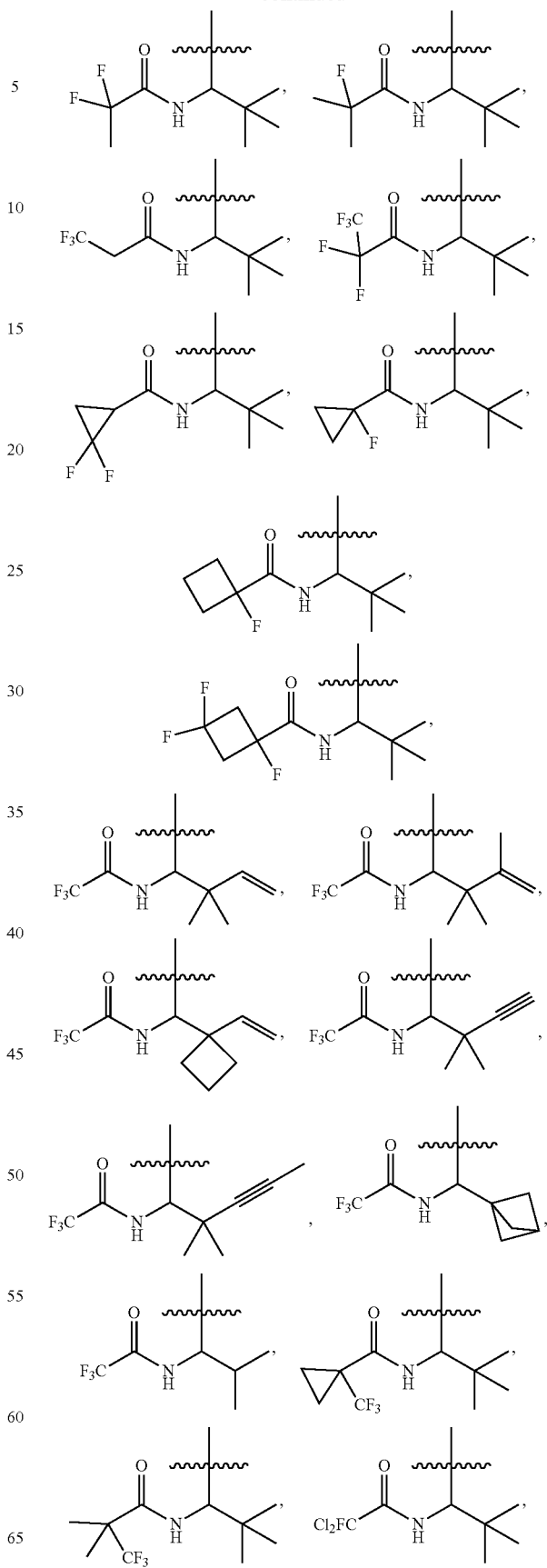

-continued
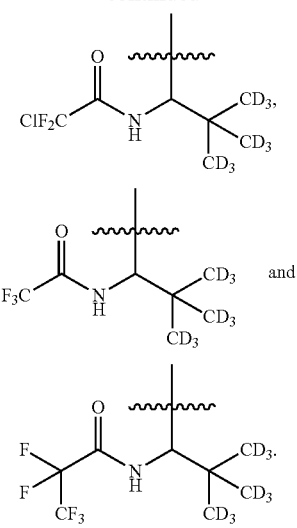
20. The compound of claim 19, wherein $R^2$ is hydrogen; and $R^4$ is hydrogen.
21. The compound of claim 20, wherein $R^1$ is cyano.
22. The compound of claim 21, wherein $R^3$ is an unsubstituted or a substituted monocyclic nitrogen-containing heterocyclyl($C_{1-4}$ alkyl).
23. The compound of claim 22, wherein $R^3$ is selected from the group consisting of:
-continued
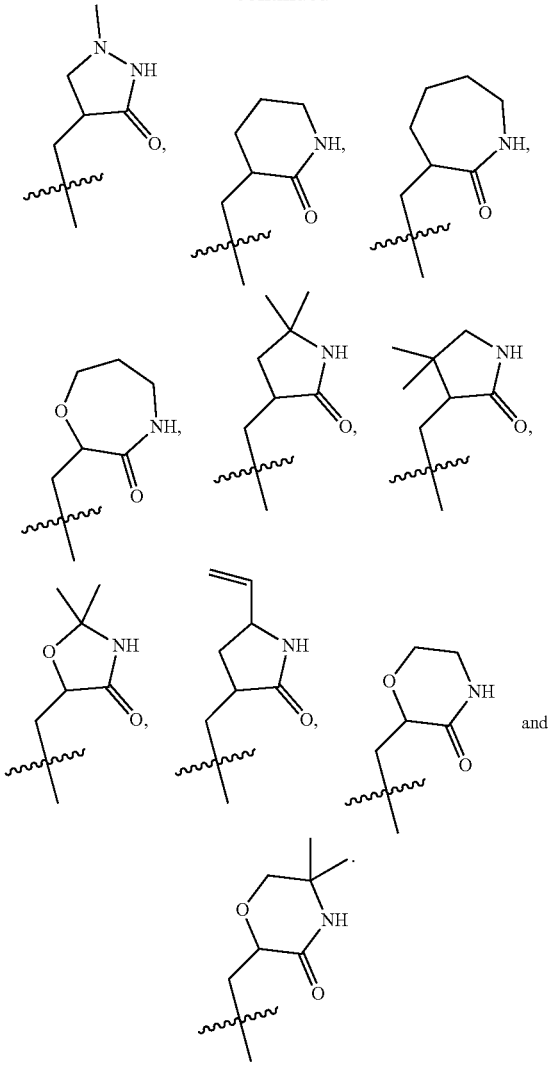
* * * * *